(12) United States Patent
Tesar et al.

(10) Patent No.: US 10,966,798 B2
(45) Date of Patent: Apr. 6, 2021

(54) SURGICAL VISUALIZATION SYSTEMS AND DISPLAYS

(71) Applicant: CamPlex, Inc., Germantown, TN (US)

(72) Inventors: John Tesar, Tucson, AZ (US); William B. Austin, Germantown, TN (US)

(73) Assignee: CamPlex, Inc., Germantown, TN (US)

( * ) Notice: Subject to any disclaimer, the term of this patent is extended or adjusted under 35 U.S.C. 154(b) by 5 days.

(21) Appl. No.: 15/360,565

(22) Filed: Nov. 23, 2016

(65) Prior Publication Data

US 2017/0143442 A1 May 25, 2017

Related U.S. Application Data

(60) Provisional application No. 62/260,221, filed on Nov. 25, 2015, provisional application No. 62/399,237, (Continued)

(51) Int. Cl.
*H04N 13/344* (2018.01)
*A61B 90/00* (2016.01)
(Continued)

(52) U.S. Cl.
CPC .......... *A61B 90/37* (2016.02); *H04N 5/2256* (2013.01); *H04N 5/2354* (2013.01);
(Continued)

(58) Field of Classification Search
CPC ......... A61B 90/37; A61B 34/20; A61B 90/25; A61B 2090/306; A61B 2090/309; A61B 2090/371; A61B 2090/373; A61B 2017/00207; A61B 2017/00216; A61B 2017/00973; H04N 5/2256;
(Continued)

(56) References Cited

U.S. PATENT DOCUMENTS

| 497,064 A | 5/1893 | Van Meter |
| 2,826,114 A | 3/1958 | Bryan |

(Continued)

FOREIGN PATENT DOCUMENTS

| CN | 2336380 Y | 9/1999 |
| CN | 101518438 | 9/2009 |

(Continued)

OTHER PUBLICATIONS

Aesculap Inc.; Aesculap Neurosurgery Pneumatic Kerrison; http://www.aesculapusa.com/assets/base/doc/doc763-pneumatic_kerrison_brochure.pdf; 2008; in 12 pages.

(Continued)

*Primary Examiner* — Eileen M Adams
(74) *Attorney, Agent, or Firm* — Knobbe, Martens, Olson & Bear, LLP

(57) ABSTRACT

A medical apparatus is described for providing visualization of a surgical site. The medical apparatus includes an electronic display disposed within a display housing. The medical apparatus includes a display optical system disposed within the display housing, the display optical system comprising a plurality of lens elements disposed along an optical path. The display optical system is configured to receive images from the electronic display.

41 Claims, 72 Drawing Sheets

Related U.S. Application Data filed on Sep. 23, 2016, provisional application No. 62/401,781, filed on Sep. 29, 2016.

(51) Int. Cl.

| | | |
|---|---|---|
| H04N 5/232 | (2006.01) | |
| H04N 5/235 | (2006.01) | |
| H04N 5/225 | (2006.01) | |
| H04N 5/33 | (2006.01) | |
| H04N 13/398 | (2018.01) | |
| A61B 90/25 | (2016.01) | |
| A61B 90/30 | (2016.01) | |
| A61B 17/00 | (2006.01) | |
| A61B 34/20 | (2016.01) | |

(52) U.S. Cl.
CPC ......... *H04N 5/23293* (2013.01); *H04N 5/332* (2013.01); *H04N 13/344* (2018.05); *H04N 13/398* (2018.05); *A61B 34/20* (2016.02); *A61B 90/25* (2016.02); *A61B 2017/00207* (2013.01); *A61B 2017/00216* (2013.01); *A61B 2017/00973* (2013.01); *A61B 2090/306* (2016.02); *A61B 2090/309* (2016.02); *A61B 2090/371* (2016.02); *A61B 2090/373* (2016.02); *H04N 2005/2255* (2013.01)

(58) Field of Classification Search
CPC .. H04N 5/23293; H04N 5/2354; H04N 5/332; H04N 13/044; H04N 13/0497; H04N 2005/2255
See application file for complete search history.

(56) References Cited

U.S. PATENT DOCUMENTS

| | | |
|---|---|---|
| 3,050,870 A | 8/1962 | Heilig |
| 3,108,781 A | 10/1963 | Saffir |
| 3,128,988 A | 4/1964 | Mandroian |
| 3,141,650 A | 7/1964 | Saffir |
| 3,405,990 A | 10/1968 | Nothnagle et al. |
| 3,409,346 A | 11/1968 | Stapsy |
| 3,664,330 A | 5/1972 | Deutsch |
| 4,056,310 A | 11/1977 | Shimizu et al. |
| 4,063,557 A | 12/1977 | Wuchinich et al. |
| 4,087,198 A | 5/1978 | Theis, Jr. |
| 4,167,302 A | 9/1979 | Karasawa |
| 4,176,453 A | 12/1979 | Abbott |
| 4,223,676 A | 9/1980 | Wuchinich et al. |
| 4,226,228 A | 10/1980 | Shin et al. |
| 4,344,746 A | 8/1982 | Leonard |
| 4,354,734 A | 10/1982 | Nkahashi |
| 4,395,731 A | 7/1983 | Schoolman |
| 4,562,832 A | 1/1986 | Wilder et al. |
| 4,651,201 A | 3/1987 | Schoolman |
| 4,655,557 A | 4/1987 | Takahashi |
| 4,665,391 A | 5/1987 | Spani |
| 4,684,224 A | 8/1987 | Yamashita et al. |
| 4,703,314 A | 10/1987 | Spani |
| 4,718,106 A | 1/1988 | Weinblatt |
| 4,750,488 A | 6/1988 | Wuchinich et al. |
| 4,750,902 A | 6/1988 | Wuchinich et al. |
| 4,779,968 A | 10/1988 | Sander |
| 4,783,156 A | 11/1988 | Yokota |
| 4,786,155 A | 11/1988 | Fantone et al. |
| 4,813,927 A | 3/1989 | Morris et al. |
| 4,873,572 A | 10/1989 | Miyazaki et al. |
| 4,900,301 A | 2/1990 | Morris et al. |
| 4,905,670 A | 3/1990 | Adair |
| 4,920,336 A | 4/1990 | Meijer |
| 4,922,902 A | 5/1990 | Wuchinich et al. |
| 4,986,622 A | 1/1991 | Martinez |
| 4,989,452 A | 2/1991 | Toon et al. |
| 5,016,098 A | 5/1991 | Cooper et al. |
| 5,032,111 A | 7/1991 | Morris et al. |
| 5,047,009 A | 9/1991 | Morris et al. |
| 5,098,426 A | 3/1992 | Sklar et al. |
| 5,143,054 A | 9/1992 | Adair |
| 5,151,821 A | 9/1992 | Marks |
| 5,176,677 A | 1/1993 | Wuchinich et al. |
| 5,201,325 A | 4/1993 | McEwen et al. |
| 5,221,282 A | 6/1993 | Wuchinich |
| 5,251,613 A | 10/1993 | Adair |
| 5,327,283 A | 7/1994 | Zobel |
| 5,354,314 A | 10/1994 | Hardy et al. |
| 5,417,210 A | 5/1995 | Funda et al. |
| 5,441,059 A | 8/1995 | Dannan |
| 5,464,008 A | 11/1995 | Kim |
| 5,523,810 A | 6/1996 | Volk |
| 5,537,164 A | 7/1996 | Smith |
| 5,553,995 A | 9/1996 | Martinez |
| 5,575,789 A | 11/1996 | Bell et al. |
| 5,584,796 A | 12/1996 | Cohen |
| 5,593,402 A | 1/1997 | Patrick |
| 5,601,549 A | 2/1997 | Miyagi |
| 5,625,493 A | 4/1997 | Matsumura et al. |
| 5,634,790 A | 6/1997 | Pathmanabhan et al. |
| 5,667,481 A | 9/1997 | Villalta et al. |
| 5,697,891 A | 12/1997 | Hori |
| 5,712,995 A | 1/1998 | Cohn |
| 5,716,326 A | 2/1998 | Dannan |
| 5,743,731 A | 4/1998 | Lares et al. |
| 5,743,846 A | 4/1998 | Takahashi et al. |
| 5,747,824 A | 5/1998 | Jung et al. |
| 5,751,341 A | 5/1998 | Chaleki |
| 5,797,403 A | 8/1998 | DiLorenzo |
| 5,803,733 A | 9/1998 | Trott et al. |
| 5,822,036 A | 10/1998 | Massie et al. |
| 5,825,534 A | 10/1998 | Strahle |
| 5,835,266 A | 11/1998 | Kitajima |
| 5,841,510 A | 11/1998 | Roggy |
| 5,861,983 A | 1/1999 | Twisselman |
| 5,889,611 A | 3/1999 | Zonneveld |
| 5,897,491 A | 4/1999 | Kastenbauer et al. |
| 5,909,380 A | 6/1999 | Dubois |
| 5,913,818 A | 6/1999 | Co et al. |
| 5,928,139 A | 7/1999 | Koros et al. |
| 5,949,388 A | 9/1999 | Atsumi |
| 5,982,532 A | 11/1999 | Mittelstadt et al. |
| 6,016,607 A | 1/2000 | Morimoto et al. |
| 6,023,638 A | 2/2000 | Swanson |
| 6,088,154 A | 7/2000 | Morita |
| 6,139,493 A | 10/2000 | Koros et al. |
| 6,152,736 A | 11/2000 | Schmidinger |
| 6,152,871 A | 11/2000 | Foley et al. |
| 6,176,825 B1 | 1/2001 | Chin et al. |
| 6,217,188 B1 | 4/2001 | Wainwright et al. |
| 6,246,898 B1 | 6/2001 | Vesely et al. |
| 6,293,911 B1 | 9/2001 | Imaizumi et al. |
| 6,317,260 B1 | 11/2001 | Ito |
| 6,319,223 B1 | 11/2001 | Wortrich et al. |
| 6,340,363 B1 | 1/2002 | Bolger et al. |
| 6,350,235 B1 | 2/2002 | Cohen et al. |
| 6,354,992 B1 | 3/2002 | Kato |
| 6,398,721 B1 | 6/2002 | Nakamura |
| 6,405,072 B1 | 6/2002 | Cosman |
| 6,434,329 B1 | 8/2002 | Dube et al. |
| 6,443,594 B1 | 9/2002 | Marshall et al. |
| 6,450,706 B1 | 9/2002 | Chapman |
| 6,450,950 B2 | 9/2002 | Irion |
| 6,491,661 B1 | 12/2002 | Boukhny et al. |
| 6,508,759 B1 | 1/2003 | Taylor et al. |
| 6,517,207 B2 | 2/2003 | Chapman |
| 6,525,310 B2 | 2/2003 | Dunfield |
| 6,525,878 B1 | 2/2003 | Takahashi |
| 6,527,704 B1 | 3/2003 | Chang et al. |
| 6,538,665 B2 | 3/2003 | Crow et al. |
| 6,549,341 B2 | 4/2003 | Nomura et al. |
| 6,561,999 B1 | 5/2003 | Nazarifar et al. |
| 6,582,358 B2 | 6/2003 | Akui et al. |
| 6,587,711 B1 | 7/2003 | Alfano et al. |
| 6,589,168 B2 | 7/2003 | Thompson |
| 6,618,207 B2 | 9/2003 | Lei |

(56) References Cited

U.S. PATENT DOCUMENTS

| | | |
|---|---|---|
| 6,626,445 B2 | 9/2003 | Murphy et al. |
| 6,633,328 B1 | 10/2003 | Byrd et al. |
| 6,635,010 B1 | 10/2003 | Lederer |
| 6,636,254 B2 | 10/2003 | Onishi et al. |
| 6,661,571 B1 | 12/2003 | Shioda et al. |
| 6,668,841 B1 | 12/2003 | Chou |
| 6,698,886 B2 | 3/2004 | Pollack et al. |
| 6,720,988 B1 | 4/2004 | Gere et al. |
| 6,757,021 B1 | 6/2004 | Nguyen-Nhu |
| 6,805,127 B1 | 10/2004 | Karasic |
| 6,817,975 B1 | 11/2004 | Farr et al. |
| 6,824,525 B2 | 11/2004 | Nazarifar et al. |
| 6,847,336 B1 | 1/2005 | Lemelson et al. |
| 6,869,398 B2 | 3/2005 | Obenchain et al. |
| 6,873,867 B2 | 3/2005 | Vilsmeier |
| 6,892,597 B2 | 5/2005 | Tews |
| 6,903,883 B2 | 6/2005 | Amanai |
| 6,908,451 B2 | 6/2005 | Brody et al. |
| 6,985,765 B2 | 1/2006 | Morita |
| 6,996,460 B1 | 2/2006 | Krahnstoever et al. |
| 7,034,983 B2 | 4/2006 | Desimone et al. |
| 7,050,225 B2 | 5/2006 | Nakamura |
| 7,050,245 B2 | 5/2006 | Tesar et al. |
| 7,054,076 B2 | 5/2006 | Tesar et al. |
| 7,116,437 B2 | 10/2006 | Weinstein et al. |
| 7,125,119 B2 | 10/2006 | Farberov |
| 7,150,713 B2 | 12/2006 | Shener et al. |
| 7,150,714 B2 | 12/2006 | Myles |
| 7,154,527 B1 | 12/2006 | Goldstein et al. |
| 7,155,316 B2 | 12/2006 | Sutherland |
| 7,163,543 B2 | 1/2007 | Smedley et al. |
| 7,226,451 B2 | 6/2007 | Shluzas et al. |
| 7,244,240 B2 | 7/2007 | Nazarifar et al. |
| 7,278,092 B2 | 10/2007 | Krzanowski |
| 7,298,393 B2 | 11/2007 | Morita |
| 7,306,559 B2 | 12/2007 | Williams |
| 7,307,799 B2 | 12/2007 | Minefuji |
| 7,326,183 B2 | 2/2008 | Nazarifar et al. |
| 7,471,301 B2 | 12/2008 | Lefevre |
| 7,480,872 B1 | 1/2009 | Ubillos |
| 7,494,463 B2 | 2/2009 | Nehls |
| 7,518,791 B2 | 4/2009 | Sander |
| 7,537,565 B2 | 5/2009 | Bass |
| 7,538,939 B2 | 5/2009 | Zimmerman et al. |
| 7,559,887 B2 | 7/2009 | Dannan |
| 7,621,868 B2 | 11/2009 | Breidenthal et al. |
| 7,633,676 B2 | 12/2009 | Brunner et al. |
| 7,644,889 B2 | 1/2010 | Johnson |
| 7,651,465 B1 | 1/2010 | Sperling et al. |
| 7,713,237 B2 | 5/2010 | Nazarifar et al. |
| 7,764,370 B2 | 7/2010 | Williams et al. |
| 7,766,480 B1 | 8/2010 | Graham et al. |
| 7,777,941 B2 | 8/2010 | Zimmer |
| 7,785,253 B1 | 8/2010 | Arambula |
| 7,786,457 B2 | 8/2010 | Gao |
| 7,806,865 B1 | 10/2010 | Wilson |
| 7,844,320 B2 | 11/2010 | Shahidi |
| 7,872,746 B2 | 1/2011 | Gao et al. |
| 7,874,982 B2 | 1/2011 | Selover et al. |
| 7,896,839 B2 | 3/2011 | Nazarifar et al. |
| 7,907,336 B2 | 3/2011 | Abele et al. |
| 7,927,272 B2 | 4/2011 | Bayer et al. |
| 7,932,925 B2 | 4/2011 | Inbar et al. |
| 7,956,341 B2 | 6/2011 | Gao |
| 8,009,141 B1 | 8/2011 | Chi et al. |
| 8,012,089 B2 | 9/2011 | Bayat |
| 8,018,523 B2 | 9/2011 | Choi |
| 8,018,579 B1 | 9/2011 | Krah |
| 8,027,710 B1 | 9/2011 | Dannan |
| 8,038,612 B2 | 10/2011 | Paz |
| 8,070,290 B2 | 12/2011 | Gille et al. |
| 8,088,066 B2 | 1/2012 | Grey et al. |
| 8,136,779 B2 | 3/2012 | Wilson et al. |
| 8,149,270 B1 | 4/2012 | Yaron et al. |
| 8,159,743 B2 | 4/2012 | Abele et al. |
| 8,169,468 B2 | 5/2012 | Scott et al. |
| 8,187,167 B2 | 5/2012 | Kim |
| 8,187,180 B2 | 5/2012 | Pacey |
| 8,194,121 B2 | 6/2012 | Blumzvig et al. |
| 8,221,304 B2 | 7/2012 | Shioda et al. |
| 8,229,548 B2 | 7/2012 | Frangioni |
| 8,294,733 B2 | 10/2012 | Eino |
| 8,295,693 B2 | 10/2012 | McDowall |
| 8,351,434 B1 | 1/2013 | Fukuda et al. |
| 8,358,330 B2 | 1/2013 | Riederer |
| 8,405,733 B2 | 3/2013 | Saijo |
| 8,408,772 B2 | 4/2013 | Li |
| 8,409,088 B2 | 4/2013 | Grey et al. |
| 8,419,633 B2 | 4/2013 | Koshikawa et al. |
| 8,419,634 B2 | 4/2013 | Nearman et al. |
| 8,430,840 B2 | 4/2013 | Nazarifar et al. |
| 8,439,830 B2 | 5/2013 | McKinley et al. |
| 8,460,184 B2 | 6/2013 | Nearman et al. |
| 8,464,177 B2 | 6/2013 | Ben-Yoseph et al. |
| 8,482,606 B2 | 7/2013 | Razzaque |
| 8,498,695 B2 | 7/2013 | Westwick et al. |
| 8,521,331 B2 | 8/2013 | Itkowitz |
| 8,702,592 B2 | 4/2014 | Langlois et al. |
| 8,702,602 B2 | 4/2014 | Berci et al. |
| 8,734,328 B2 | 5/2014 | McDowall |
| 8,786,946 B2 | 7/2014 | Nakamura |
| 8,827,899 B2 | 9/2014 | Farr et al. |
| 8,827,902 B2 | 9/2014 | Dietze, Jr. et al. |
| 8,836,723 B2 | 9/2014 | Tsao et al. |
| 8,858,425 B2 | 10/2014 | Farr et al. |
| 8,876,711 B2 | 11/2014 | Lin et al. |
| 8,878,924 B2 | 11/2014 | Farr |
| 8,882,662 B2 | 11/2014 | Charles |
| 8,976,238 B2 | 3/2015 | Ernsperger et al. |
| 8,979,301 B2 | 3/2015 | Moore |
| 9,033,870 B2 | 5/2015 | Farr et al. |
| 9,216,068 B2 | 12/2015 | Tesar |
| 9,492,065 B2 | 11/2016 | Tesar et al. |
| 9,615,728 B2 | 4/2017 | Charles et al. |
| 9,629,523 B2 | 4/2017 | Tesar et al. |
| 9,642,606 B2 | 5/2017 | Charles et al. |
| 9,681,796 B2 | 6/2017 | Tesar et al. |
| 9,723,976 B2 | 8/2017 | Tesar |
| 9,782,159 B2 | 10/2017 | Tesar |
| 9,936,863 B2 | 4/2018 | Tesar |
| 10,022,041 B2 | 7/2018 | Charles et al. |
| 10,028,651 B2 | 7/2018 | Tesar |
| 10,231,607 B2 | 3/2019 | Charles et al. |
| 10,555,728 B2 | 2/2020 | Charles et al. |
| 10,568,499 B2 | 2/2020 | Tesar |
| 10,702,353 B2 | 7/2020 | Tesar |
| 2001/0055062 A1 | 12/2001 | Shioda et al. |
| 2002/0013514 A1 | 1/2002 | Brau |
| 2002/0049367 A1 | 4/2002 | Irion et al. |
| 2002/0065461 A1 | 5/2002 | Cosman |
| 2002/0082498 A1 | 6/2002 | Wendt et al. |
| 2003/0055410 A1 | 3/2003 | Evans et al. |
| 2003/0059097 A1 | 3/2003 | Abovitz et al. |
| 2003/0078494 A1 | 4/2003 | Panescu et al. |
| 2003/0088179 A1 | 5/2003 | Seeley et al. |
| 2003/0102819 A1 | 6/2003 | Min et al. |
| 2003/0103191 A1 | 6/2003 | Staurenghi et al. |
| 2003/0142204 A1* | 7/2003 | Rus .......... H04N 5/23216 348/65 |
| 2003/0147254 A1 | 8/2003 | Yoneda et al. |
| 2004/0017607 A1 | 1/2004 | Hauger et al. |
| 2004/0027652 A1 | 2/2004 | Erdogan et al. |
| 2004/0036962 A1 | 2/2004 | Brunner et al. |
| 2004/0070822 A1 | 4/2004 | Shioda et al. |
| 2004/0087833 A1 | 5/2004 | Bauer et al. |
| 2004/0111183 A1 | 6/2004 | Sutherland |
| 2004/0196553 A1 | 10/2004 | Banju et al. |
| 2004/0230191 A1 | 11/2004 | Frey et al. |
| 2005/0018280 A1 | 1/2005 | Richardson |
| 2005/0019722 A1 | 1/2005 | Schmid et al. |
| 2005/0026104 A1 | 2/2005 | Takahashi |
| 2005/0031192 A1 | 2/2005 | Sieckmann |
| 2005/0033117 A1 | 2/2005 | Ozaki et al. |

(56) References Cited

U.S. PATENT DOCUMENTS

| | | |
|---|---|---|
| 2005/0052527 A1* | 3/2005 | Remy ............... H04N 7/181 348/14.08 |
| 2005/0063047 A1 | 3/2005 | Obrebski et al. |
| 2005/0064936 A1 | 3/2005 | Pryor |
| 2005/0065435 A1 | 3/2005 | Rauch et al. |
| 2005/0095554 A1 | 5/2005 | Wilkinson |
| 2005/0107808 A1 | 5/2005 | Evans et al. |
| 2005/0171551 A1 | 8/2005 | Sukovich et al. |
| 2005/0215866 A1 | 9/2005 | Kim |
| 2005/0228231 A1 | 10/2005 | MacKinnon et al. |
| 2005/0228232 A1 | 10/2005 | Gillinov et al. |
| 2005/0279355 A1 | 12/2005 | Loubser |
| 2006/0004261 A1 | 1/2006 | Douglas |
| 2006/0020213 A1 | 1/2006 | Whitman et al. |
| 2006/0025656 A1 | 2/2006 | Buckner et al. |
| 2006/0069315 A1 | 3/2006 | Miles et al. |
| 2006/0069316 A1 | 3/2006 | Dorfman et al. |
| 2006/0085969 A1 | 4/2006 | Bennett et al. |
| 2006/0092178 A1 | 5/2006 | Tanguya, Jr. et al. |
| 2006/0114411 A1 | 6/2006 | Wei et al. |
| 2006/0129140 A1 | 6/2006 | Todd et al. |
| 2006/0152516 A1 | 7/2006 | Plummer |
| 2006/0235279 A1 | 10/2006 | Hawkes et al. |
| 2006/0236264 A1 | 10/2006 | Cain et al. |
| 2006/0241499 A1 | 10/2006 | Irion et al. |
| 2006/0276693 A1 | 12/2006 | Pacey |
| 2006/0293557 A1 | 12/2006 | Chuanggui et al. |
| 2007/0010716 A1 | 1/2007 | Malandain |
| 2007/0019916 A1 | 1/2007 | Takami |
| 2007/0038080 A1 | 2/2007 | Salisbury, Jr. et al. |
| 2007/0086205 A1 | 4/2007 | Krupa et al. |
| 2007/0129608 A1 | 6/2007 | Sandhu |
| 2007/0129719 A1 | 6/2007 | Kendale et al. |
| 2007/0153541 A1 | 7/2007 | Bennett et al. |
| 2007/0173853 A1 | 7/2007 | MacMillan |
| 2007/0238932 A1 | 10/2007 | Jones et al. |
| 2007/0282171 A1 | 12/2007 | Karpowicz et al. |
| 2008/0015417 A1 | 1/2008 | Hawkes et al. |
| 2008/0058606 A1 | 3/2008 | Miles et al. |
| 2008/0081947 A1 | 4/2008 | Irion et al. |
| 2008/0091066 A1 | 4/2008 | Sholev |
| 2008/0094583 A1* | 4/2008 | Williams ............ G03B 21/26 353/94 |
| 2008/0096165 A1 | 4/2008 | Virnicchi et al. |
| 2008/0097467 A1 | 4/2008 | Gruber et al. |
| 2008/0123183 A1* | 5/2008 | Awdeh ............. G02B 21/368 359/368 |
| 2008/0151041 A1 | 6/2008 | Shafer et al. |
| 2008/0183038 A1 | 7/2008 | Tilson et al. |
| 2008/0195128 A1 | 8/2008 | Orbay et al. |
| 2008/0221394 A1 | 9/2008 | Melkent et al. |
| 2008/0221591 A1 | 9/2008 | Farritor et al. |
| 2008/0266840 A1 | 10/2008 | Nordmeyer et al. |
| 2008/0269564 A1 | 10/2008 | Gelnett |
| 2008/0269730 A1* | 10/2008 | Dotson ............... A61F 9/0079 606/5 |
| 2008/0278571 A1 | 11/2008 | Mora |
| 2008/0300465 A1 | 12/2008 | Feigenwinter et al. |
| 2008/0303899 A1 | 12/2008 | Berci |
| 2008/0310181 A1 | 12/2008 | Gurevich et al. |
| 2008/0319266 A1 | 12/2008 | Poll et al. |
| 2009/0030436 A1 | 1/2009 | Charles |
| 2009/0034286 A1 | 2/2009 | Krupa et al. |
| 2009/0040783 A1 | 2/2009 | Krupa et al. |
| 2009/0052059 A1 | 2/2009 | Lin |
| 2009/0105543 A1 | 4/2009 | Miller et al. |
| 2009/0137893 A1 | 5/2009 | Seibel et al. |
| 2009/0137989 A1 | 5/2009 | Kataoka |
| 2009/0149716 A1 | 6/2009 | Diao et al. |
| 2009/0156902 A1 | 6/2009 | Dewey et al. |
| 2009/0185392 A1 | 7/2009 | Krupa et al. |
| 2009/0190209 A1 | 7/2009 | Nakamura |
| 2009/0190371 A1 | 7/2009 | Root et al. |
| 2009/0209826 A1 | 8/2009 | Sanders et al. |
| 2009/0238442 A1* | 9/2009 | Upham ............ G01R 31/2896 382/145 |
| 2009/0244259 A1 | 10/2009 | Kojima et al. |
| 2009/0245600 A1 | 10/2009 | Hoffman et al. |
| 2009/0248036 A1 | 10/2009 | Hoffman et al. |
| 2009/0258638 A1 | 10/2009 | Lee |
| 2009/0304582 A1 | 12/2009 | Rousso et al. |
| 2009/0318756 A1 | 12/2009 | Fisher et al. |
| 2009/0326322 A1 | 12/2009 | Diolaiti |
| 2009/0326331 A1 | 12/2009 | Rosen |
| 2010/0013910 A1 | 1/2010 | Farr |
| 2010/0013971 A1 | 1/2010 | Amano |
| 2010/0081919 A1 | 4/2010 | Hyde et al. |
| 2010/0107118 A1 | 4/2010 | Pearce |
| 2010/0128350 A1 | 5/2010 | Findlay et al. |
| 2010/0161129 A1 | 6/2010 | Costa et al. |
| 2010/0168520 A1 | 7/2010 | Poll et al. |
| 2010/0182340 A1 | 7/2010 | Bachelder et al. |
| 2010/0198014 A1 | 8/2010 | Poll et al. |
| 2010/0198241 A1 | 8/2010 | Gerrah et al. |
| 2010/0208046 A1 | 8/2010 | Takahashi |
| 2010/0245557 A1 | 9/2010 | Luley, III et al. |
| 2010/0249496 A1 | 9/2010 | Cardenas et al. |
| 2010/0286473 A1 | 11/2010 | Roberts |
| 2010/0305409 A1 | 12/2010 | Chang |
| 2010/0312069 A1 | 12/2010 | Sutherland et al. |
| 2010/0318099 A1 | 12/2010 | Itkowitz et al. |
| 2010/0331855 A1 | 12/2010 | Zhao et al. |
| 2011/0034781 A1 | 2/2011 | Loftus |
| 2011/0038040 A1 | 2/2011 | Abele et al. |
| 2011/0042452 A1* | 2/2011 | Cormack ............... B65D 1/22 235/375 |
| 2011/0046439 A1 | 2/2011 | Pamnani et al. |
| 2011/0063734 A1 | 3/2011 | Sakaki |
| 2011/0065999 A1 | 3/2011 | Manzanares |
| 2011/0071359 A1 | 3/2011 | Bonadio et al. |
| 2011/0080536 A1 | 4/2011 | Nakamura et al. |
| 2011/0115882 A1 | 5/2011 | Shahinian et al. |
| 2011/0115891 A1 | 5/2011 | Trusty |
| 2011/0144436 A1 | 6/2011 | Nearman et al. |
| 2011/0178395 A1 | 7/2011 | Miesner et al. |
| 2011/0184243 A1 | 7/2011 | Wright et al. |
| 2011/0190588 A1 | 8/2011 | McKay |
| 2011/0234841 A1 | 9/2011 | Akeley et al. |
| 2011/0249323 A1 | 10/2011 | Tesar et al. |
| 2011/0257488 A1 | 10/2011 | Koyama et al. |
| 2011/0263938 A1 | 10/2011 | Levy |
| 2011/0264078 A1 | 10/2011 | Lipow et al. |
| 2011/0288560 A1 | 11/2011 | Shohat et al. |
| 2011/0298704 A1 | 12/2011 | Krah |
| 2011/0301421 A1 | 12/2011 | Michaeli et al. |
| 2011/0316994 A1 | 12/2011 | Lemchen |
| 2012/0029280 A1 | 2/2012 | Kucklick |
| 2012/0035423 A1 | 2/2012 | Sebastian et al. |
| 2012/0035638 A1 | 2/2012 | Mathaneswaran et al. |
| 2012/0040305 A1 | 2/2012 | Karazivan et al. |
| 2012/0041272 A1 | 2/2012 | Dietze, Jr. et al. |
| 2012/0041534 A1 | 2/2012 | Clerc et al. |
| 2012/0059222 A1 | 3/2012 | Yoshida |
| 2012/0065468 A1 | 3/2012 | Levy et al. |
| 2012/0087006 A1 | 4/2012 | Signaigo |
| 2012/0088974 A1 | 4/2012 | Maurice |
| 2012/0089093 A1 | 4/2012 | Trusty |
| 2012/0097567 A1 | 4/2012 | Zhao et al. |
| 2012/0108900 A1 | 5/2012 | Viola et al. |
| 2012/0116173 A1 | 5/2012 | Viola |
| 2012/0127573 A1 | 5/2012 | Robinson et al. |
| 2012/0130399 A1 | 5/2012 | Moll et al. |
| 2012/0134028 A1 | 5/2012 | Maruyama |
| 2012/0157775 A1 | 6/2012 | Yamaguchi |
| 2012/0157787 A1 | 6/2012 | Weinstein et al. |
| 2012/0157788 A1 | 6/2012 | Serowski et al. |
| 2012/0158015 A1 | 6/2012 | Fowler et al. |
| 2012/0190925 A1 | 7/2012 | Luiken |
| 2012/0197084 A1 | 8/2012 | Drach et al. |
| 2012/0230668 A1 | 9/2012 | Vogt |
| 2012/0232352 A1 | 9/2012 | Lin et al. |
| 2012/0245432 A1 | 9/2012 | Karpowicz et al. |
| 2012/0265023 A1 | 10/2012 | Berci et al. |

(56) References Cited

U.S. PATENT DOCUMENTS

| | | | |
|---|---|---|---|
| 2012/0320102 A1 | 12/2012 | Jorgensen | |
| 2012/0330129 A1 | 12/2012 | Awdeh | |
| 2013/0012770 A1 | 1/2013 | Su | |
| 2013/0027516 A1 | 1/2013 | Hart et al. | |
| 2013/0041226 A1 | 2/2013 | McDowall | |
| 2013/0041368 A1 | 2/2013 | Cunningham et al. | |
| 2013/0060095 A1 | 3/2013 | Bouquet | |
| 2013/0066304 A1 | 3/2013 | Belson et al. | |
| 2013/0072917 A1 | 3/2013 | Kaschke et al. | |
| 2013/0076863 A1 | 3/2013 | Rappel | |
| 2013/0077048 A1 | 3/2013 | Mirlay | |
| 2013/0085337 A1 | 4/2013 | Hess et al. | |
| 2013/0159015 A1* | 6/2013 | O'Con | G06Q 50/24 705/3 |
| 2013/0197313 A1 | 8/2013 | Wan | |
| 2013/0245383 A1 | 9/2013 | Friedrich et al. | |
| 2013/0298208 A1* | 11/2013 | Ayed | G06F 21/00 726/6 |
| 2013/0331730 A1 | 12/2013 | Fenech et al. | |
| 2014/0005488 A1 | 1/2014 | Charles et al. | |
| 2014/0081659 A1 | 3/2014 | Nawana et al. | |
| 2014/0168785 A1 | 6/2014 | Belgum | |
| 2014/0168799 A1 | 6/2014 | Hurbert et al. | |
| 2014/0179998 A1 | 6/2014 | Pacey et al. | |
| 2014/0187859 A1 | 7/2014 | Leeuw et al. | |
| 2014/0198190 A1 | 7/2014 | Okumu | |
| 2014/0247482 A1 | 9/2014 | Doi et al. | |
| 2014/0275801 A1 | 9/2014 | Menchaca et al. | |
| 2014/0276008 A1 | 9/2014 | Steinbach et al. | |
| 2014/0285403 A1 | 9/2014 | Kobayashi | |
| 2014/0316209 A1 | 10/2014 | Overes et al. | |
| 2014/0327742 A1 | 11/2014 | Kiening et al. | |
| 2014/0347395 A1 | 11/2014 | Tsao et al. | |
| 2014/0362228 A1* | 12/2014 | McCloskey | H04N 5/33 348/164 |
| 2014/0378843 A1 | 12/2014 | Valdes et al. | |
| 2015/0025324 A1 | 1/2015 | Wan | |
| 2015/0080982 A1* | 3/2015 | Van Funderburk | A61N 1/37217 607/59 |
| 2015/0087918 A1 | 3/2015 | Vasan | |
| 2015/0094533 A1 | 4/2015 | Kleiner et al. | |
| 2015/0112148 A1 | 4/2015 | Bouquet | |
| 2015/0141755 A1 | 5/2015 | Tesar | |
| 2015/0238073 A1 | 8/2015 | Charles | |
| 2015/0297311 A1 | 10/2015 | Tesar | |
| 2015/0300816 A1 | 10/2015 | Yang et al. | |
| 2016/0018598 A1 | 1/2016 | Hansson | |
| 2016/0089026 A1 | 3/2016 | Heerren | |
| 2016/0139039 A1 | 5/2016 | Ikehara et al. | |
| 2016/0220324 A1 | 8/2016 | Tesar | |
| 2017/0020627 A1 | 1/2017 | Tesar | |
| 2017/0258550 A1 | 9/2017 | Vazales | |
| 2018/0055348 A1 | 3/2018 | Tesar et al. | |
| 2018/0055502 A1 | 3/2018 | Charles et al. | |
| 2018/0064316 A1 | 3/2018 | Charles et al. | |
| 2018/0064317 A1 | 3/2018 | Tesar | |
| 2018/0070804 A1 | 3/2018 | Tesar | |
| 2018/0256145 A1 | 9/2018 | Tesar | |
| 2018/0318033 A1 | 11/2018 | Tesar | |
| 2018/0353059 A1 | 12/2018 | Tesar | |
| 2018/0368656 A1 | 12/2018 | Austin et al. | |
| 2019/0046021 A1 | 2/2019 | Charles et al. | |
| 2019/0053700 A1 | 2/2019 | Tesar | |
| 2019/0380566 A1 | 12/2019 | Charles | |
| 2020/0318810 A1 | 10/2020 | Tesar | |

FOREIGN PATENT DOCUMENTS

| | | |
|---|---|---|
| CN | 102495463 | 6/2012 |
| CN | 202920720 | 5/2013 |
| DE | 103 41 125 | 4/2005 |
| DE | 10 2010 030 285 | 12/2011 |
| DE | 10 2010 044 502 | 3/2012 |
| EP | 0 293 228 | 11/1988 |
| EP | 0 233 940 | 11/1993 |
| EP | 0 466 705 | 6/1996 |
| EP | 1 175 106 | 1/2002 |
| EP | 1 333 305 | 8/2003 |
| EP | 2 641 561 | 9/2013 |
| JP | 49-009378 | 3/1974 |
| JP | 03-018891 | 1/1991 |
| JP | 06-315487 | 11/1994 |
| JP | 07-194602 | 8/1995 |
| JP | 07-261094 | 10/1995 |
| JP | 08-131399 | 5/1996 |
| JP | 2001-087212 | 4/2001 |
| JP | 2001-117049 | 4/2001 |
| JP | 2001-161638 | 6/2001 |
| JP | 2001-161640 | 6/2001 |
| JP | 2002-011022 | 1/2002 |
| JP | 3402797 | 5/2003 |
| JP | 2003-322803 | 11/2003 |
| JP | 2004-024835 | 1/2004 |
| JP | 3549253 | 8/2004 |
| JP | 2004-305525 | 11/2004 |
| JP | 2007-068876 | 3/2007 |
| JP | 2009-288296 | 12/2009 |
| JP | 4503748 | 7/2010 |
| JP | 2010-206495 | 9/2010 |
| JP | 2011-118741 | 6/2011 |
| WO | WO 87/001276 | 3/1987 |
| WO | WO 91/012034 | 8/1991 |
| WO | WO 99/017661 | 4/1999 |
| WO | WO 00/078372 | 12/2000 |
| WO | WO 01/072209 | 10/2001 |
| WO | WO 2007/047782 | 4/2007 |
| WO | WO 2008/073243 | 6/2008 |
| WO | WO 2009/051013 | 4/2009 |
| WO | WO 2010/079817 | 7/2010 |
| WO | WO 2010/114843 | 10/2010 |
| WO | WO 2010/123578 | 10/2010 |
| WO | WO 2011/069469 | 6/2011 |
| WO | WO 2012/047962 | 4/2012 |
| WO | WO 2012/078989 | 6/2012 |
| WO | WO 2013/049679 | 4/2013 |
| WO | WO 2013/109966 | 7/2013 |
| WO | WO 2013/116489 | 8/2013 |
| WO | WO 2014/004717 | 1/2014 |
| WO | WO 2014/060412 | 4/2014 |
| WO | WO 2014/189969 | 11/2014 |
| WO | WO 2015/042460 | 3/2015 |
| WO | WO 2015/042483 | 3/2015 |
| WO | WO 2015/100310 | 7/2015 |
| WO | WO 2016/090336 | 6/2016 |
| WO | WO 2016/154589 | 9/2016 |
| WO | WO 2017/091704 | 6/2017 |
| WO | WO 2018/208691 | 11/2018 |
| WO | WO 2018/217951 | 11/2018 |

OTHER PUBLICATIONS

Aliaga, Daniel G.; "Image Morphing and Warping"; Department of Computer Science; Purdue University; Spring 2010; in 61 pages.

"Arri Medical Shows SeeFront 3D Display with HD 3D Surgical Microscope"; dated Jun. 9, 2013; downloaded from http://www.seefront.com/news-events/article/arri-medical-shows-seefront-3d-display-with-hd-3d-surgical-microscope/ in 2 pages.

"Arriscope: A New Era in Surgical Microscopy"; Arriscope Brochure published May 20, 2014 in 4 pages.

AustriaMicroSystems; "AS5050: Smallest Magnetic Rotary Encoder for µA Low Power Applications"; www.austriamicrosystems.com/AS5050 printed Nov. 2012 in 2 pages.

Bayonet Lock Video; 00:16 in length; Date Unknown; [Screenshots captured at 00:00, 00:02, 00:05, 00:08, and 00:16].

BellowsTech; "Actuators"; www.bellowstech.com/metal-bellows/actuators/ printed Jul. 17, 2012 in 4 pages.

"Carl Zeiss Unveils $99 VR One Virtual Reality Headset"; www.electronista.com/articles/14/10/10/zeiss.vr.one.able.to.accept.variety.of.smartphones.using.custom.trays printed Oct. 13, 2014 in 2 pages.

Design boom; "Bright LED"; http://www.designboom.com/project/fiber-optics-light-glove/; Sep. 28, 2007.

(56) References Cited

OTHER PUBLICATIONS

Fei-Fei, Li; Lecture 10: Multi-View Geometry; Stanford Vision Lab; Oct. 24, 2011; in 89 pages.
"Fuse™. Full Spectrum Endoscopy™"; http://www.endochoice.com/Fuse printed Oct. 7, 2013 in 3 pages.
Hardesty, Larry; "3-D Cameras for Cellphones: Clever math could enable a high-quality 3-D camera so simple, cheap and power-efficient that it could be incorporated into handheld devices"; MIT News Office; http://web.mit/edu/newsoffice/2011/lldar-3d-camera-cellphones-0105.html; Jan. 5, 2012; in 4 pages.
Hartley et al.; "Multiple View Geometry in Computer Vision: Chapter 9—Epipolar Geometry and the Fundamental Matrix"; http://www.robots.ox.ac.uk/~vgg/hzbook/hzbook2/HZepipolar.pdf; Mar. 2004; 2nd Edition; Ch. 9; pp. 239-261.
Heidelberg Engineering; "MultiColor: Scanning Laser Imaging"; http://www.heidelbergengineering.com/us/products/spectralls-models/imaging-modes/multicolor/; Copyright © 2013; printed Apr. 5, 2013.
Kramer, Jennifer; "The Right Filter Set Gets the Most out of a Microscope"; Biophotonics International; Jan./Feb. 1999; vol. 6; pp. 54-58.
Krishna, Golden; "Watch: What Good is a Screen?"; http://www.cooper.com/author/golden_krishna printed Jul. 9, 2014 in 62 pages.
Lang et al.; "Zeiss Microscopes for Microsurgery"; Springer-Verlag; Berlin, Heidelberg; 1981.
Leica Microsystems; "Images TrueVision Integrated 3D"; http://www.leica-microsystems.com/products/surgical-microscopes/neurosurgery-spine/details/products/truevision-integrated-3d/gallery; Nov. 26, 2014; in 3 pages.
Leica Microsystems; "Leica Microsystems' Ophthalmic Surgical Microscopes with TrueVision 3D Technology Available Globally"; http://www.leica-microsystems.com/products/surgical-microscops/neurosurgery-spine/details/products/truevision-integrated-3d/news/; Sep. 18, 2014; in 5 pages.
Lutze et al.; "Microsystems Technology for Use in a Minimally Invasive Endoscope Assisted Neurosurgical Operating System—MINOP II"; 2005; http://web.archive.org/web/20151120215151/http://www.meditec.hia.rwth-aachen.de/fileadmin/content/meditec/bilder/forschung/aktuelle_projekte/robotische/Exoscope_Aesculap.pdf; Nov. 20, 2015 in 4 pages.
Male Bayonet Video; 00:04 in length; Date Unknown; [Screenshots captured at 00:00, 00:01, 00:02, 00:03, and 00:04].
MediTec; "MINOP II—Robotical Microscope Platform"; http://web.archive.org/web/20151120213932/http://www.meditec.hia.rwth-aachen.de/en/research/former-projects/minop-ii/; Nov. 20, 2015 in 3 pages.
Melexis; "MLX75031 Optical Gesture and Proximitu Sensing IC"; http://melexis.com/optical-sensors/optical-sensing.mlx75031/815.aspx?sta printed Mar. 15, 2013 in 1 page.
MMR Technologies; "Micro Miniature Refrigerators"; http://www.mmr-tech.com/mmr_overview.php; Copyright © 2011; printed Feb. 11, 2013.
Moog; "Surgical Handpieces: Therapeutic Ultrasonic Devices"; http://www.moog.com/products/surgical-hpieces/ printed Sep. 25, 2013 in 1 page.
Morita; "TwinPower Turbine® High Speed Handpieces Standard, 45°, and Ultra Series Head Designs"; J. Morita Mfg. Corp., http://www.morita.com/usa/root/img/pool/pdf/product_brochures/twinpower_brochure_1-264_0512_web.pdf; May 2012; in 20 pages.
"Narrow Band Imaging"; http://web.archive.org/web/20150701233623/https://en.wikipedia.org/wiki/Narrow_band_imaging printed Jul. 1, 2015 in 1 page.
Olympus; "Olympus Introduces the World's First and Only Monopolar, Disposable Tonsil Adenoid Debrider (DTAD)"; http://www.olympususamerica.com/corporate/corp_presscenter_headline.asp?pressNo=926; Sep. 11, 2012; in 2 pages.
OmniVision; "OV2722 full HD (1080p) product brief: 1/6-Inch Native 1080p HD CameraChip Sensor for Ultra-Compact Applications"; http://web.archive.org/web/20120730043057/http://www.ovt.com/download_document.php?type=sensor&sensorid=119; May 2012 in 2 pages.
Orthofix; "ProView MAP System Retractors"; www.us.orthofix.com/products/proviewretractors.asp?cid=39; Copyright © 2010; printed Apr. 1, 2013.
OrtusTech; "Sample Shipment Start: World's Smallest Size Full-HD Color TFT LCD"; http://ortustech.co.jp/english/notice/20120427.html printed May 22, 2012 in 2 pages.
"Portion"; Definition; American Heritage® Dictionary of the English Language; Fifth Edition; 2016; Retrieved Apr. 12, 2018 from https://www.thefreedictionary.com/portion in 1 page.
Purcher, Jack; "Apple Wins a Patent for an Oculus Rift-Like Display System"; http://www.patentlyapple.com/patently-apple/2014/09/apple-wins-a-patent-for-an-oculus-rift-like-display-system.html; Sep. 9, 2014.
Rustum, Dr. Abu; "ICG Mapping Endometrial Cancer"; Pinpoint Endometrium Ca Lenfedenektomi MSKCC May 2013; Memorial Sloan Kettering Cancer Center; May 2013; Published to YouTube.com Sep. 1, 2013; in 2 pages; http://web.archive.org/web/20150402210857/https://www.youtbube.com/watch?v=DhChvaUCe4I.
Saab, Mark; "Applications of High-Pressure Balloons in the Medical Device Industry"; http://www.ventionmedical.com/documents/medicalballoonpaper.pdf; Copyright © 1999; in 19 pages.
Savage, Lynn; "Sound and Light, Signifying Improved Imaging"; www.photonics.com/Article.aspx?AID=45039; Nov. 1, 2010; in 6 pages.
Sun et al.; "Neurotoxin-Directed Synthesis and in Vitro Evaluation of Au Nanoclusters"; RSC Advances, 2015; vol. 5, No. 38; pp. 29647-29652.
Timm, Karl Walter; "Real-Time View Morphing of Video Streams"; University of Illinois; Chicago, Illinois; 2003; in 168 pages.
TrueVision Microscopes; http://truevisionmicroscopes.com/images/productsnews/081a-f.jpg; printed Nov. 26, 2014 in 1 page.
TrueVision; "About TrueVision"; http://web.archive.org/web/20071208125103/http://www.truevisionsys.com/about.html; as viewed Dec. 8, 2007 in 2 pages.
TrueVision; "Leica Microsystems and TrueVision® 3D Surgical create the first 3D digital hybrid microscope"; Press Release; Oct. 5, 2012; in 2 pages.
TrueVision; "TrueVision Technology"; http://web.archive.org/web/20071208125125/http://www.truevisionsys.com/technology.html; as viewed Dec. 8, 2007 in 2 pages.
Whitney et al.; "Pop-up book MEMS"; Journal of Micromechanics and Microengineering; Oct. 14, 2011; vol. 21; No. 115021; in 7 pages.
Wikipedia; "Zoom Lens"; http://en.wikipedia.org/wiki/Optical_Zoom; printed Oct. 7, 2014 in 3 pages.
Zeiss; "Informed for Medical Professionals, Focus: Fluorescence"; Carl Zeiss; 2nd Issue; Oct. 2006; 30-801-LBW-GFH-X-2006; Printed in Germany; in 32 pages.
Zeiss; "Ophthalmic Surgery in Its Highest Form, OPMI® VISU 210"; Carl Zeiss, 2005, 30-097/III-e/USA Printed in Germany AW-TS-V/2005 Uoo; in 19 pages.
Zeiss; "SteREO Discovery. V12, Expanding the Boundaries"; Carl Zeiss, Sep. 2004; 46-0008 e Sep. 2004, in 6 pages.
Zeiss; "Stereomicroscopes: Stemi SV 6, SV 11, SV 11 Apo"; The Profile; 1999; in 30 pages.
Zeiss; "Time for a Change: OPMI® pico for ENT"; Carl Zeiss, 2005, 30-451/III-e Printed in Germany LBW-TS-V/2005 Uoo, in 8 pages.
Zhang, Michael; "LIFX: A WiFi-Enabled LED Bulb that May Revolutionize Photographic Lighting"; http://www.petalpixel.com/2012/09/22/lifx-a-wifi-enabled-led-bulb-that-may-revolutionize-photographic-lighting/ printed Sep. 28, 2012 in 9 pages.
Zhang, Sarah; "The Obscure Neuroscience Problem That's Plaguing VR"; http://web.archive.org/web/20150812172934/http://www.wired.com/2015/08/obscure-neuroscience-problem-thats-plaguing-vr/; Aug. 11, 2015 in 5 pages.
Preliminary Amendment in U.S. Appl. No. 14/411,068, dated Aug. 13, 2015.
Office Action in U.S. Appl. No. 14/411,068, dated Aug. 17, 2017.

(56) References Cited

OTHER PUBLICATIONS

Amendment in U.S. Appl. No. 14/411,068, dated Feb. 16, 2018.
Office Action in U.S. Appl. No. 14/411,068, dated Apr. 6, 2018.
Amendment in U.S. Appl. No. 14/411,068, dated Oct. 5, 2018.
Notice of Allowance in U.S. Appl. No. 14/411,068, dated Oct. 26, 2018.
Corrected Notice of Allowance in U.S. Appl. No. 14/411,068, dated Dec. 7, 2018.
Official Communication in European Application No. 13808996.6, dated Jan. 4, 2016.
Official Communication in European Application No. 13808996.6, dated Apr. 14, 2016.
Official Communication in European Application No. 13808996.6, dated Feb. 21, 2017.
Official Communication in European Application No. 13808996.6, dated Jun. 6, 2017.
Official Communication in European Application No. 13808996.6, dated Jun. 15, 2018.
Official Communication in Japanese Application No. 2015-520471, dated May 9, 2017.
Official Communication in Japanese Application No. 2015-520471, dated Nov. 21, 2017.
Notice of Decision or Rejection in Japanese Application No. 2015-520471, dated Jul. 24, 2018.
International Search Report and Written Opinion in PCT Application No. PCT/US2013/047972, dated Jan. 3, 2014.
International Preliminary Report on Patentability in PCT Application No. PCT/US2013/047972, dated Jan. 8, 2015.
Preliminary Amendment in U.S. Appl. No. 15/483,995, dated Nov. 21, 2017.
Office Action in U.S. Appl. No. 15/483,995, dated Mar. 9, 2018.
Amendment in U.S. Appl. No. 15/483,995, dated Sep. 7, 2018.
Final Office Action in U.S. Appl. No. 15/483,995, dated Nov. 29, 2018.
Office Action in U.S. Appl. No. 15/645,589, dated Feb. 9, 2018.
Amendment in U.S. Appl. No. 15/645,589, dated Aug. 7, 2018.
Final Office Action in U.S. Appl. No. 15/645,589, dated Nov. 28, 2018.
Preliminary Amendment filed in U.S. Appl. No. 16/036,665, dated Nov. 1, 2018.
Office Action in U.S. Appl. No. 15/626,516, dated Mar. 14, 2018.
Amendment in U.S. Appl. No. 15/626,516, dated Sep. 13, 2018.
Final Office Action in U.S. Appl. No. 15/626,516, dated Jan. 15, 2019.
Amendment in U.S. Appl. No. 15/589,058, dated Nov. 15, 2017.
Office Action in U.S. Appl. No. 15/589,058, dated Dec. 8, 2017.
Amendment in U.S. Appl. No. 15/589,058, dated Jun. 7, 2018.
Final Office Action in U.S. Appl. No. 15/589,058, dated Aug. 27, 2018.
Official Communication in European Application No. 14800423.7, dated Feb. 8, 2017.
International Search Report and Written Opinion in PCT Application No. PCT/US2014/038839, dated Oct. 17, 2014.
International Preliminary Report on Patentability in PCT Application No. PCT/US2014/038839, dated Dec. 3, 2015.
Preliminary Amendment in U.S. Appl. No. 14/491,935, dated Feb. 5, 2015.
Restriction Requirement in U.S. Appl. No. 14/491,935, dated Sep. 8, 2017.
Restriction Requirement and Election of Species Response in U.S. Appl. No. 14/491,935, dated Jan. 8, 2018.
Partial Supplementary European Search Report in European Application No. 14845427.5, dated May 4, 2017.
Extended European Search Report in European Application No. 14845427.5, dated Aug. 8, 2017.
Extended European Search Report in European Application No. 14846410.0, dated Jun. 23, 2017.
Official Communication in European Application No. 14846410.0, dated Jul. 18, 2018.
Official Communication in Japanese Application No. 2016-544032, dated Jun. 26, 2018.
International Search Report and Written Opinion in PCT Application No. PCT/US2014/056643, dated Dec. 11, 2014.
International Preliminary Report on Patentability and Written Opinion in PCT Application No. PCT/US2014/056643, dated Mar. 31, 2016.
Invitation to Pay Additional Fees in PCT Application No. PCT/US2014/056681, dated Jan. 14, 2015.
International Search Report and Written Opinion in PCT Application No. PCT/US2014/056681, dated Mar. 20, 2015.
International Preliminary Report on Patentability and Written Opinion in PCT Application No. PCT/US2014/056681, dated Mar. 31, 2016.
Preliminary Amendment in U.S. Appl. No. 14/581,779, dated Jul. 6, 2015.
Restriction Requirement in U.S. Appl. No. 14/581,779, dated Oct. 31, 2017.
Restriction Requirement and Election of Species Response in U.S. Appl. No. 14/581,779, dated Jan. 2, 2018.
Office Action in U.S. Appl. No. 14/581,779, dated Apr. 24, 2018.
Amendment in U.S. Appl. No. 14/581,779, dated Sep. 24, 2018.
Final Office Action in U.S. Appl. No. 14/581,779, dated Jan. 4, 2019.
Extended European Search Report in European Application No. 14873324.9, dated Aug. 25, 2017.
Official Communication in Japanese Application No. 2016-542194, dated Nov. 6, 2018.
Invitation to Pay Additional Fees in PCT Application No. PCT/US2014/072121, dated Mar. 2, 2015.
International Search Report and Written Opinion in PCT Application No. PCT/US2014/072121, dated May 1, 2015.
International Preliminary Report on Patentability and Written Opinion in PCT Application No. PCT/US2014/072121, dated Jul. 7, 2016.
Preliminary Amendment in U.S. Appl. No. 14/960,276, dated Apr. 18, 2016.
Office Action in U.S. Appl. No. 14/960,276, dated Jul. 28, 2017.
Amendment in U.S. Appl. No. 14/960,276, dated Jan. 26, 2018.
Office Action in U.S. Appl. No. 14/960,276, dated Mar. 8, 2018.
Amendment in U.S. Appl. No. 14/960,276, dated Sep. 7, 2018.
Office Action in U.S. Appl. No. 14/960,276, dated Nov. 2, 2018.
Extended European Search Report in European Application No. 15865454.1, dated Jun. 27, 2018.
International Search Report and Written Opinion in PCT Application No. PCT/US2015/064133, dated Feb. 9, 2016.
International Preliminary Report on Patentability and Written Opinion in PCT Application No. PCT/US2015/064133, dated Jun. 15, 2017.
Preliminary Amendment in U.S. Appl. No. 15/081,653, dated Oct. 11, 2016.
Office Action in U.S. Appl. No. 15/081,653, dated Mar. 28, 2018.
Amendment in U.S. Appl. No. 15/081,653, dated Sep. 27, 2018.
Final Office Action in U.S. Appl. No. 15/081,653, dated Nov. 16, 2018.
Extended European Search Report in European Application No. 16769809.1, dated Nov. 23, 2018.
International Search Report and Written Opinion in PCT Application No. PCT/US2016/024330, dated Jul. 1, 2016.
International Preliminary Report on Patentability and Written Opinion in PCT Application No. PCT/US2016/024330, dated Oct. 5, 2017.
Invitation to Pay Additional Fees in PCT Application No. PCT/US2016/063549, dated Feb. 2, 2017.
International Search Report and Written Opinion in PCT Application No. PCT/US2016/063549, dated Apr. 14, 2017.
International Preliminary Report on Patentability and Written Opinion in PCT Application No. PCT/US2016/063549, dated Jun. 7, 2018.
International Search Report and Written Opinion in PCT Application No. PCT/US2018/031442, dated Sep. 14, 2018.
International Search Report and Written Opinion in PCT Application No. PCT/US2018/034227, dated Jul. 30, 2018.

(56) References Cited

OTHER PUBLICATIONS

Preliminary Amendment in U.S. Appl. No. 16/357,081, dated Sep. 4, 2019.
Official Communication in European Application No. 13808996.6, dated May 13, 2019.
Amendment in U.S. Appl. No. 15/483,995, dated May 28, 2019.
Office Action in U.S. Appl. No. 15/483,995, dated Jun. 13, 2019.
Amendment in U.S. Appl. No. 15/645,589, dated May 28, 2019.
Office Action in U.S. Appl. No. 15/645,589, dated Jun. 13, 2019.
Preliminary Amendment filed in U.S. Appl. No. 16/036,665, dated Sep. 5, 2019.
Office Action in U.S. Appl. No. 16/036,665, dated Sep. 26, 2019.
Response in U.S. Appl. No. 15/626,516, dated Jul. 15, 2019.
Restriction Requirement in U.S. Appl. No. 15/495,484, dated May 14, 2019.
Amendment in U.S. Appl. No. 15/589,058, dated Feb. 26, 2019.
Office Action in U.S. Appl. No. 15/589,058, dated Mar. 5, 2019.
Amendment in U.S. Appl. No. 15/589,058, dated Sep. 5, 2019.
Notice of Allowance in U.S. Appl. No. 15/589,058, dated Sep. 25, 2019.
Preliminary Amendment filed in U.S. Appl. No. 15/724,100, dated Jun. 5, 2018.
Office Action in U.S. Appl. No. 15/724,100, dated Oct. 9, 2019.
Preliminary Amendment in U.S. Appl. No. 16/042,318, dated Nov. 8, 2018.
Office Action in U.S. Appl. No. 16/042,318, dated May 8, 2019.
Amendment in U.S. Appl. No. 16/042,318, dated Sep. 9, 2019.
Notice of Allowance in U.S. Appl. No. 16/042,318, dated Oct. 9, 2019.
Office Action in U.S. Appl. No. 14/491,935, dated May 13, 2019.
Official Communication in European Application No. 14846410.0, dated Mar. 20, 2019.
Amendment in U.S. Appl. No. 14/581,779, dated Jul. 2, 2019.
Office Action in U.S. Appl. No. 14/581,779, dated Aug. 5, 2019.
Decision of Rejection in Japanese Application No. 2016-542194, dated May 14, 2019.
Amendment in U.S. Appl. No. 14/960,276, dated May 2, 2019.
Final Office Action in U.S. Appl. No. 14/960,276, dated Jun. 7, 2019.
Final Amendment in U.S. Appl. No. 15/081,653, dated May 15, 2019.
Office Action in U.S. Appl. No. 15/081,653, dated Jul. 12, 2019.
Extended European Search Report in European Application No. 16869253.1, dated May 29, 2019.
Office Action in U.S. Appl. No. 15/973,433, dated Jun. 28, 2019.
International Preliminary Report on Patentability and Written Opinion in PCT Application No. PCT/US2018/031442, dated Nov. 21, 2019.
Office Action in U.S. Appl. No. 16/357,081, dated Jul. 8, 2020.
Official Communication in Japanese Application No. 2018-218745, dated Feb. 25, 2020.
Amendment in U.S. Appl. No. 15/483,995, dated Dec. 12, 2019.
Final Office Action in U.S. Appl. No. 15/483,995, dated Feb. 20, 2020.
Office Action in U.S. Appl. No. 15/645,589, dated Dec. 26, 2019.
Amendment in U.S. Appl. No. 15/645,589, dated Jun. 26, 2020.
Notice of Allowance in U.S. Appl. No. 15/645,589, dated Jul 14, 2020.
Amendment filed in U.S. Appl. No. 16/036,665, dated Mar. 26, 2020.
Office Action in U.S. Appl. No. 16/036,665, dated Jul. 13, 2020.
Amendment in U.S. Appl. No. 15/626,516, dated Jan. 24, 2020.
Notice of Allowance in U.S. Appl. No. 15/626,516, dated Mar. 9, 2020.
Notice of Allowance in U.S. Appl. No. 15/626,516, dated Jun. 29, 2020.
Response to Restriction Requirement in U.S. Appl. No. 15/495,484, dated Nov. 13, 2019.
Office Action in U.S. Appl. No. 15/495,484, dated Nov. 27, 2019.
Amendment in U.S. Appl. No. 15/495,484, dated May 27, 2020.
Notice of Allowance in U.S. Appl. No. 15/495,484, dated Jun. 16, 2020.
Restriction Requirement in U.S. Appl. No. 15/948,842, dated Jan. 22, 2020.
Amendment filed in U.S. Appl. No. 15/724,100, dated Apr. 9, 2020.
Office Action in U.S. Appl. No. 15/724,100, dated Apr. 22, 2020.
Notice of Allowance in U.S. Appl. No. 15/724,100, dated Jul. 6, 2020.
Amendment in U.S. Appl. No. 14/491,935, dated Nov. 13, 2019.
Final Office Action in U.S. Appl. No. 14/491,935, dated Feb. 24, 2020.
Amendment in U.S. Appl. No. 14/581,779, dated Feb. 4, 2020.
Final Office Action in U.S. Appl. No. 14/581,779, dated Apr. 29, 2020.
Amendment in U.S. Appl. No. 15/081,653, dated Jan. 10, 2020.
Final Office Action in U.S. Appl. No. 15/081,653, dated Jan. 31, 2020.
Amendment in U.S. Appl. No. 15/081,653, dated Jul. 30, 2020.
Amendment in U.S. Appl. No. 15/973,433, dated Sep. 30, 2019.
Notice of Allowance in U.S. Appl. No. 15/973,433, dated Jan. 28, 2020.
Notice of Allowance in U.S. Appl. No. 15/973,433, dated Jun. 25, 2020.
International Preliminary Report on Patentability and Written Opinion in PCT/US2018/034227, dated Dec. 5, 2019.
Burle Industries, Technical Memorandum 100-Fiber Optics: Theory and Applications, archived Feb. 21, 2007, in 20 pages http://web.archive.org/web/20070221125354/http://www.burle.com/cgi-bin/byteserver.pl/pdf/100r.pdf.
Decision to Refuse received in European Application No. 13808996.6, dated Oct. 19, 2020.
Amendment in U.S Appl. No. 15/483,995, dated Aug. 19, 2020.
Office Action in U.S. Appl. No. 15/483,995, dated Sep. 4, 2020.
Notice of Allowance in U.S. Appl. No. 15/626,516, dated Oct. 13, 2020.
Notice of Allowance in U.S. Appl. No. 15/495,484, dated Sep. 29, 2020.
Supplemental Notice of Allowance in U.S. Appl. No. 15/495,484, dated Oct. 13, 2020.
Amendment in U.S. Appl. No. 16/786,054, dated Sep. 25, 2020.
Response to Restriction Requirement in U.S. Appl. No. 15/948,842, dated Jul. 21, 2020.
Office Action in U.S. Appl. No. 15/948,842, dated Aug. 24, 2020.
Amendment in U.S. Appl. No. 15/724,100, dated Jun. 22, 2020.
Notice of Allowance in U.S. Appl. No. 15/724,100, dated Oct. 15, 2020.
Amendment in U.S. Appl. No. 16/799,168, dated Oct. 9, 2020.
Amendment in U.S. Appl. No. 14/491,935, dated Aug. 24, 2020.
Notice of Allowance in U.S. Appl. No. 14/491,935, dated Sep. 2, 2020.
Office Action in U.S. Appl. No. 15/081,653, dated Sep. 17, 2020.
Notice of Allowance in U.S. Appl. No. 15/973,433, dated Oct. 15, 2020.
Amendment in U.S. Appl. No. 16/677,441, dated Jun. 26, 2020.

* cited by examiner

The display provides a horizon consistent with an ergonomically advantageous viewing position for the user. The isocenter is defined as the postion bewtween the two eyes parallel to the display's horizon.

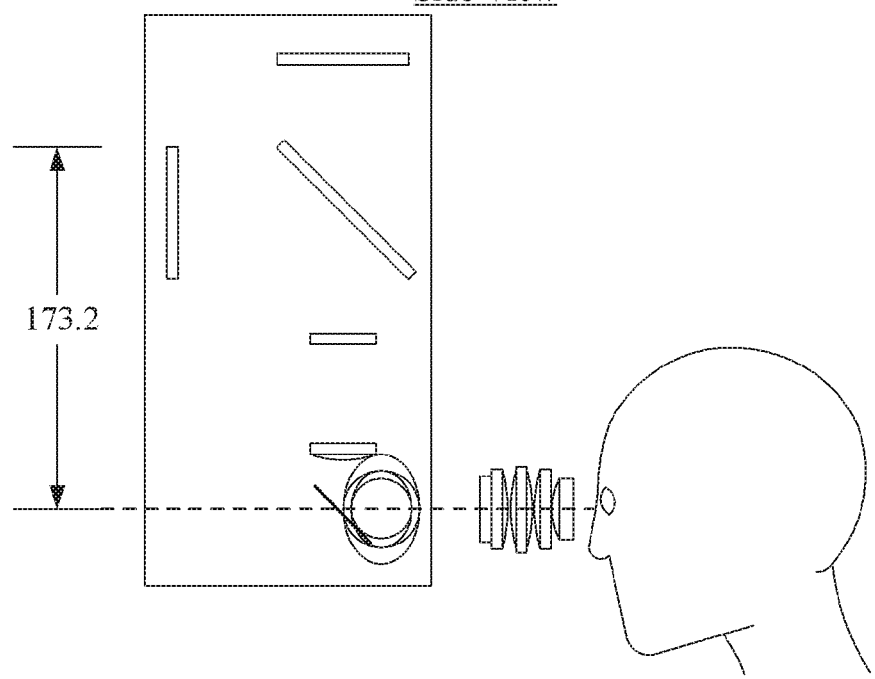
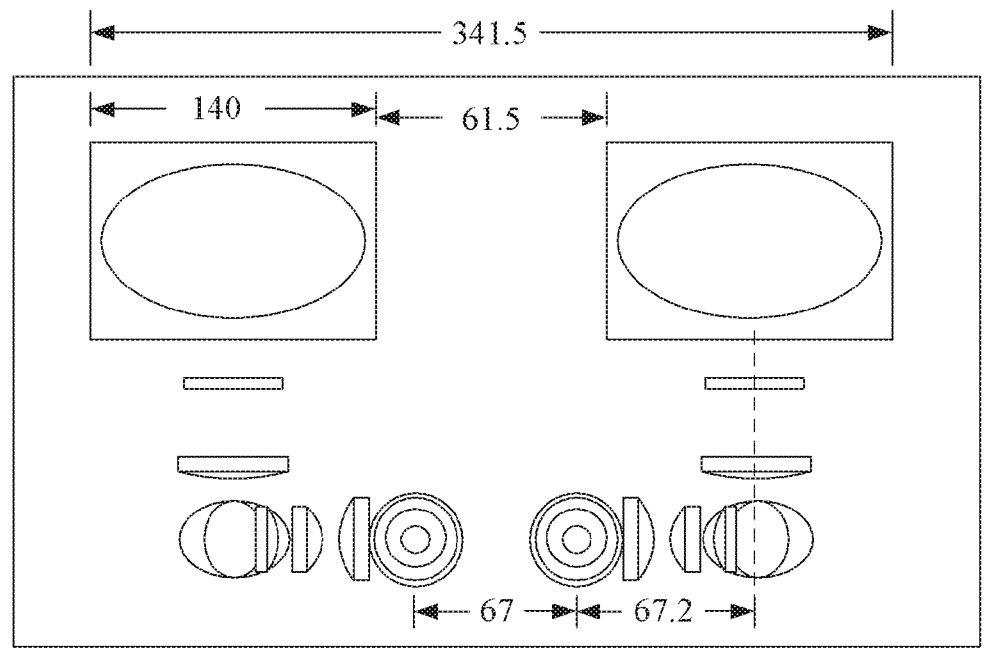
FIG. 13B1

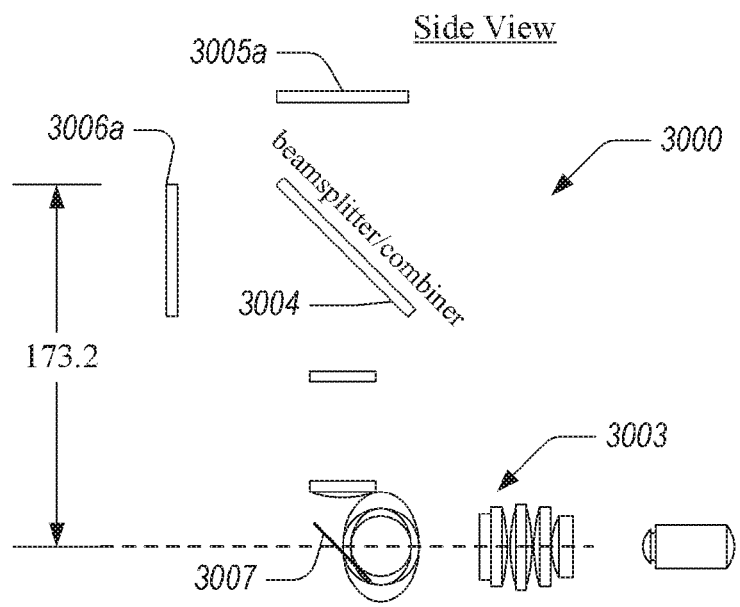
FIG. 13B1-a
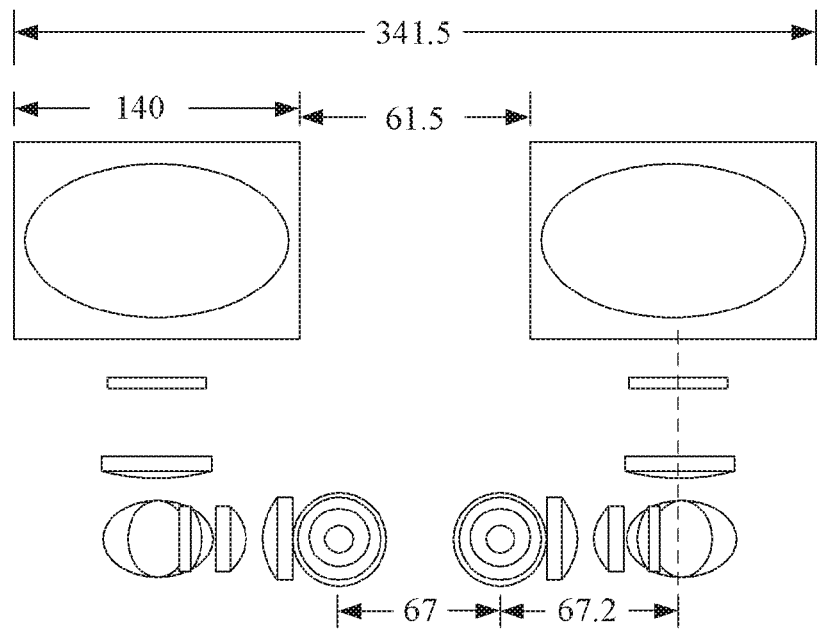
FIG. 13B1-b

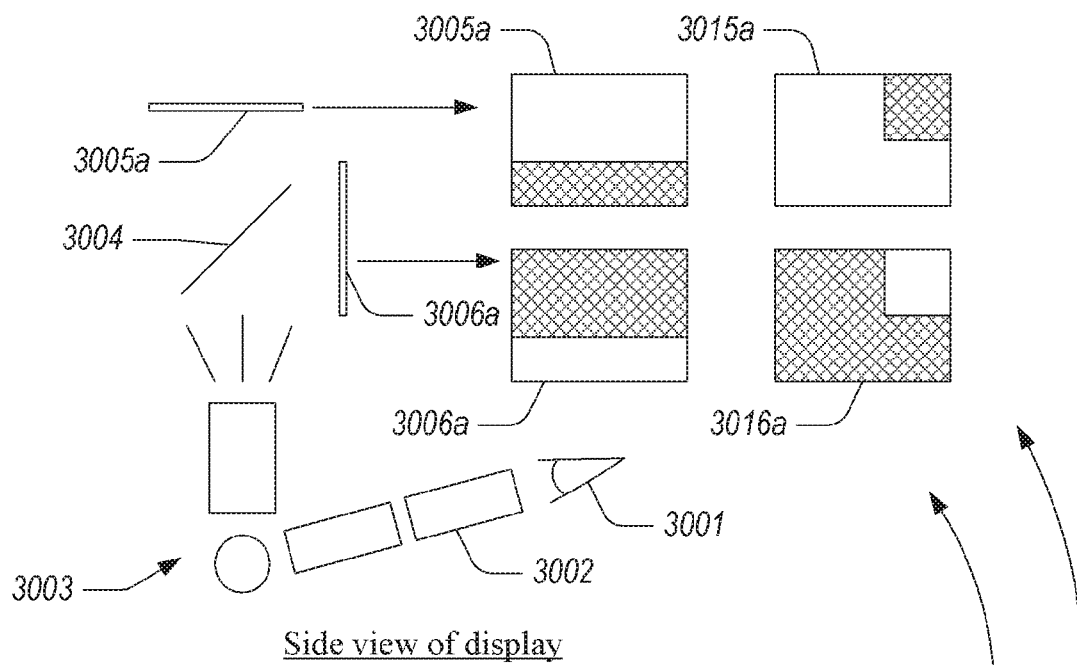
Side view of display
FIG. 13B1-c
one eye's view shown from side
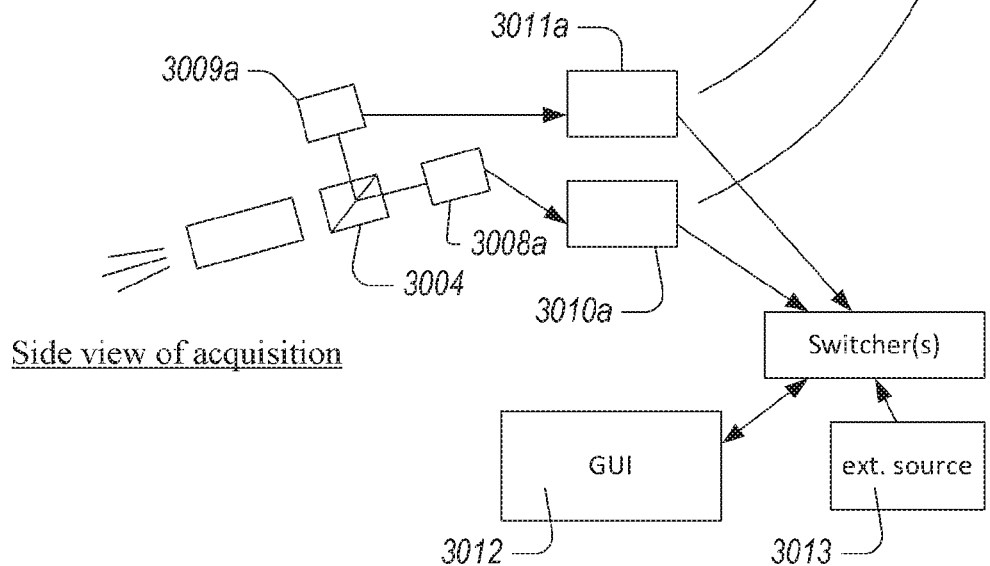
Side view of acquisition
FIG. 13B1-d

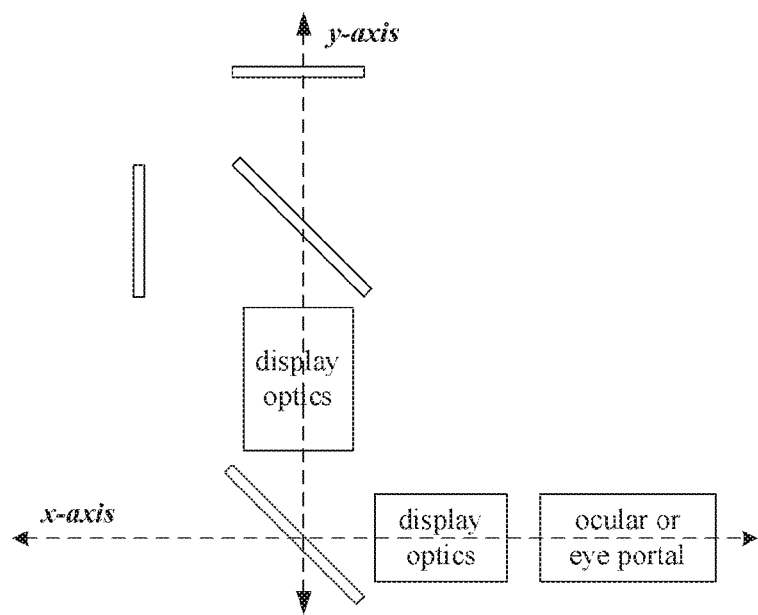
FIG. 13B1-e
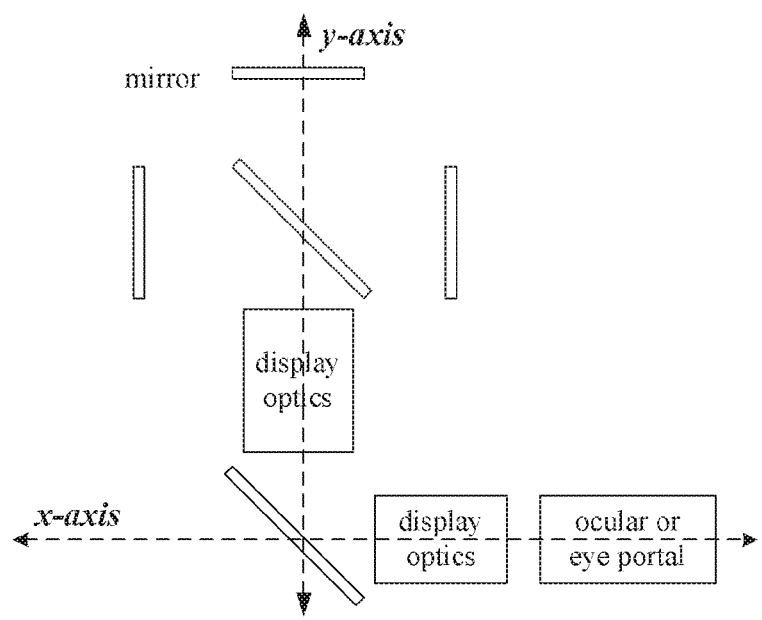
FIG. 13B1-f

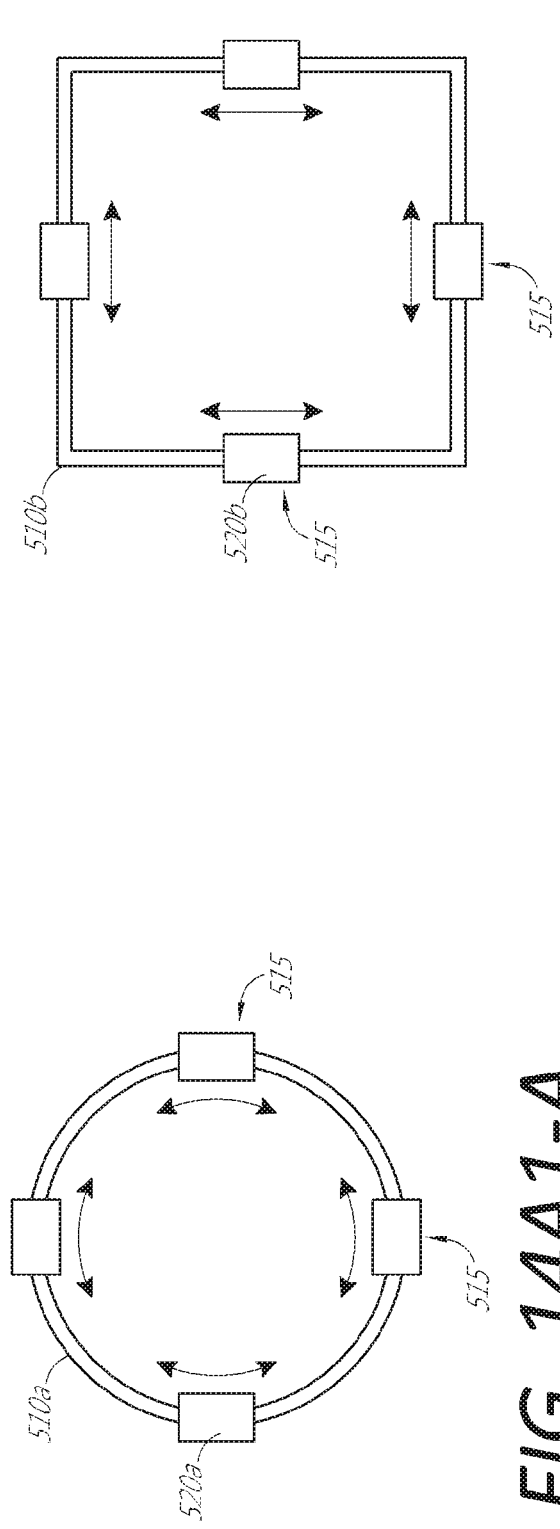
FIG. 14A1-B
FIG. 14A1-C
FIG. 14A1-A

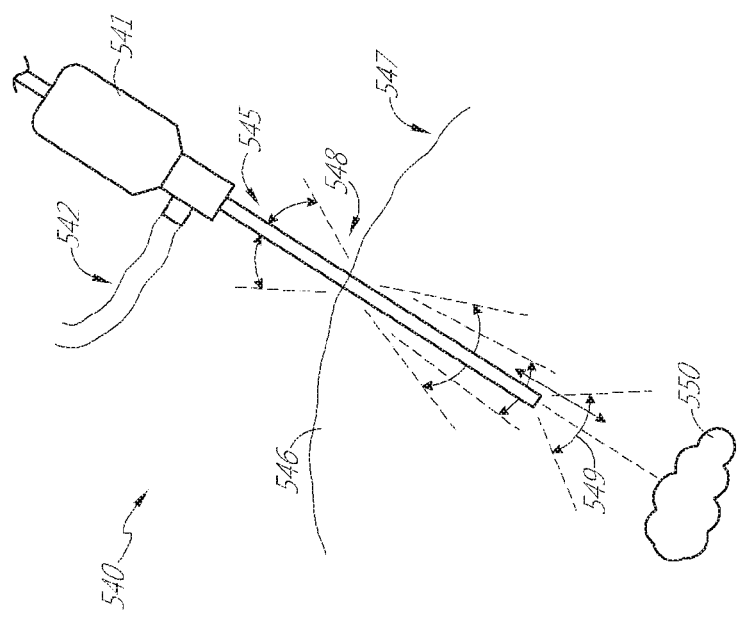
FIG. 14B1-A
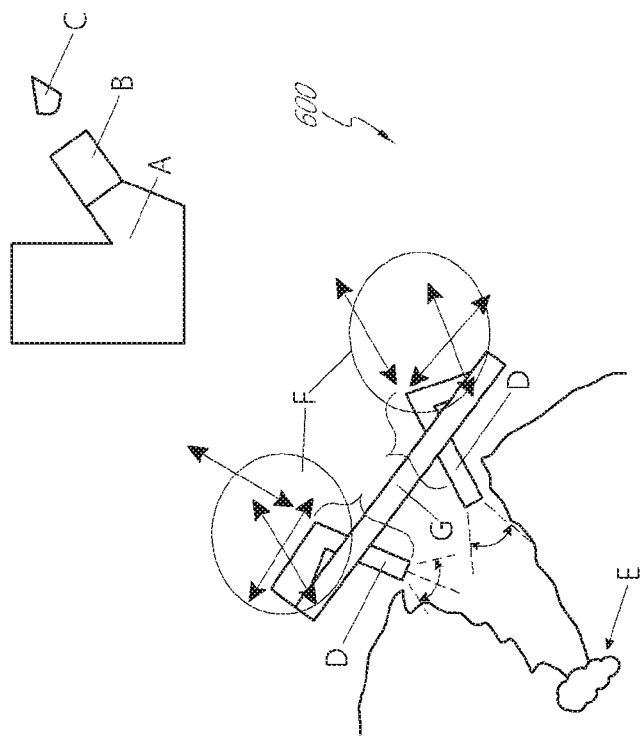
FIG. 14B1-B

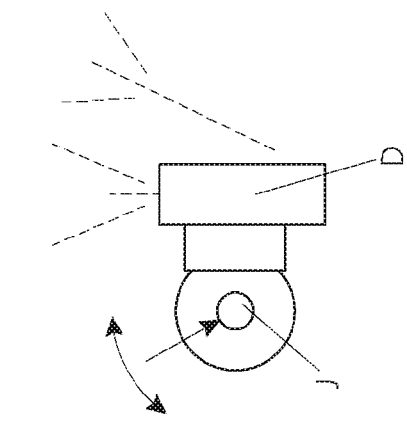
FIG. 14B2-A
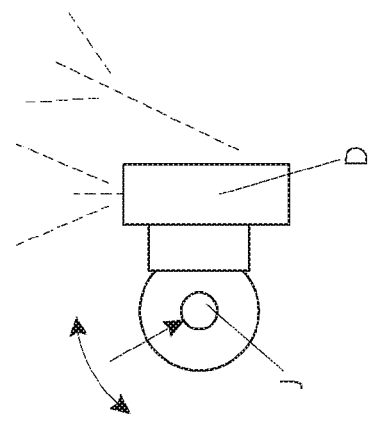
FIG. 14B2-B
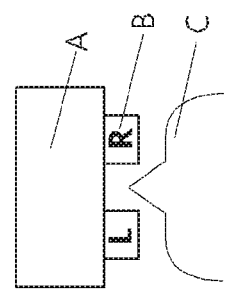
FIG. 14B2-C
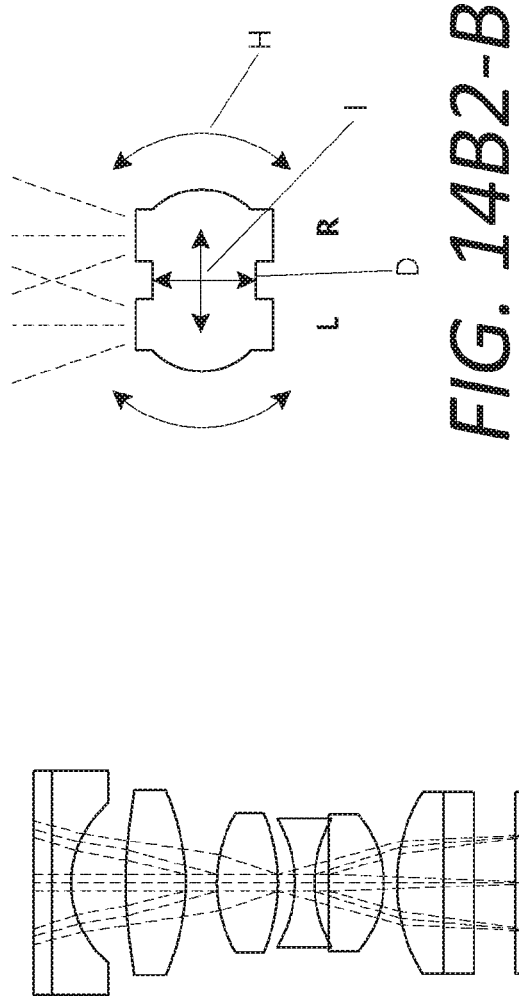
FIG. 14B2-D
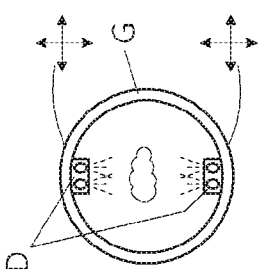
FIG. 14B2-E

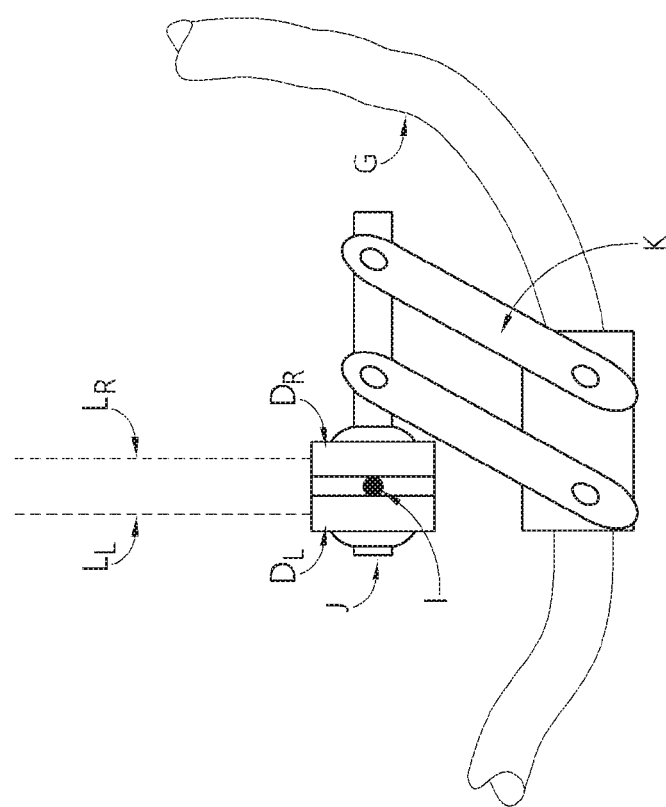
FIG. 14B2-F

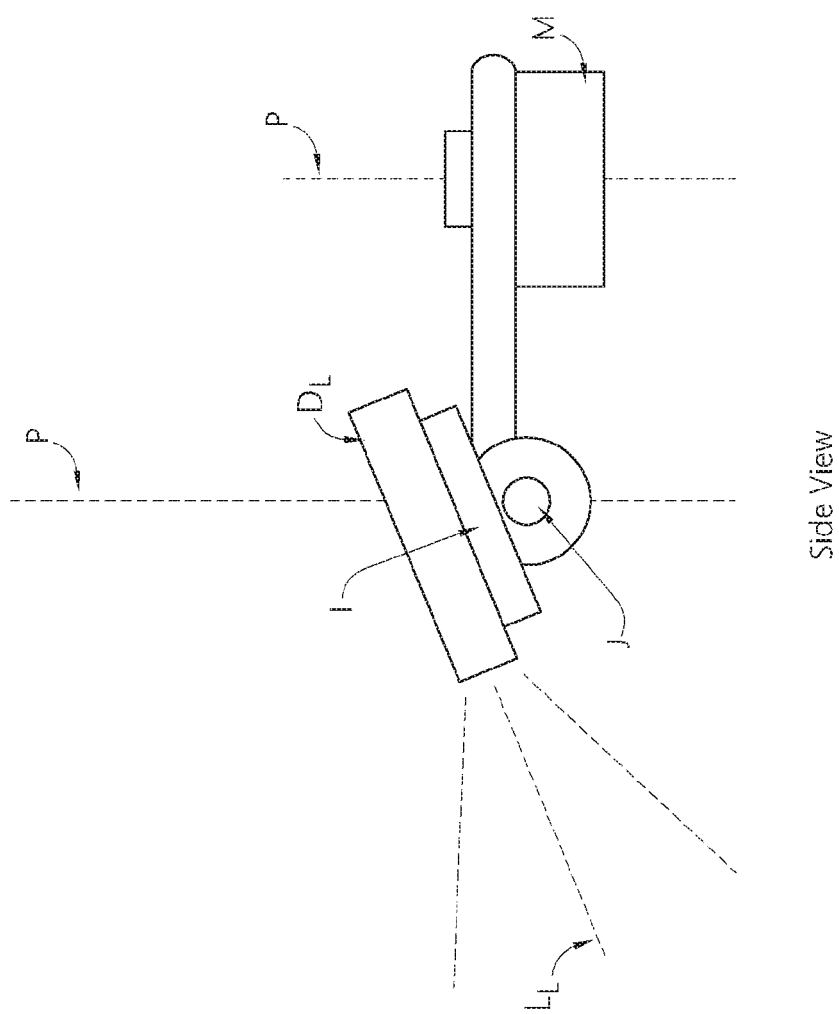
FIG. 14B2-G

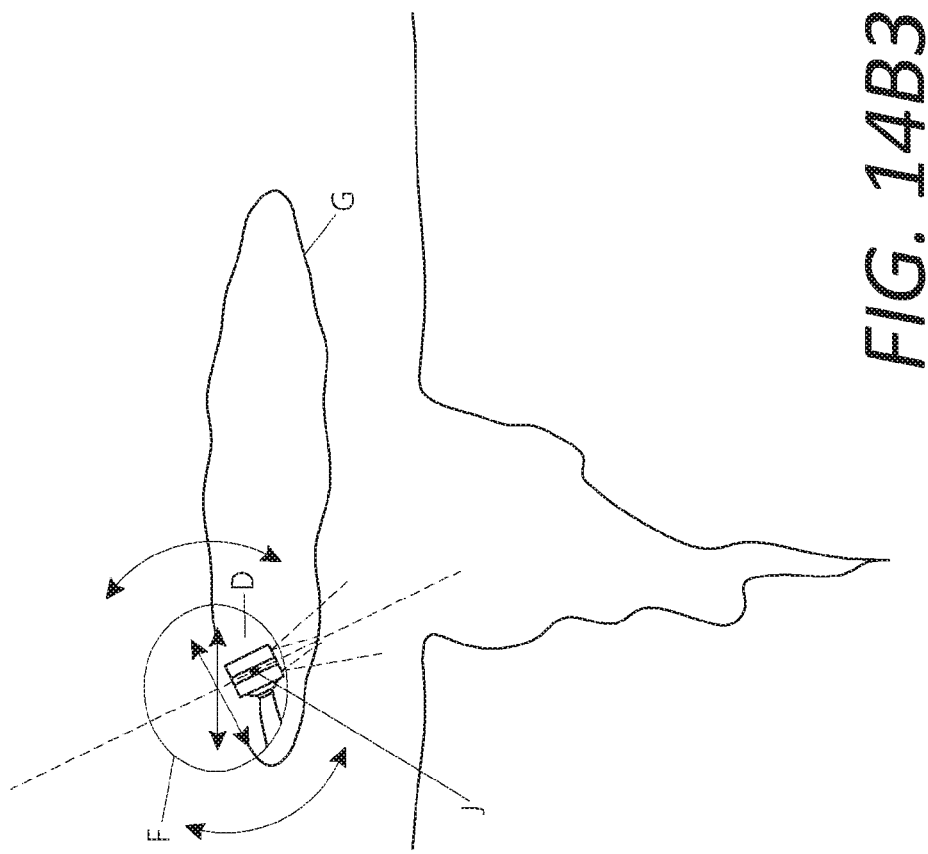
FIG. 14B3

SURGICAL VISUALIZATION SYSTEMS AND DISPLAYS

CROSS-REFERENCE TO RELATED APPLICATIONS

This application claims the benefit of priority to U.S. Provisional Application No. 62/260,221, entitled "SURGICAL VISUALIZATION SYSTEMS," filed on Nov. 25, 2015; U.S. Provisional Application No. 62/399,237, entitled "SURGICAL VISUALIZATION SYSTEMS AND DISPLAYS," filed on Sep. 23, 2016; and U.S. Provisional Application No. 62/401,781, entitled "SURGICAL VISUALIZATION SYSTEMS AND DISPLAYS," filed on Sep. 29, 2016. The entirety of each application referenced in this paragraph is incorporated herein by reference.

BACKGROUND

Field

Embodiments of the present disclosure relate to visualization systems and displays for use during surgery.

Description of Related Art

Some surgical operations involve the use of large incisions. These open surgical procedures provide ready access for surgical instruments and the hand or hands of the surgeon, allowing the user to visually observe and work in the surgical site, either directly or through an operating microscope or with the aid of loupes. Open surgery is associated with significant drawbacks, however, as the relatively large incisions result in pain, scarring, and the risk of infection as well as extended recovery time. To reduce these deleterious effects, techniques have been developed to provide for minimally invasive surgery. Minimally invasive surgical techniques, such as endoscopy, laparoscopy, arthroscopy, pharyngo-laryngoscopy, as well as small incision procedures utilizing an operating microscope for visualization, utilize a significantly smaller incision than typical open surgical procedures. Specialized tools may then be used to access the surgical site through the small incision. However, because of the small access opening, the surgeon's view and workspace of the surgical site is limited. In some cases, visualization devices such as endoscopes, laparoscopes, and the like can be inserted percutaneously through the incision to allow the user to view the surgical site.

The visual information available to a user without the aid of visualization systems and/or through laparoscopic or endoscopic systems contains trade-offs in approach. Accordingly, there is a need for improved visualization systems, for use in open and/or minimally invasive surgery.

SUMMARY

Disclosed herein are systems, devices, and methods for surgery and surgical visualization and display. Image acquisition and image display, for example, are described. Such image acquisition may be performed by, such as for example but not limited to, one or more cameras on a surgical tool, frame or support just a few centimeters above the patient's body and/or surgical site, as well as camera systems farther from the patient including camera systems from about 15 cm to about 45 cm from the patient's body and/or the surgical site. In various embodiments, these cameras may be stereo or mono cameras. A variety of camera designs may be employed. Different types of displays and display designs including binocular displays may also be used. Various combinations of components and features are possible. For example, one or more embodiment or feature described or referenced in any one or more of the different sections of the present disclosure may be used with, combined with, incorporated into, and/or are otherwise compatible with one or more embodiments and features described in any one or more other of the sections of the present disclosure. Similarly, embodiments or features described or referenced in any section of the present disclosure may be used with, combined with, incorporated into, and/or are otherwise compatible with any other embodiment or feature also described or referenced in that section. Additionally any one or more embodiments or features described or referenced in any section may be used with, combined with, incorporated into, be applicable to, and/or are otherwise compatible with a wide range of medical or surgical devices which may or may not be introduced into the body including but not limited to endoscopes, laparoscopes, and arthroscopes. Use of the various features and embodiments and combination thereof with other medical devices is also possible.

Multi-Display/Binocular Display Assembly

1. A medical apparatus comprising:
   a first display portion configured to display a first image;
   a second display portion configured to display a second image;
   electronics configured to receive one or more signals corresponding to images from a plurality of sources and to drive said first and second display portions to produce said first and second images based at least in part on said images from said plurality of sources; and
   a first beam combiner configured to receive said first and second images from said first and second display portions and to combine said first and second images for viewing.

2. The medical apparatus of Claim 1, wherein said first and second display portions comprise first and second displays, respectively.

3. The medical apparatus of Claim 1 or 2, further comprising a housing and a first ocular for viewing the combined first and second images within said housing.

4. The medical apparatus of Claim 3, further comprising a second ocular for viewing an additional image within said housing.

5. The medical apparatus of any of the preceding claims, further comprising imaging optics disposed to collect light from both said first and second display portions.

6. The medical apparatus of Claim 5, wherein said imaging optics are configured to form images at infinity.

7. The medical apparatus of any of the preceding claims, wherein said plurality of sources comprises at least one camera providing a surgical microscope view.

8. The medical apparatus of any Claim 7, further comprising said at least one camera providing said surgical microscope view.

9. The medical apparatus of any of the preceding claims, wherein said plurality of sources comprises at least one camera disposed on a surgical tool.

10. The medical apparatus of any Claim 9, further comprising said at least one camera disposed on said surgical tool.

11. The medical apparatus of any of the preceding claims, wherein said plurality of sources comprises at least one source providing data, a computed tomography scan, a computer aided tomography scan, magnetic resonance imaging, an x-ray, or ultrasound imaging.

12. The medical apparatus of any Claim 11, further comprising said at least one source providing said data, computed tomography scan, computer aided tomography scan, magnetic resonance imaging, x-ray, or ultrasound imaging.

13. The medical apparatus of any of the preceding claims, wherein said first image comprises a fluorescence image and said second image comprises a non-fluorescence image.

14. The medical apparatus of Claim 1, further comprising:
a third display portion configured to display a third image;
a fourth display portion configured to display a fourth image; and
a second beam combiner configured to receive said third and fourth images from said third and fourth display portions and to combine said third and fourth images for viewing.

15. The medical apparatus of Claim 14, wherein said third and fourth display portions comprise third and fourth displays.

16. The medical apparatus of Claim 14 or 15, further comprising a housing, a first ocular for viewing the combined first and second images within said housing, and a second ocular for viewing the combined third and fourth images within said housing.

17. The medical apparatus of any of Claims 14-16, further comprising additional electronics configured to receive one or more signals corresponding to images from another plurality of sources and to drive said third and fourth display portions to produce said third and fourth images based at least in part on said images from said another plurality of sources.

18. The medical apparatus of any of Claims 14-17, further comprising imaging optics disposed to collect light from both said third and fourth display portions.

19. The medical apparatus of Claim 18, wherein said imaging optics are configured to form images at infinity.

20. The medical apparatus of any of Claims 17-19, wherein said another plurality of sources comprises at least one camera providing a surgical microscope view.

21. The medical apparatus of any Claim 20, further comprising said at least one camera providing said surgical microscope view.

22. The medical apparatus of any of Claims 17-21, wherein said another plurality of sources comprises at least one camera disposed on a surgical tool.

23. The medical apparatus of Claim 22, further comprising said at least one camera disposed on said surgical tool.

24. The medical apparatus of any of Claims 17-23, wherein said another plurality of sources comprises at least one source providing data, a computed tomography scan, a computer aided tomography scan, magnetic resonance imaging, an x-ray, or ultrasound imaging.

25. The medical apparatus of any Claim 24, further comprising said at least one source providing said data, computed tomography scan, computer aided tomography scan, magnetic resonance imaging, x-ray, or ultrasound imaging.

26. The medical apparatus of any of Claims 14-25, wherein said third image comprises a fluorescence image and said fourth image comprises a non-fluorescence image.

27. The medical apparatus of any of the preceding claims, wherein said medical apparatus provides 3D viewing of a surgical field.

28. The medical apparatus of any of the preceding claims, wherein the combined first and second images for viewing comprises a composite image of said first and second images, wherein said first beam combiner is configured to produce said first image as a background image of said composite image, and to produce said second image as a picture-in-picture (PIP) of said composite image.

29. The medical apparatus of any of Claims 14-28, wherein the combined third and fourth images for viewing comprises a composite image of said third and fourth images, wherein said second beam combiner is configured to produce said third image as a background image of said composite image, and to produce said fourth image as a picture-in-picture (PIP) of said composite image.

Different Types of Displays

30. The medical apparatus of any of Claims 1-29, wherein said first display portion has a different resolution than said second display portion.

31. The medical apparatus of any of Claims 1-29, wherein said first display portion has a different pixel count than said second display portion.

32. The medical apparatus of any of Claims 1-29, wherein said first display portion has a different size than said second display portion.

33. The medical apparatus of any of Claims 1-29, wherein said first display portion has a different frame rate than said second display portion.

34. The medical apparatus of any of Claims 1-29, wherein said first display portion has different timing than said second display portion.

35. The medical apparatus of any of Claims 1-29, wherein at least said first display portion is configured to be moved with respect to said second display portion such that said first image is moved with respect to said second image after combining by the first beam combiner.

36. The medical apparatus of any of Claims 1-29, wherein at least said first display portion is configured to be re-oriented with respect to said second display portion such that said first image is re-oriented with respect to said second image after combining by the first beam combiner.

37. The medical apparatus of any of Claims 1-29, further comprising a movable mount to which said first display is coupled, said movable mount being configured to be moved such that when said at least said first display portion is moved with respect to said second display portion such that said first image is moved with respect to said second image after combining by the first beam combiner.

38. The medical apparatus of Claim 37, wherein said movable mount is configured to be moved by hand.

39. The medical apparatus of Claim 37, further comprising electrically driven actuators configured to control movement of said movable mount with electronic signals.

40. The medical apparatus of any of Claims 1-29, further comprising processing electronics configured to combine said first and second images in addition to said combining by said beam combiner.

41. The medical apparatus of Claim 40, wherein said processing electronics are configured to direct said combined first and second images to at least one additional display for viewing by another viewer.

42. The medical apparatus of any of Claims 1-41, wherein said medical apparatus is configured to provide a view of a surgical site and comprises a binocular viewing assembly comprising a housing and a plurality of oculars, at least one of said oculars configured to provide views of said first and second display portions disposed in the housing, said binocular viewing assembly configured so as not to provide a view of said surgical site through the oculars via an optical pathway that passes through the housing.

43. The medical apparatus of any of Claims 1-41, wherein said medical apparatus is configured to provide a view of a surgical site and does not provide an optical path to said surgical site.

44. The medical apparatus of any of Claims 1-41, wherein said medical apparatus is configured to provide a view of a surgical site and comprise a binocular viewing assembly comprising a housing and a plurality of oculars, said at least one of said plurality of oculars configured to provide views of said first and second display portions disposed in the housing, wherein a line of sight of the plurality of oculars is decoupled from a line of sight of the binocular viewing assembly.

45. The medical apparatus of any of Claims 1-41, comprising a binocular viewing assembly including said first and second display portions, at least one of said display portions configured to display a surgical microscope view of said surgical site provided by a surgical microscope camera.

46. The medical apparatus of Claim 45, wherein said oculars can be moved away from the surgical site by at least 2 feet and provide views of the surgical site from said camera while the camera remain within a foot of said surgical site.

47. The medical apparatus of Claim 45, wherein said oculars can be moved away from the surgical site by at least 3 feet and provide views of the surgical site from said camera while the camera remain within a foot of said surgical site.

48. The medical apparatus of Claim 45, wherein said oculars can be moved away from the surgical site by at least 4 feet and provide views of the surgical site from said camera while the camera remain within 2 feet of said surgical site.

49. The medical apparatus of Claim 45, wherein said oculars can be moved away from the surgical site by at least 5 feet and provide views of the surgical site from said camera while the camera remain within 2 feet of said surgical site.

50. The medical apparatus of Claim 45, wherein said oculars can be moved away from the surgical site by at least 5 feet and provide views of the surgical site from said camera while the camera remain within a foot of said surgical site.

51. The medical apparatus of any of Claims 1-41, comprising a binocular viewing assembly including said displays and oculars, at least one of said oculars providing a view of said first and second display portions, at least one of said displays configured to display a surgical microscope view of said surgical site provided by a surgical microscope camera, wherein said oculars do not provide a direct optical path to said surgical site.

52. The medical apparatus of any of Claims 1-41, wherein said medical apparatus is configured for viewing a surgical site using at least one of said first and second display portions and said medical apparatus does not provide a direct optical path therethrough to said surgical site.

53. The medical apparatus of any of Claims 1-41, further comprising a port for outputting a video signal from a camera that provides input to said first display portion.

54. The medical apparatus of any of Claims 1-41, further comprising first and second ports for outputting a video signals from first and second cameras that provide input to said first and second display portions respectively.

55. The medical apparatus of any of Claims 1-41, further comprising first and second ports for outputting a video signals from first and second sources that provide input to said first and second display portions respectively.

56. The medical apparatus of any of Claims 53-55, further comprising an interface for receiving user input for recording video from said port.

57. The medical apparatus of any of Claims 53-56, further comprising a recording device coupled to said port.

58. The medical apparatus of Claim 2, wherein said first display has a different resolution than said second display.

59. The medical apparatus of Claim 2, wherein said first display has a different pixel count than said second display.

60. The medical apparatus of Claim 2, wherein said first display has a different size than said second display portion.

61. The medical apparatus of Claim 2, wherein said first display has a different frame rate than said second display.

62. The medical apparatus of Claim 2, wherein said first display has different timing than said second display.

63. The medical apparatus of Claim 2, wherein at least said first display is configured to be moved with respect to said second display such that said first image is moved with respect to said second image after combining by the first beam combiner.

64. The medical apparatus of any of Claim 2, wherein at least said first display is configured to be re-oriented with respect to said second display such that said first image is re-oriented with respect to said second image after combining by the first beam combiner.

65. The medical apparatus of any of Claim 2, further comprising a movable mount to which said first display is coupled, said movable mount being configured to be moved such that when said at least said first display is moved with respect to said second display such that said first image is moved with respect to said second image after combining by the first beam combiner.

66. The medical apparatus of Claim 65, wherein said movable mount is configured to be moved by hand.

67. The medical apparatus of Claim 65, further comprising electrically driven actuators configured to control movement of said movable mount with electronic signals.

68. The medical apparatus of Claim 2, further comprising processing electronics configured to combine said first and second images in addition to said combining by said beam combiner.

69. The medical apparatus of Claim 68, wherein said processing electronics are configured to direct said combined first and second images to at least one additional display for viewing by another viewer.

70. The medical apparatus of any of Claim 2, wherein said medical apparatus is configured to provide a view of a surgical site and comprises a binocular viewing assembly comprising a housing and a plurality of oculars, at least one of said oculars configured to provide views of said first and second displays disposed in the housing, said binocular viewing assembly configured so as not to provide a view of said surgical site through the oculars via an optical pathway that passes through the housing.

71. The medical apparatus of Claim 2, wherein said medical apparatus is configured to provide a view of a surgical site and does not provide an optical path to said surgical site.

72. The medical apparatus of Claim 2, wherein said medical apparatus is configured to provide a view of a surgical site and comprise a binocular viewing assembly comprising a housing and a plurality of oculars, said at least one of said plurality of oculars configured to provide views of said first and second displays disposed in the housing, wherein a line of sight of the plurality of oculars is decoupled from a line of sight of the binocular viewing assembly.

73. The medical apparatus of Claim 2, comprising a binocular viewing assembly including said first and second display portions, at least one of said display configured to display a surgical microscope view of said surgical site provided by a surgical microscope camera.

74. The medical apparatus of Claim 73, wherein said oculars can be moved away from the surgical site by at least 2 feet and provide views of the surgical site from said camera while the camera remain within a foot of said surgical site.

75. The medical apparatus of Claim 73, wherein said oculars can be moved away from the surgical site by at least 3 feet and provide views of the surgical site from said camera while the camera remain within a foot of said surgical site.

76. The medical apparatus of Claim 73, wherein said oculars can be moved away from the surgical site by at least 4 feet and provide views of the surgical site from said camera while the camera remain within 2 feet of said surgical site.

77. The medical apparatus of Claim 73, wherein said oculars can be moved away from the surgical site by at least 5 feet and provide views of the surgical site from said camera while the camera remain within 2 feet of said surgical site.

78. The medical apparatus of Claim 73, wherein said oculars can be moved away from the surgical site by at least 5 feet and provide views of the surgical site from said camera while the camera remain within a foot of said surgical site.

79. The medical apparatus of Claim 2, comprising a binocular viewing assembly including said displays and oculars, at least one of said oculars providing a view of said first and second displays, at least one of said displays configured to display a surgical microscope view of said surgical site provided by a surgical microscope camera, wherein said oculars do not provide a direct optical path to said surgical site.

80. The medical apparatus of Claim 2, wherein said medical apparatus is configured for viewing a surgical site using at least one of said first and second displays and said medical apparatus does not provide a direct optical path therethrough to said surgical site.

81. The medical apparatus of Claim 2, further comprising a port for outputting a video signal from a camera that provides input to said first display.

82. The medical apparatus of Claim 2, further comprising first and second ports for outputting a video signals from first and second cameras that provide input to said first and second displays respectively.

83. The medical apparatus of Claim 2, further comprising first and second ports for outputting a video signals from first and second sources that provide input to said first and second displays, respectively.

84. The medical apparatus of any of Claims 81-83, further comprising an interface for receiving user input for recording video from said port.

85. The medical apparatus of any of Claims 81-83, further comprising a recording device coupled to said port.

86. The medical apparatus of any of the preceding claims, wherein said electronics is configured to provide surgical navigational guidance by providing images.

87. The medical apparatus of Claim 86, wherein said images change with movement of a surgical tool.

88. The medical apparatus of Claim 86 or 87, wherein said images comprise text.

89. The medical apparatus of any of Claims 86-88, wherein said images are from a 3D model.

Mobile Display Devices

1. A medical apparatus comprising:
    a first display portion configured to display a first image of a surgical site;
    electronics configured to receive one or more signals corresponding to said first image from a camera and to drive said first display portion to produce said first image;
    a docking station configured to receive a cell phone or tablet comprising a second display portion having a second image;
    a beam combiner configured to receive and combine said first image and at least a portion of said second image for viewing; and
    a viewing assembly comprising a housing and first and second oculars for viewing the combined images within said housing through said first ocular.

2. The medical apparatus of Claim 1, wherein the combined images for viewing comprise a composite image of at least a portion of said first image and said at least a portion of said second image, wherein said beam combiner is configured to produce said first image as a background image of said composite image, and to produce at least a portion of said at least a portion of said second image as a picture-in-picture (PIP) of said composite image.

3. The medical apparatus of Claim 1, wherein said beam combiner is configured to produce said first image adjacent said at least a portion of said second image.

4. The medical apparatus of any of the preceding claims, wherein said camera provides a surgical microscope view.

5. The medical apparatus of any of the preceding claims, wherein said camera has a work distance between 150 and 450 mm.

6. The medical apparatus of any of the preceding claims, wherein said camera provides a zoom magnification.

7. The medical apparatus of any of the preceding claims, wherein said camera provides an image of a field (or lateral dimension).

8. The medical apparatus of any of the preceding claims, wherein said camera is disposed on a surgical tool.

9. The medical apparatus of any of the preceding claims, further comprising a third display portion configured to display a third image, said third image comprising another image of said surgical site, wherein said second ocular is configured for viewing said third image within said housing.

10. The medical apparatus of Claim 9, further comprising additional electronics configured to receive one or more signals corresponding to said third image from another camera and to drive said third display portion to produce said third image.

11. The medical apparatus of Claim 9 or 10, wherein said another camera provides a surgical microscope view.

12. The medical apparatus of Claim 9 or 10, wherein said another camera is disposed on a surgical tool.

13. The medical apparatus of any of Claims 9-12, wherein said first and third display portions are configured to provide 3D viewing of images of said surgical site through said first and second oculars.

14. The medical apparatus of any of Claims 9-13, wherein said cameras provide different views from different perspectives to produce 3D visualization for a viewer viewing the first and third display portions through the first and second oculars.

15. The medical apparatus of any of Claims 9-12, further comprising:
    an additional beam combiner configured to receive and combine said at least a portion of said second image and at least a portion of said third image for viewing within said housing through said second ocular.

16. The medical apparatus of Claim 15, wherein the combined second and third images for viewing comprises a composite image of said at least a portion of said second image and at least a portion of said third image, wherein said additional beam combiner is configured to produce at least a portion of said third image as a background image of said composite image, and to produce said at least a portion of said second image as a picture-in-picture (PIP) of said composite image.

17. The medical apparatus of Claim 15, wherein said additional beam combiner is configured to produce said at least a portion of third image adjacent said at least a portion of said second image.

18. The medical apparatus of any of Claims 9-14, further comprising:
    an additional beam combiner configured to receive and combine another perspective of at least a portion of said second image and at least a portion of said third image for viewing within said housing through said second ocular.

19. The medical apparatus of Claim 17, wherein said at least a portion of said second image and said another perspective of at least a portion of said second image are different stereo views of said second image.

20. The medical apparatus of Claim 18 or 19, wherein said additional beam combiner is configured to produce said third image as a background image of a composite image, and to produce said another perspective of at least a portion of said second image as a picture-in-picture (PIP) of said composite image.

21. The medical apparatus of Claim 18 or 19, wherein said additional beam combiner is configured to produce at least a portion of said third image adjacent said another perspective of said at least a portion of said second image.

22. The medical apparatus of any of the preceding Claims, further comprising an optical pathway between said second display portion and said beam combiner such that said beam combiner is capable of optically receiving said at least a portion of said second image from said second display portion.

23. The medical apparatus of any of the preceding claims, further comprising:
    a fourth display portion configured to display said at least a portion of said second image;
    further electronics configured to receive one or more signals corresponding to said at least a portion of said second image and to drive said fourth display portion to produce said at least a portion of said second image, wherein said beam combiner is configured to receive said at least a portion of said second image from said fourth display portion.

24. The medical apparatus of any of the preceding claims, further comprising a fifth display portion configured to display a fifth image, said fifth image comprising another image of said surgical site, wherein said first ocular is configured for viewing said fifth image within said housing.

25. The medical apparatus of Claim 24, further comprising additional electronics configured to receive one or more signals corresponding to said fifth image from another camera and to drive said fifth display portion to produce said fifth image.

26. The medical apparatus of Claim 24 or 25, wherein said another camera provides a surgical microscope view.

27. The medical apparatus of Claim 24 or 25, wherein said another camera is disposed on a surgical tool.

28. The medical apparatus of any of Claims 24-27, further comprising:
    another beam combiner configured to receive and combine said at least a portion of said second image and at least a portion of said fifth image for viewing within said housing through said first ocular.

29. The medical apparatus of any of Claims 24-27, further comprising a sixth display portion configured to display a sixth image, said sixth image comprising another image of said surgical site, wherein said second ocular is configured for viewing said sixth image within said housing.

30. The medical apparatus of Claim 29, further comprising additional electronics configured to receive one or more signals corresponding to said sixth image from another camera and to drive said sixth display portion to produce said sixth image.

31. The medical apparatus of Claim 29 or 30, wherein said another camera provides a surgical microscope view.

32. The medical apparatus of Claim 29 or 30, wherein said another camera is disposed on a surgical tool.

33. The medical apparatus of any of Claims 29-32, further comprising:
    a beam combiner configured to receive and combine said at least a portion of said second image and at least a portion of said sixth image for viewing within said housing through said second ocular.

34. The medical apparatus of any of Claims 29-32, wherein said fifth and sixth display portions are configured to provide 3D viewing of images of said surgical site through said first and second oculars.

35. The medical apparatus of any of Claims 29-34, wherein said cameras provide different views from different perspectives to produce 3D visualization for viewer viewing the fifth and sixth display portions through the first and second oculars.

36. The medical apparatus of any of the preceding claims, wherein said at least a portion of said second image comprises an e-mail message.

37. The medical apparatus of any of the preceding claims, wherein said at least a portion of said second image comprises an at text message.

38. The medical apparatus of any of the preceding claims, wherein said at least a portion of said second image comprises a medical communication.

39. The medical apparatus of any of the preceding claims, wherein said at least a portion of said second image comprises medical data.

40. The medical apparatus of any of the preceding claims, wherein said at least a portion of said second image comprises news.

41. The medical apparatus of any of the preceding claims, wherein said at least a portion of said second image comprises financial data.

42. The medical apparatus of any of the preceding claims, wherein said at least a portion of said second image comprises business information.

43. The medical apparatus of any of the preceding claims, wherein said at least a portion of said second image comprises business data.

44. The medical apparatus of any of the preceding claims, wherein said docking station is configured to allow said cell phone or tablet to provide navigational guidance or ergonomic control.

45. The medical apparatus of any of the preceding claims, wherein said viewing assembly does not provide a view of said surgical site through said first and second oculars via an optical pathway that passes through said housing.

46. The medical apparatus of any of the preceding claims, wherein said viewing assembly is ergonomically decoupled from said camera that provide video to said first display that is viewed through said first ocular of said viewing assembly.

47. The medical apparatus of any of the preceding claims, wherein said docking station is configured to allow said at least a portion of said second image from said cell phone or tablet to be displayed on an external monitor.

48. The medical apparatus of any of the preceding claims, wherein said docking station is configured to allow said cell phone or tablet to receive and record images of said surgical site from said camera.

49. The medical apparatus of any of the preceding claims, wherein said docking station is in electrical communication with said cell phone or tablet.

50. The medical apparatus of any of the preceding claims, wherein said docking station includes a port for electrical communication with said cell phone or tablet.

51. The medical apparatus of any of the preceding claims, wherein said docking station includes a port providing power to said cell phone or tablet.

52. The medical apparatus of any of the preceding claims, further comprising imaging lenses for imaging said display portions.

53. The medical apparatus of Claim 52, wherein said imaging lenses are disposed between respective beam combiners and display portions.

54. The medical apparatus of any of the preceding claims, further comprising a remote control configured to control said cell phone or tablet.

55. The medical apparatus of Claim 54, wherein the remote control is disposed on said viewing assembly.

56. The medical apparatus of Claim 54 or 55, wherein the remote control includes a handgrip, a handle, a joystick, buttons, haptics, or a touchpad.

57. The medical apparatus of any of Claims 54-56, wherein said remote control is configured to control the second image displayed on the second display portion of said cell phone or tablet.

High Intensity Displays

1. A medical apparatus comprising:
    a first display portion configured to display a first image;
    a second display portion configured to display a second image;
    electronics configured to receive one or more signals corresponding to images from a plurality of sources and to drive said first and second display portions to produce said first and second images based at least in part on said images from said plurality of sources; and
    a first beam combiner configured to receive said first and second images from said first and second display portions and to combine said first and second images for viewing,
    wherein the first display portion has a power between 0.5 watts and 6 watts.

2. The medical apparatus of Claim 1, wherein said second display portion has a power between 0.5 watts and 6 watts.

3. The medical apparatus of Claim 1 or 2, wherein said first and second display portions comprise first and second displays, respectively.

4. The medical apparatus of Claim 1-3, further comprising a housing and a first ocular for viewing the combined first and second images within said housing.

5. The medical apparatus of Claim 1-4, further comprising a second ocular for viewing an additional image within said housing.

6. The medical apparatus of any of the preceding claims, further comprising imaging optics disposed to collect light from both said first and second display portions.

7. The medical apparatus of Claim 6, wherein said imaging optics are configured to form images at infinity.

8. The medical apparatus of any of the preceding claims, wherein said plurality of sources comprises at least one camera providing a surgical microscope view.

9. The medical apparatus of any Claim 8, further comprising said at least one camera providing said surgical microscope view.

10. The medical apparatus of any of the preceding claims, wherein said plurality of sources comprises at least one camera disposed on a surgical tool.

11. The medical apparatus of any Claim 10, further comprising said at least one camera disposed on said surgical tool.

12. The medical apparatus of any of the preceding claims, wherein said plurality of sources comprises at least one source providing data, a computed tomography scan, a computer aided tomography scan, magnetic resonance imaging, an x-ray, or ultrasound imaging.

13. The medical apparatus of any Claim 12, further comprising said at least one source providing said data, computed tomography scan, computer aided tomography scan, magnetic resonance imaging, x-ray, or ultrasound imaging.

14. The medical apparatus of any of the preceding claims, wherein said first image comprises a fluorescence image and said second image comprises a non-fluorescence image.

15. The medical apparatus of Claim 1, further comprising:
    a third display portion configured to display a third image;
    a fourth display portion configured to display a fourth image; and
    a second beam combiner configured to receive said third and fourth images from said third and fourth display portions and to combine said third and fourth images for viewing.

16. The medical apparatus of Claim 15, wherein said third and fourth display portions comprise third and fourth displays.

17. The medical apparatus of Claim 15 or 16, further comprising a housing, a first ocular for viewing the combined first and second images within said housing, and a second ocular for viewing the combined third and fourth images within said housing.

18. The medical apparatus of any of Claims 15-17, further comprising additional electronics configured to receive one or more signals corresponding to images from another plurality of sources and to drive said third and fourth display portions to produce said third and fourth images based at least in part on said images from said another plurality of sources.

19. The medical apparatus of any of Claims 15-18, further comprising imaging optics disposed to collect light from both said third and fourth display portions.

20. The medical apparatus of Claim 19, wherein said imaging optics are configured to form images at infinity.

21. The medical apparatus of any of Claims 18-20, wherein said another plurality of sources comprises at least one camera providing a surgical microscope view.

22. The medical apparatus of any Claim 21, further comprising said at least one camera providing said surgical microscope view.

23. The medical apparatus of any of Claims 18-22, wherein said another plurality of sources comprises at least one camera disposed on a surgical tool.

24. The medical apparatus of Claim 23, further comprising said at least one camera disposed on said surgical tool.

25. The medical apparatus of any of Claims 18-24, wherein said another plurality of sources comprises at least one source providing data, a computed tomography scan, a computer aided tomography scan, magnetic resonance imaging, an x-ray, or ultrasound imaging.

26. The medical apparatus of any Claim 25, further comprising said at least one source providing said data, computed tomography scan, computer aided tomography scan, magnetic resonance imaging, x-ray, or ultrasound imaging.

27. The medical apparatus of any of Claims 15-26, wherein said third image comprises a fluorescence image and said fourth image comprises a non-fluorescence image.

28. The medical apparatus of any of the preceding claims, wherein said medical apparatus provides 3D viewing of a surgical field.

29. The medical apparatus of any of the preceding claims, wherein the combined first and second images for viewing comprises a composite image of said first and second images, wherein said first beam combiner is configured to produce said first image as a background image of said composite image, and to produce said second image as a picture-in-picture (PIP) of said composite image.

30. The medical apparatus of any of Claims 15-29, wherein the combined third and fourth images for viewing comprises a composite image of said third and fourth images, wherein said second beam combiner is configured to produce said third image as a background image of said composite image, and to produce said fourth image as a picture-in-picture (PIP) of said composite image.

31. The medical apparatus of any of Claims 15-30, wherein the third display portion has a power between 0.5 watts and 6 watts, or wherein the fourth display portion has a power between 0.5 watts and 6 watts.

32. The medical apparatus of any of Claims 1-31, further comprising one or more light sources configured to illuminate the first or second display portion.

33. The medical apparatus of any of Claims 15-31, further comprising one or more light sources configured to illuminate the third or fourth display portion.

34. The medical apparatus of Claim 32 or 33, wherein said one or more light sources are configured to provide between 0.5 to 10 watts of power.

Neuro-Monitoring & Vital Sign Monitoring

1. A medical apparatus comprising:
   a first display portion configured to display a first image;
   a second display portion configured to display a second image; and
   electronics configured to receive one or more signals corresponding to images from a plurality of sources and to drive said first and second display portions to produce said first and second images based at least in part on said images from said plurality of sources;
   wherein said plurality of sources comprises a source providing neuro-monitoring.

2. The medical apparatus of Claim 1, wherein said first and second display portions comprise first and second displays, respectively.

3. The medical apparatus of Claim 1 or 2, further comprising a housing and a first ocular for viewing the combined first and second images within said housing.

4. The medical apparatus of Claim 3, further comprising a second ocular for viewing an additional image within said housing.

5. The medical apparatus of any of the preceding claims, further comprising imaging optics disposed to collect light from both said first and second display portions.

6. The medical apparatus of Claim 5, wherein said imaging optics are configured to form images at infinity.

7. The medical apparatus of any of the preceding claims, wherein said plurality of sources comprises at least one camera providing a surgical microscope view.

8. The medical apparatus of any Claim 7, further comprising said at least one camera providing said surgical microscope view.

9. The medical apparatus of any of the preceding claims, wherein said plurality of sources comprises at least one camera disposed on a surgical tool.

10. The medical apparatus of any Claim 9, further comprising said at least one camera disposed on said surgical tool.

11. The medical apparatus of claims 1-10, wherein the source comprises a source providing electroencephalography or electromyography.

12. The medical apparatus of Claim 35 or 36, further comprising the source providing neuro-monitoring.

13. The medical apparatus of any of Claims 17-23, wherein said another plurality of sources comprises a source providing neuro-monitoring.

14. The medical apparatus of Claim 38, wherein the source comprises a source providing electroencephalography or electromyography.

15. The medical apparatus of Claim 38 or 39, further comprising the source providing neuro-monitoring.

16. The medical apparatus of any of Claims 1-11, wherein said plurality of sources comprises a source providing vital sign monitoring.

17. The medical apparatus of Claim 16, the source comprises a source providing heart rate, blood pressure, body temperature, or weight.

18. The medical apparatus of any of the preceding claims, further comprising a beam combiner configured to receive said first and second images from said first and second display portions and to combine said first and second images for viewing.

Pair of Mobile Displays in FOV

1. A binocular display for viewing a surgical field, said binocular display comprising:
   a left-eye view channel comprising a first cell phone having:
     a first camera configured to produce a left-eye view image of said surgical field;
     a first display configured to display said left-eye view image of said surgical field; and
     a first controller configured to receive one or more input signals corresponding to said left-eye view image from said first camera and/or receive input from cameras viewing the surgical field and to drive said first display to produce said left-eye view image; and
   a right-eye view channel comprising a second cell phone having:
     a second camera configured to produce a right-eye view image of said surgical field;
     a second display configured to display said right-eye view image of said surgical field; and
     a second controller configured to receive one or more input signals corresponding to said right-eye view image from said second camera and/or receive input from cameras viewing the surgical field and to drive said second display to produce said right-eye view image.

2. The binocular display of Claim 1, further comprising a viewing assembly comprising a housing and first and second oculars for viewing said left-eye and right-eye view images within said housing through said first and second oculars respectively.

3. The binocular display of Claim 2, further comprising optical elements in said left-eye and right-eye view channels configured to direct light from said first and second displays to said first and second oculars respectively.

4. The binocular display of Claim 3, wherein said optical elements include a mirror or a lens.

5. The binocular display of any of the preceding claims, wherein said left-eye view image and said right-eye view image are different stereo views of said surgical field.

6. The binocular display of any of Claims 2-5, further comprising a remote control configured to control said first or second cell phone.

7. The binocular display of Claim 6, wherein said remote control is disposed on said viewing assembly.

8. The binocular display of Claim 6 or 7, wherein said remote control includes a handgrip, a handle, a joystick, buttons, haptics, or a touchpad.

9. The binocular display of any of Claims 6-8, wherein said remote control is configured to control said left-eye or right-eye view image displayed on said first or second display of said first or second cell phone.

10. The binocular display of any of the preceding claims, wherein the binocular display is disposed on an articulating arm.

Multiple Displays in FOV

1. A medical apparatus for viewing a surgical field, said medical apparatus comprising:
   a viewing assembly comprising:
   a housing;
   an ocular having a field of view;
   a first display within said field of view for viewing a first image of said surgical field within said housing through said ocular; and
   a second display within said field of view for viewing a second image within said housing through said ocular;
   a first controller configured to receive one or more signals corresponding to said first image and to drive said first display to produce said first image; and
   a second controller configured to receive one or more signals corresponding to said second image to drive said second display to produce said second image.

2. The medical apparatus of Claim 1, further comprising:
   a third display within said field of view for viewing a third image within said housing through said ocular; and
   a third controller configured to receive one or more signals corresponding to said third image to drive said third display to produce said third image.

3. The medical apparatus of Claim 1 or 2, wherein said first image is provided by a camera.

4. The medical apparatus of Claim 3, wherein said camera is disposed on a surgical tool.

5. The medical apparatus of Claim 3, wherein said camera is an endoscope.

6. The medical apparatus of any of Claims 1-5, wherein said second image comprises another image of said surgical field.

7. The medical apparatus of any of Claims 1-5, wherein said second image comprises at least one of an image from a mobile display device, data, a computed tomography scan, a computer aided tomography scan, magnetic resonance imaging, an x-ray, ultrasound imaging, a fluorescence image, neuro-monitoring, or vital sign monitoring.

8. The medical apparatus of any of the preceding claims, further comprising a switching system configured to switch said first or second image to another image.

9. The medical apparatus of any of Claims 1-8, wherein said viewing assembly further comprises:
   another ocular having another field of view;
   a fourth display within said another field of view for viewing a fourth image of said surgical field within said housing through said another ocular; and
   a fifth display within said another field of view for viewing a fifth image within said housing through said another ocular;
   a fourth controller configured to receive one or more signals corresponding to said fourth image and to drive said fourth display to produce said fourth image; and
   a fifth controller configured to receive one or more signals corresponding to said fifth image to drive said fifth display to produce said fifth image.

10. The medical apparatus of Claim 9, further comprising:
    a sixth display within said field of view for viewing a sixth image within said housing through said another ocular; and
    a sixth controller configured to receive one or more signals corresponding to said sixth image to drive said six display to produce said sixth image.

11. The medical apparatus of Claim 9 or 10, wherein said fourth image is provided by another camera.

12. The medical apparatus of Claim 11, wherein said another camera is disposed on a surgical tool.

13. The medical apparatus of Claim 11, wherein said another camera is an endoscope.

14. The medical apparatus of any of Claims 9-13, wherein said fourth image comprises another image of said surgical field.

15. The medical apparatus of any of Claims 9-14, wherein said fifth image comprises at least one of an image from a mobile display device, data, a computed tomography scan, a computer aided tomography scan, magnetic resonance imaging, an x-ray, ultrasound imaging, a fluorescence image, neuro-monitoring, or vital sign monitoring.

16. The medical apparatus of any of Claims 9-15, further comprising a switching system configured to switch said fourth or fifth image to another image.

17. The medical apparatus of any of the preceding claims, wherein the medical apparatus is not associated with a direct view surgical microscope.

18. The medical apparatus of any of the preceding claims, wherein the medical apparatus is not a binocular viewing assembly.

19. The medical apparatus of any of the preceding claims, wherein the medical apparatus provides a mono view of said surgical field.

20. The medical apparatus of any of the preceding claims, wherein the medical apparatus provides a surgical microscope view.

21. The medical apparatus of any of the preceding claims, wherein the second display is adjacent to the first display in the field of view.

22. The medical apparatus of Claim 21, wherein the second display is spaced apart from the first display in the field of view by a distance between about 5-10 mm.

23. The medical apparatus of Claim 21, wherein the second display is spaced apart from the first display in the field of view by a distance between about 1-5 mm.

24. The medical apparatus of any of the preceding claims, wherein a display surface of the first display that produces the first image is parallel to a display surface of the second display that produces the second image.

25. The medical apparatus of Claim 24, wherein the display surfaces of the first display and the second display are square or rectangular and have parallel sides.

26. The medical apparatus of Claim 24, wherein surface normals to the display surfaces of the first display and the second display are within 5 degrees of each other.

27. The medical apparatus of Claim 24, wherein the display surfaces are coplanar 28. The medical apparatus of any of the preceding claims, wherein light from the first display and light from the second display are not combined with a beam combiner.

29. The medical apparatus of any of the preceding claims, wherein said first or second controller is configured to provide surgical navigational guidance by providing images.

30. The medical apparatus of Claim 29, wherein said images change with movement of a surgical tool.

31. The medical apparatus of Claim 29 or 30, wherein said images comprise text.

32. The medical apparatus of any of Claims 29-31, wherein said images are from a 3D model.

Robotic Surgery

1. A medical apparatus comprising:
    a surgical microscope camera configured to provide a surgical microscope view of a surgical site, said surgical microscope camera not coupled to a direct view surgical microscope;
    a viewing assembly comprising a housing and separate left and right eye oculars for left and right eyes of a viewer, said left and right eye oculars configured to provide views of at least one display disposed in said housing, the viewing assembly configured to be disposed over or adjacent said surgical site;
    an image processing system in communication with said surgical microscope camera, and said at least one display, said image processing system comprising processing electronics,
    wherein said image processing system is configured to:
        receive images acquired by said surgical microscope camera, and
        present output images based on at least one of said received images on said at least one display so that said output images are viewable through said separate left and right eye oculars by a viewer viewing the surgical site;
    at least one robotic surgical device disposed adjacent said viewing assembly; and a control system configured to control the at least one robotic surgical device.

2. The medical apparatus of Claim 1, further comprising another viewing assembly comprising another housing and other left and right eye oculars for left and right eyes of another viewer, said other left and right eye oculars configured to provide views of at least one other display disposed in said another housing, the another viewing assembly configured to be disposed over or adjacent said surgical site.

3. The medical apparatus of Claim 1 or 2, wherein the control system is disposed on a side of the viewing assembly.

4. The medical apparatus of Claim 1 or 2, wherein the control system is disposed remotely from said at least one robotic surgical device.

5. The medical apparatus of any of the preceding claims, wherein the at least one robotic surgical device comprises a first and second robotic hand or tool.

6. The medical apparatus of Claim 5, wherein the first and second robotic hands or tools comprise hands or tools configured for port access.

7. The medical apparatus of any of the preceding claims, wherein, when in use, a surgeon can ergonomically perform surgery at the surgical site while viewing through the oculars.

8. The medical apparatus of any of Claims 1-3, wherein, when in use, a surgeon can operate the control system to control the at least one robotic surgical device while viewing through the oculars.

Illumination

1. An imaging system configured to generate images of a surgical site, said imaging system comprising:
    an illumination control configured to control light provided to said surgical site such that said provided light adjusts between light of different wavelength ranges;
    at least one objective configured to receive light from said surgical site;
    a left eye optical path comprising left eye optics configured to direct a portion of said received light within said left eye optical path; and
    a right eye optical path comprising right eye optics configured to direct another portion of said received light within said right eye optical path,
    wherein for each of said left eye and right eye optical paths, said imaging system is configured to generate first and second images of said surgical site, said first image at a first wavelength range and said second image at a second wavelength range.

2. The imaging system of Claim 1, wherein said first wavelength range overlaps said second wavelength range.

3. The imaging system of Claim 1, wherein said first wavelength range does not overlap said second wavelength range.

4. The imaging system of any of Claims 1-3, further comprising a viewing assembly comprising a housing and first and second oculars for viewing said generated images in said left eye and right eye optical paths within said housing through said first and second oculars respectively.

5. The imaging system of Claim 4, wherein said illumination control is disposed on said viewing assembly.

6. The imaging system of any of the preceding claims, wherein said illumination control comprises at least one knob, dial, button, switch, joystick, haptic, or touchpad.

7. The imaging system of any of the preceding claims, wherein said illumination control comprises at least one or more handles.

8. The imaging system of any of the preceding claims, wherein said illumination control comprises at least one of a virtual touch screen, voice command recognition, eye tracking, or head tracking.

9. The imaging system of any of the preceding claims, wherein said illumination control is configured to control at least one illumination source.

10. The imaging system of Claim 9, wherein said at least one illumination source comprises a visible light source.

11. The imaging system of Claim 9 or 10, wherein said at least one illumination source comprises an ultraviolet light source.

12. The imaging system of any of Claims 9-11, wherein said at least one illumination source comprises an infrared light source.

13. The imaging system of Claim 9, wherein said at least one illumination source comprises a fluorescence light source.

14. The imaging system of Claim 9, wherein said at least one illumination source comprises one or more lasers.

15. The imaging system of Claim 9, wherein said at least one illumination source comprises one or more light emitting diodes.

16. The imaging system of Claim 9, wherein said at least one illumination source comprises a white-light light source.

17. The imaging system of any of the preceding claims, wherein said illumination control comprises at least one filter configured to remove unwanted wavelengths from said light being provided to said surgical site.

18. The imaging system of Claim 17, wherein said at least one filter comprises a dichroic filter.

19. The imaging system of Claim 17, wherein said at least one filter comprises a notch filter.

20. The imaging system of any of Claims 1-9, wherein said provided light comprises a pump wavelength to excite fluorescence.

21. The imaging system of Claim 20, further comprising a filter configured to remove said pump wavelength from said light after provided to said surgical site.

22. The imaging system of any of the preceding claims, wherein said illumination control is configured to adjust said provided light between light of different wavelength ranges within 5 seconds.

23. The imaging system of Claim 9, wherein said provided light from said illumination source passes through said objective prior to and after illuminating said surgical site.

24. The imaging system of any of the preceding claims, further comprising a sensing system configured to detect light of said first and second wavelength ranges in said left eye and right eye optical paths.

25. An imaging system configured to generate images of a surgical site, said imaging system comprising:
at least one objective configured to receive light from said surgical site;
a left eye optical path comprising left eye optics configured to direct a portion of said received light within said left eye optical path;
a right eye optical path comprising right eye optics configured to direct another portion of said received light within said right eye optical path; and
a sensing system configured to detect light of first and second wavelength ranges in said left eye and right eye optical paths, wherein said imaging system is configured to generate first and second images of said surgical site based on said detected light, said first image at said first wavelength range and said second image at said second wavelength range, said first wavelength range different from said second wavelength range.

26. The imaging system of Claim 25, wherein said surgical site is illuminated with light having a pump wavelength to excite fluorescence.

27. The imaging system of Claim 26, further comprising one or more filters configured to remove said pump wavelength from said light that illuminated said surgical site.

28. The imaging system of any of Claims 24-27, wherein said sensing system is configured to detect said light of said first and second wavelength ranges in said left eye optical path on a portion of said sensing system and said light of said first and second wavelength ranges in said right eye optical path on another portion of said sensing system.

29. The imaging system of any of Claims 24-27, wherein said sensing system comprises first and second sensors, said first sensor configured to detect said light of said first wavelength range and said second sensor configured to detect said light of said second wavelength range.

30. The imaging system of any of the preceding claims, wherein each of said left eye and right eye optical paths comprises a plurality of optical paths for imaging at said first and second wavelength ranges.

31. The imaging system of any of the preceding claims, wherein said first or second wavelength ranges include infrared or near infrared ranges.

32. The imaging system of any of the preceding claims, wherein said first or second wavelength ranges include ultraviolet ranges.

33. The imaging system of any of the preceding claims, wherein said first or second wavelength ranges include a visible range between 400-700 nm.

34. The imaging system of any of the preceding claims, wherein said first or second wavelength ranges include bands within the visible range.

35. The imaging system of Claim 34, wherein said bands within said visible range include 440-460 nm and 540-560 nm.

36. The imaging system of any of the preceding claims, wherein said generated images in said left eye and right eye optical paths are different stereo views of said surgical field.

37. The imaging system of any of the preceding claims, wherein said imaging system provides a surgical microscope view.

38. The imaging system of Claim 37, wherein said imaging system providing a surgical microscope view comprise a camera having a work distance between 150 and 450 mm.

39. The imaging system of Claim 37, wherein said imaging system providing a surgical microscope view comprise a camera having a focal length between 150 and 450 mm.

40. The imaging system of any of the preceding claims, wherein said imaging system is not associated with a direct view surgical microscope.

41. The imaging system of any of the preceding claims, wherein said at least one objective is a common objective for said left eye and right eye optical paths.

42. The imaging system of any of the preceding claims, wherein said at least one objective collimates said received light.

43. The imaging system of Claim 25, wherein the first said first wavelength range overlaps said second wavelength range.

44. The imaging system of Claim 25, wherein said first wavelength range does not overlap said second wavelength range.

45. The imaging system of any of the preceding claims, wherein said first wavelength range comprises the entire visible range and said second wavelength range does not comprise the entire visible range.

46. The imaging system of Claim 30, further comprising a dichroic beamsplitter configured to provide said plurality of optical paths.

47. The imaging system of Claim 46, further comprising a filter assembly configured to hold said dichroic beamsplitter and one or more filters.

48. The imaging system any of the preceding claims, configured to alternately provide illumination at a first wavelength and a second wavelength.

Software Image Processing

1. A medical apparatus for viewing a surgical field, the medical apparatus comprising:

a viewing assembly comprising:
   an ocular comprising a field of view;
   a first display for viewing a first image of the surgical field within the field of view; and
   a second display for viewing a second image within the field of view, the second image comprising a feature in coordination with the first image of the surgical field;
wherein the second image is superimposed over or adjacent to the first image to produce a single image within the field of view.

2. The medical apparatus of Claim 1, wherein the feature comprises at least one feature selected from the group of fiducials, drawings, annotations, and virtual alignment of implants.

3. The medical apparatus of Claim 1, further comprising one or more assistant displays, a panel display viewable in the room, or one or more displays located remotely.

4. The medical apparatus of Claim 3, wherein the feature is configured to appear on the one or more assistant displays, panel display viewable in the room, or one or more displays located remotely.

5. The medical apparatus of Claim 1, wherein the feature comprises fiducial markers, the fiducial markers comprise at least one fiducial marker selected from the group of a mark, a pattern, a line, a set of marks, a set of lines, an image, and set of images.

6. The medical apparatus of Claim 1, wherein the feature comprises fiducial markers, the fiducial markers comprise a ruler or a grid pattern.

7. The medical apparatus of Claim 1, wherein the feature comprises virtual alignment of implants comprising an implant image, wherein the implant image can be manipulated by a user to move the implant image over the first image of the surgical field.

8. The medical apparatus of Claim 7, wherein the implant image is stored or retrieved based on user selection of the type of implant.

9. The medical apparatus of Claim 7, further comprising input controls utilized by the user configured to move the implant image in any direction relative to the first image of the surgical field.

10. The medical apparatus of Claim 7, wherein the implant image is configured to be displayed at a predetermined size corresponding to the actual size of the implant.

11. The medical apparatus of Claim 1, wherein the first image and second image are calibrated electronically.

12. The medical apparatus of Claim 1, wherein the first image and second image are mechanically calibrated by input controls utilized by a user.

13. The medical apparatus of Claim 1, further comprising:
a third display for viewing a third image, wherein the third image is superimposed over or adjacent to the first image and the second image to produce a single image within the field of view.

14. A medical apparatus for viewing a surgical field, the medical apparatus comprising:
   a viewing assembly comprising:
      an ocular comprising a field of view, the field of view is configured to view the surgical field within the field of view; and
      a first display for viewing an image within the field of view, the image comprising a feature in coordination with the surgical field;
   wherein the image is projected onto the surgical field and is superimposed over or adjacent to the surgical field, the projected image is configured to produce the image within the field of view for viewing the surgical field.

15. The medical apparatus of Claim 14, wherein the feature comprises at least one feature selected from the group of fiducials, drawings, annotations, and virtual alignment of implants.

16. The medical apparatus of Claim 14, further comprising one or more assistant displays, a panel display viewable in the room, or one or more displays located remotely.

17. The medical apparatus of Claim 16, wherein the feature is configured to appear on the one or more assistant displays, panel display viewable in the room, or one or more displays located remotely.

18. The medical apparatus of Claim 14, wherein the feature comprises fiducial markers, the fiducial markers comprise at least one fiducial marker selected from the group of a mark, a pattern, a line, a set of marks, a set of lines, an image, and set of images.

19. The medical apparatus of Claim 14, wherein the feature comprises fiducial markers, the fiducial markers comprise a ruler or a grid pattern.

20. The medical apparatus of Claim 14, wherein the feature comprises virtual alignment of implants comprising an implant image, wherein the implant image can be manipulated by a user to move the implant image over the surgical field.

21. The medical apparatus of Claim 20, wherein the implant image is stored or retrieved based on user selection of the type of implant.

22. The medical apparatus of Claim 20, further comprising input controls utilized by the user configured to move the implant image in any direction relative to the surgical field.

23. The medical apparatus of Claim 20, wherein the implant image is configured to be displayed at a predetermined size corresponding to the actual size of the implant.

24. The medical apparatus of Claim 14, wherein the surgical field and the image are calibrated electronically.

25. The medical apparatus of Claim 14, wherein the surgical field and the image are mechanically calibrated by input controls utilized by a user.

26. The medical apparatus of Claim 14, further comprising:
   a second display for viewing a second image, wherein the second image is superimposed over or adjacent to the image of the first display and the surgical field to produce a single image within the field of view.

Example Optical Systems for Binocular Viewing Assemblies

1. A medical apparatus comprising:
   one or more electronic displays comprising a plurality of pixels configured to produce a two-dimensional image;
   first and second imaging optics disposed respectively in first and second optical paths from said one or more electronic displays to form respective first and second collimated optical beams and images disposed at infinity;
   a primary housing at least partially enclosing said displays and said imaging optics;
   wherein said first and second imaging optics are configured to direct said first and second beams such that the beams are substantially parallel to each other and have cross-sections with centers separated from each other by between about 22 mm and 25 mm
   (in some Claims, the housing can include an opening, and the first and second imaging optics can be configured to direct the first and second beams through the opening, and the first and second beams can be substantially parallel to each other at the opening).

2. The medical apparatus of Claim 1, wherein said one or more electronic displays comprise first and second electronic displays.

3. The medical apparatus of Claim 1, wherein said one or more electronic displays comprise first and second portions of a single electronic display.

4. The medical apparatus of Claim 1, wherein said one or more electronic displays comprise at least one emissive display or at least one spatial light modulator.

5. The medical apparatus of Claim 1, wherein said one or more electronic displays comprise at least one liquid crystal display or at least one light emitting diode display.

6. The medical apparatus of Claim 1, further comprising a plurality of reflective surfaces in the optical paths of the optical beams to fold the optical beams.

7. The medical apparatus of Claim 6, wherein said plurality of reflective surfaces comprise mirrors.

8. The medical apparatus of Claim 6, wherein said plurality of reflective surfaces comprise between about 2 and 6 mirrors per side of said reflective surfaces in each of said first and second optical paths.

9. The medical apparatus of Claim 1, further comprising a plurality of reflective surfaces to fold the optical beams.

10. The medical apparatus of Claim 1, further comprising at least one mirror between said one or more electronic displays and said imaging optics.

11. The medical apparatus of Claim 1, further comprising between 0 and 2 mirrors between said one or more electronic displays and said imaging optics.

12. The medical apparatus of Claim 1, wherein said imaging optics comprise a plurality of lenses.

13. The medical apparatus of Claim 12, further comprising at least one mirror between said imaging optics and an exit pupil of said imaging optics.

14. The medical apparatus of Claim 13, wherein said at least one mirror comprises at least one mirror between said electronic display and said imaging optics, and at least one mirror disposed between lenses in said imaging optics, said former mirror being larger than said latter mirror.

15. The medical apparatus of Claim 1, wherein said imaging optics comprise between about 2 and 11 lenses.

16. The medical apparatus of Claim 1, wherein said imaging optics comprise positive lenses.

17. The medical apparatus of Claim 1, wherein said imaging optics have positive power.

18. The medical apparatus of Claim 1, wherein said imaging optics comprise a first lens configured to reduce a cross-section of the first beam.

19. The medical apparatus of Claim 18, wherein said first lens is configured to substantially collimate said first beam.

20. The medical apparatus of Claim 18, wherein said first lens has positive power.

21. The medical apparatus of Claim 18, wherein a lens in said imaging optics other than said first lens has an aperture size smaller than said first lens.

22. The medical apparatus of Claim 18, wherein lenses in said imaging optics other than said first lens have aperture sizes smaller than said first lens.

23. The medical apparatus of Claim 1, wherein said imaging optics is configured to produce a collimated view of the right eye and left eye display.

24. The medical apparatus of Claim 1, wherein said imaging optics has a field of view between about 3-10° at the exit pupil side.

25. The medical apparatus of Claim 1, wherein said first and second imaging optics have exit pupils and said first and second electronic displays are not parallel to said exit pupils.

26. The medical apparatus of Claim 1, wherein said first and second imaging optics have exit pupils having centers and said first and second electronic displays have centers, said center of said exit pupils being displaced from said centers of said electronic displays.

27. The medical apparatus of Claim 1, wherein said first and second imaging optics have exit pupils and an optical path length from said one or more electronic displays to said exit pupils is between about 10 mm and 24 mm.

28. The medical apparatus of Claim 1, wherein an optical path length from said one or more electronic displays to said imaging optics is between about 100 mm and 400 mm.

29. The medical apparatus of Claim 1, wherein the imaging optics comprise a plurality of lenses including a first lens and a last lens in said optical paths and said imaging optics has an optical path length from said first lens to the last lens that is between about 50 mm and 250 mm.

30. The medical apparatus of Claim 1, wherein the imaging optics comprise a plurality of lenses including a first lens and an exit pupil in said optical paths and said imaging optics has an optical path length from said first lens to the exit pupil that is between about 10 mm and 50 mm.

31. The medical apparatus of Claim 1, wherein said one or more electronic displays comprise first and second electronic displays having centers spaced apart by a distance, $W_{display}$, wherein said first and second imaging optics have exit pupils having centers spaced apart by a distance a distance of about, $W_{eye}$ paths, and wherein $W_{display} > W_{eye}$ paths.

32. The medical apparatus of Claim 1, wherein said one or more electronic displays comprise first and second electronic displays having centers spaced apart by a distance between about 100 mm and 200 mm.

33. The medical apparatus of Claim 1, wherein said first and second imaging optics have exit pupils having centers spaced apart by a distance of between about 22 mm and 25 mm.

34. The medical apparatus of Claim 1, wherein said first and second imaging optics have produce beams having centers spaced apart by a distance of between about 50 mm and 200 mm over most of a distance through the imaging optics.

35. The medical apparatus of Claim 1, wherein said first and second imaging optics have optical axes spaced apart over most of a distance through the imaging optics by a distance of between about 50 mm and 200 mm.

36. The medical apparatus of Claim 1, wherein said first and second beams have cross-sections having centers spaced apart over most of a distance through the imaging optics by a distance of between about 15 mm and 35 mm.

37. The medical apparatus of Claim 1, wherein said first and second imaging optics have first and second exit pupils disposed a longitudinal distance along the length of the beam that is between about 0 mm and 45 mm from the opening.

38. The medical apparatus of Claim 1, wherein said housing has internal sidewalls darker than external sidewalls.

39. The medical apparatus of Claim 1, wherein said housing has dark internal sidewalls.

40. The medical apparatus of Claim 1, wherein said housing has black internal sidewalls.

41. The medical apparatus of Claim 1, further comprising baffles in said housing for reducing stray light.

42. The medical apparatus of Claim 1, wherein said opening comprises a mounting face configured to connect to a binocular assembly.

43. The medical apparatus of Claim 1, wherein said opening is between about 50 mm and 100 mm wide.

44. The medical apparatus of Claim 1, wherein said opening is circular.

45. The medical apparatus of Claim 1, wherein said opening is between about 66 mm and 70 mm in diameter.

46. The medical apparatus of Claim 1, wherein said opening comprises a mounting face having a size and shape configured to mate with a binocular assembly for a surgical microscope. (in some Claims, wherein said opening and mounting face can be located on the top, bottom or front face of the apparatus in some Claims.)

47. The medical apparatus of Claim 1, further comprising a binocular assembly comprising first and second objectives, first and second beam positioning optics, and first and second oculars.

48. The medical apparatus of Claim 47, wherein said binocular assembly has a magnification at the ocular of between 8× and 13×.

49. The medical apparatus of Claim 47, wherein said binocular assembly has a magnification at the ocular of between 10× and 12.5×.

50. The medical apparatus of Claim 47, wherein said imaging optics and said binocular assembly including oculars provide an apparent field of view of between 100-120°.

51. The medical apparatus of Claim 47, wherein said imaging optics and said binocular assembly including oculars provide an apparent field of view of about 110°.

52. The medical apparatus of Claim 47, wherein said imaging optics and said binocular assembly including oculars provide an apparent field of view of between 60-70°.

53. The medical apparatus of Claim 47, wherein said first and second beam positioning optics comprise prisms.

54. The medical apparatus of Claim 47, wherein said imaging optics have exit pupils having centers and said binocular assembly have entrance pupils having centers, and said centers of said entrance pupils are separated by a distance that is substantially the same as the separation between said centers of said exit pupils.

55. The medical apparatus of Claim 47, wherein said binocular assembly has entrance pupils having centers, and said centers of said entrance pupils are separated by a distance of between about 22 mm and 25 mm.

56. The medical apparatus of Claim 47, wherein said imaging optics have exit pupils and said binocular assembly have entrance pupils, and said entrance pupils are smaller than said exit pupils.

57. The medical apparatus of Claim 47, wherein said imaging optics have exit pupils and said binocular assembly have entrance pupils, and said entrance pupils are the same size as said exit pupils.

58. The medical apparatus of Claim 47, wherein said binocular assembly has entrance pupils, and said entrance pupils are 15 mm to 20 mm in diameter.

59. The medical apparatus of Claim 47, wherein said oculars on said binocular assembly have adjustable tilt to accommodate different heights of surgeons.

60. The medical apparatus of Claim 47, wherein said binocular assembly has a housing with an opening and said opening is configured to interface with and connect to the opening of said primary housing.

61. The medical apparatus of Claim 47, wherein said imaging optics have exit pupils disposed in an exit pupil plane and said binocular assembly have entrance pupils disposed in an entrance pupil plane, and said entrance pupil plane and said exit pupil plane are substantially coplanar.

62. The medical apparatus of Claim 47, wherein said entrance pupil plane and said exit pupil plane are separated by less than about 0 mm to 30 mm.

63. The medical apparatus of Claim 62, wherein said entrance pupil plane and said exit pupil plane are separated by less than 0 mm to 15 mm.

64. The medical apparatus of Claim 1, further comprising an articulated arm supporting said primary housing of said one or more electronic displays.

65. The medical apparatus of Claim 1, further comprising processing electronics configured to communicate with said one or more electronic displays to provide images for said one or more electronic displays.

66. The medical apparatus of Claim 65, wherein said electronics is configured to receive images from one or more cameras on a surgical device.

67. The medical apparatus of Claim 65, wherein said electronics is configured to receive images from one or more cameras on a surgical tool and/or endoscope.

68. The medical apparatus of Claim 65, wherein said electronics is configured to receive images from one or more cameras on a surgical retractor.

69. The medical apparatus of Claim 65, wherein said electronics is configured to receive images from one or more cameras that provide a surgical microscope view.

70. The medical apparatus of Claim 69, wherein said camera is supported by an articulated arm that supports said primary housing for said electronic displays.

71. The medical apparatus of Claim 69, wherein said primary housing for said displays is supported by an articulated arm and said one or more cameras that provide a surgical view are supported by a separate platform that is configured to be able to be stationary with movement of said articulated arm.

72. The medical apparatus of Claim 65, wherein said first and second displays receive input images from said processing electronics corresponding respectively to left and right channels on a stereo camera and display said input images on said first and second electronic displays respectively.

73. The medical apparatus of Claim 72, further comprising a binocular assembly that receives said first and second beams from said first and second imaging optics and has oculars that output images from said first and second electronics display so as to render a three-dimensional image visible to a viewer peering through said oculars.

74. The medical apparatus of Claim 65, wherein said processing electronics are configured to receive images from memory that store previously recorded images.

75. The medical apparatus of Claim 65, wherein said processing electronics are configured to present images sources other than cameras.

76. The medical apparatus of Claim 65, wherein said processing electronics are configured to present images sources other than cameras in addition to images from cameras for simultaneous viewing by a viewer.

77. The medical apparatus of Claim 75 or 76, wherein said sources of images other than cameras comprises Computer Aided Tomography (CAT) scan, MRI, x-ray, and ultrasound imaging instruments.

78. The medical apparatus of Claim 75 or 76, wherein said source comprises a source of artificially generated image data.

79. The medical apparatus of Claim 1, further comprising at least one beam splitter disposed in one or both of said first and second optical paths configured to receiving images to be viewable by a binocular assembly connected to said primary housing in addition to images from said electronics displays.

80. The medical apparatus of Claim 79, further comprising at least one separate electronic display disposed with respect to said at least one beam splitter such that said one or both of said first and second optical paths receives images produced on said at least one electronic display through said at least one beam splitter for viewing through said binocular assembly connected to said housing in addition so images from said electronics displays.

81. The medical apparatus of Claim 80, wherein said at least one beam splitter comprises first and second beam splitters and said at least one separate electronic display comprises first and second displays configured to display a pair of two-dimensional images which together when viewed through said binocular assembly produces a three-dimensional image.

82. The medical apparatus of Claim 1, further comprising an assistant display housing containing at least one assistant electronic display and assistant display imaging optics for imaging images produced on said at least one assistant electronic display.

83. The medical apparatus of Claim 82, wherein said assistant display housing contains first and second assistant electronic displays and first and second assistant display imaging optics for imaging images produced on said first and second electronic displays.

84. The medical apparatus of Claim 82, wherein said primary housing and said assistant housing are supported by a common articulated arm.

85. The medical apparatus of Claim 82, wherein said assistant housing and said primary housing are connected via a support post such that said assistant housing can rotate with respect said primary housing.

86. The medical apparatus of Claim 82, wherein said assistant housing is configured to rotate with respect to said primary housing without moving said primary housing.

87. The medical apparatus of Claim 82, wherein said assistant housing is configured to rotate with respect to said primary housing to accommodate an assistant on opposite side of surgeon facing surgeon.

88. The medical apparatus of Claim 82, wherein said assistant housing is configured to rotate with respect to said primary housing to accommodate an assistant on left or right sides of a primary surgeon.

89. The medical apparatus of Claim 82, wherein said assistant housing is configured to rotate through at least 180° with respect to said primary housing.

90. The medical apparatus of Claim 89, wherein said assistant housing can rotate from +90° with respect to said primary housing to at least 270° with respect to said primary housing.

91. The medical apparatus of Claim 82, wherein said assistant housing is smaller than said primary housing.

92. The medical apparatus of Claim 82, wherein said at least one electronic display in said assistant housing is smaller than said one or more electronic displays in said primary housing.

93. The medical apparatus of Claim 82, wherein said imaging optics in said assistant housing are smaller than said imaging optics in said primary housing.

94. The medical apparatus of Claim 82, wherein said primary housing and said assistant housing are stacked, one over the other.

95. The medical apparatus of Claim 82, wherein said primary housing is disposed over said assistant housing.

96. The medical apparatus of Claim 82, wherein said assistant housing is disposed over said primary housing.

97. The medical apparatus of Claim 82, wherein said assistant housing is disposed between said primary housing and a camera that provides surgical microscope views.

98. The medical apparatus of Claim 97, wherein said assistant housing is disposed between said primary housing and movable support for said camera that provides surgical microscope views.

99. The medical apparatus of Claim 82, wherein first and second optical paths in said assistant display rotate with respect to first and second optical paths of said assistant housing.

100. The medical apparatus of Claim 82, wherein said at least one electronic displays in said assistant display rotates with respect to said at least one electronic display of said assistant housing.

101. The medical apparatus of Claim 82, further comprising processing electronics in communication with said at least one electronic displays in said assistant display configured to adjust the images presented on said at least one electronic displays in said assistant display based on the orientation of the assistant display housing with respect to the primary housing.

102. The medical apparatus of Claim 101, further comprising sensors to determine an orientation of the assistant housing that provides input to said processing electronics to adjust the images presented on said at least one assistant electronic display depending on said orientation.

103. The medical apparatus of Claim 102, further comprising at least four cameras for providing a surgical microscope view, said processing electronics selecting images from different pairs of said four cameras depending on said orientation of said assistant housing.

104. The medical apparatus of Claim 103, wherein said least four cameras comprise four cameras in a square 2×2 array and said electronics select a pair of said four cameras depending on said orientation of said assistant housing.

105. The medical apparatus of Claim 1, wherein said primary housing has a width between about 110 mm and 250 mm.

106. The medical apparatus of Claim 82, wherein said assistant housing has a width between about 50 mm and 150 mm.

107. The medical apparatus of Claim 1, wherein said primary housing has a length between about 150 mm and 350 mm.

108. The medical apparatus of Claim 82, wherein said assistant housing has a length between about 75 mm and 175 mm.

109. The medical apparatus of Claim 2, wherein said first and second electronic displays present left and right two-dimensional images having parallax such that a viewer viewing through a binocular assembly receiving light from said imaging optics can see a three-dimensional image.

110. The medical apparatus of Claim 1, wherein said one or more electronic displays comprise first and second electronic displays having centers spaced apart by a distance, $W_{display}$, of between about 75 mm and 200 mm.

111. The medical apparatus of Claim 1 or 110, wherein said first and second imaging optics have exit pupils having centers spaced apart by a distance a distance, $W_{eye}$, of between about 15 mm to 35 mm.

112. The medical apparatus of Claim 1, wherein said one or more electronic displays comprise first and second electronic displays having centers spaced apart by a distance, $W_{display}$, wherein said first and second imaging optics have exit pupils having centers spaced apart by a distance a distance of about, $W_{eye}$ paths, and wherein the radio of $W_{display}$ to $W_{eye}$ paths is between about 2 and 15.

113. The medical apparatus of Claim 1, wherein said one or more electronic displays comprise first and second electronic displays having centers spaced apart by a distance, $W_{display}$, wherein said first and second imaging optics have exit pupils having centers spaced apart by a distance a distance of about, $W_{eye}$ paths, and wherein the radio of $W_{display}$ to $W_{eye}$ paths is between about 4 and 12.

114. The medical apparatus of Claim 1, wherein there is no intermediate images of said first and second display between the first and second display and said exit pupils.

115. The medical apparatus of Claim 1, wherein there is no intermediate images of said first and second display between the first and second display and a field stop in said binocular assembly.

116. The medical apparatus of Claim 1, wherein said binocular assembly has a field stop between about 22 and 25 mm in sizes.

117. The medical apparatus of Claim 1, wherein said first or second display is between about 3 and 6 mm.

118. The medical apparatus of Claim 1, wherein said first or second display is between about 5 mm.

119. The medical apparatus of Claim 1, wherein said binocular assembly has a field stop and the ratio of the field stop to said first or second displays is between about 3 and 8.

120. The medical apparatus of Claim 1, wherein said binocular assembly has a field stop and the ratio of the field stop to said first or second displays is between about 4 and 6.

121. The medical apparatus of Claim 1, wherein a real image of said first and second displays is formed by light from said displays prior to exiting said oculars.

122. A medical apparatus comprising:
one or more electronic displays comprising a plurality of pixels configured to produce a two-dimensional image;
first and second imaging optics disposed respectively in first and second optical paths from said one or more electronic displays to form respective first and second substantially collimated optical beams;
a primary housing at least partially enclosing said displays and said imaging optics;
an opening in said housing,
wherein said first and second imaging optics are configured to direct said first and second beams through said opening.

Periscope Design

1. A medical apparatus comprising:
a plurality of electronic displays each comprising a plurality of pixels configured to produce a two-dimensional image;
first and second imaging optics disposed respectively in first and second optical paths from said plurality of electronic displays;
a primary housing at least partially enclosing said displays and said imaging optics;
a pair of oculars coupled to the primary housing, the pair of oculars configured to provide a view of the plurality of displays with a left eye and a right eye,
wherein, in use, said plurality of electronic displays are positioned above said pair of oculars.

2. The medical apparatus of Claim 1, wherein the first and second imaging optics each comprise a mirror configured to redirect an optical axis from the plurality of electronic displays to the pair of oculars.

3. The medical apparatus of Claim 2, wherein the mirrors of the respective first and second imaging optics are configured to redirect the optical axis from being substantially horizontal to being substantially vertical.

4. The medical apparatus of Claim 1, wherein, in use, the primary housing does not extend below the shoulders of a surgeon looking through the pair of oculars.

5. The medical apparatus of Claim 1, wherein the primary housing has a horizontal depth that is less than its height.

Contoured BDU

1. A medical apparatus comprising:
one or more electronic displays each comprising a plurality of pixels configured to produce a two-dimensional image;
first and second imaging optics disposed respectively in first and second optical paths from said one or more electronic displays;
a primary housing at least partially enclosing said electronic displays and said imaging optics;
a pair of oculars coupled to the primary housing, the pair of oculars configured to provide a view of the one or more electronic displays with a left eye and a right eye; and
a surgical microscope camera assembly configured to be positionable and/or orientable independent of the position and/or orientation of the primary housing,
wherein the primary housing includes a contoured bottom surface that allows the surgical microscope camera to be positioned below the primary housing without contacting the housing such that, in use, a surgeon that is viewing the one or more electronic displays through the pair of oculars is provided a surgical microscope view acquired with the surgical microscope camera assembly positioned above a surgical site,
wherein the surgeon can access the surgical site with surgical tools with arms positioned in a comfortable and/or ergonomic manner.

2. The medical apparatus of Claim 1, wherein the surgeon's arms are bent at approximately 90 degrees at the elbow and the upper arm is approximately vertical.

3. The medical apparatus of Claim 1, wherein the surgical microscope camera is configure to be positioned about 15 cm to about 45 cm above the surgical site.

4. The medical apparatus of Claim 1, wherein the primary housing is attached to a first positionable structure and the surgical microscope camera assembly is coupled to a second positionable structure.

5. The medical apparatus of Claim 4, wherein each of the first and second positionable structures are attached to a common support structure.

6. The medical apparatus of Claim 4, wherein each of the first and second positionable structures are attached to separate support structures.

7. The medical apparatus of Claim 4, wherein each of the first and second positionable structures are independently positionable.

8. The medical apparatus of Claim 1, wherein, in use, the surgical microscope camera assembly is positioned adjacent to the primary housing at the contoured bottom surface without contacting the primary housing.

9. The medical apparatus of Claim 1, wherein the surgical microscope camera assembly is configured to move up and down to adjust a working distance of the surgical microscope camera assembly.

10. The medical apparatus of Claim 9, wherein the working distance of the surgical microscope camera assembly is less than or equal to about 45 cm when the surgical microscope camera assembly is adjacent to the contoured bottom surface of the primary housing.

11. A medical apparatus comprising:
one or more electronic displays each comprising a plurality of pixels configured to produce a two-dimensional image;
first and second imaging optics disposed respectively in first and second optical paths from said one or more electronic displays;
a primary housing at least partially enclosing said electronic displays and said imaging optics;
a pair of oculars coupled to the primary housing, the pair of oculars configured to provide a view of the one or more electronic displays with a left eye and a right eye; and
a surgical microscope camera assembly configured to be positionable and/or orientable independent of the position and/or orientation of the primary housing,
wherein the primary housing includes a contoured surface that allows the surgical microscope camera to be positioned adjacent to the primary housing without contacting the housing such that, in use, a surgeon that is viewing the one or more electronic displays through the pair of oculars is provided a surgical microscope view acquired with the surgical microscope camera assembly positioned above a surgical site,
wherein surgical microscope camera is configured to fit within a vacated region formed by the contoured surface.

12. The medical apparatus of Claim 11, wherein the vacated region formed by the contoured surface has a depth that is at least 30% and less than or equal to 70% of the depth of the primary housing at a bottom surface.

13. The medical apparatus of Claim 11, wherein the vacated region formed by the contoured surface has a height that is at least 20% and less than or equal to 60% of the height of the primary housing at a distal surface of the primary housing.

14. The medical apparatus of Claim 11, wherein the surgeon's arms are bent at approximately 90 degrees at the elbow and the upper arm is approximately vertical.

15. The medical apparatus of Claim 11, wherein the surgical microscope camera is configured to be positioned about 15 cm to about 45 cm above the surgical site.

16. The medical apparatus of Claim 11, wherein the primary housing is attached to a first positionable structure and the surgical microscope camera assembly is coupled to a second positionable structure.

17. The medical apparatus of Claim 16, wherein each of the first and second positionable structures are attached to a common support structure.

18. The medical apparatus of Claim 16, wherein each of the first and second positionable structures are attached to separate support structures.

19. The medical apparatus of Claim 16, wherein each of the first and second positionable structures are independently positionable.

20. The medical apparatus of Claim 11, wherein, in use, the surgical microscope camera assembly is positioned within the vacated region without contacting the primary housing.

21. The medical apparatus of Claim 11, wherein the surgical microscope camera assembly is configured to move up and down to adjust a working distance of the surgical microscope camera assembly.

22. The medical apparatus of Claim 21, wherein working distance of the surgical microscope camera assembly is less than or equal to about 45 cm when the surgical microscope camera assembly is adjacent to the contoured surface of the primary housing.

Virtual User Interface and Display

1. A medical apparatus comprising:
one or more electronic displays each comprising a plurality of pixels configured to produce a two-dimensional image;
first and second imaging optics disposed respectively in first and second optical paths from said one or more electronic displays;
a primary housing at least partially enclosing said electronic displays and said imaging optics;
a pair of oculars coupled to the primary housing, the pair of oculars configured to provide a view of the one or more electronic displays with a left eye and a right eye; and
a user interface projector configured to project images onto a surgical site;
a user interface camera configured to acquire images of a surgeon's hands and/or tools along with at least a portion of the projected images,
wherein images acquired with the user interface camera are processed to determine virtual interactions between elements of the projected images with the surgeon's hands or tools.

Four Image Sensors

1. A medical apparatus comprising:
a common objective lens;
a left image acquisition optical system comprising imaging optics from the common objective lens to first and second left channel image sensors;
a right image acquisition optical system comprising imaging optics from the common objective lens to first and second right channel image sensors,
wherein the left image acquisition optical system comprises a spectral splitting optical component configured to direct light within a first spectral band to the first left channel image sensor and to direct light within a second spectral band to the second left channel image sensor,
wherein the right image acquisition optical system comprises a spectral splitting optical component configured to direct light within a first spectral band to the first right channel image sensor and to direct light within a second spectral band to the second right channel image sensor.

2. The medical apparatus of Claim 1, wherein the first spectral band comprises visible light and the second spectral band comprises near infrared light.

3. The medical apparatus of Claim 1, wherein the second spectral band comprises fluoresced light.

4. The medical apparatus of Claim 1, wherein the first spectral band and the second spectral band do not significantly overlap.

5. The medical apparatus of Claim 1, wherein the first spectral band and the second spectral band at least partially overlap.

6. The medical apparatus of Claim 1, wherein each of the left image acquisition optical system and the right image acquisition optical system comprise a zoom lens group.

7. The medical apparatus of Claim 6, wherein the left and right lens groups are configured to provide collimated light.

8. The medical apparatus of Claim 6, wherein each of the left image acquisition optical system and the right image acquisition optical system comprise first and second video coupler lens groups positioned after the left and right spectral splitting optical components, the first and second video coupler lens groups configured to generate respectively first and second images for each of the left and right image acquisition optical systems.

9. The medical apparatus of Claim 8, wherein each of the left image acquisition optical system and the right image acquisition optical system comprise an aperture positioned between the zoom lens group and the spectral splitting optical component.

10. The medical apparatus of Claim 8, wherein each of the left image acquisition optical system and the right image acquisition optical system comprise a first image sensor and a second image sensor positioned on an image side of the first and second video coupler lens groups at an image plane of said video coupler lens groups.

11. The medical apparatus of Claim 6, wherein each of the left image acquisition optical system and the right image acquisition optical system comprise a redirection element positioned between the common objective lens and the zoom lens groups.

12. The medical apparatus of Claim 1, wherein the common objective lens comprises an air-spaced triplet.

13. The medical apparatus of Claim 1, wherein the common objective lens comprises doublet.

14. The medical apparatus of Claim 1, wherein the common objective lens comprises an achromat.

15. The medical apparatus of Claim 1, wherein each of the left image acquisition optical system and the right image acquisition optical system comprise an afocal zoom lens group.

16. The medical apparatus of Claim 1, further comprising an illumination source directed through the common objective lens to a surgical site.

17. The medical apparatus of Claim 1, wherein the first spectral band includes the entire visible spectrum.

Switchable Ports

1. A medical apparatus comprising:
   a first image acquisition system comprising a surgical microscope camera;
   an input port for receiving video image data from an endoscope camera;
   a plurality of electronic displays each comprising a plurality of pixels configured to produce a two-dimensional image;
   first and second imaging optics disposed respectively in first and second optical paths from said plurality of electronic displays;
   a primary housing at least partially enclosing said displays and said imaging optics;
   a pair of oculars coupled to the primary housing, the pair of oculars configured to provide a view of the plurality of displays with a left eye and a right eye,
   wherein in a first mode the plurality of electronic displays are configured to display video images acquired with the first image acquisition system and in a second mode the plurality of electronic displays are configured to display video images acquired with the endoscope camera.

2. The medical apparatus of Claim 1, wherein a switch is used to switch between the first mode and the second mode.

Remote Control

1. A medical apparatus comprising:
   a surgical microscope camera configured to provide a surgical microscope view of a surgical site, said surgical microscope camera not coupled to a direct view surgical microscope;
   a viewing assembly comprising a housing and separate left and right eye portals for left and right eyes of a viewer, said left and right eye portals configured to provide views of at least one display disposed in said housing;
   an image processing system in communication with said surgical microscope camera, and said at least one display, said image processing system comprising processing electronics,
   wherein said image processing system is configured to:
      receive images acquired by said surgical microscope camera,
      receive one or more signals corresponding to images from a plurality of sources; and
      present output images based on at least one of said received images or one or more signals on said at least one display so that said output images are viewable through said separate left and right eye portals by a viewer viewing the surgical site; and a control system configured to control at least the surgical microscope camera or the
   viewing assembly based on monitoring eye or head movement of the viewer.

2. The medical apparatus of Claim 1, wherein the control system is disposed on the medical apparatus.

3. The medical apparatus of Claim 1, wherein the control system comprises at least one of an eye tracking system, a gaze tracking system, a head movement detecting system or a gesture recognition system.

4. The medical apparatus of Claim 3, wherein the control system comprises a pair of handgrips with buttons, each handgrip disposed on a side of the viewing assembly.

5. The medical apparatus of Claim 4, wherein the control system is configured to provide hands free control.

6. The medical apparatus of Claim 5, wherein the hands free control includes a virtual touch screen or a voice command recognition system.

7. The medical apparatus of Claim 1, wherein at least one of the plurality of sources comprises a camera disposed on a surgical tool.

8. The medical apparatus of Claim 7, wherein the surgical tool comprises an endoscope.

9. A medical apparatus comprising:
   a binocular display assembly comprising one or more display portions configured to display one or more images of a surgical site;
   electronics configured to receive one or more signals corresponding to images from a plurality of sources and to drive said one or more display portions to produce said one or more images of the surgical site, the electronics comprising a switching module configured to switch between one or more of the plurality of sources to produce said one or more images; and
   a control system configured to control at least one parameter of the one or more of the plurality of sources based on monitoring eye or head movement of a user viewing the surgical site.

10. The medical apparatus of Claim 9, wherein at least one of the plurality of sources comprises a camera disposed on a surgical tool.

11. The medical apparatus of Claim 9, wherein at least one of the plurality of sources comprises a surgical microscope camera configured to provide a surgical microscope view of the surgical site.

12. The medical apparatus of Claim 9, wherein the control system comprises at least one of an eye tracking system, a gaze tracking system, a head movement detecting system or a gesture recognition system.

13. The medical apparatus of Claim 9, wherein the control system is configured to provide hands free control.

14. The medical apparatus of Claim 13, wherein the hands free control includes a virtual touch screen or a voice command recognition system.

Separate Display Controllers

1. A binocular display for viewing a surgical field, said binocular display comprising:
   a left-eye view channel comprising one or more left-eye display portions configured to display one or more left-eye images of a surgical site;
   a right-eye view channel comprising one or more right-eye display portions configured to display one or more right-eye images of the surgical site;
   a left-eye display controller comprising hardware electronics, the left-eye display controller configured to receive one or more signals corresponding to images from a plurality of sources and to drive said one or more left-eye display portions to produce said one or more left-eye images of the surgical site; and
   a right-eye display controller comprising hardware electronics, the right-eye display controller configured to receive one or more signals corresponding to images from the plurality of sources and to drive said one or more right-eye display portions to produce said one or more right-eye images of the surgical site.

2. The binocular display of Claim 1, wherein the left-eye display controller further comprises a left-eye switching module configured to switch between one or more of the plurality of sources to produce said one or more left-eye images.

3. The binocular display of Claim 1, wherein the right-eye display controller further comprises a right-eye switching module configured to switch between one or more of the plurality of sources to produce said one or more right-eye images.

4. The binocular display of Claim 1, further comprising a viewing assembly comprising a housing and first and second oculars for viewing said left-eye and right-eye view images within said housing through said first and second oculars respectively.

5. The binocular display of Claim 4, further comprising optical elements in said left-eye and right-eye view channels configured to direct light from said one or more left-eye and right-eye display portions to said first and second oculars respectively.

6. The binocular display of Claim 5, wherein said optical elements include a mirror or a lens.

7. The binocular display of any of the preceding claims, wherein said left-eye view image and said right-eye view image are different stereo views of said surgical site.

8. The binocular display of any of Claims 1-7, further comprising a remote control configured to control said left-eye display controller, right-eye display controller or at least one parameter of the one or more of the plurality of sources.

9. The binocular display of Claim 4-8, wherein said remote control is disposed on said viewing assembly.

10. The binocular display of Claim 8 or 9, wherein said remote control includes a handgrip, a handle, a joystick, buttons, haptics, or a touchpad.

11. The binocular display of any of Claims 8-10, wherein said remote control is configured to control said left-eye or right-eye view image displayed on said one or more left-eye and right-eye display portions.

12. The binocular display of any of the preceding claims, wherein the binocular display is disposed on an articulating arm.

Display Designs

1. A medical apparatus comprising:
   a binocular display assembly comprising one or more display portions configured to display one or more images of a surgical site, the binocular display assembly comprising:
   a housing;
   a left-eye view channel comprising imaging optics configured to direct light from said one or more display portions to a left ocular disposed within the housing and form one or more images of the surgical site on a retina of a left-eye of a user viewing the surgical site; and
   a right-eye view channel comprising imaging optics configured to direct light from said one or more display portions to a right ocular disposed within the housing and form one or more images of the surgical site on a retina of a right-eye of the user viewing the surgical site; and
   electronics configured to receive one or more signals corresponding to images from a plurality of sources and to drive said one or more display portions to produce said one or more images of the surgical site,
   wherein the left ocular and the right ocular and/or the optical elements of left-eye view channel and the right-eye view channel respectively are configured to correct optical aberrations in the one or more images of the surgical site formed on the retina of the left-eye and the right-eye of the user.

2. The medical apparatus of Claim 1, wherein the one or more images of the surgical site that are formed on the retina of the user viewing the surgical site are real images.

3. The medical apparatus of Claim 1, wherein the one or more images of the surgical site are corrected for optical aberrations resulting from myopia, hyperopia and/or presbyopia.

4. The medical apparatus of Claim 1, wherein said imaging optics comprise a mirror or a lens.

5. The medical apparatus of Claim 1, further comprising a left field stop disposed between the imaging optics of the left-eye view channel and the left ocular.

6. The medical apparatus of Claim 1, further comprising a right field stop disposed between the imaging optics of the right-eye view channel and the right ocular.

7. The medical apparatus of Claim 5 or 6, wherein the imaging optics of the left-eye view channel and the right-eye view channel are configured to produce a real image at the left and right field stops respectively.

8. The medical apparatus of Claim 7, wherein the left ocular and the right ocular are configured to produce a conjugate image of the real image produced at the left and right field stops respectively.

9. The medical apparatus of any of the preceding claims, wherein the imaging optics of the left-eye view channel and the right-eye view channel are configured to collimate light from said one or more display portions.

10. The medical apparatus of any of the preceding claims, wherein the left-eye view channel and the right-eye view channel comprise optical elements configured to produce an eye box comprising multiple laterally displaced pupils such that the user can view the one or more display portions over a range of lateral positions.

11. The medical apparatus of Claim 10, wherein the left and the right eye of the user can be positioned at a variable distance from the left ocular and the right ocular respectively.

12. The medical apparatus of Claim 10, wherein the optical elements comprise reflective optical elements.

13. The medical apparatus of Claim 10, wherein the optical elements comprise aspheric optical elements.

14. The medical apparatus of Claim 10, wherein the optical elements are configured to provide a secondary display outside the binocular display assembly.

15. The medical apparatus of Claim 14, wherein the secondary display optical elements are configured to provide a secondary display outside the binocular display assembly.

16. The medical apparatus of Claim 15, wherein the secondary display can be laterally displaced from the binocular display assembly.

17. The medical apparatus of Claim 10, wherein the optical elements comprise a partially transmissive mirror.

18. The medical apparatus of any of the preceding claims, wherein the one or more images formed on the retina of said left-eye and said right-eye are different stereo views of said surgical site.

19. The medical apparatus of any of the preceding claims, further comprising a left-eye display controller comprising hardware electronics configured to drive said one or more display portions to produce said one or more images of the surgical site on the retina of the left-eye.

20. The medical apparatus of Claim 19, wherein the left-eye display controller further comprises a left-eye switching module configured to switch between one or more of the plurality of sources to produce said one or more images of the surgical site on the retina of the left-eye.

21. The medical apparatus of any of the preceding claims, further comprising a right-eye display controller comprising hardware electronics configured to drive said one or more display portions to produce said one or more images of the surgical site on the retina of the right-eye.

22. The medical apparatus of Claim 19, wherein the right-eye display controller further comprises a right-eye switching module configured to switch between one or more of the plurality of sources to produce said one or more images of the surgical site on the retina of the right-eye.

23. The medical apparatus of any of preceding claims, further comprising a remote control configured to control said left-eye display controller, right-eye display controller or at least one parameter of the one or more of the plurality of sources.

24. The medical apparatus of Claim 23, wherein said remote control is disposed on said display assembly.

25. The medical apparatus of Claim 23 or 24, wherein said remote control includes a handgrip, a handle, a joystick, buttons, haptics, or a touchpad.

Surgical Visualization System with Cameras Rotating about Central Aperture

1. A surgical visualization system comprising:
a primary surgeon optical assembly comprising a primary surgeon camera and primary surgeon optics comprising an objective lens, the primary surgeon camera configured to acquire images of a surgical site from outside the surgical site;
an assistant surgeon optical assembly comprising an assistant surgeon camera configured to provide a view of the surgical site from outside the surgical site; and
a rotatable structure configured to rotate about a longitudinal axis of the objective lens,
wherein the assistant surgeon optical assembly is mounted to the rotatable structure.

2. The system of Claim 1, wherein the rotatable structure is attached to the objective lens so that rotation of the rotatable structure causes the objective lens to rotate.

3. The system of Claim 1, wherein the rotatable structure is configured to rotate while the objective lens remains stationary.

4. The system of Claim 1, wherein an optical axis of the primary surgeon optical assembly and an optical axis of the assistant surgeon optical assembly are substantially parallel.

5. The system of Claim 1, wherein an optical axis of the primary surgeon optical assembly and an optical axis of the assistant surgeon optical assembly are configured to be directed to a similar region of the surgical site.

6. The system of Claim 1 further comprising an electronic motor coupled to the rotatable structure to control rotation of the rotatable structure.

7. The system of Claim 1, wherein the rotatable structure is configured to be manually manipulated.

8. The system of Claim 1 further comprising a pivoting system coupled to the rotatable structure and the assistant surgeon optical assembly, the pivoting system configured to provide additional degrees of freedom of movement for the assistant surgeon optical assembly relative to the objective lens.

9. The system of Claim 1 further comprising a control system configured to control rotation of the rotatable structure.

10. The system of Claim 9, wherein the control system is configured to determine rotations of the rotatable structure that reduce a likelihood that cables become entangled.

11. The system of Claim 1, wherein the primary surgeon optical assembly is coupled to a binocular display assembly.

12. A surgical visualization system comprising:
a primary surgeon optical assembly comprising a primary surgeon camera and primary surgeon optics comprising a pair of converging optical trains, the primary surgeon camera configured to acquire images of a surgical site from outside the surgical site;
an assistant surgeon optical assembly comprising an assistant surgeon camera configured to provide a view of the surgical site from outside the surgical site; and
a rotatable structure configured to rotate about an axis bisecting the pair of converging optical trains,
wherein the assistant surgeon optical assembly is mounted to the rotatable structure.

13. The system of Claim 12, wherein the rotatable structure is attached to the pair of converging optical trains so that rotation of the rotatable structure causes the pair of converging optical trains to rotate.

14. The system of Claim 12, wherein the rotatable structure is configured to rotate while the pair of converging optical trains remains stationary.

15. The system of Claim 12, wherein an optical axis of the primary surgeon optical assembly and an optical axis of the assistant surgeon optical assembly are substantially parallel.

16. The system of Claim 12, wherein an optical axis of the primary surgeon optical assembly and an optical axis of the assistant surgeon optical assembly are configured to be directed to a similar region of the surgical site.

17. The system of Claim 12 further comprising an electronic motor coupled to the rotatable structure to control rotation of the rotatable structure.

18. The system of Claim 12, wherein the rotatable structure is configured to be manually manipulated.

19. The system of Claim 12 further comprising a pivoting system coupled to the rotatable structure and the assistant surgeon optical assembly, the pivoting system configured to provide additional degrees of freedom of movement for the assistant surgeon optical assembly relative to the pair of converging optical trains.

20. The system of Claim 12 further comprising a control system configured to control rotation of the rotatable structure.

21. The system of Claim 20, wherein the control system is configured to determine rotations of the rotatable structure that reduce a likelihood that cables become entangled.

22. The system of Claim 12, wherein the primary surgeon optical assembly is coupled to a binocular display assembly.

Optical Systems for Surgical Microscope Cameras

1. A surgical visualization system comprising:
a binocular viewing assembly comprising a housing and a pair of eyepieces, said eyepieces configured to provide a view of at least one display disposed in the housing;
an optical assembly configured to provide a surgical microscope view of a surgical site, the optical assembly comprising an optical train configured to direct light from the surgical site to an image sensor; and
an image processing system configured to receive video data of the surgical site from the image sensor and to provide output video data of the surgical site to the at least one display,
wherein the optical train comprises a zoom lens assembly and a field stop positioned after the zoom lens assembly along an optical axis from the surgical site to the image sensor,
wherein the zoom lens assembly comprises lenses each having a diameter that is less than or equal to half of a width of the image sensor.

2. The system of Claim 1, wherein the lenses of the zoom lens assembly each have a diameter that is less than or equal to about 0.25 inches.

3. The system of Claim 1, wherein the width of the image sensor is less than or equal to about 0.5 inches.

4. The system of Claim 1, wherein the optical train further comprises a beamsplitter configured to split light into different spectral components.

5. The system of Claim 1, wherein the optical train further comprises filter block.

Autoclavable Microscope Head

1. A surgical visualization system comprising:
a binocular viewing assembly comprising a housing and a pair of eyepieces, said eyepieces configured to provide a view of at least one display disposed in the housing;
a microscope head comprising a housing;
an optical assembly positioned within the housing of the microscope head, the optical assembly configured to provide a surgical microscope view of a surgical site, the optical assembly comprising an optical train configured to direct light from the surgical site to an image sensor; and
an image processing system configured to receive video data of the surgical site from the image sensor and to provide output video data of the surgical site to the at least one display,
wherein the microscope head is configured to be sterilized using an autoclave between uses.

2. The system of Claim 1, wherein the microscope head comprises materials configured to withstand heats and pressures in the autoclave.

3. The system of Claim 2, wherein the materials include one or more of polypropylene, polymethylpentene, PTFE resin, polycarbonate, and polymethyl methacrylate.

4. The system of Claim 1, wherein the microscope head is configured to be sealable.

5. The system of Claim 1, wherein the optical assembly is configured to maintain alignment after undergoing the autoclaving process.

6. The system of Claim 1, wherein the optical assembly is configured to maintain focal location after undergoing the autoclaving process.

7. The system of Claim 1, wherein the microscope head is configured to maintain its structural integrity after 100 times through an autoclaving process.

8. The system of Claim 1, wherein the microscope head is configured to maintain its structural integrity after 200 times through an autoclaving process.

9. The system of Claim 1, wherein the microscope head is configured to maintain its structural integrity after 300 times through an autoclaving process.

Degrees of Freedom of Movement

1. A medical apparatus comprising:
a viewing assembly comprising a pair of oculars and at least one display viewable through the pair of oculars;
an optical assembly comprising at least one stereo camera configured to provide a view of a surgical site;
a viewing assembly positioning system coupled to the viewing assembly and configured to move the viewing assembly;
an optical assembly positioning system coupled to the optical assembly and configured to move the optical assembly; and
an image processing system configured to receive input video from the at least one stereo camera and to provide output video to the at least one display,
wherein the viewing assembly positioning system is configured to provide less than or equal to five degrees of freedom of movement to the viewing assembly.

2. The medical apparatus of Claim 1, wherein the five degrees of freedom of movement includes translation along three orthogonal axes and rotation about two of the three orthogonal axes.

3. The medical apparatus of Claim 2, wherein the rotational degrees of freedom include pitch and yaw.

4. The medical apparatus of Claim 2, wherein the rotational degrees of freedom do not include roll.

5. The medical apparatus of Claim 2, wherein the three orthogonal axes comprise:
an x-axis corresponding to a horizontal direction parallel to a line of site of a person looking through the ocular;
a y-axis corresponding to a horizontal direction orthogonal to the x-axis; and
a z-axis corresponding to a vertical direction orthogonal to both the x-axis and the y-axis,
wherein the viewing assembly positioning system is configured to rotate the viewing assembly with the y-axis as the axis of rotation, to rotate the viewing assembly with the z-axis as the axis of rotation, and to restrict rotation of the viewing assembly with the x-axis as the axis of the restricted rotation.

6. The medical apparatus of Claim 1, wherein the viewing assembly positioning system is configured to maintain the pair of oculars in a horizontal configuration.

7. The medical apparatus of Claim 1, wherein the viewing assembly positioning system includes arms coupled to the viewing assembly to restrict roll of the viewing assembly.

8. The medical apparatus of Claim 1, wherein movement of the viewing assembly positioning system is decoupled from movement of the optical assembly positioning system.

9. A medical apparatus comprising:
a viewing assembly comprising a pair of oculars and at least one display viewable through the pair of oculars;
an optical assembly comprising at least one stereo camera configured to provide a view of a surgical site;
a viewing assembly positioning system coupled to the viewing assembly and configured to move the viewing assembly;
an optical assembly positioning system coupled to the optical assembly and configured to move the optical assembly; and
an image processing system configured to receive input video from the at least one stereo camera and to provide output video to the at least one display,
wherein the optical assembly positioning system is configured to provide less than or equal to five degrees of freedom of movement to the viewing assembly.

10. The medical apparatus of Claim 9, wherein the five degrees of freedom of movement includes translation along three orthogonal axes and rotation about two of the three orthogonal axes.

11. The medical apparatus of Claim 10, wherein the rotational degrees of freedom include pitch and yaw.

12. The medical apparatus of Claim 10, wherein the rotational degrees of freedom do not include roll.

13. The medical apparatus of Claim 10, wherein the three orthogonal axes comprise:
an x-axis corresponding to a horizontal direction parallel to a line of site of a person looking through the ocular;
a y-axis corresponding to a horizontal direction orthogonal to the x-axis; and
a z-axis corresponding to a vertical direction orthogonal to both the x-axis and the y-axis,
wherein the optical assembly positioning system is configured to rotate the optical assembly with the y-axis as the axis of rotation, to rotate the optical assembly with the z-axis as the axis of rotation, and to restrict rotation of the optical assembly with the x-axis as the axis of the restricted rotation.

14. The medical apparatus of Claim 9, wherein the optical assembly positioning system is configured to maintain the at least one stereo camera in a horizontal configuration.

15. The medical apparatus of Claim 9, wherein the optical assembly positioning system includes arms, positioners, or mounts coupled to the optical assembly to restrict roll of the optical assembly.

16. The medical apparatus of Claim 9, wherein movement of the viewing assembly positioning system is decoupled from movement of the optical assembly positioning system.

17. The medical apparatus of Claim 9, wherein the at least one stereo camera includes an endoscope camera.

18. The medical apparatus of Claim 9, wherein the optical assembly is configured to provide a surgical microscope view of the surgical site from outside the surgical site.

19. The medical apparatus of Claim 9, wherein the optical assembly positioning system includes mechanical fixtures configured to limit the degrees of freedom of movement of the at least one stereo camera.

20. The medical apparatus of Claim 19, wherein the mechanical fixtures include a mount configured to restrict roll of the at least one stereo camera to maintain a horizon of the at least one stereo camera substantially constant throughout movements of the optical assembly.

Fixed Working Distance Objectives

1. A surgical visualization system comprising:
a viewing assembly comprising a pair of oculars and at least one display viewable through the pair of oculars, wherein the viewing assembly does not provide an optical path from the pair of oculars to a surgical site;
an optical assembly configured to provide a surgical microscope view of a surgical site, the optical assembly comprising a camera configured to acquire images of the surgical site from outside the surgical site, the camera comprising an image sensor and a microscope objective having a fixed working distance; and
an image processing system configured to receive input video from the camera and to provide output video to the at least one display,
wherein the microscope objective has a first fixed work distance, and
wherein the optical assembly is configured to switch out the microscope objective and replace it with a second microscope objective having a second fixed work distance different from the first fixed work distance 2. The surgical visualization system of Claim 1, wherein the first and second fixed working distance is at least 150 mm.

3. The surgical visualization system of Claim 1, wherein the first and second fixed working distance is less than or equal to 450 mm.

4. The surgical visualization system of Claim 1, wherein the first and second fixed working distance is at least 150 mm and less than or equal to 450 mm.

5. The surgical visualization system of Claim 1, wherein the camera is a stereo camera and light for left and right channels of the stereo camera passes through the microscope objective.

6. The surgical visualization system of Claim 1, wherein the camera is a stereo camera and light for left and right channels of the stereo camera pass through respective left and right microscope objectives.

7. A surgical visualization system comprising:
a viewing assembly comprising a pair of oculars and at least one display viewable through the pair of oculars;
an optical assembly configured to provide a surgical microscope view of a surgical site, the optical assembly comprising a camera configured to acquire images of the surgical site from outside the surgical site, the camera comprising an image sensor and an interchangeable microscope objective; and
an image processing system configured to receive input video from the camera and to provide output video to the at least one display,
wherein the camera is configured to receive different interchangeable microscope objectives, individual interchangeable microscope objectives having a fixed working distance.

8. The surgical visualization system of Claim 7, wherein the fixed working distance of the individual interchangeable microscope objectives is at least 150 mm.

9. The surgical visualization system of Claim 7, wherein the fixed working distance of the individual interchangeable microscope objectives is less than or equal to 450 mm.

10. The surgical visualization system of Claim 7, wherein the fixed working distance of the individual interchangeable microscope objectives is at least 150 mm and less than or equal to 450 mm.

11. The surgical visualization system of Claim 7, wherein the camera comprises a mechanical interface to facilitate convenient interchangeability of the interchangeable microscope objective.

12. The surgical visualization system of Claim 11, wherein the mechanical interface comprises threading or clamps.

13. The surgical visualization system of Claim 7, wherein the camera is a stereo camera and light for left and right channels of the stereo camera passes through the microscope objective.

14. The surgical visualization system of Claim 7, wherein the camera is a stereo camera and light for left and right channels of the stereo camera pass through respective left and right microscope objectives.

Laser Distance Positioning Guide

1. A surgical visualization system comprising:
    a viewing assembly comprising a pair of oculars and at least one display viewable through the pair of oculars;
    an optical assembly configured to provide a surgical microscope view of a surgical site, the optical assembly comprising:
        a camera configured to acquire images of the surgical site from outside the surgical site, the camera having a working distance; and
        an alignment system configured to provide an indication of a position of the camera with respect to the surgical site;
    an optical assembly positioning system configured to move the optical assembly so that the camera is positioned at a distance from the surgical site that is substantially equal to the working distance; and
    an image processing system configured to receive input video from the camera and to provide output video to the at least one display.

2. The system of Claim 1, wherein the alignment system is configured to project beams of light.

3. The system of Claim 2, wherein the projected beams of light intersect at a position that has a distance from the camera that is substantially equal to the working distance.

4. The system of Claim 2, wherein the projected beams of light intersect at a position that is aligned near a center of a field of view of the camera and that has a distance from the camera that is substantially equal to the working distance.

5. The system of Claim 2, wherein the projected beams of light are provided by lasers.

6. The system of Claim 5, wherein the lasers comprise a pair of lasers mounted on the optical assembly, the pair of lasers configured to provide laser beams that overlap at the working distance from the camera.

7. The system of Claim 6, wherein the pair of laser beams form orthogonal lines that intersect at the working distance from the camera to form a crosshair pattern.

8. The system of Claim 6, wherein the each laser beam forms a crosshair pattern.

9. The system of Claim 2, wherein the projected beams of light have a spectral output primarily within the infrared wavelength band.

10. The system of Claim 9, wherein the optical assembly further comprises an infrared sensor and the image processing system is further configured to receive video from the infrared sensor and to provide video acquired by the infrared sensor of the projected beams of light on the at least one display.

11. The system of Claim 1, wherein the camera further comprises an objective lens system.

12. The system of Claim 11, wherein the alignment system is configured to project a beam of light through the objective lens system of the camera to focus the projected beam of light.

13. The system of Claim 12, wherein the projected beam of light is focused at a distance from the camera that is substantially equal to the working distance.

14. The system of Claim 11, wherein the alignment system is configured to project a pair of parallel, collimated beams of light through the objective lens system of the camera.

15. The system of Claim 14, wherein the parallel beams of light are focused at a distance from the camera that is substantially equal to the working distance.

16. The system of Claim 14, wherein the parallel beams of light are focused such that they overlap at a distance from the camera that is substantially equal to the working distance.

17. The system of Claim 11, wherein the objective lens system of the camera is configured to be interchangeable.

18. The system of Claim 1, wherein the alignment system comprises a laser range finder.

19. The system of Claim 18, wherein output of the laser range finder is configured to be displayed on the at least one display.

20. The system of Claim 18, wherein output of the laser range finder is configured to be displayed a range finder display positioned outside the viewing assembly or mounted to the viewing assembly.

21. The system of Claim 18, wherein output of the laser range finder is configured to be projected onto a surface at the surgical site.

22. The system of Claim 18, wherein output of the laser range finder is configured to be used to display information corresponding whether it is necessary to increase or decrease distance of the camera to the surgical site to match the working distance.

23. The system of Claim 22, wherein the displayed information includes an indication when a distance between the camera and the surgical site substantially matches the working distance.

Multi-View Switching Visualization System

1. A surgical visualization system comprising:
    a first viewing assembly comprising a pair of oculars and at least one display viewable through the pair of oculars when looking through the pair of oculars along a first line of sight;
    a second viewing assembly comprising a pair of oculars and at least one display viewable through the pair of oculars when looking through the pair of oculars along a second line of sight;
    a first display positioned outside of the first viewing assembly;
    a second display positioned outside of the second viewing assembly;
    a plurality of cameras configured to acquire video of a surgical site;
    an image processing system configured to receive input video from the plurality of cameras and to provide output video to the at least one display in the first viewing assembly and the at least one display in the second viewing assembly; and
    a control system configured to receive user input to respectively control the output video provided to the at least one display in the first viewing assembly and provided to the at least one display in the second viewing assembly,
    wherein the first display is positioned in a line of sight of a person looking over the first viewing assembly in a direction parallel to the first line of sight, wherein the second display is positioned in a line of sight of a person looking over the second viewing assembly in a direction parallel to the second line of sight.

2. The system of Claim 1, wherein the plurality of cameras includes an endoscope.

3. The system of Claim 1, wherein the plurality of cameras includes an auxiliary camera configured to provide a surgical microscope view of a surgical site.

4. The system of Claim 1, wherein the first viewing assembly includes a user interface feature to provide user input to the control system.

5. The system of Claim 4, wherein the user interface feature is configured to provide user input to the control system to control the output video provided to the at least one display in the first viewing assembly and provided to the at least one display in the second viewing assembly.

6. The system of Claim 4, wherein the user interface feature is configured to provide user input to the control system to control the output video provided to one of the at least one display in the first viewing assembly or to the at least one display in the second viewing assembly.

7. The system of Claim 4, wherein the user interface feature is configured to provide user input to the control system to control a picture-in-picture feature of the at least one display in the first viewing assembly or the at least one display in the second viewing assembly.

8. The system of Claim 4, wherein the user interface feature comprises a button on a handle of the first viewing assembly.

9. A surgical visualization system comprising:
a first viewing assembly comprising a pair of oculars and at least one display viewable through the pair of oculars when looking through the pair of oculars along a first line of sight;
a second viewing assembly comprising a pair of oculars and at least one display viewable through the pair of oculars when looking through the pair of oculars along a second line of sight;
a plurality of cameras configured to acquire video of a surgical site;
an image processing system configured to receive input video from the plurality of cameras and to provide output video to the at least one display in the first viewing assembly and the at least one display in the second viewing assembly; and
a control system configured to receive user input to respectively control the output video provided to the at least one display in the first viewing assembly and provided to the at least one display in the second viewing assembly.

10. The system of Claim 9, wherein the plurality of cameras includes an endoscope.

11. The system of Claim 9, wherein the plurality of cameras includes an auxiliary camera configured to provide a surgical microscope view of a surgical site.

12. The system of Claim 9, wherein the first viewing assembly includes a user interface feature to provide user input to the control system.

13. The system of Claim 12, wherein the user interface feature is configured to provide user input to the control system to control the output video provided to the at least one display in the first viewing assembly and provided to the at least one display in the second viewing assembly.

14. The system of Claim 12, wherein the user interface feature is configured to provide user input to the control system to control the output video provided to one of the at least one display in the first viewing assembly or to the at least one display in the second viewing assembly.

15. The system of Claim 12, wherein the user interface feature is configured to provide user input to the control system to control a picture-in-picture feature of the at least one display in the first viewing assembly or the at least one display in the second viewing assembly.

16. The system of Claim 12, wherein the user interface feature comprises a button on a handle of the first viewing assembly.

17. The system of Claim 9, wherein user input received by the control system can be configured to control the output video provided to the at least one display in each of the first and second viewing assemblies.

18. The system of Claim 9, wherein user input received by the control system is provided through a user interface element associated with the first viewing assembly and the user input can be configured to control the output video provided to the at least one display in the second viewing assembly.

19. The system of Claim 9, wherein user input received by the control system is provided through a user interface element associated with the first viewing assembly and the user input can be configured to only control the output video provided to the at least one display in the first viewing assembly.

20. The system of Claim 9, wherein user input received by the control system can be configured to control the output video provided to the at least one display in each of the first and second viewing assemblies so that the output video for each viewing assembly is the same.

21. The system of Claim 9, wherein user input received by the control system can be configured to control the output video provided to the at least one display in each of the first and second viewing assemblies so that the output video for each viewing assembly is different.

22. The system of Claim 1, wherein user input received by the control system can be configured to control the output video provided to the at least one display in each of the first and second viewing assemblies.

23. The system of Claim 1, wherein user input received by the control system is provided through a user interface element associated with the first viewing assembly and the user input can be configured to control the output video provided to the at least one display in the second viewing assembly.

24. The system of Claim 1, wherein user input received by the control system is provided through a user interface element associated with the first viewing assembly and the user input can be configured to only control the output video provided to the at least one display in the first viewing assembly.

25. The system of Claim 1, wherein user input received by the control system can be configured to control the output video provided to the at least one display in each of the first and second viewing assemblies so that the output video for each viewing assembly is the same.

26. The system of Claim 1, wherein user input received by the control system can be configured to control the output video provided to the at least one display in each of the first and second viewing assemblies so that the output video for each viewing assembly is different.

User Control Systems & Control of Image Intensity

1. A visualization system comprising:
a plurality of communication ports configured to be operatively coupled to a plurality of image acquisition subsystem;

at least one image output port configured to be operatively coupled to at least one image display subsystem;

at least one user input port configured to be operatively coupled to at least one user input device; and at least one circuit operatively coupled to the plurality of communication ports, the at least one image output port, and the at least one user input port, the at least one circuit configured to receive data signals from the plurality of image acquisition subsystems, to transmit control signals to the plurality of image acquisition subsystems, and to transmit output image signals to the at least one image display subsystem, the at least one circuit further configured to receive at least one first user input signal and a plurality of second user input signals from the at least one user input device, the at least one circuit responsive at least in part to the received at least one first user input signal by:

selecting an image acquisition subsystem from the plurality of image acquisition subsystems, transmitting the output image signals to the at least one image display subsystem in response to the data signals received from the selected image acquisition subsystem, and generating the control signals and transmitting the control signals to the selected image acquisition subsystem.

2. The visualization system of claim 1, wherein the plurality of image acquisition subsystems comprises a plurality of cameras configured to generate the data signals indicative of an image of a surgical site, the at least one image display subsystem comprises a display configured to present an image of the surgical site to a user in response to the output image signals, the at least one user input device comprises a remote control device configured to generate the first user input signal and configured to generate the plurality of second user input signals.

3. The visualization system of claim 2, wherein the at least one circuit is within a housing of the at least one image display subsystem or within a housing of the at least one user input device.

4. The visualization system of claim 2 or claim 3, wherein the at least one circuit generates the control signals in response to the received at least one first user signal and the received plurality of second user input signals.

5. The visualization system of claims 2 to 4, wherein the plurality of cameras comprises at least one endoscope camera and at least one surgical microscope camera.

6. The visualization system of any of claims 2 to 5, wherein the camera is responsive to the control signals by varying one or more features of the camera, the at least one circuit further configured to respond to the received at least one first user input signal being in a first state by generating control signals which vary a first set of features of the camera and to respond to the received at least one first user input signal being in a second state by generating control signals which vary a second set of features of the camera.

7. The visualization system of any of claims 2 to 6, wherein one or more image acquisition subsystems of the plurality of image acquisition subsystems each comprises a camera and a light source, wherein the camera is responsive to the control signals by varying one or more features of the camera and the light source is responsive to the control signals by varying one or more features of the light source.

8. The visualization system of any of claims 2 to 7, wherein the at least one circuit is further configured to calculate a difference between an attribute of a first image provided by a first camera of the plurality of cameras and to the attribute of a second image provided by a second camera of the plurality of camera, the at least one circuit further configured to respond to the difference by generating and transmitting control signals to at least one of the first camera and the second camera to vary one or more features of the camera to reduce the difference.

9. The visualization system of any of claims 2 to 8, wherein the at least one circuit is further configured to calculate a difference between an attribute of a first image provided by a first camera of the plurality of cameras and to the attribute of a second image provided by a second camera of the plurality of camera, the at least one circuit further configured to respond to the difference by generating and transmitting output image signals to the display which reduce the difference of the attribute in the displayed first image and the displayed second image.

10. A visualization system comprising:

a plurality of communication ports configured to be operatively coupled to a plurality of image acquisition subsystem;

at least one image output port configured to be operatively coupled to at least one image display subsystem;

at least one user input port configured to be operatively coupled to at least one user input device; and at least one circuit operatively coupled to the plurality of communication ports, the at least one image output port, and the at least one user input port, the at least one circuit configured to receive data signals from the plurality of image acquisition subsystems, to transmit control signals to the plurality of image acquisition subsystems, and to transmit output image signals to the at least one image display subsystem, the at least one circuit further configured to receive at least one first user input signal and a plurality of second user input signals from the at least one user input device, the at least one circuit responsive at least in part to the received at least one first user input signal by:

selecting an image acquisition subsystem from the plurality of image acquisition subsystems, transmitting the output image signals to the at least one image display subsystem in response to the data signals received from the selected image acquisition subsystem, calculating a difference between an attribute of a first image provided by a first image acquisition subsystem of the plurality of image acquisition subsystems and to the attribute of a second image provided by a second image acquisition subsystem of the plurality of image acquisition subsystems, and responding to the difference by either generating and transmitting control signals to at least one of the first image acquisition subsystem and the second image acquisition subsystem to vary one or more features of the image acquisition subsystem to reduce the difference or generating and transmitting output image signals to the display which reduce the difference of the attribute in the displayed first image and the displayed second image.

11. A visualization system comprising:

a plurality of communication ports configured to be operatively coupled to at least one source of non-visible light and at least one sensor of non-visible light, the at least one source configured to irradiate a surgical site with the non-visible light, the at least one sensor having a capture rate and configured to detect emissions from the surgical site;

at least one image output port configured to be operatively coupled to at least one image display subsystem; and at least one circuit operatively coupled to the plurality of communication ports and to the at least one image output port, the at least one circuit configured to receive data signals from the at least one sensor, to transmit output image signals to the at least one image display subsystem, and to transmit control signals to the at least one source, the control signals configured to adjust a pulse rate of the at least one source, the at least one circuit determining the pulse rate by analyzing the data signals from the at least one sensor and selecting a pulse rate.

12. The system of claim 11, wherein the at least one source comprises an infrared light source, the at least one sensor comprises a fluorescence camera, and the at least one circuit is configured to control the pulsing of the infrared light source so that the at least one sensor captures a peak emission response from the surgical site.

13. A surgical visualization system comprising:
at least one image acquisition system and at least one image storage system configured to provide images to be displayed;
an electronic display system with one or more displays;
an electronic video switching system;
a controller; and
one or more remote control units that provide remote control of one or more of the following functions for one or more of the images provided by the at least one image acquisition system and the at least one storage system: zoom, focus, iris, tilt, pan, brightness, contrast, and acquisition selection, wherein the one or more functions provided by the remote control unit automatically change to a image acquisition or storage system selected for display, such that one remote control unit is able to function for multiple image acquisition or storage systems.

14. The system of claim 13, wherein the image acquisition or storage systems comprise at least one camera, at least one sensor, at least one image storage medium, or electronics accessing at least one image storage medium.

15. The system of claim 13 or 14, wherein the remote control unit incorporates one or more indicators that operate the same function on each image acquisition or storage system.

16. The system of claim 15, wherein the one or more indicators comprises one or more switches, buttons, or touchscreens.

17. The system of claim 13, wherein the remote control unit incorporates one or more indicators that operate a first function when a first image acquisition or storage system is selected and a second function when a second image acquisition or storage system is selected.

18. The system of claim 13, wherein a first remote control unit operates a variety of functions with a reduced number of indicators by using a first indicator to change the function of a second indicator.

19. The system of claim 18, wherein when the first indicator is open, the second indicator affects a first function and when the first indicator is closed, the second indicator affects a second function.

20. The system of Claim 18, wherein initially the second indicator affects a first function, but when the first indicator is operated, the controller is changed so the second indicator affects a second function, and when the first indicator is operated again, the controller is changed so the second indicator operates a third function.

21. The system of claim 20, wherein after further operation of the first indicator, the controller is changed so the second indicator operates the first function.

22. A surgical visualization system comprising:
at least one image acquisition system and at least one image storage system configured to provide images to be displayed;
an electronic display system with at least one display;
an integrated lighting system;
an electronic video switching system; and
a control unit that allows the user to switch which image acquisition or storage system presents an image in the display, wherein the lighting system has programmed settings for a particular light intensity of each light source to match the optical demands of each image acquisition and storage system, and wherein the control unit switches the lighting system to the programmed setting for the selected image acquisition or storage system in conjunction with switching the display to the selected image acquisition or storage system.

23. The system of claim 22, wherein the image acquisition or storage systems comprise at least one camera, at least one sensor, at least one image storage medium, or electronics accessing at least one image storage medium.

24. The system of claim 22, wherein the light intensity is adjusted by turning a portion of the light sources in the system on while leaving an additional portion off.

25. The system of claim 22, wherein the light intensity is adjusted by cycling at least one light source rapidly between off and on with the apparent intensity related to the ratio of the cycle time the light is on versus the cycle time the light is off.

26. The system of claim 22, wherein the light intensity of at least one light source is variable.

27. The system of claim 22, wherein at least one light source generates non-visible light.

28. The system of claim 27, wherein the non-visible light is in the infrared spectrum.

29. The system of claim 27, wherein the non-visible light has a wavelength from about 700 nm to about 1000 nm.

30. The system of claim 27, wherein the non-visible light is in the near infrared spectrum.

31. The system of claim 27, wherein the non-visible light has a wavelength from about 700 nm to about 800 nm.

32. The system of claim 27, wherein the non-visible light is in the ultraviolet spectrum.

33. The system of claim 27, wherein the non-visible light has a wavelength from about 10 nm to about 400 nm.

34. The system of claim 27, wherein the non-visible light is in the near ultraviolet spectrum.

35. The system of claim 27, wherein the non-visible light has a wavelength from about 300 nm to about 400 nm.

36. The system of claim 27, wherein the control unit cycles at least one non-visible light source with a rapid rate between off and on.

37. The system of claim 36, wherein the rate is concurrent with and synchronized to the image capture rate of a camera.

38. The system of claim 36, wherein the rate is selected such that the fluorescence response is captured by the image acquisition system.

39. The system of claim 22, wherein the control unit allows for adjustment of the programmed settings of the lighting system.

40. A visualization system comprising:
a plurality of communication ports configured to be operatively coupled to a plurality of image acquisition subsystems configured to image a surgical site;

at least one image output port configured to be operatively coupled to at least one image display subsystem;

at least one user input port configured to be operatively coupled to at least one user input device; and at least one circuit operatively coupled to the plurality of communication ports, the at least one image output port, and the at least one user input port, the at least one circuit configured to receive data signals from the plurality of image acquisition subsystems, to transmit control signals to the plurality of image acquisition subsystems, and to transmit output image signals to the at least one image display subsystem, the at least one circuit further configured to receive at least one first user input signal and a plurality of second user input signals from the at least one user input device, the at least one circuit responsive at least in part to the received at least one first user input signal by:

selecting an image acquisition subsystem from the plurality of image acquisition subsystems, transmitting the output image signals to the at least one image display subsystem in response to the data signals received from the selected image acquisition subsystem, calculating a difference between an attribute of a first image provided by a first image acquisition subsystem of the plurality of image acquisition subsystems and to the attribute of a second image provided by a second image acquisition subsystem of the plurality of image acquisition subsystems, and responding to the difference by either generating and transmitting control signals to at least one of the first image acquisition subsystem and the second image acquisition subsystem to vary one or more features of a light source illumination the surgical site to reduce the difference or generating and transmitting output image signals to the display subsystem which reduce the difference of the attribute in the displayed first image and the displayed second image.

41. The visualization system of any of claims 10, wherein the image acquisition subsystem comprises a light source configured to provide illumination to a surgical site and varying one or more features of said image acquisition subsystem comprises varying one or more features of said light source illumination.

42. The visualization system of any of claims 10, wherein the image acquisition subsystem comprises an optical sensor configured to detect light and varying one or more features of said image acquisition subsystem comprises varying one or more features of said optical sensor.

43. The visualization system of any of claims 10, wherein varying one or more features of said optical sensor comprising varying gain.

44. A visualization system comprising:

a plurality of communication ports configured to be operatively coupled to a plurality of image acquisition subsystems configured to image a surgical site;

at least one image output port configured to be operatively coupled to at least one image display subsystem;

at least one user input port configured to be operatively coupled to at least one user input device; and at least one circuit operatively coupled to the plurality of communication ports, the at least one image output port, and the at least one user input port, the at least one circuit configured to receive data signals from the plurality of image acquisition subsystems, to transmit control signals to the plurality of image acquisition subsystems, and to transmit output image signals to the at least one image display subsystem, the at least one circuit further configured to receive at least one first user input signal and a plurality of second user input signals from the at least one user input device, the at least one circuit responsive at least in part to the received at least one first user input signal by:

selecting an image acquisition subsystem from the plurality of image acquisition subsystems, transmitting the output image signals to the at least one image display subsystem in response to the data signals received from the selected image acquisition subsystem, calculating a difference between an attribute of a first image provided by a first image acquisition subsystem of the plurality of image acquisition subsystems and to the attribute of a second image provided by a second image acquisition subsystem of the plurality of image acquisition subsystems, and responding to the difference by either generating and transmitting control signals to at least one of the first image acquisition subsystem and the second image acquisition subsystem to vary one or more features of at least one image display subsystem to reduce the difference of the attribute in the displayed first image and the displayed second image.

45. The system of any of the preceding claims, comprising a binocular viewing assembly including at least one display disposed in a housing and oculars, at least one of said oculars providing a view of first and second display portions for viewing images of a surgical site, wherein said oculars do not provide an optical path to said surgical site.

46. The system of any of the preceding claims, wherein at least one of said display portions is configured to display a surgical microscope view of said surgical site provided by a surgical microscope camera, wherein said surgical microscope camera does not have a direct optical path to said surgical site through said housing.

47. The system of any of the preceding claims, wherein said system is configured to switch among input received from a plurality of different cameras disposed to image a surgical site.

48. The system of any of the preceding claims, further comprising a camera providing a surgical microscope view.

49. The system of any of the preceding claims, wherein said camera providing a surgical microscope view is not associated with a direct view surgical microscope that includes oculars do provide an optical path to said surgical site.

50. The system of any of the preceding claims, wherein said camera providing a surgical microscope view has a work distance in the range of from 150 mm to 450 mm.

51. The system of any of the preceding claims, wherein said camera providing a surgical microscope view comprises a stereo camera.

52. The system of any of the preceding claims, wherein said system is configured to switch among input received from an endoscope camera and said camera providing surgical microscope views.

53. The system of any of claims 13-21, wherein the multiple image acquisition or storage systems comprise one image acquisition system and one image storage system.

54. The system of any of claims 22-39, wherein the system is configured to maintain a consistent brightness on the display.

55. A surgical visualization system comprising:
  at least one image acquisition system and at least one image storage system configured to provide images to be displayed;
  an electronic display system with at least one display;
  an electronic video switching system; and
  a control unit that allows the user to switch which image acquisition or storage system presents an image in the display, wherein the system is configured to vary a parameter of the image in the display when switched.

56. The system of claim 55, wherein the image acquisition or storage systems comprise at least one camera, at least one sensor, at least one image storage medium, or electronics accessing at least one image storage medium.

57. The system of claim 55 or 56, wherein the parameter comprises one or more of zoom, focus, iris, tilt, pan, brightness, or contrast.

58. The system of claim 57, wherein the system is configured to maintain a consistent brightness on the display.

User Control Systems & Control of Image Intensity-II

1. A surgical visualization system comprising:
  a plurality of cameras configured to provide video of a surgical site;
  a viewing assembly comprising a pair of oculars and at least one display viewable through the pair of oculars, wherein the viewing assembly does not provide an optical path from the pair of oculars to the surgical site;
  an image processing system configured to receive acquired video of the surgical site from the plurality of cameras and to provide output video to the at least one display of the viewing assembly; and
  at least one user input device configured to be operatively coupled to the image processing system;
  wherein the image processing system is configured to:
  select a camera from the plurality of cameras;
  generate output video based on video acquired with the selected camera;
  transmit the output video to the at least one display
  generate control signals; and
  transmit the control signals to the selected camera.

2. The system of claim 1, wherein the at least one user input device comprises a remote control device configured to generate a plurality of user input signals.

3. The system of claim 2, wherein the image processing system is within a housing of the viewing assembly or within a housing of the at least one user input device.

4. The system of claim 2 or claim 3, wherein the image processing system generates the control signals in response to the received plurality of user input signals.

5. The system of claims 2 to 4, wherein the plurality of cameras comprises at least one endoscope camera and at least one surgical microscope camera.

6. The system of any of claims 2 to 5, wherein the camera is responsive to the control signals by varying one or more features of the camera, the image processing system further configured to respond to the received user input signals by generating control signals which vary a first set of features of the selected camera.

7. The system of any of claims 2 to 6, wherein one or more cameras includes a light source, wherein the selected camera is responsive to the control signals by varying one or more features of the camera and the light source is responsive to the control signals by varying one or more features of the light source.

8. The system of any of claims 2 to 7, wherein the image processing system is further configured to calculate a difference between an attribute of a first image provided by a first camera of the plurality of cameras and to the attribute of a second image provided by a second camera of the plurality of camera, the image processing system further configured to respond to the difference by generating and transmitting control signals to at least one of the first camera and the second camera to vary one or more features of the camera to reduce the difference.

9. The system of any of claims 2 to 8, wherein the image processing system is further configured to calculate a difference between an attribute of a first image provided by a first camera of the plurality of cameras and to the attribute of a second image provided by a second camera of the plurality of camera, the image processing system further configured to respond to the difference by generating and transmitting output image signals to the display which reduce the difference of the attribute in the displayed first image and the displayed second image.

10. A surgical visualization system comprising:
  a plurality of communication ports configured to be operatively coupled to a plurality of cameras configured to provide views of a surgical site;
  at least one image output port configured to be operatively coupled to at least one display housed in a viewing assembly comprising a pair of oculars, the viewing assembly configured to not provide an optical path from the pair of oculars to the surgical site;
  at least one user input port configured to be operatively coupled to at least one user input device; and
  an image processing system comprising at least one circuit operatively coupled to the plurality of communication ports, the at least one image output port, and the at least one user input port, the at least one circuit configured to receive data signals from the plurality of cameras, to transmit control signals to the plurality of cameras, and to transmit output image signals to the at least one display, the at least one circuit further configured to receive at least one first user input signal and a plurality of second user input signals from the at least one user input device, the at least one circuit responsive at least in part to the received at least one first user input signal by:
  selecting a camera from the plurality of cameras,
  transmitting the output image signals to the at least one display in response to the data signals received from the selected camera,
  calculating a difference between an attribute of a first image provided by a first camera of the plurality of cameras and to the attribute of a second image provided by a second camera of the plurality of cameras, and
  responding to the difference by either generating and transmitting control signals to at least one of the first camera and the second camera to vary one or more features of the camera to reduce the difference or generating and transmitting output image signals to the display which reduce the difference of the attribute in the displayed first image and the displayed second image.

11. A surgical visualization system comprising:
  a plurality of communication ports configured to be operatively coupled to at least one source of non-visible light and at least one sensor of non-visible light, the at least one source configured to irradiate a surgical site with the non-visible light, the at least one sensor having a capture rate and configured to detect emissions from the surgical site;

at least one image output port configured to be operatively coupled to at least one camera configured to acquire video of the surgical site; and an image processing system comprising at least one circuit operatively coupled to the plurality of communication ports and to the at least one image output port, the at least one circuit configured to receive data signals from the at least one sensor, to transmit output image signals to the at least one camera, and to transmit control signals to the at least one source, the control signals configured to adjust a pulse rate of the at least one source, the at least one circuit determining the pulse rate by analyzing the data signals from the at least one sensor and selecting a pulse rate.

12. The system of claim 11, wherein the at least one source comprises an infrared light source, the at least one sensor comprises a fluorescence camera, and the at least one circuit is configured to control the pulsing of the infrared light source so that the at least one sensor captures a peak emission response from the surgical site.

13. A surgical visualization system comprising:
two or more cameras configured to acquire video of a surgical site;
an electronic display system with one or more displays housed in a viewing assembly comprising a pair of oculars configured to provide a view of the one or more displays, wherein there is no optical path from the pair of oculars to the surgical site;
an integrated lighting system;
an electronic video switching system;
a controller; and
one or more remote control units that provide remote control of one or more of the following functions for one or more of the cameras: zoom, focus, iris, tilt, pan, and acquisition selection, wherein the one or more functions provided by the remote control unit automatically change to a camera selected for display, such that one remote control unit is able to function for multiple cameras.

14. The system of claim 13, wherein the two or more cameras comprise at least one camera or at least one sensor.

15. The system of claim 13, wherein the remote control unit incorporates one or more indicators that operate the same function on each camera.

16. The system of claim 15, wherein the one or more indicators comprises one or more switches, buttons, or touchscreens.

17. The system of claim 13, wherein the remote control unit incorporates one or more indicators that operate a first function when a first camera is selected and a second function when a second camera is selected.

18. The system of claim 13, wherein a first remote control unit operates a variety of functions with a reduced number of indicators by using a first indicator to change the function of a second indicator.

19. The system of claim 18, wherein when the first indicator is open, the second indicator affects a first function and when the first indicator is closed, the second indicator affects a second function.

20. The system of claim 18, wherein initially the second indicator affects a first function, but when the first indicator is operated, the controller is changed so the second indicator affects a second function, and when the first indicator is operated again, the controller is changed so the second indicator operates a third function.

21. The system of claim 20, wherein after further operation of the first indicator, the controller is changed so the second indicator operates the first function.

22. A surgical visualization system comprising:
two or more cameras;
an electronic display system with one or more displays;
an integrated lighting system;
an electronic video switching system; and
a control unit that allows the user to switch which camera presents an image in the display, wherein the lighting system has programmed settings for a particular light intensity of each light source to match the optical demands of each camera, and wherein the control unit switches the lighting system to the programmed setting for the selected camera in conjunction with switching the display to the selected camera.

23. The system of claim 22, wherein the two or more cameras comprise at least one camera or at least one sensor.

24. The system of claim 22, wherein the light intensity is adjusted by turning a portion of the light sources in the system on while leaving an additional portion off.

25. The system of claim 22, wherein the light intensity is adjusted by cycling at least one light source rapidly between off and on with the apparent intensity related to the ratio of the cycle time the light is on versus the cycle time the light is off.

26. The system of claim 22, wherein the light intensity of at least one light source is variable.

27. The system of claim 22, wherein at least one light source generates non-visible light.

28. The system of claim 27, wherein the non-visible light is in the infrared spectrum.

29. The system of claim 27, wherein the non-visible light has a wavelength from about 700 nm to about 1000 nm.

30. The system of claim 27, wherein the non-visible light is in the near infrared spectrum.

31. The system of claim 27, wherein the non-visible light has a wavelength from about 700 nm to about 800 nm.

32. The system of claim 27, wherein the non-visible light is in the ultraviolet spectrum.

33. The system of claim 27, wherein the non-visible light has a wavelength from about 10 nm to about 400 nm.

34. The system of claim 27, wherein the non-visible light is in the near ultraviolet spectrum.

35. The system of claim 27, wherein the non-visible light has a wavelength from about 300 nm to about 400 nm.

36. The system of claim 27, wherein the control unit cycles at least one non-visible light source with a rapid rate between off and on.

37. The system of claim 36, wherein the rate is concurrent with and synchronized to the image capture rate of the camera.

38. The system of claim 36, wherein the rate is selected such that the fluorescence response is captured by the camera.

39. The system of claim 22, wherein the control unit allows for adjustment of the programmed settings of the lighting system.

40. A surgical visualization system comprising:
a plurality of cameras configured to provide video of a surgical site;
at least one light source configured to provide illumination to the surgical site;
a viewing assembly comprising a pair of oculars and at least one display viewable through the pair of oculars, wherein the viewing assembly is not associated with a direct view surgical microscope having an optical path from the pair of oculars to the surgical site;

an image processing system configured to receive acquired video of the surgical site from the plurality of cameras and to provide output video to the at least one display of the viewing assembly; and wherein the image processing system is configured to:

switch between providing output video based on video acquired by a first camera of the plurality of cameras to providing output video based on video acquired with a second camera of the plurality of cameras;

determine a difference between the video acquired with the first camera and the video acquired with the second camera; and adjust a property of the camera, the at least one display, or the at least one light source to reduce the determined differences.

41. A surgical visualization system comprising:

a plurality of cameras configured to provide video of a surgical site;

a viewing assembly comprising a pair of oculars and at least one display viewable through the pair of oculars, wherein the viewing assembly is not associated with a direct view surgical microscope having an optical path from the pair of oculars to the surgical site;

an image processing system configured to receive acquired video of the surgical site from the plurality of cameras and to provide output video to the at least one display of the viewing assembly; and wherein the image processing system is configured to:

switch between providing output video based on video acquired by a first camera of the plurality of cameras to providing output video based on video acquired with a second camera of the plurality of cameras;

determine a difference between the video acquired with the first camera and the video acquired with the second camera; and adjust a property of the camera, the at least one display, or the at least one light source to reduce the determined differences.

42. The surgical visualization systems of any of claim 1 or 2, wherein the property of the camera includes a sensor gain, the property of the at least one display includes display brightness, and the property of the property of the at least one light source includes light intensity.

Additional Numbered Example Embodiments

The following is a numbered list of example embodiments that are within the scope of this disclosure. The example embodiments that are listed should in no way be interpreted as limiting the scope of the embodiments. Various features of the example embodiments that are listed can be removed, added, or combined to form additional embodiments, which are part of this disclosure:

1. A stereo viewing system in which multiple sources of synchronized or a-synchronized video streams emanating from endoscopes, proximal cameras, external sources or stand-off cameras can be seen as a pair of stereo views with a right eye and left eye perspectives to an object comprising:

an eye path comprised respectively of lenses, mirrors and beam combiners merging one or more independent video sources to one or more displays.

a second eye path comprised respectively of lenses, mirrors and beam combiners merging one or more independent video sources to one or more displays.

said right and left eye paths have at least one display panel, such as a liquid crystal display or DMD containing a convergent perspective view from a source so that when viewed the 2 eye paths yield a stereo or 3D image.

2. The Stereo viewing system of claim 1, wherein each of the said eye paths to each eye contains alignment means, such as beam splitters or pellicle mirrors to register the 2 or more displays with respect to each other so that all or part of the combined pair of displays for each eye are seen by the viewer as one scene for each eye, the combined eye paths yield a stereo or 3D view.

3. The Stereo viewing system of claim 1, wherein the said combined eye paths contain a pair of displays, among the combined displays, displaying an object in the visible waveband, nominally 400-700 nm, as seen by 2 or more detectors producing a convergent perspective excited by a visible source.

4. The Stereo viewing system of claim 1, wherein the said combined eye paths contain a pair of displays, among the combined displays, displaying an object in the visible waveband, nominally 400-700 nm, as seen by one detector which receives a right eye image on one portion of the detector and a left eye image on the remainder of the detector producing a convergent perspective excited by a visible source.

5. The Stereo viewing system of claim 1, wherein the said combined eye paths contain a pair of displays, among the combined displays, displaying an object in the near infrared waveband, nominally 700-1100 nm, as seen by two or more detectors producing a convergent perspective excited by an infrared source.

6. The Stereo viewing system of claim 1, wherein the said combined eye paths contain a pair of displays, among the combined displays, displaying an object in the near infrared waveband, nominally 700-1100 nm, as seen by one detector which receives a right eye image on one portion of the detector and a left eye image on the remainder of the detector producing a convergent perspective excited by an infrared source.

7. The Stereo viewing system of claim 1, wherein the said combined eye paths contain a pair of displays, among the combined displays, displaying an object in the visible waveband, nominally 400-700 nm, as seen by two or more detectors producing a convergent perspective excited by visible source with filters selected to pass light of wavelengths of 440 nm to 460 nm and 540 to 560 nm, or other subsets of 400-700 nm, to the object of interest.

8. A stereo viewing system in which multiple light sources can be independently powered to produce images illuminated entirely by visible light, or subset of visible, e.g., narrow band imaging such as 440 nm to 460 nm and 540 nm to 560 nm, or by near infrared sources.

9. A stereo viewing system in which multiple light sources can be coordinated by control means to combine simultaneous sources of different wavebands to be selectively displayed to each eye to form visible images with overlays of subsets of visible or altered visible or infrared images and whose emphasis can be controlled by means of regulating the power provided to the different light sources.

10. A stereo viewing system in which multiple displays can be combined by means of pellicle mirrors, beamsplitters, optics and prisms to add text or graphics or notations over a primary scene for one or both eyes.

11. A stereo viewing system in which one or more displays can wirelessly transmit its view to an external monitor.

12. A stereo viewing system in which the brightness contrast gamma and other camera and light source and system settings are projected by means of a pico projector into part of the sterile field so that the user does not break sterile field to control the system.

13. A stereo viewing system in claim 12, wherein the projected controls are visible in the stereo display system by means of one or more cameras so that the operator does not look away from the display.

14. A stereo viewing system in claim 12, wherein the projected controls are touched by the user and an image processing unit detects the users hands and fingers and actives or adjusts the buttons or other projected menus of the system.

15. A stereo viewing system in which each eye paths components, lenses, mirrors, prisms, pellicles, and discrete displays lie substantially above the users line of sight or eye level to permit a direct view of the patient when the user is not looking into the eye ports.

16. A stereo viewing system in which each eye path is comprised of an ocular unit directed to a real image at a field stop of between 16 and 30 mm yielding an apparent field of view of between 50 degrees and 90 degrees with an eye relief of at least 18 mm.

17. A stereo viewing system where the backlit display panels are replaced by deformable mirror arrays and RGB illumination directed at each DMD with prisms, beam splitters or pellicle mirrors to combine 2 or more DMD's per eye driven by synchronous or a-synchronous sources.

18. A stereo viewing system where the backlit display panels are illuminated by LED's continuously on the back side of the panel with high power, e.g. 1 W, 2-4 W's, or 5-6 W's.

Combinations

19. Any of the above Claims as part of a surgical visualization system comprising:
   a binocular viewing assembly comprising a housing and a pair of eyepieces, said eyepieces configured to provide a view of at least one display disposed in the housing;
   an optical assembly configured to provide a surgical microscope view of a surgical site, the optical assembly comprising at least one auxiliary camera;
   a positioning system, the binocular viewing assembly attached to the positioning system, the positioning system configured to allow adjustment of a position and/or orientation of the binocular viewing assembly and/or the optical assembly; and
   an image processing system in communication with the display, the image processing system comprising at least one physical processor,
   wherein the image processing system is configured to:
   receive video images acquired by at least the auxiliary camera,
   provide output video images based on the received video images, and
   present the output video images on the display so that the output video images are viewable through the eyepiece,
   wherein the optical assembly is configured to provide a working distance that is between about 15 cm and about 45 cm.

The systems, methods and devices described herein each have innovative aspects, no single one of which is solely responsible for the desirable attributes disclosed herein.

BRIEF DESCRIPTION OF THE DRAWINGS

Throughout the drawings, reference numbers can be reused to indicate general correspondence between reference elements. The drawings are provided to illustrate example embodiments described herein and are not intended to limit the scope of the disclosure.

FIG. 13B1 shows an illustration of an example medical apparatus according to certain embodiments described herein.

FIG. 13B1-*a* shows a larger view of the side view of FIG. 13B1.

FIG. 13B1-*b* shows a larger view of the front view of FIG. 13B1.

FIG. 13B1-*c* shows the example medical apparatus of FIG. 13B1.

FIG. 13B1-*d* shows an illustration of a beam combiner, a first camera, and a second camera.

FIGS. 13B1-*e* and 13B1-*f* illustrate example display units and optical paths of a medical apparatus.

FIG. 14A1-*a*, FIG. 14A1-*b*, and FIG. 14A1-*c* schematically illustrates cameras mounted to a circular frame, a square frame, or a L-shaped frame respectively.

FIG. 14B1-*a* shows an illustration of an imaging system comprising a camera, fiber optics, and a laparoscope.

FIG. 14B1-*b* shows an illustration of certain embodiments of a medical apparatus having one or more proximal camera D on a frame.

FIG. 14B2-*a* schematically illustrates imaging optics of an example imaging system compatible with certain embodiments of cameras as described herein.

FIG. 14B2-*b* shows an illustration of an example top-down view of certain embodiments disclosed herein.

FIG. 14B2-*c* shows an illustration of an example side-view of one optical channel of the apparatus shown in FIG. 14B2-*b*.

FIG. 14B2-*d* shows an illustration of an example proximal camera arrangement in accordance with certain embodiments described herein.

FIG. 14B2-*e* schematically illustrates a display viewable through portals.

FIG. 14B2-*f* shows an illustration of an example planar four-bar mechanism.

FIG. 14B2-*g* shows an illustration of the side-view of FIG. 14B2-*f*.

FIG. 14B3 shows an illustration of an oblique camera orientation.

DETAILED DESCRIPTION

The following description is directed to certain embodiments for the purposes of describing the innovative aspects of this disclosure. However, a person having ordinary skill in the art will readily recognize that the teachings herein can be applied in a multitude of different ways. The described embodiments may be implemented in any device or system that can be configured to provide visualization of a surgical site. Thus, the teachings are not intended to be limited to the embodiments depicted solely in the figures and described herein, but instead have wide applicability as will be readily apparent to one having ordinary skill in the art.
Surgical Visualization System To provide improved visualization of a surgical site, a surgical device can be provided with multiple integrated cameras. Each of the cameras may capture a distinct view of the surgical site. In some embodiments, imagery from the plurality of cameras may be displayed to facilitate operation in a surgical site. Tiled, individual, and/or stitched imagery from the multiple cameras can provide the user with a view of the surgical site. The user can select the imagery to be displayed and the manner in which it is displayed for enhanced utility during surgery. As used herein, the term imagery and images includes video and/or images captured from one or more video cameras. Images from video are often referred to as video images or simply images. The term images may also refer to still images or snap shots. Video feed or video stream may also be used to describe the video images such as video images from a camera.

The video cameras may comprise, for example, CCD or CMOS sensor arrays or other types of detector arrays. A frame grabber may be configured to capture data from the cameras. For example, the frame grabber may be a Matrox Solios eA/XA, 4 input analog frame grabber board. Image processing of the captured video may be undertaken. Such image processing can be performed by, for example, the Matrox Supersight E2 with Matrox Supersight SHB-5520 with two Intel Six Core Xeon E5645 2.4 GHz processors with DDR3-1333SDRAM. This system can be designed to support eight or more camera inputs using two Matrox Solios eA/XA, 4 input, analog frame grabber boards. More or fewer cameras may be employed. In some implementations, a field programmable gate array ("FPGA") can be used to capture and/or process video received from the cameras. For example, the image processing can be performed by Xilinx series 7 FPGA boards. Other hardware devices can be used as well, including ASIC, DSP, computer processors, a graphics board, and the like. The hardware devices can be standalone devices or they can be expansion cards integrated into a computing system through a local computer bus, e.g., a PCI card or PCIe card.

Figure 1:
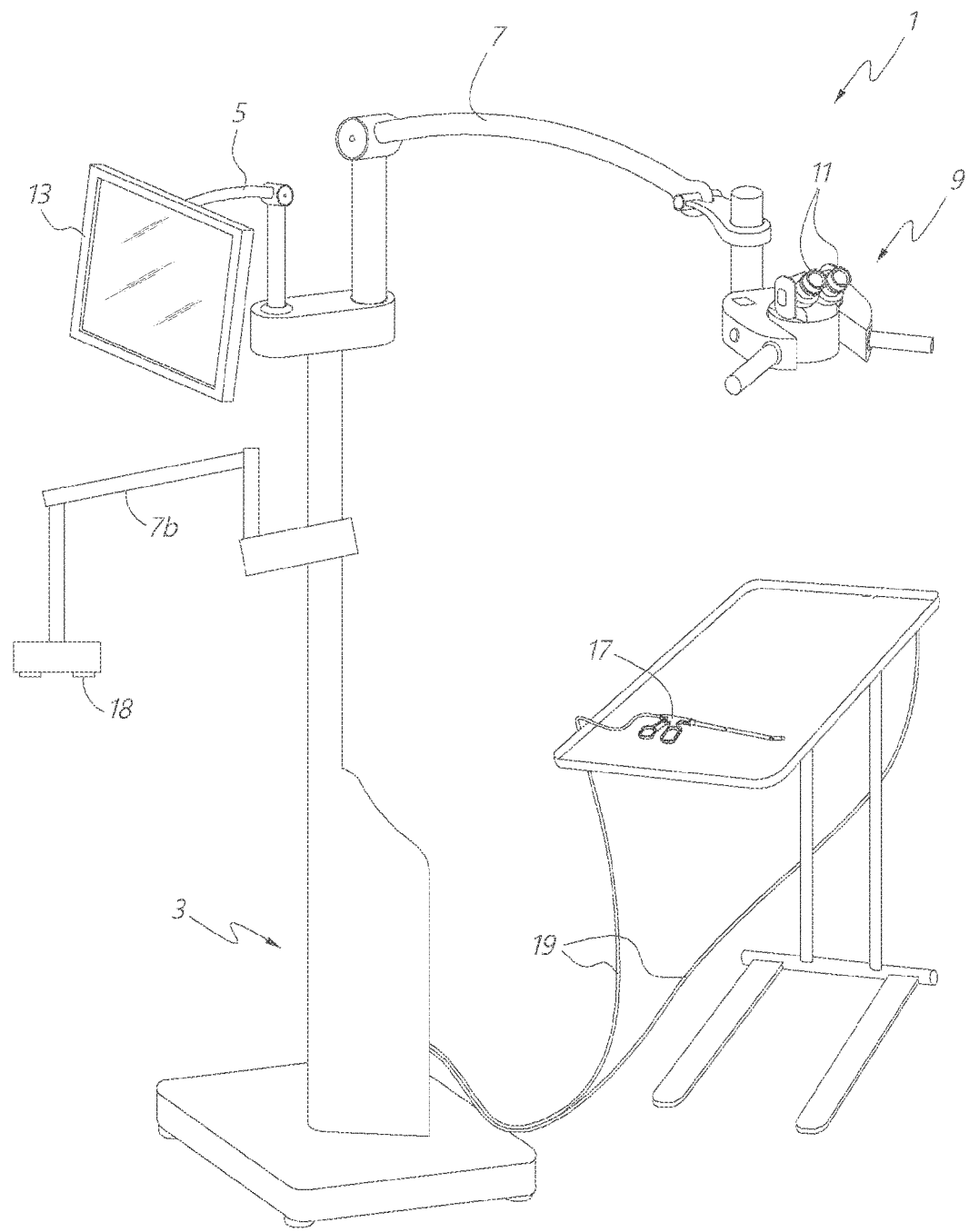
FIG. 1 illustrates an embodiment of the surgical visualization system having an imaging system that can be configured to provide imagery similar to a direct-view surgery microscope.

FIG. 1 shows an example embodiment of a surgical visualization system 1. As illustrated, the system 1 includes a console and electronics 3 from which three arms 5, 7 and 7b extend. The first arm 7 has mounted to its distal end a viewing platform 9. The viewing platform may include two oculars 11 and be configured similarly to a standard surgical microscope viewing platform. In some embodiments, however, unlike a conventional surgical microscope or a head mounted display the viewing platform 9 is not a direct view device where the surgeon or other user sees directly through the platform, e.g., an aperture in the platform. In some embodiments, regardless whether the user can view directly through the viewing platform, the surgical visualization system 1 can be configured to display video in a manner that the video displayed is decoupled from movement of the surgical microscope cameras such that a user can adjust the position and/or orientation of the surgical microscope cameras without moving the oculars 11 or the user adjusting position. As discussed in more detail below, the viewing platform 9 may include displays that receive signals from cameras that the surgeon or user employs to view the surgical site.

In some embodiments, cameras can be mounted to the viewing platform 9 and the cameras can be configured to provide imagery of the surgical site. Accordingly, the cameras can be used to provide imagery similar to a conventional surgical microscope. For example, the cameras on the viewing platform 9 can be configured to provide a working distance, or a distance from the viewing platform 9 to the patient, that can vary using zooming. The virtual working distance can vary, where the working distance can be at least about 150 mm and/or less than or equal to about 450 mm, at least about 200 mm and/or less than or equal to about 400 mm, or at least about 250 mm and/or less than or equal to about 350 mm. The working distance can be selected and/or changed by the surgeon. In some embodiments, changing the working distance does not affect the position and/or orientation of the oculars 11 with respect to the user or surgeon. In various embodiments, different objectives having different work distances can be employed for different procedures. One objective can be switched out for another objective to provide a different work distance for a different procedure. In some embodiments, zoom lens systems are included to provide the ability to vary working distance. In some embodiments, the cameras mounted on the viewing platform 9 can be used to provide gesture recognition to allow a surgeon to virtually interact with imagery provided by the display using the surgeon's hands, a surgical tool, or both, as described in greater detail herein.

The second arm 5 has mounted to its distal end an input and display device 13. In some embodiments, the input and display device 13 comprises a touchscreen display having various menu and control options available to a user. In some embodiments, the touchscreen can be configured to receive multi-touch input from ten fingers simultaneously, allowing for a user to interact with virtual objects on the display. For example, an operator may use the input device 13 to adjust various aspects of the displayed image. In various embodiments, the surgeon display incorporating a video camera providing a surgical microscope view may be mounted on a free standing arm, from the ceiling, on a post, or the like. The flat panel display touch screen 13 may be positioned on a tilt/rotate device on top of the electronics console.

A surgical tool 17 can be connected to the console 3 by electrical cable 19. The surgical tool 17 includes, for example, a cutting tool, a cleaning tool, a device used to cut patients, or other such devices. In other embodiments, the surgical tool 17 may be in wireless communication with the console 3, for example via WiFi (e.g., IEEE 802.11a/b/g/n), Bluetooth, NFC, WiGig (e.g., IEEE 802.11ad), etc. The surgical tool 17 may include one or more cameras configured to provide imagery, e.g., image and/or video data. In various embodiments, video data can be transmitted to a video switcher, camera control unit (CCU), video processor, or image processing module positioned, for example, within the console 3. The video switching module may then output a display video to the viewing platform 9. The operator may then view the displayed video through the oculars 11 of the viewing platform 9. In some embodiments, the binoculars permit 3D viewing of the displayed video. As discussed in more detail below, the displayed video viewed through the viewing platform 9 may comprise a composite video formed (e.g., stitched or tiled) from two or more of the cameras on the surgical tool 17.

In use, an operator may use the surgical tool 17 to perform open and/or minimally invasive surgery. The operator may view the surgical site by virtue of the displayed video in the viewing platform 9. Accordingly, the viewing platform (surgeon display system) 9 may be used in a manner similar to a standard surgical microscope although, as discussed above, the viewing platform 9 need not be a direct view device wherein the user sees directly through the platform 9 to the surgical site via an optical path from the ocular through an aperture at the bottom of the viewing platform 9. Rather, in various embodiments, the viewing platform 9 includes a plurality of displays, such as liquid crystal or light emitting diode displays (e.g., LCD, AMLCD, LED, OLED, etc.) that form an image visible to the user by peering into the ocular. Accordingly, one difference, however, is that the viewing platform 9 itself need not necessarily include a microscope objective or a detector or other image-capturing mechanisms. Rather, the image data can be acquired via the cameras of the surgical tool 17. The image data can then be processed by a camera control unit, video processor, video switcher or image processor within the console 3 and displayed imagery may then be viewable by the operator at the viewing platform 9 via the display devices, e.g., liquid crystal or LED displays, contained therein. In some embodiments, the viewing platform 9 can provide a view similar to a standard surgical microscope using cameras and displays and can be used in addition to or in conjunction with a standard surgical microscope optical pathway in the viewing platform. In certain embodiments, the viewing platform 9 can provide a surgical microscope view wherein changes in the viewing angle, viewing distance, work distance, zoom setting, focal setting, or the like is decoupled from movement of the viewing platform 9. In certain embodiments, changes in the position, pitch, yaw, and/or roll of the imaging system 18 are decoupled from the viewing platform 9 such that the imaging system 18 can move and/or re-orient while the surgeon can remain stationary while viewing video through the oculars 11.

The third arm 7b can include an imaging system 18 that can be configured to provide video similar to a direct-view surgery microscope. The imaging system 18 can be configured, then, to provide a surgical imaging system configured to provide an electronic microscope-like view that can comprise video of the work site or operational site from a position above the site (e.g., about 15-45 cm above the surgical site) or from another desired angle. By decoupling the imagers 18 from the display, the surgeon can manipulate the surgical imaging system to provide a desired or selected viewpoint without having to adjust the viewing oculars. This can advantageously provide an increased level of comfort, capability, and consistency to the surgeon compared to traditional direct-view operating microscope systems. In some embodiments, as described herein, the imagers 18 can be located on the viewing platform 9, on a dedicated arm 7b, on a display arm 5, on a separate post, a separate stand, supported from an overhead structure, supported from the ceiling or wall, or detached from other systems. The imagers 18 can comprise a camera configured to be adjustable to provide varying levels of magnification, viewing angles, monocular or stereo imagery, convergence angles, working distance, or any combination of these.

The viewing platform 9 can be equipped with wide field-of-view oculars 11 that are adjustable for refractive error and presbyopia. In some embodiments, the oculars 11, or eyepieces, may additionally include polarizers in order to provide for stereoscopic vision. The viewing platform 9 can be supported by the arm 7 or 7b, such that it may be positioned for the user to comfortably view the display 13 through the oculars 11 while in position to perform surgery. For example, the user can pivot and move the arm 7 or 7b to re-orient and/or re-position the viewing platform 9. In some embodiments, the viewing platform 9 can be positioned above the patient while in use by the surgeon or other user. The surgeon can then be positioned next to the patient while performing surgery.

In some embodiments, the image processing system and the display system are configured to display imagery placed roughly at infinity to reduce or eliminate accommodation and/or convergence when viewing the display. For example, the display system can be configured with sufficient eye relief for the user to reduce fatigue associated with using the display system. A display optical system can include one or more lenses and one or more redirection elements (e.g., mirrors, prisms) and can be configured to provide light from the display that can be imaged by a binocular viewing assembly comprising a pair of oculars, objectives, and/or turning prisms or mirrors. The display devices such as liquid crystal displays can be imaged with the objective and the pair of oculars and display optical system within the viewing platform 9. The binocular assembly and display optical system can be configured to produce an image of the displays at infinity. Such arrangements may potentially reduce the amount of accommodation by the surgeon. The oculars can also have adjustments (e.g., of focus or power) to address myopia or hyperopia of the surgeon. Accordingly, the surgeon or other users may view the displays through the oculars without wearing glasses even if ordinarily prescription glasses were worn for other activities.

In certain implementations, the display optical system does not include a pair of oculars but instead includes two or more chambers that are optically separate to form left and right eye paths. In such implementations, the display optical system can be baffled to prevent light communication between the left and right eye channels. To adjust for different accommodations, the displays within the display system can be configured to move toward and/or away from the viewer along the optical path. This can have an effect similar to varying focal lengths of lenses in an ocular system. In some embodiments, the display housing with the electronic displays can change to move the displays closer or further from the viewer along the optical path. In some embodiments, both the display housing and the electronic displays are configured to be adjustable along the optical path to adjust for accommodation.

Figure 2:
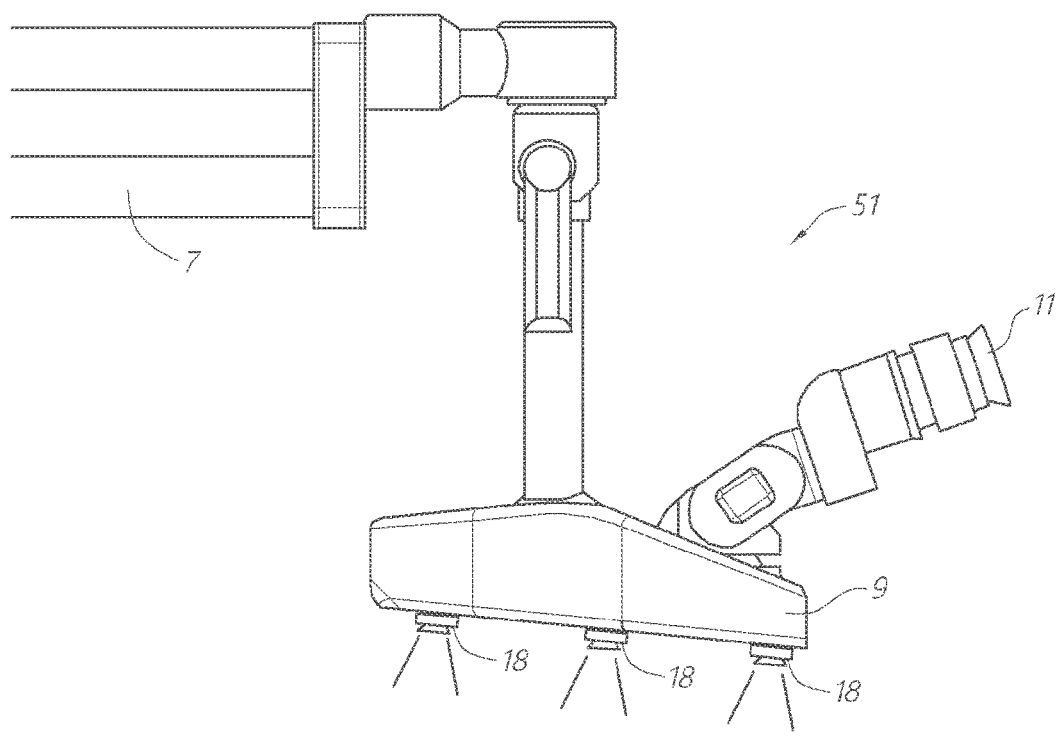
FIG. 2 illustrates an example surgical viewing system attached to an articulating arm, the system including one or more cameras mounted on a binocular viewing platform.

In some embodiments, the viewing platform 9 can include one or more imagers configured to provide electronic microscope-like imaging capabilities. FIG. 2 illustrates an example surgical imaging system 51 attached to an arm 7, the system 51 including one or more cameras 18 mounted on a viewing platform 9. The cameras 18 can be configured to provide imagery of a worksite. The image data can be presented on a display that the user can view using oculars 11 mounted on the viewing platform 9. This design can be used to mimic other direct-view microscopes, but it can also be configured to provide additional capabilities. For example, the surgical imaging system 51 can be configured to have a variable working distance without adjusting the viewing platform 9 or the articulating arm 7. In some embodiments, the working distance can be adjusted by adjusting one or more elements of imaging optics of the camera(s) 18 mounted on the viewing platform 9. In certain implementations, the working distance can be adjusted by adjusting a zoom or focal length of a zoom optical apparatus. The surgical imaging system 51 can be configured to provide image processing capabilities such as electronic zooming and/or magnification, image rotation, image enhancement, stereoscopic imagery, and the like. Furthermore, the imagery from the cameras 18 can be combined with imagery from cameras on the surgical device 17. In some embodiments, the surgical imaging system 51 can provide fluorescence images.

Although the discussion considers images from surgical tools, numerous embodiments may involve at least one auxiliary video camera 18 and one or more other cameras that are not disposed on surgical tools but are disposed on other medical devices. These medical devices may include devices introduced into the body such as endoscopes, laparoscopes, arthroscopes, etc.

Accordingly, one or more displays such as the at least one display 13 included in the viewing platform 9 may be used to provide a surgical microscope view using one or more cameras such as the auxiliary video camera(s) 18 as well as to display views from one or more cameras located on such medical devices other than surgical tools. In some embodiments, cameras from a variety of sources, e.g., surgical tools and other medical devices, in any combination, may be viewed on the display(s) on the surgical platform together with the surgical microscope view from the auxiliary video cameras 18. As described herein, the displays may provide 3D thus any of the images and graphics may be provided in 3D.

In various embodiments, a virtual touchscreen may be provided by the auxiliary video cameras 18 or other virtual touchscreen cameras mounted to the viewing platform 9. Accordingly, in some embodiments a user may provide a gesture in the field of view of the auxiliary video cameras and/or virtual touchscreen cameras and the processing module can be configured to recognize the gesture as an input. Although the virtual display has been described in the context of the auxiliary video cameras 18, other cameras, e.g., virtual reality input cameras, possibly in addition to the auxiliary video cameras 18 may be used. These cameras may be disposed on the viewing platform 9 or elsewhere, such as the third arm 7b. As described herein the displays may provide 3D thus the virtual reality interface may appear in 3D. This may increase the immersive quality of the viewing experience, enhancing the detail and/or realistic presentation of video information on the display.

Figure 3A:
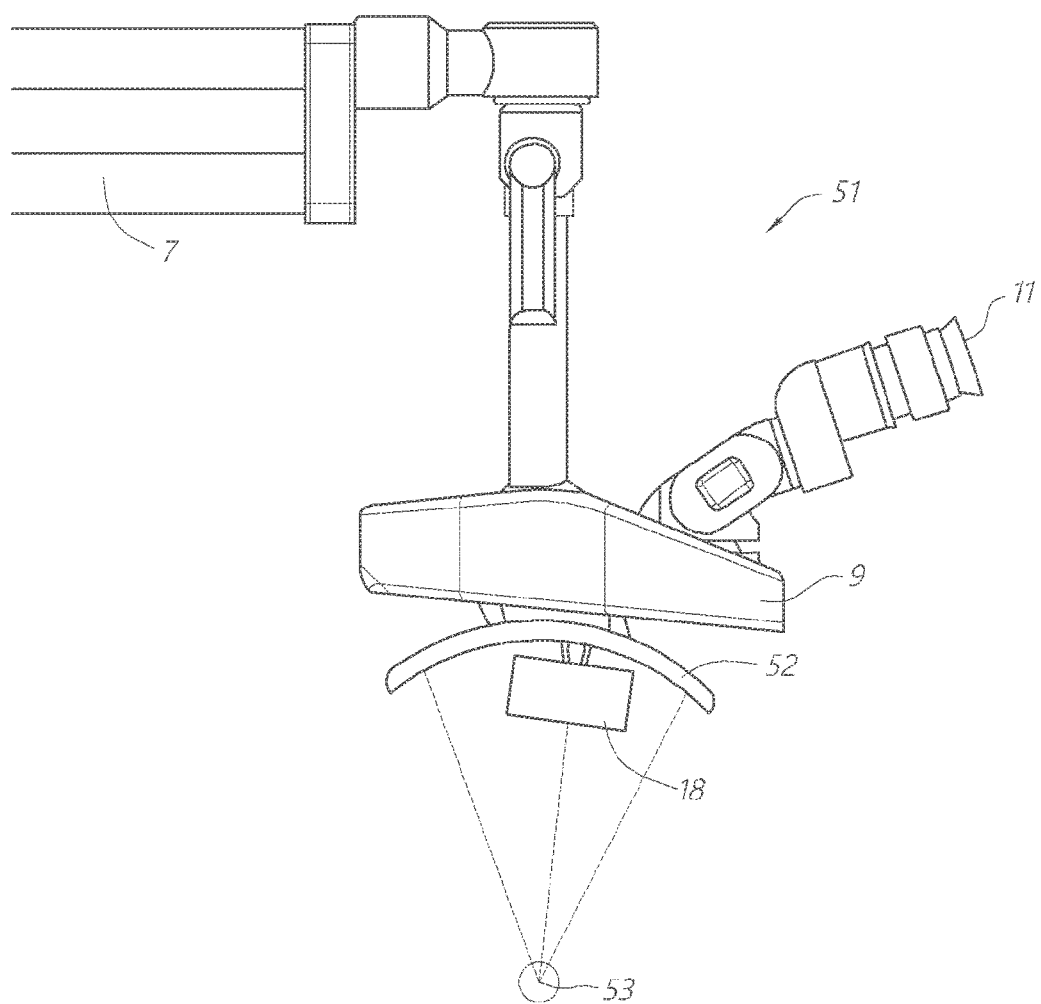
FIGS. 3A and 3B illustrate an example surgical viewing system that includes an isocenter positioning system attached to the binocular viewing platform.
Figure 3B:
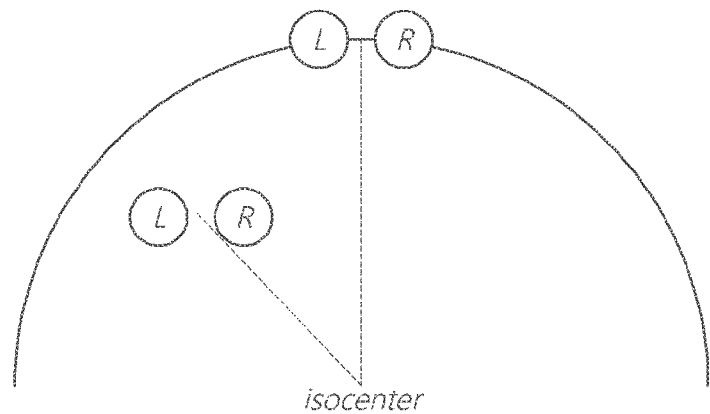

In some embodiments, as illustrated in FIG. 3A, the surgical imaging system 51 includes an isocenter positioning system 52 attached to the viewing platform 9. The isocenter positioning system 52 can include a single track or guide configured to move and orient the cameras 18 such that they are substantially pointed at a single point 53, the isocenter. In some embodiments, a second track or guide can be attached to the first guide in an orthogonal manner to provide movement along two dimensions while substantially maintaining the pointing angle towards the isocenter 53. Other configurations can be used to provide isocenter pointing capabilities, such as articulating arms, electro-mechanical elements, curved friction plates, etc. In some embodiments, as illustrated in FIG. 3B, the imaging system is configured to move in an isocenter manner. This can be used to enhance dexterity of the user of the system because hand-eye coordination is increased or maximized. Such enhanced dexterity can be vital for prolonged and/or difficult surgery. In the displayed embodiment, the horizons of the acquisition systems are configured to be horizontal to match the horizon of the display system and the user. As shown in FIG. 3B, in various embodiments, a stereo imaging system may be maintained in a horizontal configuration as it is moved across a range of locations to avoid confusion for the user viewing the video from the stereo camera. By maintaining a common relative horizon between the display and the acquisition system, the user can relatively easily translate hand motion to manipulation of objects in the display, which may not be the case where translation of the acquisition system is accompanied by a relative rotation between the display and the acquisition system.

In the embodiments illustrated in FIGS. 3A and 3B, the isocenter assemblies can be a part of the display system or a separate, independent system. For example, the viewing platform 9 can be mounted on a separate arm from the cameras 18. Thus, the display and the image acquisition of the surgical imaging system can be decoupled, similar to the embodiment illustrated in FIG. 1. By decoupling the isocenter cameras 18 from the display ergonomic benefits are provided such as, for example, the surgeon does not need to be looking through binoculars for an extended period of time or at an uncomfortable position or angle. In various embodiments, a common relative horizon for both the display and the acquisition system may also be employed.

In some embodiments, the distance between the surgical site of interest and the imagers, e.g., the working distance, can be at least about 20 cm and/or less than or equal to about 450 cm, at least about 10 cm and/or less than or equal to about 50 cm, or at least about 5 cm and/or less than or equal to about 1 m, although values outside this range are possible.

The user can interact with the surgical imaging system 51 to select a working distance, which can be fixed throughout the procedure or which can be adjusted at any point in time. Changing the working distance can be accomplished using elements on a user interface, such as a graphical user interface, or using physical elements such as rotatable rings, knobs, pedals, levers, buttons, etc. In some embodiments, the working distance is selected by the system based at least in part on the cables and/or tubing being used in the surgical visualization system. For example, the cables and/or tubing can include an RFID chip or an EEPROM or other memory storage that is configured to communicate information to the surgical imaging system 51 about the kind of procedure to be performed. For an ENT/Head/Neck procedure, the typical working distance can be set to about 40 cm. In some embodiments, the user's past preferences are remembered and used, at least in part, to select a working distance.

In some embodiments, the working distance can be changed by translating an imaging lens or imaging lenses along a longitudinal axis (e.g., a z-axis parallel to gravity). The imaging lens(es) can be translated in an orthogonal and/or transverse direction (e.g., x- and/or y-axis) to adjust a convergence angle with changes in the working distance. In this way, the viewing platform 9 and/or the position of the cameras 18 can remain relatively fixed with changes in working distance. This can also provide for stereoscopic image acquisition, thereby providing 3D video to the surgeon while being able to change working distance.

In some embodiments, gross focus adjustment can be accomplished manually by positioning the cameras 18 and arm 7. The fine focus adjustment can be done using other physical elements, such as a fine focusing ring, or it can be accomplished electronically.

In some embodiments, the magnification of the surgical imaging system 51 can be selected by the user using physical or virtual user interface elements. The magnification can change and can range between about 1× and about 6×, between about 1× and about 4×, or between about 1× and about 2.5×. Embodiments may be able to change between any of these such as between 2.5× and 6× or between 2.5× and 6×. Values outside these ranges are also possible. For example, the system 51 can be configured to provide magnification and demagnification and image inversion, with a range from about −2× to about 10×, from about −2× to about 8×, from about −2× to about 4×, from about −0.5× to about 4×, or from about −0.5× to about 10×. The surgical imaging system 51 can be configured to decouple zoom features and focus adjustments, to overcome problems with traditional operating room microscopes. In some embodiments, the surgical visualization system 51 can be used to provide surgical microscope views. In some embodiments, the surgical imaging system 51 can decouple instrument myopia by providing an electronic display instead of a direct view of a scene. The electronic displays can be configured to be focused at varying levels of magnification allowing the user to view the displays without adjusting the oculars between magnification adjustments. Moreover, in various embodiments, the oculars can be configured to provide continuous views at infinity. In some embodiments, however, the principal user of the surgical imaging system may select an accommodation level for the oculars, rather than using a relaxed view provided by the electronic displays. The electronic displays, in various embodiments, however, can remain in focus and the ocular adjustments do not affect the focus of the various video acquisition systems. Thus, adjustments by the principal user do not affect the views of the other users of the system viewing, for example, other displays showing the video, as the cameras/acquisition systems can remain focused. In some embodiments, the surgical imaging system 51 can be focused at a relatively close working distance (e.g., a distance with a relatively narrow depth of field) such that the image remains focused when moving to larger working distances (e.g., distances with broader depth of field). Thus, the surgical imaging system 51 can be focused over an entire working range, reducing or eliminating the need to refocus the system after magnification or zoom adjustments are made.

In some embodiments, the surgical imaging system 51 includes an afocal zoom assembly to provide changes in magnification. The afocal zoom assembly comprises an afocal system that can be used to provide variations in magnification at a fixed working distance and/or to provide variations in magnification with changes in working distance. In certain embodiments, the surgical imaging system 51 includes a common objective for left and right optical paths (e.g., left and right lens systems) corresponding to left and right imaging sensors configured to produce images for the left and right eyes of the user. The left and right lens systems can each comprise one or more lenses or lens groups disposed in each of the respective left and right paths. The common objective (e.g., a single lens, compound lens, or lens group) can be configured to have a focal length corresponding to a distance to the object. The afocal zoom assembly can thus receive collimated light from the objective and produce collimated light while changing a magnification of the optical system of the surgical imaging system 51. The zoom or variable magnification can provide selectable magnification or zoom. In certain embodiments, the surgical imaging system 51 includes a variable diaphragm to adjust the aperture of the optical system. The variable diaphragm can be adjusted to increase or decrease the f-number of the optical system or the variable diaphragm can be adjusted to maintain a relatively constant f-number with changes in the magnification of the optical system.

In some embodiments, the surgical imaging system 51 includes a zoom optical system that functions to change working distance and/or magnification. The surgical imaging system 51 can also include a zoom objective lens and one or more afocal zoom assemblies.

The surgical imaging system 51 can include a gimbal system to point the camera(s), for example, objective as desired. In various embodiments, the gimbal system is configured to provide isocentric views of the worksite or surgical site. The gimbal system can be configured to change the relative position and/or orientation of imaging optics to maintain a isocentric views. In some embodiments, the gimbal system can be configured to move the imaging system (e.g., the optical assembly) while maintaining the isocentric view while also maintaining the position and/or orientation of the oculars of the surgical imaging system 51 relatively motionless.

Figure 4A:
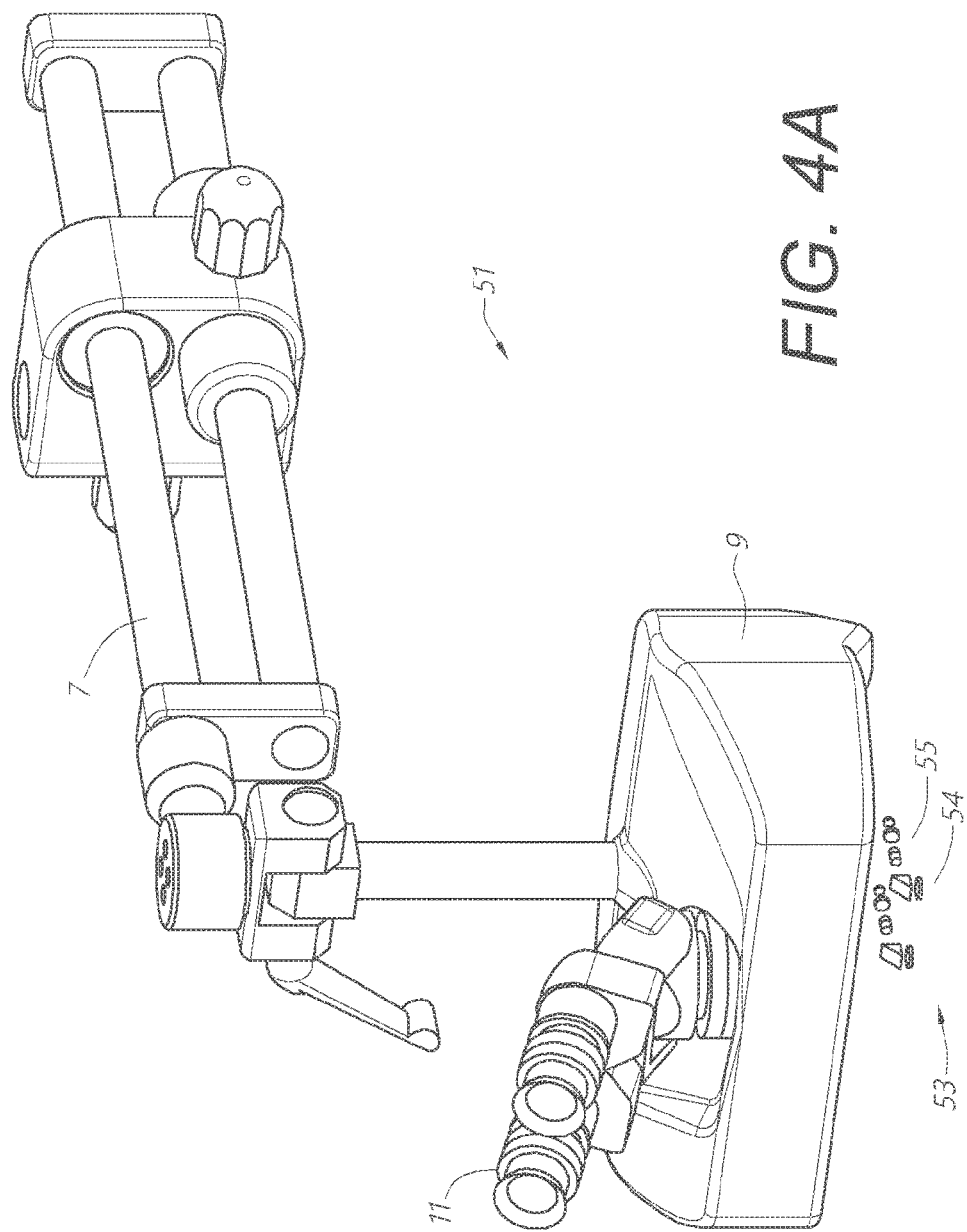
FIGS. 4A and 4B illustrate an embodiment of a surgical visualization system having an optical imaging system mounted under the binocular viewing platform.
Figure 4B:
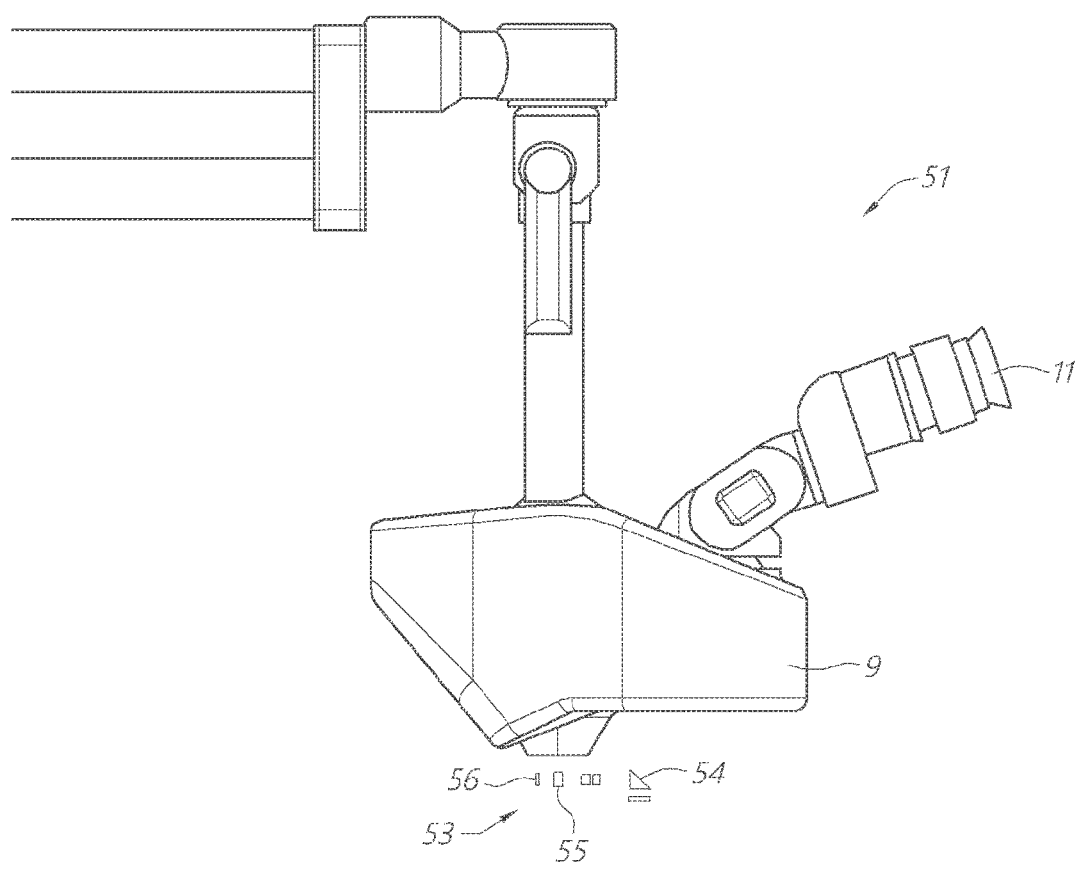

FIGS. 4A and 4B illustrate an embodiment of the surgical imaging system 51 having an optical system 53 mounted under the viewing platform 9. As illustrated, the optical components are shown as free-standing to show the structure of the components, but in practice the optical components 53 will be mounted within or on a structure attached to the viewing platform. In some embodiments, the optical system 53 and/or the cameras 18 (discussed above) can be modular and can be selected and swapped for use with the surgical imaging system 51.

The optical system 53 is configured to provide stereo image data to the imaging system 51. The optical system 53 includes a turning prism 54 to fold the optical path underneath the viewing platform 9 to decrease the physical extent (e.g., length) of the imaging system under the viewing platform 9. The turning prism 54 can be configured to fold the optical path from vertical to horizontal. This design can reduce the thickness (e.g., vertical dimension) of the optical system 53. This configuration can also reduce the size of any housing used to house the optical system 53. This approach can also reduce the size of the viewing platform 9, for example, where the optical system is incorporated into the housing of the viewing platform 9.

The optical system 53 can include, in some embodiments, an objective lens or objective lens group, an afocal zoom lens group, an imaging lens or lens group, and an image sensor or other similar detector. The afocal zoom lens group can be adjusted or manipulated to receive and produce a collimated beam wherein the adjustments alter the zoom or magnification of the optical system 53. The optical system 53 can include a common objective lens or objective lens group for both right and left optical paths (e.g., corresponding to right and left eye views for a stereoscopic display). Alternatively, the optical system 53 can include a separate objective lenses or lens groups for both right and left optical paths (e.g., corresponding to right and left eye views for a stereoscopic display). In various embodiments, the objective provides a collimated beam to the afocal zoom. The afocal zoom may also output a collimated beam in certain embodiments. In some embodiments, the optical system 53 is configured to translate the imaging lens or imaging lens group along a longitudinal axis or vertical axis (e.g., a z-axis) to change the working distance. The optical system 53 can also be configured to translate the imaging lens or imaging lens group along a transverse or horizontal axis (e.g., a x- and/or y-axis) to alter the convergence angle. In some implementations, alterations of the convergence angle correspond to changes in the working distance to maintain appropriate convergence at a targeted location or distance. For example, as the working distance decreases, the convergence angle can be made to increase. In certain embodiments, the convergence angle of the optical system 53 can be about 3 degrees at about 300 mm working distance, or between about 2 degrees and about 5 degrees at between about 150 mm and about 500 mm working distance, or between about 1 degree and about 10 degrees at between about 50 mm and about 1000 mm working distance. Values outside these ranges are also possible.

In some embodiments, the optical system 53 includes a zoom optical system that functions to change working distance and/or magnification. The optical system 53 can also include a zoom objective lens and one or more afocal zoom assemblies.

In some embodiments, the optical system 53 comprises a Greenough-style system wherein the optical paths for each eye have separate optical components. In some embodiments, the optical system 53 comprises a Galilean-style system wherein the optical paths for each eye pass through a common objective. The Greenough-style system may be preferable where imaging sensors are being used to capture and convey the image data as compared to the Galilean-style system. The Galilean system can introduce aberrations into the imagery by virtue of the rays for each eye's optical path passing through a periphery of the objective lens. This does not happen in the Greenough-style system as each optical path has its own optics. In addition, the Galilean system can be more expensive as the objective used can be relatively expensive based at least in part on the desired optical quality of the lens and its size.

The optical system 53 can include two right-angle prisms 54, two zoom systems 55, and two image sensors 56. This folding is different from a traditional operating room microscope because the optical path leads to image sensors rather than to a direct-view optical system.

In some embodiments, the optical system 53 can have a relatively constant F-number. This can be accomplished, for example, by varying the focal length and/or aperture of the system based on working distance and/or magnification. In one embodiment, as the focal length changes, the eye paths can move laterally apart (or together), the prisms 54 can rotate to provide an appropriate convergence angle, and the apertures can change their diameters to maintain the ratio of the focal length to the diameter a relatively constant value. This can produce a relatively constant brightness at the image sensor 56, which can result in a relatively constant brightness being displayed to the user. This can be advantageous in systems, such as the surgical visualization systems described herein, where multiple cameras are being used and changing an illumination to compensate for changes in focal length, magnification, working distance, and/or aperture can adversely affect imagery acquired with other cameras in the system. In some embodiments, the illumination can change to compensate for changes in the focal length and/or the aperture so as to provide a relatively constant brightness at the image sensors 56. In some embodiments, illumination can be provided through the objective lens or objective lens group of the optical assembly 53.

The optical assembly 53 can include a zoom system 55 configured to provide a variable focal distance and/or zoom capabilities. A Galilean-style stereoscopic system generally includes a common objective for the two eye paths. When this optical system is imaged with image sensors 56, it can create aberrations, wedge effects, etc. that can be difficult to compensate for. In some embodiments, the surgical imaging system 51 can include a Galilean-style optical system configured to re-center at least one of the stereo paths to a central location through the objective lens, which can be advantageous in some applications.

In some embodiments, the real-time visualization system utilizes a Greenough-style system. This can have separate optical components for each stereo path. The optical assembly 53 can be configured to provide variable magnification and/or afocal zoom and can be configured to operate in a magnification range from about 1× to about 6×, or from about 1× to about 4×, or from about 1× to about 2.5×.

The distal-most portion of the Greenough assembly 53 can be similar in functionality to an objective lens of a typical, direct-view operating room microscope with the working distance set approximately to that of the focal length. The working distance, and in some implementations the focal length, can be between about 20 cm and about 40 cm, for example. In some embodiments the work distance may be adjustable from 15 cm to 40 cm or to 45 cm. Other values outside these ranges are also possible. In some embodiments, the surgical imaging system 51 includes an opto-mechanical focus element configured to vary the focal length of a part of the optical assembly 53 or the whole optical assembly 53.

Figure 5A:
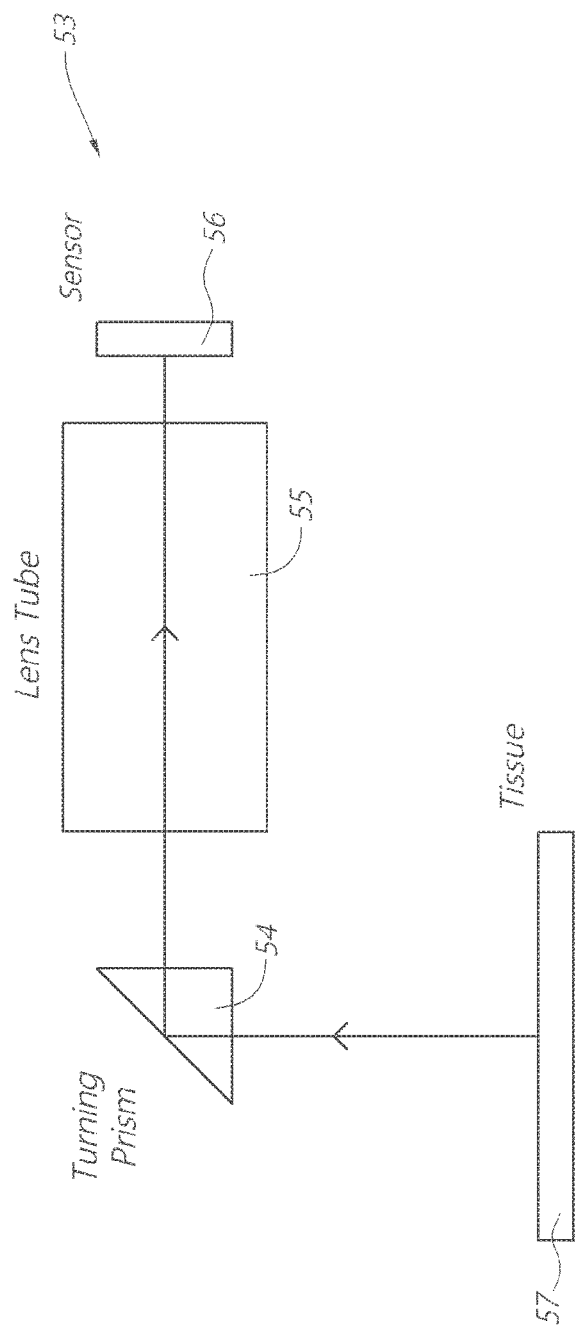
FIG. 5A illustrates an example embodiment of an optical imaging system for use in a stereoscopic surgical viewing system, such as those illustrated in FIGS. 4A and 4B.

FIG. 5A illustrates an example embodiment of an optical assembly 53 for use in a stereoscopic surgical imaging system, such as those described herein with reference to FIGS. 4A-4B. FIG. 5A illustrates a side view of an example optical assembly 53 configured to use a turning prism 54 to fold an optical path from a tissue 57 to a sensor 56 along a lens train 55 that is situated near or adjacent to a viewing platform 9. This can advantageously provide a relatively long optical path in a relatively compact distance.

In some embodiments, the optical assembly 53 includes a source of illumination, such as a fiber optic or light emitting diode (LED) or other type of light source providing light through one or more of the optical elements of the optical assembly 53. In certain implementations, the light source (e.g., fiber optic, LED, etc.) provides illumination through the objective lens or objective lens group to provide illumination to the worksite. (A beamsplitter or beam combiner may be used to couple light into the optical path or the light source may itself be disposed in the optical path.) This arrangement can be useful as the light from the light source (e.g., fiber optic, LED, etc.) can be directed to the worksite along a similar optical path as light arriving from the worksite. This configuration can help the user to control the location and/or amount of illumination provided by the light source (e.g. fiber optic, LED, etc.). For example, the user can direct the illumination to the same location that the user is viewing. As another example, changes in the relative positions of the objective lens and light source (e.g., fiber optic, LED, etc.) can change the divergence of the light to increase or decrease the amount of light per unit area at the worksite. As another example, changes in the focal length of the objective lens group can change the divergence of the light from the light source (e.g., fiber optic, LED, etc.) to control illumination at the worksite. In some embodiments, additional optics such as beam shaping optics may be included for the light source. One or more lenses may for example be disposed forward of the fiber optic or LED or other light source and may be adjustable, to control divergence and/or beam size.

In some embodiments, the source of illumination can be controlled using a gimbal. The light source may be mounted on a gimbal or one or more other translation/rotation devices to provide the ability to controllably redirect the beam into different directions. The gimbal or other orientation control device may be moved manually or have electrically driven actuators to control movement of the system and the direction of the beam. The gimbal can be used to provide illumination with variable pitch. The gimbal can also be used to steer the illumination to provide light at a targeted location, with a targeted intensity, and/or from a desired or selected angle.

Multiple light sources may be employed. These multiple light sources may, for example, be on opposite sides of the optical path. In some embodiments, different light sources are mounted on different gimbals (or motion and/or orientation control systems) such as described above and elsewhere herein. Accordingly, a plurality of beams may be controlled so that a first beam from a first light source may be directed in a first direction (possibly using a first gimbal system) and a second beam from a second light source may be directed in a second different direction (possibly using a second gimbal system) and the first and second light sources and directions can be separately changed subsequently. In some embodiments, the size of the beam at the object is less than the field of view of the camera imaging the object. The multiple light sources can be used to fill a larger portion of that field of view that is larger than the beam from a single light source. In various embodiments, the plurality of beams from the plurality of light sources fills at least as large as the field of view of the one or more cameras imaging the object.

In various embodiments, as the optical assembly changes zoom or magnification, the illumination from the light source (e.g., fiber optic or LED) can change. For example, variable divergence of the illumination can accompany changes in zoom of the optical assembly 53 to place more light energy in an area for imaging that area. In some implementations, the fiber optic illumination source can be adjusted to maintain a relatively constant divergence with changes in zoom of the optical assembly 53 by placing the illumination at a place in the optical assembly 53 or elsewhere where the optical properties remain relatively constant with changes in zoom.

In some embodiments, the optical assembly 53 can include a common objective lens with one or more zoom lenses (e.g. Galilean configuration) or can have separate objectives for separate left and right optical paths (e.g., Greenough configurations) with the fiber optic illumination or other illumination. This arrangement can be used to transform the effective numerical aperture of the fiber optic (or other type of light source) to achieve targeted or desired illumination effects. In some embodiments, the source of illumination is remote from the optical assembly 53 and may be delivered to the worksite through the fiber optic. In other embodiments, however, as described above, instead of employing a fiber optic, a light source such as a light emitting diode (LED) or other emitter (e.g., solid state emitter), with or without beam shaping optics (e.g., one or more lenses) can be employed instead of a fiber. One or more fibers and one or more light sources (such as multiple LEDs) can be employed, for example, at different location such as on opposite sides of the optical path or surgical site. Similar combination of one or more fiber and one or more light source such as one or more LEDs can be used. As described above, these can be included in the optical system in some embodiments such that the light from the fiber or light source propagates through the camera optics used for imaging (e.g., objective, afocal zoom, and/or imaging lens) to illuminate the surgical site or a portion thereof. In various embodiments, the light from the light source propagates through the objective (and not the afocal zoom and/or imaging lens) prior to being incident on the object. Such a configuration can reduce the amount of back reflected from the optical surfaces that results in light incident on the sensor. In various embodiments, a beam splitter or beam combiner (e.g., prism) may be use to couple the illumination beam into the optical path of the camera. In other cases, the light source may be disposed itself in the optical path. In some embodiments the light source (e.g., fiber, LED, etc.) is disposed adjacent to the camera and does not couple light such that the light propagates through the camera optics prior to being incident on the surgical site.

Light sources may be used in connection with providing illumination of the object for the one or more proximal cameras disposed above the surgical site or body by, e.g., 25-40 mm, for one or more cameras mounted on a surgical tool, as well as for one or more cameras that provide a surgical microscope view, for other cameras or for any combination thereof. The light sources and illumination configurations including for example the gimbals or other positioning orientation devices may be useful for any of these applications (e.g., one or more proximal cameras, one or more cameras on a surgical tool(s), etc.) and may be used for other types of cameras (stereo or otherwise) as well. As discussed above, the cameras may have a Galilean or Greenough like configuration and illumination may be provided through at least a portion of the camera optics (e.g., one or more camera lenses) in either the left or right channels or both in the case of stereo cameras.

Movement Control System

Figure 6A:
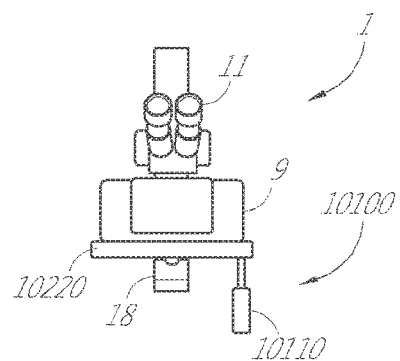
FIG. 6A is a front view of an embodiment of a surgical visualization system, a movement control system, and an imager.
Figure 6A:
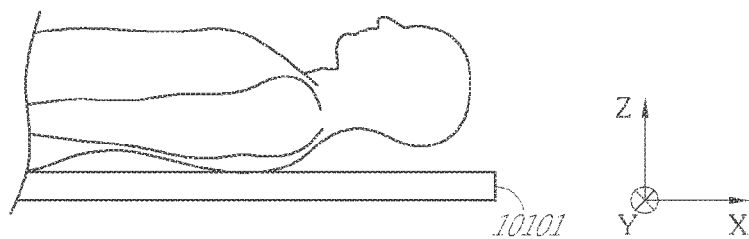
Figure 6B:
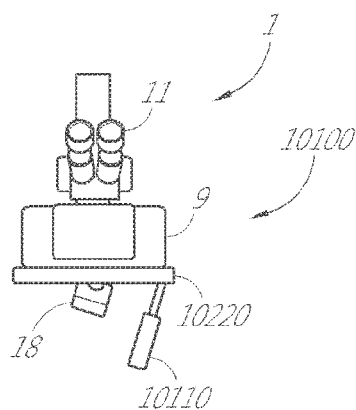
FIG. 6B is a front view of the embodiment of FIG. 6A with the movement control system and imager shifted.
Figure 6B:
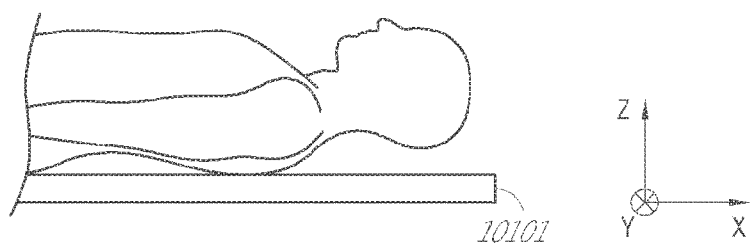
Figure 6C:
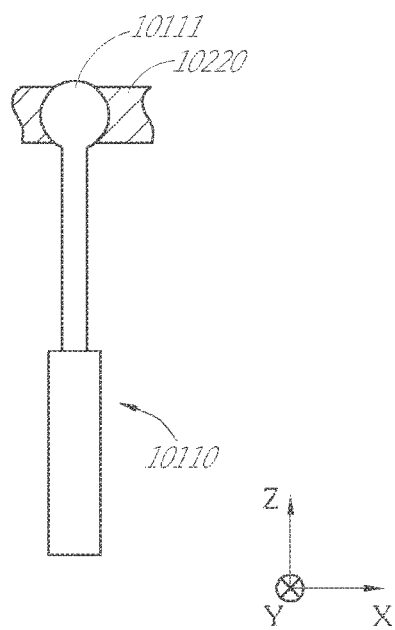
FIG. 6C is a partial section view of the embodiment of a movement control system of FIG. 6A.

FIGS. 6A-C illustrate embodiments of components of a movement control system 10100 that can be configured to allow an operator of the surgical visualization system 1, such as a medical professional or assistant, to control the movement of one or more imagers 18. Such imagers may comprise cameras that provide a surgical microscope view through the oculars 11 or eyepieces of the binocular display unit 9. In various embodiments, the movement control system can enable the imagers 18 to be moved without changing the positioning of oculars 11, and thus an operator can remain in an ergonomic position while changing the view provided by the imager 18. The imager 18 can be on the binocular display unit 9 or located elsewhere such as on a separate platform or articulated arm. Additionally, unlike conventional articulated optical systems which are generally unwieldy, complex, and have the potential for introducing optical aberrations, use of the movement control system 10100 with the surgical visualization system 1 can result in a simplified system with greater optical clarity and range of movement. It should be appreciated by one of skill in the art that, while the description of the movement control system 10100 is described herein in the context of medical procedures, the movement control system 10100 can be used for other types of visualization and imaging systems. Movement of the imagers 18 can be performed prior to and/or during the activity, such as surgical procedures, dental procedures, and the like. Movement of the imagers 18 can advantageously allow a medical professional or other operator to alter the view through oculars 11, for example, to provide different surgical microscope-like electronic visualizations which might be beneficial during the course of a medical procedure or for different surgical procedures.

In some embodiments, control of the movement of the imager 18 can be achieved using a single control member such as 10110. This provides the advantage of allowing single-handed operation of the movement control system 10100 which can, for example, allow a medical professional to move one or more imagers 18 using only one hand while using a second hand for other tasks such as performing surgical techniques. It should be appreciated by one of skill in the art that, while the description of the movement control system 10100 is described herein in the context of medical procedures, the movement control system 10100 can be used for other types of visualization and imaging systems.

Operation

As illustrated in FIGS. 6A-C, in some embodiments, the control member, such as a joystick, 10110 can be used to translate the imager 18, adjust the pitch, yaw, and/or roll of the imager 18, and/or adjust the working distance of the imager 18. In some embodiments, the oculars 11 can remain immobile when translating the imager 18, adjusting the pitch, yaw, and/or roll of the imager 18, and/or adjusting the working distance of the imager 18. The ability for a single control member 10110 to control translation, adjustments to pitch and/or yaw, and/or adjustments to the working distance can beneficially simplify operation of the device as an operator need not release the control member 10110 to control multiple aspects of its operation. For example, an operator can translate the imager 18 and subsequently adjust the pitch and/or yaw without having to release the control member 10110 thereby increasing ease-of-use of the system and enhancing efficiency when using this system.

As shown in FIG. 6C, one or more control members of the movement control system 10100, such as control member 10110, and/or one or more imager arms (see FIG. 7) can be attached to a component of the movement control system 10100 using various types of joints and/or can be remote from the movement control system 10100 such as a remote joystick or toggle. In some embodiments, the control member 10110 can include a joint for attachment to the movement control system 10100. For example, as shown in the illustrated embodiment, control member 10110 can include joint 10111. In some embodiments, one or more of the joints can include components for detecting movement of the control member and/or an imager arm. For example, one or more of the joints can include one or more sensors for detecting rotation and/or translation of the control member and/or the imager arm about the joint. The signals from these sensors can be used to control other components of the movement control system, such as one or more electromechanical components.

For purposes of this disclosure, rotation about joints, such as joint 10111, around the x-axis is hereinafter termed "pitch" or "tilt" and rotation about joints, such as joint 10111, around the y-axis is hereinafter termed "yaw" or "pan."

As shown in the illustrated embodiment, the joint 10111 can be spherical joints received in a socket formed in the member 10220 thereby forming a ball-and-socket attachment. As should be apparent to one of ordinary skill in the art, other types of mounting mechanisms may be used for attaching control member 10110 as well as an imager arm to components of the movement control system 10100. For example, joints such as gimbals can be used which limit the rotational degrees of freedom about the gimbal. Other types of joint can be used depending on the types of movement the movement control system is designed to allow. For example, if only pitch is needed without yaw, one can use a joint having a single rotational degree of freedom. In some embodiments, the control member 10110 can be positioned remotely from the movement control system 10100.

General Embodiment

With continued reference to FIGS. 6A and 6B, in some embodiments, the movement control system 10100 can be attached to an attachment structure, such as binocular display unit 9, and support one or more imagers 18. As shown in the illustrated embodiment, the movement control system 10100 can be oriented generally underneath the binocular display unit 9 and in some embodiments can be sized such that the movement control system 10100 does not extend significantly beyond the outer housing of the binocular display unit 9. This can advantageously provide a smaller form factor thereby reducing the likelihood that the movement control system 10100 will interfere with the medical professionals and assistants during a medical procedure. In other embodiments, the attachment structure can be other components of the surgical visualization system 1 such as, but not limited to, a dedicated articulating arm or a display arm. In some embodiments, the movement control system 10100 can extend significantly beyond the outer housing of the binocular display unit 9 or any other platform to which it is attached. This can be advantageous in situations where a greater degree of movement of the imagers 18 is desired or in embodiments where the control member 10110 is located above the attachment point between the movement control system 10100 and binocular display unit 9.

With continued reference to FIGS. 6A and 6B, as discussed in part above, the movement control system 10100 can be configured to allow translation of one or more attached imagers 18 along a plane relative to the binocular display unit 9. In some embodiments, the binocular display unit 9 can be immobile while the one or more imagers 18 are translated. For example, when attached to the binocular display unit 9 with the movement control mechanism 10100 parallel to an operating table 10101, the one or more imagers 18 can be translated along a plane parallel to the operating table 10101. As shown in the illustrated embodiment, the movement control system 10100 can be translated along both the x-axis and the y-axis (which projects perpendicularly through the sheet). This can advantageously allow the medical professional to position the view of oculars 11 for comfortable viewing by the surgeon thereby reducing physical strain on the surgeon during long procedures.

In some embodiments, defining an imager 18 centered on the movement control system 10100 (as shown in FIG. 6A) as having an x-axis, y-axis, and z-axis coordinate of zero, the movement control system 10100 can have a range of translation relative to the binocular display unit 9, of approximately ±500 mm along the x-axis and y-axis at full extension, approximately ±400 mm along the x-axis and y-axis at full extension, approximately ±300 mm along the x-axis and y-axis at full extension, approximately ±200 mm along the x-axis and y-axis at full extension, or approximately ±100 mm along the x-axis and y-axis at full extension. In some embodiments, full extension along one axis can be greater than full extension along the other axis. For example, in some embodiments, full extension along the x-axis may be approximately ±175 mm whereas the y-axis extension can be three-quarters full extension of the x-axis, one-half full extension of the x-axis, one-quarter full extension of the x-axis, or any other ratio between unity and zero. In some embodiments, the range of translation relative to the binocular display unit 9 along the y-axis can be approximately ±87.5 mm. This can be advantageous in cases where allowing the y-axis to have a full range of motion may interfere with the medical professional and/or assistants.

These ratios can be reversed such that the range of translation of the x-axis can be three-quarters full extension of the y-axis, one-half full extension of the y-axis, one-quarter full extension of the y-axis, or any ratio between unity and zero. Additionally, in some embodiments, the imager 18 can translate further in the "positive" direction than the "negative" direction. For example, along the x-axis, the imager 18 may move from −100 mm to 500 mm. Ranges of motion outside these ranges are also possible. As should be apparent to one of ordinary skill in the art, the maximum translation relative to the binocular display unit 9 along the x-axis and y-axis can be chosen to provide a balance between greater maneuverability, the yaw and/or pitch angles, working distances, size constraints, and other such factors.

As described in part above and as will be discussed in greater detail below, in some embodiments, translation of the imagers 18 can be performed by translating one or more control members, such as control member 10110, in the desired direction. In some embodiments, the control member 10110 can be electrically coupled to the movement control system 10100 to provide translation via an electromechanical system utilizing stepper motors, linear motors, or the like. For example, a joint of the control member 10110 can include components for detecting translation of the control member 10110. The signals from these sensors can be used to control other components of the movement control system, such as one or more electromechanical components such as stepper motors, linear motors, or the like to translate the imager 18. The electromechanical components can be coupled to a moveable platform to which the imager 18 can be attached. In some embodiments, the control member 10110 can be physically connected to the movement control system 10100 without any electromechanical assistance.

As should be appreciated by one of ordinary skill in the art, the movement control system 10100 need not translate solely along a plane parallel to the operating table 10101 or the x-y plane as set forth in the illustrated embodiment. In some embodiments, the plane of translation can be defined by the orientation of the mount to which the movement control system 10100 is connected. In some embodiments, the movement control system 10100 can be configured for non-planar translation and/or translation along more than one plane. In some embodiments, for example, a tip and tilt stage provides angular motion. A rotary stage can also be used to provide rotary motion.

With continued reference to FIGS. 6A and 6B, as described in part above, the movement control system 10100 can be configured to allow rotation of the one or more attached imagers 18 about a joint which can be attached to components of the movement control system 10100 and/or remotely from the movement control system 10100. In some embodiments, the movement control system 10100 can be designed to allow the control member, such as control member 10110, as well as the imager 18 and/or imager arm to "pitch" or "tilt" and "yaw" or "pan" relative to the binocular display unit 9. In some embodiments, the binocular display unit 9 can be immobile while the "tilt" and "yaw" or "pan" of the one or more imagers 18 are adjusted. Pitch or yaw can allow the imager 18 to have a line of sight that is centered (e.g., focused) on the surgical site after the imager 18 is translated. This can advantageously allow the medical professional or assistant to adjust the viewing angle during a medical procedure. This can be beneficial in circumstances where a medical professional is unable to adequately view an object due to another element obstructing the view. Under such circumstances, a medical professional can translate the imager 18 and adjust the viewing angle of the imager 18 such that the same general area is viewed from a different angle.

In some embodiments, defining an imager 18 in a perpendicular orientation to the movement control system 10100 (as shown in FIG. 6A) as having an a pitch and yaw of zero (i.e., as shown in FIG. 6A), the movement control system 10100 can allow both pitch and yaw adjustments relative to the binocular display unit 9 within the range of approximately ±60 degrees each, by approximately ±50 degrees each, by approximately ±40 degrees each, by approximately ±30 degrees each, by approximately ±20 degrees each, or approximately ±10 degrees each. In some embodiments, the pitch and yaw can have different adjustment ranges. For example, in some embodiments, the yaw can have an adjustment range of approximately ±40 degrees whereas the pitch can have an adjustment range of approximately three-quarters that of the yaw, one-half that of the yaw, one-quarter that of the yaw, or any other ratio between unity and zero. In some embodiments, the pitch can have an adjustment range of approximately ±20 degrees.

The adjustment range of yaw and pitch can correspond to the distance at full extension along both the x-axis and the y-axis. For example, in some embodiments, the pitch and yaw can be chosen such that the imager 18 can remain centered on the surgical site when the movement control system 10100 is fully extended in any direction. In some embodiments, the working distance between the imager 18 and the surgical site can be approximately 200 mm, with a range of translation along the x-axis of approximately ±175 mm, and a range of translation along the y-axis of approximately ±87.5 mm. In order to remain centered on the surgical site, the pitch adjustment range can be ±20 degrees and the yaw adjustment range can be ±40 degrees. As such, because the full extension need not be the same in both directions, the pitch and yaw adjustment ranges can also be different to match the differences in extension. In other embodiments, such as those in which the working distance can be adjusted, the pitch and yaw adjustment range can be chosen such that the imager 18 can remain centered on the surgical site when the movement control system 10100 is fully extended in any direction at least one working distance. For example, in embodiments where the working distance can be adjusted between approximately 200 mm and 400 mm, the pitch and yaw adjustment range can be approximately ±20 degrees and approximately ±10 degrees respectively to allow centering at a working distance of 400 mm.

Additionally, in some embodiments, the imager 18 can adjust further in a "positive" angle than a "negative" angle. For example, the yaw may range from −5 degrees to 15 degrees.

As described in part above and as will be discussed in greater detail below, in some embodiments, increasing or decreasing the pitch and/or yaw of the imagers 18 relative to the binocular display unit 9 can be achieved by increasing or decreasing the pitch and/or yaw of the one or more control members, such as control member 10110. In some embodiments, the control member 10110 can be electrically coupled to the movement control system 10100 to provide pitch and yaw via an electromechanical system utilizing stepper motors, linear motors, or the like. For example, a joint of the control member 10110 can include components for detecting pitch and/or yaw of the control member 10110. In some embodiments, the joint of the control member 10110 can be gimbals which can detect pitch and/or yaw of the control member 10110. The signals from these sensors can be used to control other components of the movement control system, such as one or more electromechanical components such as stepper motors, linear motors, or the like to adjust the pitch and/or yaw of the imager 18. As should be appreciated by one of ordinary skill in the art, in some embodiments, the movement control system 10100 can be configured to allow rotation along other axes such as the z-axis. In some embodiments, the control member 10110 can be physically connected to the movement control system 10100 without any electromechanical assistance.

Additionally, in some embodiments, the movement control system 10100 can be configured to adjust the working distance between the imagers 18 and the surgical site. In some embodiments, the binocular display unit 9 can remain immobile while the working distance of the imagers 18 is adjusted. In some embodiments, the working distance can range from between approximately 1 m to approximately 10 mm, from between approximately 800 mm to approximately 50 mm, from between approximately 600 mm to approximately 100 mm, or from between approximately 400 mm to approximately 200 mm. In some embodiments, the control member 10110 can be electrically coupled to the movement control system 10100 to provide working distance adjustment via an electromechanical system utilizing stepper motors, linear motors, or the like. For example, a joint of the control member 10110 can include components for detecting rotation of the control member 10110 about the longitudinal axis. The signals from these sensors can be used to control other components of the movement control system, such as one or more electromechanical components such as stepper motors, linear motors, or the like to adjust the pitch and/or yaw of the imager 18. In some embodiments, the control member 10110 can be physically connected to the movement control system 10100 without any electromechanical assistance.

In some embodiments, the movement control system 10100 can include a translation system for translating an imager 18 and/or an imager arm, a pitch-yaw adjustment system for adjusting the pitch and/or yaw of the imager 18 and/or an imager arm, a control member, such as control member 10110, and one or more imager arms to which the imager 18 can be attached. In some embodiments, a working distance adjustment system can be included which can allow adjustments in working distance of the imager 18 and/or an imager arm. It should be appreciated by one of ordinary skill in the art that the translation system, the pitch-yaw adjustment system, and/or the working distance adjustment system can be used separately or in any combination.

Operation of the translation, pitch-yaw adjustment, and/or working distance adjustment systems can be performed using a control member, such as control member 10110. In some embodiments, control member 10110 can be operatively coupled to the translation, pitch-yaw adjustment, and/or working distance adjustment systems. For example, as described above, in some embodiments, the control member can be coupled to an electromechanical system for controlling the translation, pitch-yaw adjustment, and/or working distance adjustment systems. The control member can be directly attached to a component of the movement control system 10100 or can be remotely positioned (e.g., a toggle or joystick on a separate module). In some embodiments, the control member can be coupled directly to the translation, pitch-yaw adjustment, and/or working distance adjustment systems such that no electromechanical devices are used. In some embodiments, the operator can be given the option of controlling the translation, pitch-yaw adjustment, and/or working distance adjustment systems with or without electromechanical devices. For example, the operator can control the translation, pitch-yaw adjustment, and/or working distance adjustment systems without electromechanical devices for certain portions of a procedure and use such electromechanical devices for controlling the translation, pitch-yaw adjustment, and/or working distance adjustment systems during other portions of a procedure. As another example, in some embodiments coarse control of the movement control system 10100 can be achieved without use of electromechanical devices whereas fine control of the movement control system 10100 can be achieve with use of electromechanical devices, vice-versa, or a combination of the two.

In some embodiments, the movement control system 10100 can include a control system which controls functions of the electromechanical devices. In some embodiments, the electromechanical components can be programmed such that the electromechanical components can orient the translation, pitch-yaw adjustment, and/or working distance adjustment systems in certain positions based on the operator's input. For example, the electromechanical components can be programmed such that it goes to reverts back to a pre-set or previous position upon receiving a command from the operator. As another example, the electromechanical components can be programmed such that an operator can specify a desired position for the imager 18 and the control system can control the electromechanical devices coupled to the translation, pitch-yaw adjustment, and/or working distance adjustment systems orient the imager 18 in the desired position.

Figure 7:
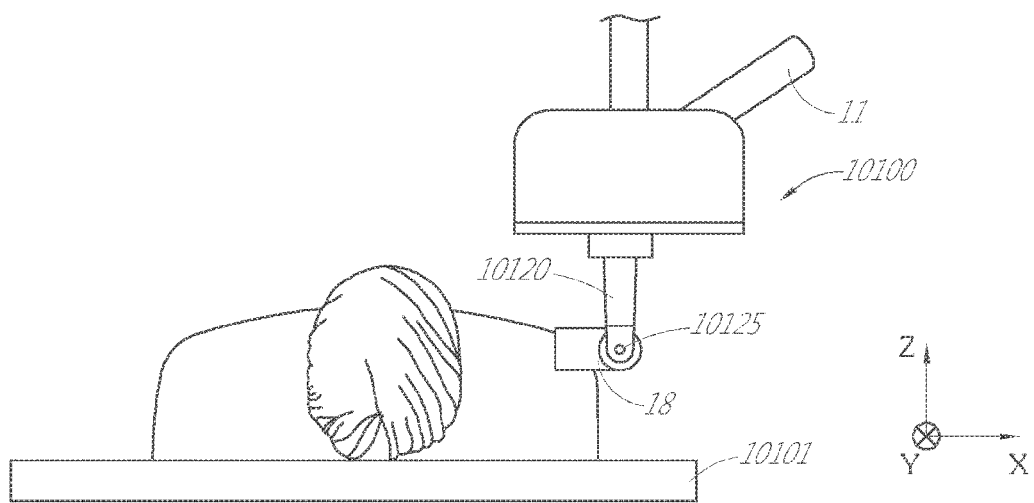
FIG. 7 is a side view of an embodiment of a surgical visualization system, a movement control system, and an imager.

With reference to FIG. 7, in some embodiments, the imager arm 10120 and the imager 18 can be attached such that the imager 18 can be directed towards the side of the head of a patient. For example, in some embodiments, the imager 18 can be attached to the imager arm 10120 using a yoke 10125 which can be designed to allow for coarse and/or fine control of pitch, yaw, and/or roll of the imager 18. In some embodiments, the yoke 10125 can have one or more pivots which can be configured to allow the imager 18 to have a viewing angle parallel to the operating room floor such that an operator can view the side of the head. In some embodiments, the yoke 10125 can be configured to allow the imager 18 to rotate such that the imager can be directed to a portion of the back of the head.

Figure 8:
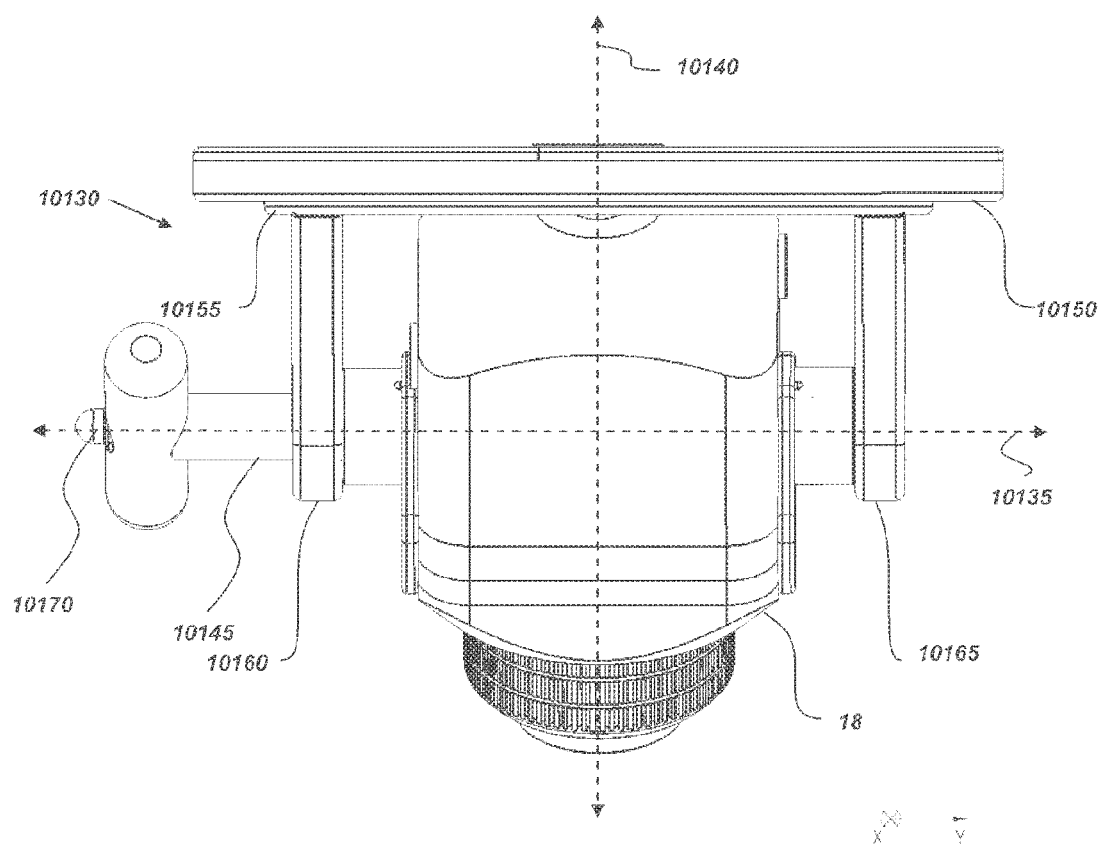
FIG. 8 is a rear view of an embodiment of an embodiment of a movement control system.

In some embodiments, the imager 18 can be positioned on a movement control system 10130 providing at least two rotational degrees of freedom and/or at least one translational degree of freedom. In some embodiments, movement control system 10130 can provide two rotational degrees of freedom and at least two translation degrees of freedom. For example, as shown in FIG. 8, the movement control system 10130 can allow for rotation along axis 10135 of the movement control system 10130 and/or along axis 10140 (which can be parallel with the z-axis). Moreover, as shown in the illustrated embodiment, the movement control system can allow translation along both the x-axis and y-axis. In some embodiments, apparatus 10130 can provide at least one translational degree of freedom.

As shown in the illustrated embodiment, the movement control system 10130 can include a one or more control members, such as control member 10145. Control member 10145 can be positioned such that the longitudinal axis of the control member 10145 is parallel with and/or collinear with axis 10135. This can advantageously allow the imager 18 to be rotated about axis 10135 by rotating the control member 10145. In some embodiments, the control member 10145 can be mechanically coupled to the imager 18. In some embodiments, the control member 10145 can be coupled to the imager 18 via an electromechanical system. For example, the control member 10145 can include sensors for detecting rotation of the control member 10145 and use data received from the sensors to rotate the imager 18 via electromechanical components such as stepper motors, linear motors, or the like.

As shown in the illustrated embodiment, the movement control system 10130 can include a first plate element 10150 and a second plate element 10155 which can be rotatable coupled. The second plate element 10155 can include first and second supports 10160, 10165 to which the imager 18 can be attached. In some embodiments, the first and second plate elements 10150, 10155 can be rotatable coupled such that the axis of rotation of the two plate elements 10150, 10155 is parallel and/or collinear with axis 10140.

In various embodiments, the gimbal advantageously allows movement of the camera without movement of the display such as the binocular display. Such movement can include pitch or yaw, as well as possibly, x, y, or z motion or any combination thereof. Despite such movement of the camera that provides surgical microscope views, the binocular display need not move similarly. Accordingly, in various embodiments a joint is provided between the camera and binocular display that permits pitch or yaw, as well as possibly, x, y, or z or any combination thereof of the stereo surgical microscope view camera without requiring the same motion (include pitch or yaw, as well as possibly, x, y, or z or any combination thereof) of the binocular display. The binocular display is thus decoupled from the camera. Such a decoupling of motion is possible, even if the camera is connected to the binocular display. For example, the camera may move laterally in the x direction and or up and down in the y direction or may be rotated about the x or y axis to introduce yaw and/or to introduce pitch, however, the binocular display (and the oculars) need not move similarly or need not move at all such that the surgeon need not reorient his or her head to view the images on the display. Movement and/or positioning and/or orientation control systems, other than gimbal systems may be employed as well. By decoupling the movement of the camera from that of the binocular display, even for camera's mounted on or connected to the binocular display, ergonomic benefits can be achieved. For example, the surgeon need not contort their neck in positions that are uncomfortable for long surgical procedures.

In various embodiments, the gimbal does not provide roll of the camera(s), for example, about the axis 10140. If for example the camera comprises a stereo camera with separate left and right cameras, such roll would raise the left channel above the right or vice versa. A horizontal line through the line of sight of the left and right channels might not therefore be parallel with the floor (perpendicular to the gravity vector). This roll might therefore cause disorientation and/or discomfort for the viewer. Accordingly, various embodiments of the gimbal or other positioning/orientation system for the camera's that provide surgical microscope views are configured not to such roll. Substantially reducing or eliminating roll might apply to use for the camera for surgery either or both in the downward view (for example, for spine surgery) as well as the oblique view (for temporal approach into the skull). Such configurations that substantially reduce or eliminate roll may be applicable for gimbal systems for other cameras including one or more proximal cameras disposed outside the surgical site a distance from the patient's body but in close proximity thereto (for example on a stereotactic frame, etc.), such as for example, a distance of between 5 mm and 50 mm, between about 20 mm and 40 mm (e.g., between 10 mm to 25 mm) from the patient's body and/or surgical site. A plurality of cameras including possibly a plurality of stereo cameras and possibly one or more mono-cameras (for example at 3, 6, 9, and 12 o'clock positions) can be repositioned and/or reoriented using positioning and orientations devices potentially in x, y, and z directions as well as in pitch and yaw and any combination thereof. However, in various embodiments such positioning and/or orientation devices do not permit the amount of roll to exceed that which would cause disorientation or do not provide for roll of the left and right channels of the stereo cameras altogether so as to reduce disorientation for the viewer.

In some embodiments, the control member 10145 can include one or more switches and/or actuators 10170 for controlling movement of the device. For example, the actuator 10170 can be coupled to mechanisms which can unlock the apparatus 10130 such that the movement control system 10130 can be manipulated to rotate and/or translate the imager 18. In some embodiments, the switches and/or actuators can be coupled to an electromechanical system to rotate and/or translate the movement control system 10130.

Figure 8A:
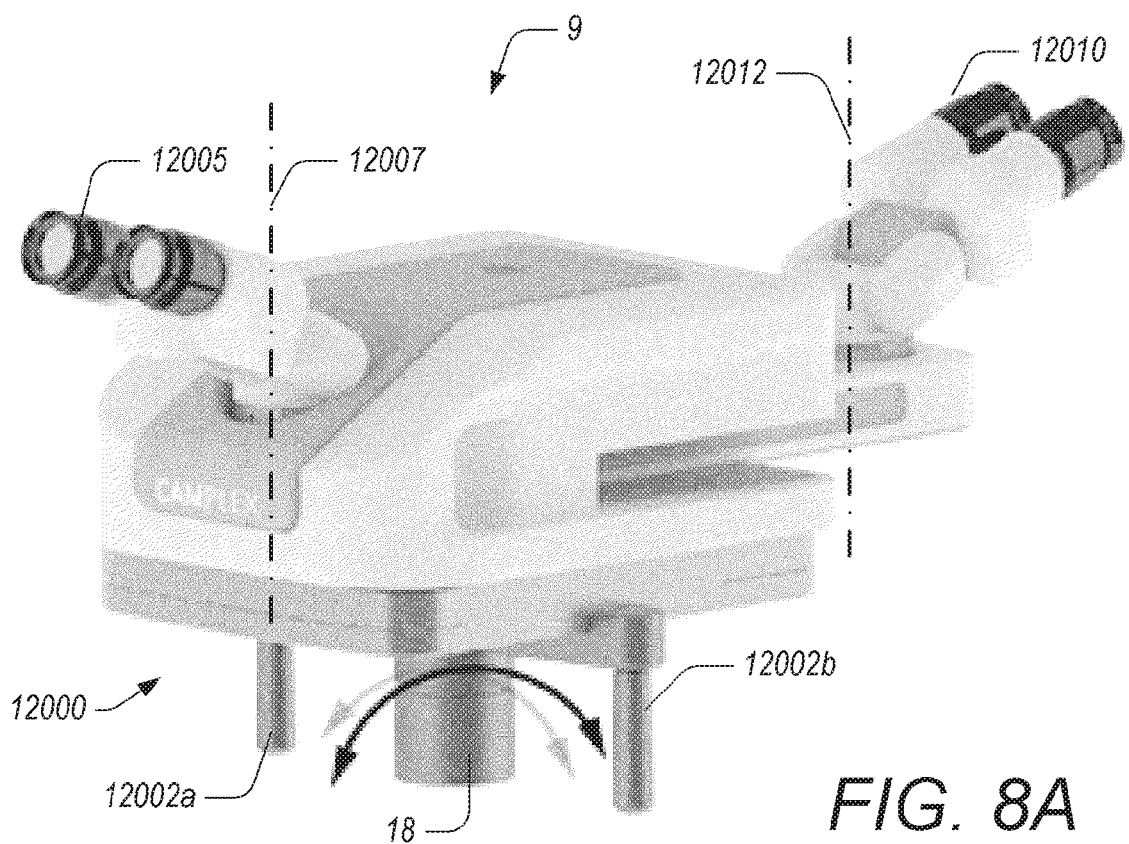
FIG. 8A illustrates a perspective view of an example gimbal system for an imager, the gimbal system coupled to a viewing assembly comprising two pairs of oculars.

FIG. 8A illustrates a perspective view of an example gimbal system 12000 for an imager 18, the gimbal system 12000 coupled to a viewing assembly 9 comprising 2 pairs of oculars, 12005, 12010. The first pair of oculars 12005 is configured to adjust its orientation about an axis 12007. The second pair of oculars 12010 is configured to adjust its orientation relative to an axis 12012 as well as relative to the first pair of oculars 12005. For example, the second pair of oculars 12010 can be oriented such that users of the two pairs of oculars face one another when using the viewing assembly 9, such as when a doctor and an assistant are on opposite sides of a patient. The second pair of oculars 12010 can also be oriented such that it is at about 90 degrees relative to the first pair of oculars 12005. Other relative orientations are also available, such as any value between about 15 degrees to about 180 degrees between the first and second pairs of oculars 12005, 12010.

The gimbal system 12000 can include a pair of handles 12002a, 12002b to allow a user to change the orientation of the imager 18. As illustrated, the user can adjust the pitch and yaw of the imager 18 using the handles 12002a, 12002b.

Figure 8B:
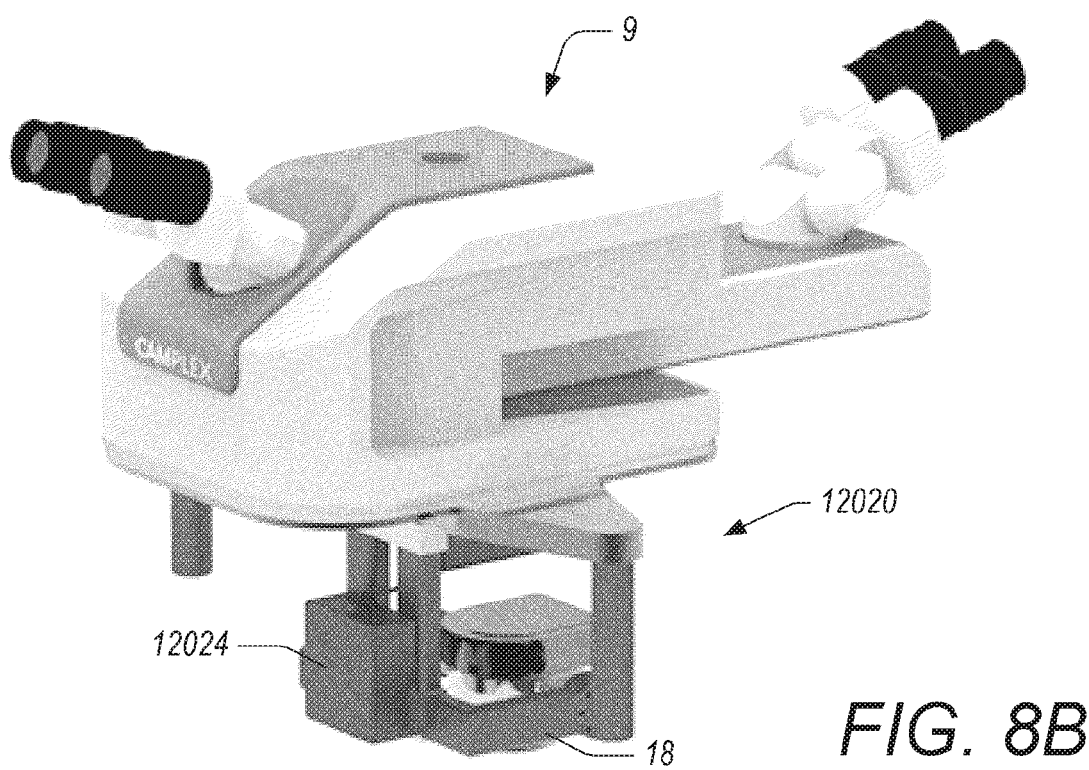
FIG. 8B illustrates a perspective view of a second example gimbal system for an imager, the gimbal system coupled to a viewing assembly.

FIG. 8B illustrates a perspective view of a second example gimbal system 12020 for an imager 18, the gimbal system 12020 coupled to a viewing assembly 9. The support structure 12024 for the imager 18 is configured to allow a user to change the orientation and position of the imager 18.

In some embodiments, the handles 12022a, 12022b are used to mechanically alter the position and/or orientation of the imager 18. In certain embodiments, the handles 12022a, 12022b are used as electronic controls to control one or more motor systems to orient and position the imager 18. In some embodiments, the handles 12022a, 12022b are a convenience or comfort for a user, and other separate controls are used to control the position and/or orientation of the imager 18 relative to the viewing assembly 9.

In some embodiments, one or more handles 12022 can include controls for controlling features of the overall system. For example the handle can include one or more controls, e.g., button(s), for altering the illumination, zoom, focus, work distance, camera view provided, arrangement of camera views or any combination of these feature or other features in the alternative or in addition.

Although a gimbal system is shown, other types of systems for position (e.g., x, y, and/or z) and orienting (e.g., pitch, yaw, and possibly roll), may be employed. In some embodiments, encoders or sensors provide signals with regard to the position and/or orientation of the camera. In some embodiments, the gimbal or positioning and/or orientation system may include motors or actuators that can be controlled by control electronics. In some embodiments the control electronics can be configured to cause to gimbal or other positioning and/or orientation system to return to a preset position and orientation. Memory, may for example be included that record certain preset positions and/or orientations. Such preset positions and/or orientations may be positions and/or orientations for certain types of surgical procedures, for certain surgeons, or combinations of both. Selection of the particular procedure or indication of the particular surgeon may cause the gimbal or position/orientation system to go to the appropriate preset position stored in memory. Such preset positions and/or orientations may also include a storage position.

Other types of positioning and/or orientation systems may include a hexapod and/or an articulated arm.

In some embodiments, light weight material may be used to form the display and/or console such as the housing. A honeycomb structure may for example be employed as a housing or cover.

The discussions above or elsewhere herein may be applicable to other types of cameras and positioning and/or orientation systems for other types of cameras including but not limited to one or more cameras on a surgical tool(s), one or more proximal cameras disposed outside a patient but within a close proximity to the patient and/or surgical site, such as 5 mm, 10 mm, 20 mm, 25 mm to 30 mm, 40 mm, 45 mm or any ranges therebetween. The distance of the proximal cameras to the patient's body and or surgical site may be greater or less than these values recited above.

Optical Systems for Displays

Figure 9A:
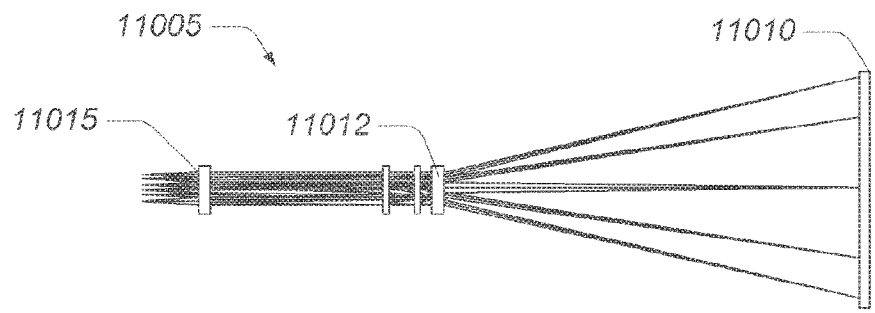
FIGS. 9A-9B illustrate example display optical systems configured to provide a view of a display or a pair of displays through oculars.
Figure 9B:
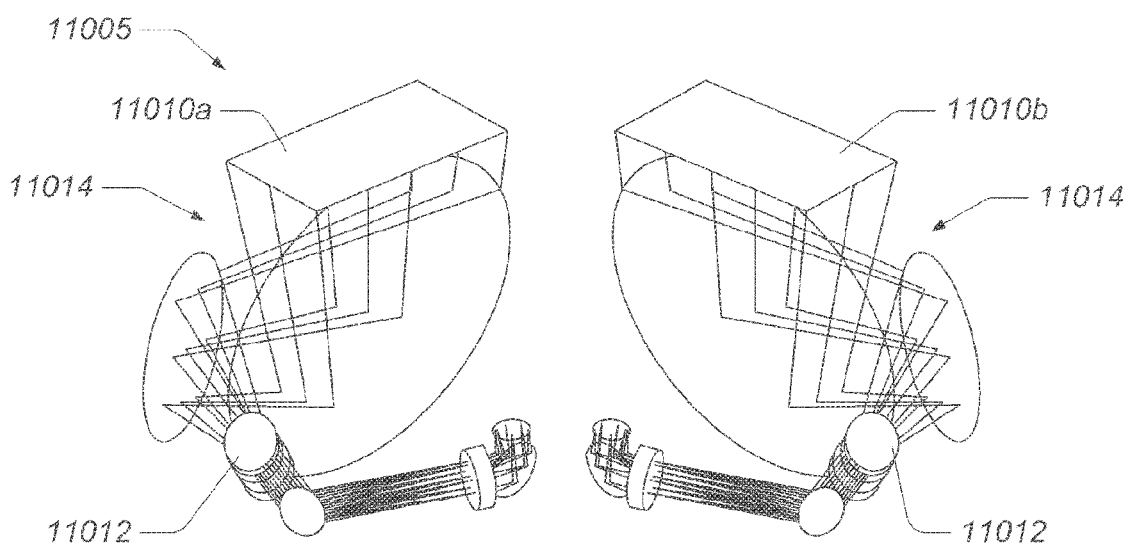

FIGS. 9A-9B illustrate example display optical systems 11005 configured to provide a view of displays 11010 through oculars (not shown) that receive light from the last lens 11015 in the display optical system 11005. The display optical system 11005 forms an exit pupil at or near the entrance pupil of the surgeon binoculars. These pupils are closely matched, for example, in size and shape. In some embodiments, the exit pupil of the display optical system 11005 can be the same size or smaller than the entrance pupil of oculars used to view the display. The oculars form an exit pupil that is matched (e.g., in size and shape) to the entrance pupil of the surgeon's eye(s). In some embodiments, the display optical system 11005 is configured to produce a beam that has a relatively constant cross-section between the first lens element 11012 and the last lens element 11015, where the cross-section is relatively small. Advantageously, this allows the display optical system 11005 to be included in a relatively small or compact package and use relatively small optical elements. In some embodiments, the last lens 11015 collimates the beam leaving the display optical system 11005. The termination of the rays shown in FIG. 9A to the left of lens 11015 is the exit pupil of the display optical system 11005. In some embodiments, the exit pupil of the display optical system 11005 is configured to be the same size or smaller than, and positioned at the same location, as an entrance pupil of a binocular viewing assembly configured to allow a user to view the display 11010.

The lenses in the display optical system 11005 form a highly color-corrected view of the display by forming the exit pupil in a position favorably disposed for the user and the binoculars. A combination of singlets and bonded lenses provide such correction. The display optical system 11005 may be designed to provide such correction while keeping a small beam column or ray bundle, which permits adding mirrors and obtaining a compact package. In various embodiments, producing an undistorted image can be difficult without such a group of lenses designed properly to provide such correction. This correction includes both color correction as well as distortion correction.

The display optical system 11005 advantageously allows a relatively small, compact lens assembly to provide a view of a relatively large display 11010. The display optical system 11005 can be configured to work with displays 11010 of varying sizes, including, without limitation, displays with a diagonal that is less than or equal to about 0.86 in. (22 mm), at least about 0.86 in. (22 mm) and/or less than or equal to about 10 in., at least about 1 in. and/or less than or equal to about 9 in., at least about 2 in. and/or less than or equal to about 8 in., or at least about 4 in. and/or less than or equal to about 6 in. The display may, for example, have a diagonal of about 5 inches or about 8 inches in some embodiments. The display can be configured to have a relatively high pixel count (e.g., 1920×1080 pixels, 1280× 720 pixels, 3840×2160 pixels, etc.). The total optical path length of the display optical system 11005 can be less than or equal to about 9 in., at least about 9 in. and/or less than or equal to about 20 in., at least about 10 in. and/or less than or equal to about 19 in., at least about 14 in. and/or less than or equal to about 18 in. The display optical system 11005 can include lenses, mirrors, prisms, and other optical elements configured to direct and manipulate light along an optical path. The display optical system 11005 can be used in conjunction with a primary display, a surgeon display, an assistant display, possibly other displays, or any combination of these.

The example display optical system 11005 illustrated in FIG. 9A has a total optical path length of about 16.2 in. (412 mm). It is configured to provide an image of a 5 in. display 11010. The display optical system 11005 can include a lens 11012 configured to direct the light from the display 11010 along a path wherein light from the display 11010 is directed along a path with a relatively narrow cross-section. In various embodiments, the light received from the display is initially substantially reduced in beam size for example by the lens 11012 or lenses closest to the display and a more narrow beam is produced. In certain embodiments, for example, the lens 11012 or lenses closest to the display collect light at an angle (half angle) in excess of 20°, 25°, 30° and reduce the beam size of the light. This design is advantageous because it allows for the elements in the display optical system 11005 to be relatively small and compact. In some embodiments, the cross-section of the optical beam after the lens 11012 in the display optical system 11005 can be configured to be relatively constant. This configuration allows folding or redirecting mirrors present in the optical path to remain small.

FIG. 9B illustrates a binocular display optical system 11005 configured to provide a view of stereo displays 11010a, 11010b through a pair of oculars. The binocular display optical system 11005 can be based on the optical design illustrated in FIG. 9A, and can include one or more elements 11014 in the optical path before the lens 11012 to reduce the physical size of the optical system while maintaining the length of the optical path. These elements can include mirrors, prisms, and/or other optical elements configured to redirect the light from the displays 11010a, 11010b to the lens 11012. In some embodiments, the elements 11014 include curved mirrors which redirect the optical path and converge the rays from the displays 11010a, 11010b. In some embodiments, the elements 11014 include mirrors or prisms (for example that may have planar reflecting surface) that do not substantially affect the convergence of the light rays, but redirect the optical path. In some embodiments, because of the shape of the beam incident on the reflective surface, for example, mirror, the reflective surface or cross-section of the mirror is non-circular, and is, for example, elliptical. Accordingly, in various embodiments the cross-section of the mirror or other reflective surface is possibly being longer in one direction than in another, for example, orthogonal direction. These elements may fold the optical path to provide for a more compact system. Such a system may therefore have an optical path length from display to ocular that is longer than the length and/or width of the viewing platform of the combination thereof.

In some embodiments, the display optical system 11005 can include at least four mirrors, or less than or equal to four mirrors. In certain implementations, two mirrors can be used to fold the optical path from the display 11010 to the exit pupil, the two mirrors positioned between the first lens 11012 and the display 11010. In some embodiments, the display optical system 11005 includes at least four lenses or less than or equal to four lenses.

In some embodiments, the display optical system 11300 can include at least four baffles or less than or equal to four baffles. In certain implementations, four baffles can be included in the optical path between the first lens and the display 11310. In some implementations, two mirrors can be included in the optical path between the first lens and the display 11310. In some embodiments, the optical path can include, in order from the display 11310, a first baffle, a first mirror, a second baffle, a second mirror, and a third baffle prior to the first lens.

In some embodiments, the display optical system can include binoculars having an optical power of about 10×. The binoculars can have a field of view of about 80 degrees to about 90 degrees. The binoculars can be configured to provide a field of view that is relatively wide (e.g., panoramic) without producing a noticeable "kidney bean" effect." The binoculars can also be configured to provide a view of the display without viewing the field stop. In some embodiments, the binoculars have a focal length of about 10 mm. The display optical system can include a field stop in the oculars. The display optical system can include a circular exit pupil with rectangular baffles.

The optics of the display optical system can include one or more optical elements configured to output collimated rays. In some embodiments, the optical elements, however, can be configured to not produce collimated light within the lens train of the display optical system. By incorporating a converging lens near the display in the display optical system, the light tube can be configured to be relatively small compared to the size of the display. This can allow the size of the viewing assembly to be relatively compact.

In some embodiments, the display can be a curved surface, for example either a projection display or recent generation of flexible LCD or OLED displays having high-resolution (e.g., in excess of 300 ppi). A curved display may provide two advantages: the imaging optics for the display can be less complex than for flat panels, and the cone or numerical aperture of each picture element in the display can be directed towards the viewing optics and in the periphery of the display, thereby providing a brighter image less subject to vignetting.

In some embodiments, the display can be a volumetric display comprising two or more transmissive display panels having a single backlight wherein the transmissive display panels are stacked to provide different planes of focus for a surgeon. The transmissive displays can be active matrix liquid crystal displays ("AMLCD") or other types of transmissive displays. The backlight can be a fluorescent lamp, LEDs, or other suitable light source. By having displays positioned in different focal planes, image data from different focal planes may be presented to the surgeon with relatively less image processing and/or compression compared to a system which combines data from multiple focal planes into a single image. In some embodiments, a number of cameras can be positioned at varying depths or having varying focal distances such that the displays at different focal planes are configured to display image data from cameras positioned or focused at different depths to create a display that assists the surgeon in identifying positions of features within displayed images.

The display can show, as an overlay, pre-operative CT, MR, or other 3D image datasets from, for example, conventional surgical navigation systems (e.g., the Medtronic StealthStation or Treon, Stryker Surgical Navigation System, or Brainlab, among others). In various embodiments, in addition to images, the display can additionally provide numerical data and/or text. For example, in various embodiments, the display can overlay information such as distance or tool measurements, transparent tool renderings, camera identification information (e.g., the portion of the composite image attributable to a specific optical sensor may generate an identifying border around that portion), up/down orientation, elapsed time, and/or one or more still images captured from one or more optical sensors from a previous time in the operation The tracking system can provide 5-DOF (degrees of freedom) or 6-DOF position and orientation information to conventional surgical navigation systems. Other information, graphic, alpha numeric, or otherwise, can be provided.

The tool image can be magnified with respect to the wide-field view image, and change in image scaling will occur as the tool is moved in and out. In some embodiments, a visual metaphor for embodiments of the display is that of a hand-held magnifying glass for inspecting and doing work on a smaller region of a larger workpiece, while seeing the larger workpiece with lower magnification (if any) in more peripheral regions of the visual field to provide situational awareness. Tool images, for example, can be superimposed on the background image thereby blocking that portion of the background image. In various embodiments, the tool images may be stereo.

Figure 10:
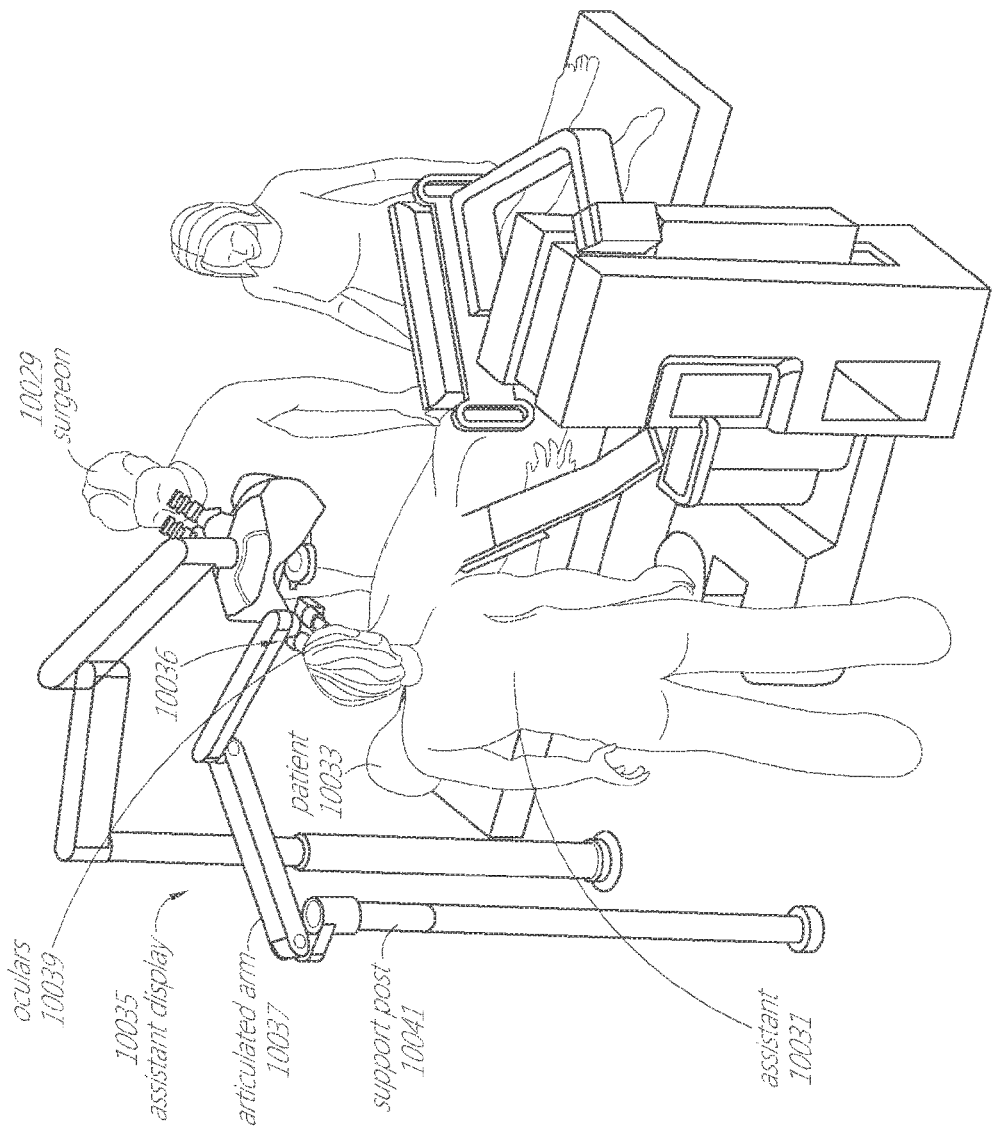
FIG. 10 is a schematic illustration of a surgical visualization system including an assistant display.

FIG. 10 is a schematic illustration of a surgical visualization system and an assistant display. In some embodiments, a separate assistant display may be provided for use by a surgical assistant or observer. As illustrated in FIG. 10, the assistant display 10035 comprises a binocular viewing platform 10036 for the assistant that includes oculars 10039 mounted on a lockable articulated arm 10037, which extends from a support post 10041. For example, the assistant 10031 and surgeon 10029 may be positioned on opposite sides of the patient 10033, as in the illustrated arrangement. In such an arrangement, the image provided in the assistant display 10035 may be rotated 180 degrees with respect to that provided to the surgeon 10029. The assistant may be at other locations, for example, in other procedures. The assistant may, for example, be located at a location 90 degrees with respect to the surgeon, as opposed to 180 degrees with respect to the surgeon. Likewise, the image provided in the assistant display 10035 may be rotated 90 degrees with respect to that provided to the surgeon 10029. Similarly the image may be reoriented as needed, possibly based on the location/position and perspective of the assistant. Additionally, the assistant display can be provided with any of the features described elsewhere herein.

In some embodiments fluorescence images can be collected and displayed. These fluorescence images may be viewed superimposed on images of the surgical site not based on fluorescence. Cameras that image in different wavelengths, such as infrared, could image the surgical site or objects contained therein. In some embodiments, features could be made to fluoresce, for example, by injecting fluorescent chemical and illuminating the area with light that will induce fluorescence. For example, in certain embodiments anatomical features may contain fluorescent dye that fluoresces, for example, when exposed to short wavelength radiation such as UV radiation. Such a technique may be useful to identify and/or highlight the location and/or boundaries of specific features of interest such as tumors, etc. The fluorescence or other wavelength of interest may be detected by the one or more cameras imaging the surgical field such as one or more camera providing a surgical microscope view or one or more cameras on a surgical tool providing a surgical tool view. For example, an optical detector that is sensitive to the wavelength of the fluorescent emission may be employed to view the fluorescent image. In some embodiments, the wavelength of fluorescent emission is in the infrared. In certain embodiments sensors sensitive to different wavelengths may be employed. In particular, one or more sensors sensitive to the fluorescing wavelength (e.g., IR) may be used in conjunction with one or more sensors not sensitive or less sensitive to the fluorescing wavelength but sensitive or more sensitive to other useful wavelengths (e.g. visible light). Light can be collected and distributed to both types of detectors for example using a beamsplitter such as a wavelength dependent beamsplitter that reflects one wavelength and passes another. The fluorescent and non-fluorescent images can be recorded by the respective sensors. In some embodiments, the fluorescent and non-fluorescent images can be superimposed when displayed on electronic displays that receive image data from both types of sensors. In various embodiments, the cameras, including fluorescent and/or non-fluorescent cameras, that provide a surgical microscope view, a surgical tool view (e.g., from a camera on a tool), or other view of the surgical site, may comprises stereo cameras and the displays may comprise stereo displays.

In some embodiments, images produced by fluorescence or other wavelengths of interest are superimposed on one or more images from other camera(s). Filtering could be provided to remove unwanted wavelengths and possibly increase contrast. For example, the filter can be used to remove excitation illumination. In some embodiments, emission image content, (e.g., fluorescing tissue) can be parsed and superimposed on image content that is not emitting (e.g., tissue that is not fluorescing), or vice versa.

In some embodiments, IR fluorescence images are superimposed over non-IR (e.g. visible) images. Other wavelengths such as other fluorescence wavelengths may be employed. In various embodiments, such as where the fluorescing wavelength is not visible (e.g., for fluorescence in the infrared), an artificial color rendition of the fluorescing content can be used in place of the actual fluorescing color so as to enable the fluorescing tissue to be visible.

Figure 11:
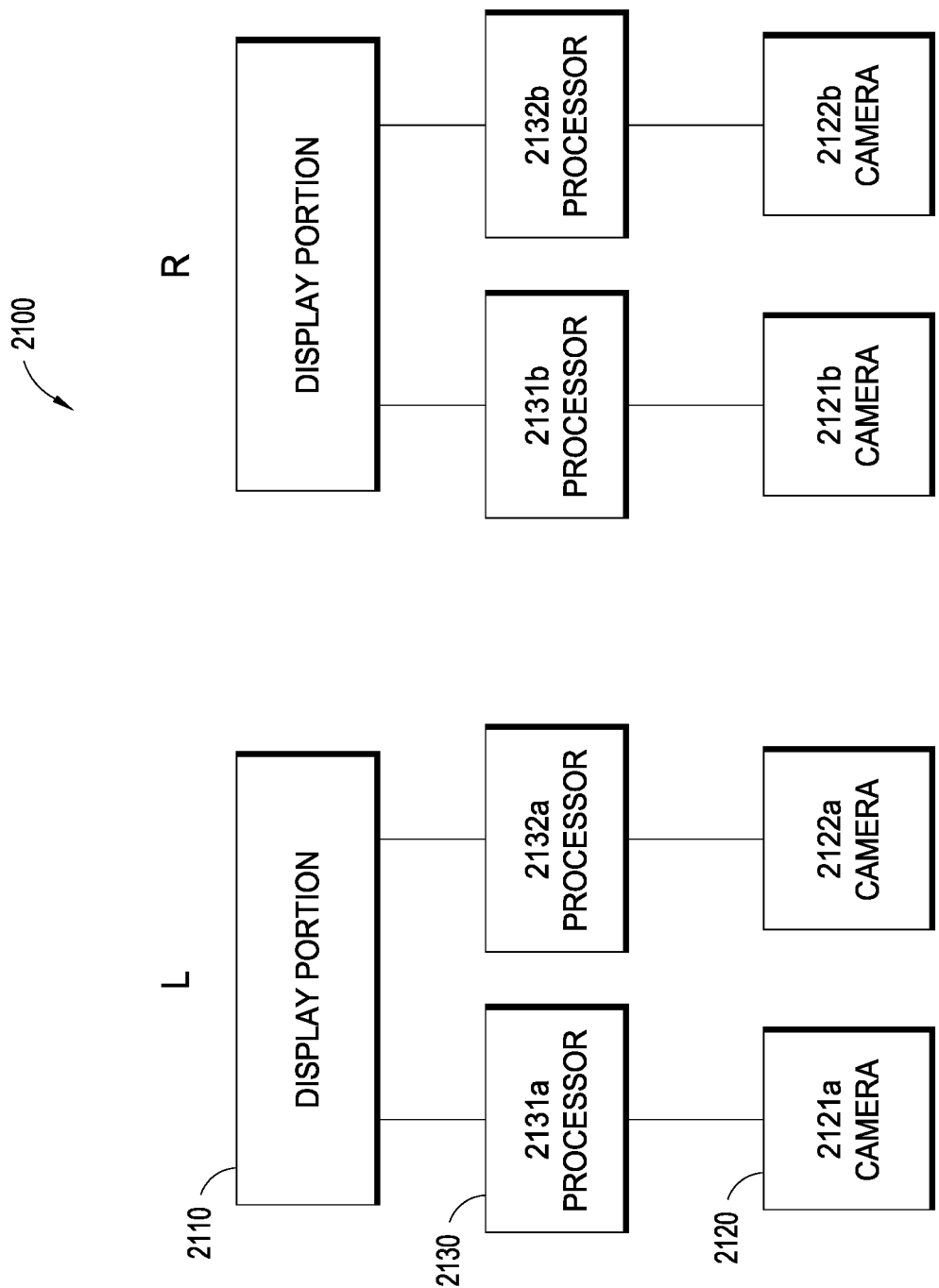
FIG. 11 schematically illustrates an example medical apparatus in accordance with certain embodiments described herein.

FIG. 11 schematically illustrates an example medical apparatus in accordance with certain embodiments described herein. The medical apparatus 2100 can comprise a display (or display portion) 2110, a plurality of cameras 2120, and one or more processors 2130. The plurality of cameras 2120 can include at least one first camera 2121*a* configured to image fluorescence in a surgical field, and at least one second camera 2122*a* configured to produce a non-fluorescence image of the surgical field. The processor 2130 can be configured to receive images from the plurality of cameras 2121*a*, 2122*a*, and to display on the display 2110 a fluorescence image from the at least one first camera 2121*a* and to display on the display 2110 the non-fluorescence image from the at least one second camera 2122*a*. As shown in FIG. 11, the processor 2130 can advantageously include a plurality of processors 2131*a*, 2132*a*, e.g., a separate processor for each camera within the plurality of cameras 2120. For example, at least one first processor 2131*a* can be configured to receive an image from at least one first camera 2121*a* and to display on the display 2110 a fluorescence image. In addition, at least one second processor 2132*a* can be configured to receive an image from at least one second camera 2122*a* and to display on the display 2110 the non-fluorescence image.

The display 2110 can be a primary display, a surgeon display, an assistant display, possibly other displays, or any combination of these. The display 2110 can include a display portion, a display, or display device as described herein. For example, in some embodiments, the display 2110 can include a display (or display portion) to be viewed through one or more oculars, e.g., a display within the viewing platform 9 of the surgical viewing system 1 shown in FIGS. 1, 2, 3A, 4A and 4B. The display (or display portion) could be within a housing. In other embodiments, the display 2110 can include a display mounted on a display arm from the ceiling or on a post, e.g., a display device 13 on display arm 5 of the surgical viewing system 1 shown in FIG. 1 or be mounted on the wall. In various embodiments, such displays comprise panel displays having a length of, for example, be between 15-70 inches, or larger or smaller.

In various embodiments, the plurality of cameras 2120 can include a camera to provide a surgical microscope view of the surgical field. In some embodiments, the plurality of cameras 2120 can include a camera disposed on a surgical tool or on another medical device. The plurality of cameras 2120 can include at least one first camera 2121*a* and at least one second camera 2122*a* configured to form a left-eye view of the surgical field. The plurality of cameras 2120 can also include at least one first camera 2121*b* and at least one second camera 2122*b* configured to form a right-eye view of the surgical field. In some embodiments, the left and right-eye views are for stereoscopic viewing of the surgical field and the cameras can be angled to provide desired convergence mimicking the human eye. One or more cameras 2121*a*, 2121*b*, 2122*a*, and/or 2122*b* of the plurality of cameras 2120 can include optical assemblies as described herein. For example, one or more cameras 2121*a*, 2121*b*, 2122*a*, and/or 2122*b* can include a turning prism 54, a lens train 55, and/or a sensor 56 as shown in FIG. 5A.

As described herein, for the left-eye view, the at least one first camera 2121*a* can be configured to image fluorescence in a surgical field, and the at least one second camera 2122*a* can be configured to produce a non-fluorescence image of the surgical field. Similarly, for the right-eye view, the at least one first camera 2121*b* can be configured to image fluorescence in a surgical field, and the at least one second camera 2122b can be configured to produce a non-fluorescence image of the surgical field.

In some embodiments, the first camera 2121a and/or 2121b can be sensitive to infrared wavelengths, ultraviolet wavelengths, or other fluorescence wavelengths. For example, an optical detector, e.g., sensor 56 or an array of sensors, of the first camera 2121a and/or 2121b can be sensitive to fluorescence wavelengths. In some embodiments, the first camera 2121a and/or 2121b sensitive to fluorescence wavelengths can include an infrared, ultraviolet, or other fluorescence light source. In some embodiments, illumination using an optical fiber can be used to provide pump radiation to induce fluorescence. In some embodiments, a filter may be used to selectively direct fluorescence wavelengths to the first camera 2121a and/or 2121b sensitive to fluorescence wavelengths. In some embodiments, the second camera 2122a and/or 2122b may not be sensitive to fluorescence wavelengths.

In some embodiments, the processor 2130 can be configured to superimpose the fluorescence image over the non-fluorescence image. In other embodiments, the processor 2130 can be configured to superimpose the non-fluorescence image over the fluorescence image. In various embodiments, the processor 2130 can electronically process and synchronize the fluorescence and non-fluorescence images together. For example, the processor 2130 can read, align, and combine together the images.

The processor 2130 can include a general all-purpose computer and in some embodiments, a single processor may drive both the left and right display portions 2110. However, various embodiments of the medical apparatus 2100 can include separate processing electronics for the left-eye and right-eye views. Such separate processing for the left and right channels can be advantageous over a processor with single processing electronics or the general all-purpose computer since time is critical in surgical procedures. For example, in some embodiments, having separate dedicated processing electronics for each channel can provide pure parallel processing, which results in faster processing of images, thereby reducing latency. In addition, addressing a failure of a general all-purpose computer may entail rebooting of the computer and involve some downtime. Furthermore, with separate processing electronics in left-eye and right-eye view channels, if one of the processing electronics were to fail, the processing electronics in the other channel can continue to provide images to the surgeon. Such redundancy can also be incorporated into a monocular viewing system. For example, in some embodiments of a monocular viewing system, two channels similar to a binocular viewing system can be provided. Images for the monocular viewing system can be split into each channel, with each channel having its own processing electronics.

Furthermore, in some even more advantageous embodiments, as shown in FIG. 11, the medical apparatus 2100 can include separate processing for each camera within each channel to further increase processing of images and reduce latency. For example, for the left-eye view, processor 2131a can be configured to receive an image from camera 2121a and to display on the display 2110 a fluorescence image from camera 2121a. Processor 2132a can be configured to receive an image from camera 2122a and to display on the display 2110 the non-fluorescence image from camera 2122a. The fluorescence and non-fluorescence images can be superimposed optically on the display 2110. Similarly, for the right-eye view, processor 2131b can be configured to receive images from camera 2121b and to display on the display 2110 a fluorescence image from camera 2121b. Processor 2132b can be configured to receive images from camera 2122b and to display on the display 2110 the non-fluorescence image from camera 2122b. The fluorescence and non-fluorescence images can be superimposed optically on the display 2110.

In certain embodiments, each of the separate processing electronics can be configured for image manipulation, e.g., to receive image data, process the image data, and output the images for display. For example, each of the processing electronics can be configured to receive one or more user inputs, receive one or more input signals corresponding to images from one or more cameras, and/or select which image to display. Each of the processing electronics can also resize, rotate, or reposition the selected image based at least in part on one or more user inputs or provide any combination of these operations. The processing electronics can also produce one or more output signals to drive one or more displays to produce one or more images. For example, each processing electronics can include a microprocessor, a field programmable gate array (FPGA), or an application specific integrated circuit (ASIC). Each processing electronics can also include a graphics processing unit (GPU) and random access memory (RAM). The processing electronics can also control the color balance, brightness, contrast, etc. of the one or more images or provide any combination of these operations.

In some embodiments, instead of superimposing fluorescence and non-fluorescence images, an image at a first wavelength range can be superimposed with an image at a second wavelength range. For example, one or more sensors can capture a first image at a first wavelength range, and one or more sensors can capture a second image at a second wavelength range. The first and second images can be superimposed optically as disclosed herein. As another example, the image at a first wavelength can be provided by narrow band imaging instead of fluorescence imaging. For example, a filter in some embodiments can allow imaging with the use of ambient light at blue (about 440 to about 460 nm) and/or green (about 540 to about 560 nm) wavelengths for the image at the first wavelength. Imaging at or near these wavelengths can improve visibility of features since the peak light absorption of hemoglobin occurs at these wavelengths. The image at the second wavelength can be provided without narrow band imaging (e.g., use of ambient light without a filter).

In further embodiments, the plurality of cameras 2120 can include different cameras for multiple views of the surgical site instead of or in addition to cameras mainly for imaging at different wavelengths. For example, in some embodiments, the plurality of cameras 2120 can include a camera providing a surgical microscope view, a camera disposed on a surgical tool (e.g. cutting tool), and a camera disposed on another medical device to provide different views of the surgical site or any combination thereof. Some embodiments can also include a switch or switching module to determine which views are to be displayed, for example, as superimposed, overlapping, adjacent, stereo or as a monocular view, etc. One or more image could also be from other sources, e.g., a data file, a computed tomography (CT) scan, a computer aided tomography (CAT) scan, magnetic resonance imaging (MRI), an x-ray, ultrasound imaging instrument, etc.

Figure 12A:
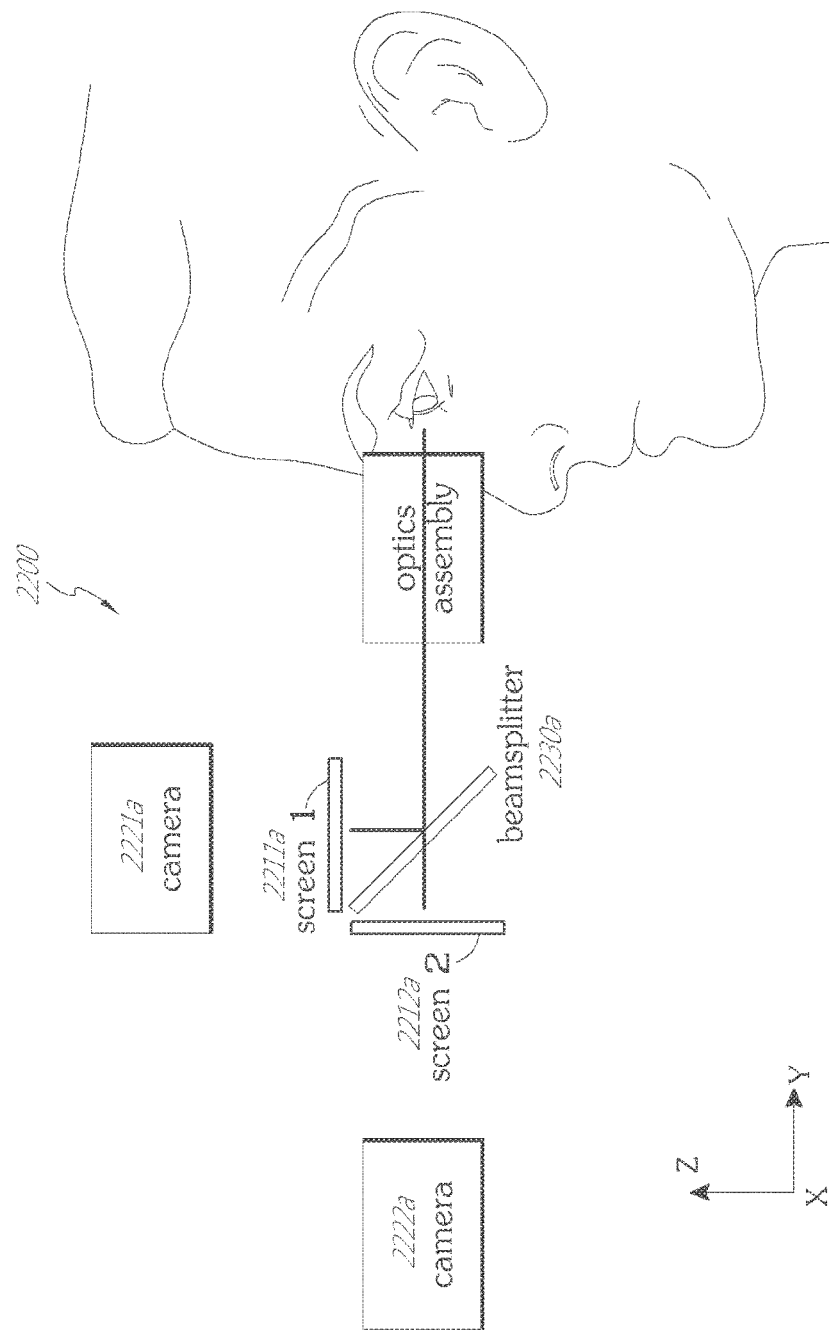
FIGS. 12A-12C schematically illustrate another example medical apparatus in accordance with certain embodiments described herein.

FIG. 12A schematically illustrates another example medical apparatus in accordance with certain embodiments described herein. Some such embodiments can also advantageously decrease the time to produce an image for viewing, which can be important in certain surgical procedures. For example, the medical apparatus 2200 can include a plurality of displays (or display portions), a plurality of cameras, and one or more beam combiners. As shown in FIG. 12A, to form a left-eye view, the plurality of cameras can include at least one first camera 2221a configured to produce a fluorescence image onto a first display 2211a and at least one second camera 2222a configured to produce a non-fluorescence image onto a second display 2212a. In some embodiments, the cameras 2221a, 2222a can produce the images onto the plurality of displays 2211a, 2212a, e.g., with a processor. However, in such embodiments, an electronic processor need not perform the combining of images. A beam combiner 2230a can be configured to receive the fluorescence and non-fluorescence images from the first 2211a and second 2212a displays and to combine or superimpose optically the fluorescence and non-fluorescence images for left-eye viewing, e.g., within a housing through an ocular or on a display device.

Figure 12B:
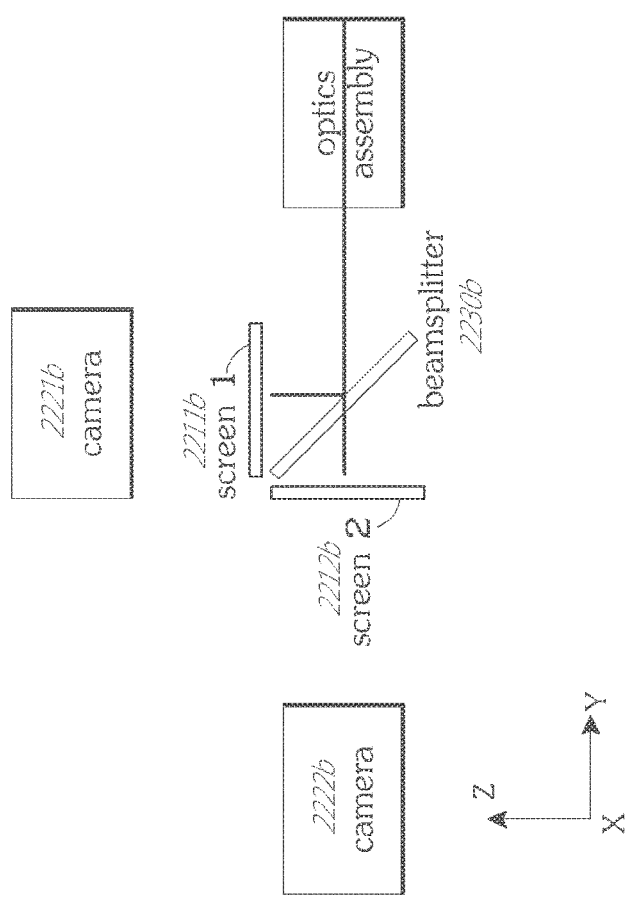

As shown in FIG. 12B, to form a right-eye view, the plurality of cameras can also include another first camera 2221b configured to produce a fluorescence image onto another first display 2211b and another second camera 2222b configured to produce a non-fluorescence image onto another second display 2212b. In some embodiments, the cameras 2221b, 2222b can obtain images that can be viewed on the plurality of displays 2211b, 2212b, for example, using processing electronics. However, in such embodiments, an electronic processor need not perform the combining of images. Combining images into a single display, for example, may involve a central processor working to a single clock. Instead, a beam combiner 2230b can be configured to receive the fluorescence and non-fluorescence images from the first 2211b and second 2212b displays and to superimpose the fluorescence and non-fluorescence images for right-eye viewing, e.g., within a housing through an ocular or on a display device. By optically combining multiple images from various sources, with or without stereo convergent characteristics, differently timed imaging signals (for example, with different frame rates) or differently resolved imaging signals (wherein, for example, the pixel count can be the full pixel count or a subset of the full pixel count) can be sent to their respective displays and viewed by the viewer as optically compatible without the need for them to be electrically made time or resolution compatible. For example, screens of different resolution such as a 5 inch screen having 1080×1920 pixels may be combined with a display for a fluorescence image wherein the display has 800×520 pixels. The different spatial resolution (and/or size) of the two displays are combined optically by the beam combiner and processed by the eye. Such an example could apply for either or both the right eye and/or left eye. Other variations in the displays are possible such as displays with different timing. For example, a high definition (HD) display operating at 60 frames per second can be optically combined with images from a fluorescence camera operating at 30 frames a second. Instead of speeding up or slowing down one of the signals with respect to the other in a single processor, images from the separate displays having different timing can be combine optically with a beamsplitter or beamcombiner. More than two displays having such different features (e.g., size, resolution, timing) can be combined optically in this manner for either or both the left eye and/or right eye.

Figure 12C:
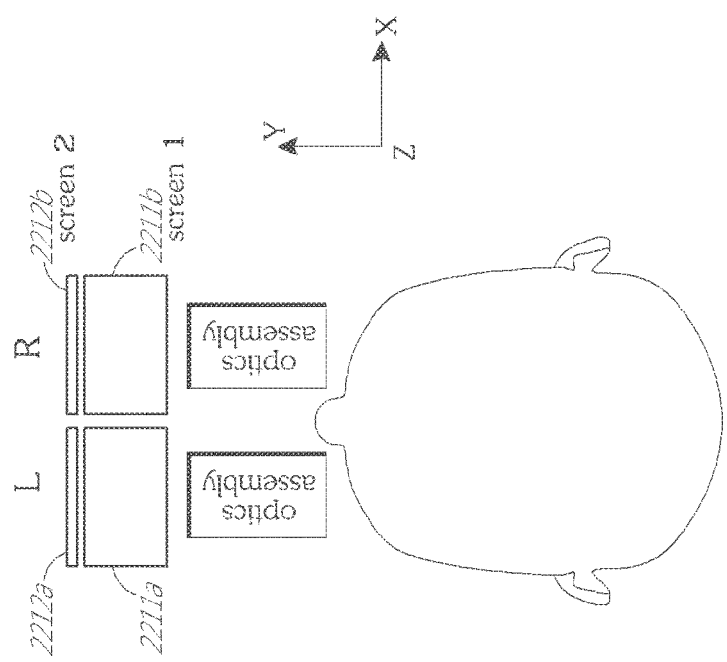

In various embodiments, the beam combiner 2230 can include a beamsplitter (e.g., a 45 degree or other angle splitter used in reverse), a dichroic beamsplitter, a prism, or other optical structure to combine the beams. As an example, a beam combiner 2230a can be placed within the left-eye optical path to receive the fluorescence and non-fluorescence images from the first 2211a and second 2212a displays and to superimpose the fluorescence and non-fluorescence images for left-eye viewing, e.g., within a housing through an ocular or on a display device. Similarly, another beam combiner 2230b can be placed in the right-eye optical path to receive the fluorescence and non-fluorescence images from the first 2211b and second 2212b displays and to superimpose the fluorescence and non-fluorescence images for right-eye viewing. Some embodiments can further include imaging optics (e.g., an optics assembly) disposed to collect light from the displays to enable the images to overlap. The imaging optics can be configured to form images at infinity. The imaging optics can be configured to be seen by an observer as though the viewer is seeing the displays at infinity with relaxed accommodation. FIG. 12C schematically illustrates a top view of an embodiment of a medical apparatus incorporating the example left and right assemblies from FIGS. 12A and 12B.

In some embodiments, instead of superimposing fluorescence and non-fluorescence images, an image at a first wavelength range can be superimposed with an image at a second wavelength range. For example, a first camera 2221a can produce a first image at a first wavelength range onto a first display 2211a, and a second camera 2222a can produce a second image at a second wavelength range onto a second display 2212a. The beam combiner 2230a can optically superimpose the first and second images. As another example, the image at a first wavelength can be provided by narrow band imaging instead of fluorescence imaging, and the image at the second wavelength can be provided without narrow band imaging as described herein.

Figure 14A:
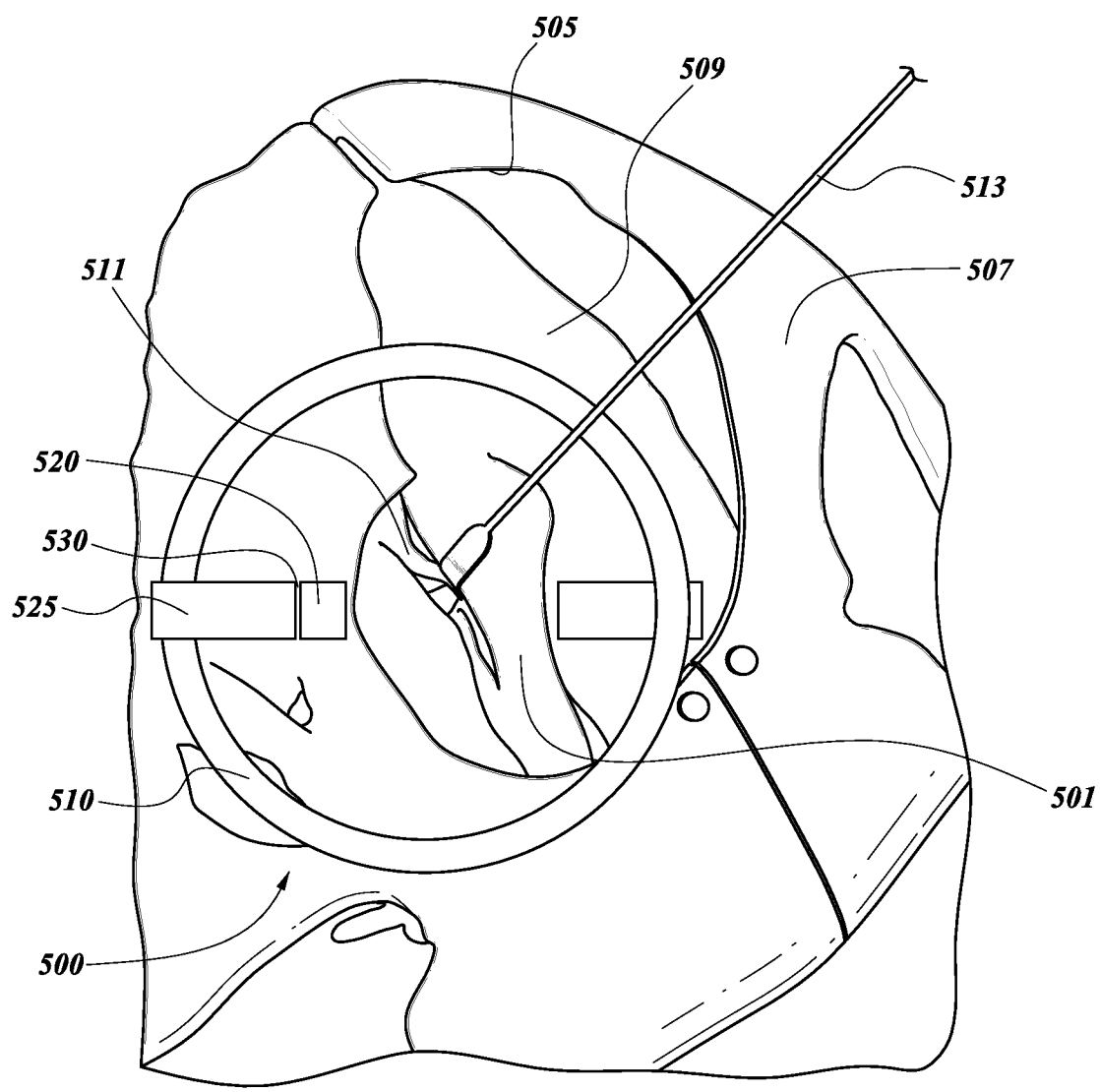
FIG. 14A shows a schematic of an example medical apparatus comprising a frame 510 disposed above a surgical site of a mock patient.

In addition, images from two different cameras of the same or substantially the same wavelength, but having other properties can be superimposed. For example, one image could be a natural image of tissue, and another view could be an unnatural image (e.g., an image with false color or an image with exaggerated or extreme contrast). In some embodiments, such superimposed images can advantageously show margins between healthy and unhealthy tissue. The example embodiments of the medical apparatuses shown in FIGS. 12 and 12A-12C can also be modified to produce a composite image of two or more images. FIG. 14A illustrates a schematic of an example composite image 2500, where a first (e.g., a background) image 2501 is produced on a first portion 2511 of the composite image 2500, and a second (e.g., a picture-in-picture (PIP)) image 2502 is produced on a second portion 2512 of the composite image 2500. In some embodiments, the images can include a fluorescence image and a non-fluorescence image. However, in other embodiments, the images are not necessarily fluorescence and non-fluorescence images. For example, one image can be a surgical microscope view of the surgical field from a camera producing the surgical microscope view. The other image can be the image of the surgical field from a camera disposed on a surgical tool (e.g. cutting tool) or other medical device. One or more image could also be from sources other than cameras, e.g., a data file, a computed tomography (CT) scan, a computer aided tomography (CAT) scan, magnetic resonance imaging (MRI), an x-ray, ultrasound imaging instrument, etc. FIG. 14B schematically illustrates a front view of an embodiment of a medical apparatus incorporating the example left and right assemblies from FIG. 11 or 12A-12C to produce a composite image of two or more images for both left and right eyes.

Figure 13A:
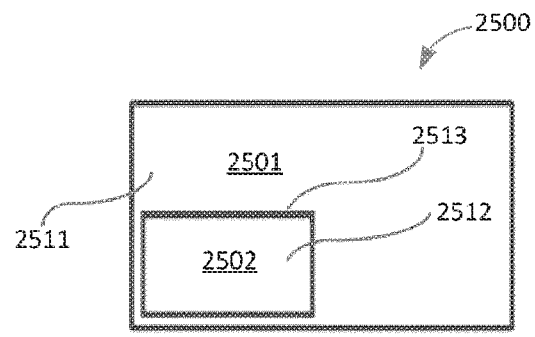
FIG. 13A illustrates a schematic of an example of a composite image with a picture-in-picture (PIP) view of a surgical field.
Figure 13B:
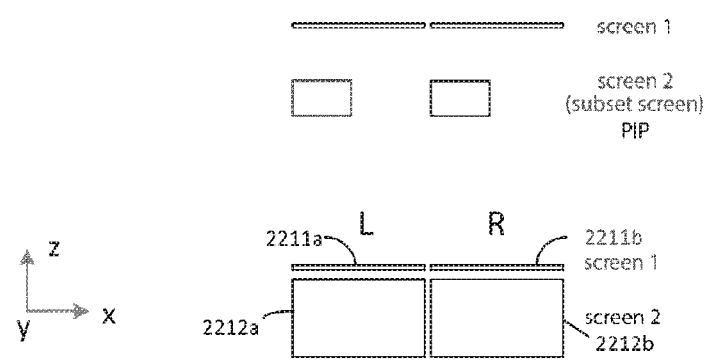
FIG. 13B schematically illustrates a front view of an embodiment of a medical apparatus incorporating left and right assemblies to produce a composite image of two or more images for both left and right eyes.
Figure 13B:
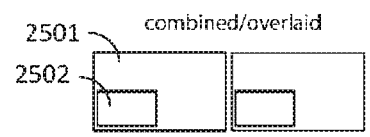

Referring to the example embodiment shown in FIG. 11, for the left-eye view, the first camera 2121a can be a camera producing a surgical microscope view, and the second camera 2122a can be a camera disposed on a surgical tool (e.g. cutting tool) or other medical device. Similarly, for the right-eye view, the first camera 2121b can be another camera producing a surgical microscope view, and the second camera 2122b can be another camera disposed on a surgical tool (e.g. cutting tool) or other medical device. For each eye's view, the first camera 2121a, 2121b can produce the background image 2501 of the composite image 2500, and the second camera 2122a, 2122b can produce the PIP image 2502 in the composite image 2500. For the left-eye view, the processor 2131a can be configured to receive an image from the first camera 2121a and to display on the display 2110 the image as the background image 2501 of the composite image 2500. In addition, the processor 2132a can be configured to receive an image from the second camera 2122a and to display on the display 2110 the image as the PIP image 2502 of the composite image 2500. For the right-eye view, the processor 2131b can be configured to receive an image from the first camera 2121b and to display on the display 2110 the image as the background image 2501 of the composite image 2500. In addition, the processor 2132b can be configured to receive an image from the second camera 2122b and to display on the display 2110 the image as the PIP image 2502 of the composite image 2500. As shown in FIG. 13B, the position of the PIP image 2502 in the composite image 2500 can be in the same or different location from that illustrated in the figures. Additional cameras or sources can also be used to produce a multiple PIP images.

Referring to the example embodiment shown in FIGS. 12A-12C, a beam combiner 2230a, 2230b can be placed within each eye's optical path to produce the composite image 2500. In some embodiments, the background image from a camera can be resized or the row count of pixels of the background image can be reduced. For example, the background image can be resized from the full frame to the size of the first portion 2511 (e.g., about ½, ⅔, ¾, etc., or any range therebetween) of the composite image 2500. The beam combiner 2230a, 2230b in each eye's optical path between the viewer and the displays can superimpose the background image with a PIP image such that the background image appears on the first portion 2511 of the composite image 2500, and the PIP image forms within the remaining portion 2512 (e.g., about ½, ⅓, ¼, etc., or any range therebetween) of the composite image 2500. In some embodiments, the remaining portion 2512 can include a border 2513 having a thickness (e.g., 1%, 2%, 3%, 5%, 10%, or 15%, of the width of the image, or any range therebetween) surrounding the PIP image 2502 to help prevent the viewer from seeing similar types of images as being falsely contiguous (e.g., similar types of tissues from multiple sources).

With reference to FIG. 12A, an example illustration using the left-eye view will be provided. The example illustration can also apply to the right-eye view in certain embodiments. For example, a first camera 2221a for providing a surgical microscope view can provide the background image on a first display 2211a, and a second camera 2222a disposed on a surgical tool or other medical device can provide the smaller image on a second display 2212a. The beam combiner 2230a can produce the background image from the first display 2211a as the first portion 2511 (e.g., about ⅔) of the composite image 2500. The beam combiner 2230a can also combine the PIP image from the second display 2212a as part of a second portion 2512 (e.g., about ⅓) of the composite image 2500. As shown in FIG. 13A, the background image 2501 can be produced in the majority (e.g., about ⅔) of the composite image 2500. The PIP image 2502 can be produced as part of, e.g., within the remaining portion 2512 (e.g., about ⅓) of the composite image 2500.

The display 2211a for the background image can be a 5" display. The smaller PIP image from the second camera 2222a can be displayed on a smaller panel viewed off from the beam combiner 2230a, or could be displayed on a 5" display using only a portion of the display (e.g., about ⅓ of the display or about part of ⅓ of the display). After properly baffling the optical pathways, the viewer can see the smaller image 2502 adjacent the background image 2501 as though it were a picture-in-picture.

The beam combiner 2230 can also produce additional PIP images from other displays as part of the composite image 2500. For example, multiple images (e.g., two, three, four, five, six, nine, twelve, etc., or any range therebetween) from multiple displays (e.g., two, three, four, five, six, nine, twelve, etc., or any range therebetween) can be viewed for each eye's view by using one or more beam combiners 2230.

In some embodiments, the smaller images can be superimposed with a dark (e.g., black) or light (e.g., clear) border to prevent the viewer from seeing similar images as being falsely contiguous (e.g., similar types of tissues from multiple sources). For example, after resizing the background image (e.g., to about ⅔ size), the remaining portion (e.g., about ⅓) of the image can be left black. The smaller images from other displays can be superimposed onto the black portion of the background image such that the images do not appear falsely contiguous. In addition, the border can help facilitate the beam combiner 2230 arrangement, making the alignment less critical in some embodiments. In various embodiments, the border to can have a thickness of between of 2% to 5% or 3% to 10% of the width of the images or larger. In some embodiments, the smaller images could be superimposed onto the background image. For example, the background image could include additional superimposed or overlapping images. Some embodiments can include a switch or switching module to determine which image to be displayed. For example, the background image could be switched off and not be displayed so that a different image(s) can be displayed in the first portion 2511 of the view 2500.

As described herein, two images can form a composite image. For example, two non-latent images, e.g., two real-time images of the surgical field, can form a composite image. In various embodiments, when the horizontal line of sight is maintained, merging of images is possible. In addition, one non-latent image (e.g., a real-time image of the surgical field) and one latent image (e.g., a data file, a CT scan, a CAT scan, an MRI, an x-ray, ultrasound image, etc.) can form a composite image. In various embodiments, the latent and/or non-latent images can be seen individually by both eyes; and one or more of the images can have convergence information for a stereo or 3D effect. For example, the images can be displayed on 2D displays that represent 2D images from the input cameras. However, with convergence information, the brain can allow the eyes to see a 3D image.

FIG. 13B1 shows an illustration of an example medical apparatus according to certain embodiments described herein. FIG. 13B1-a shows a larger view of the side view of FIG. 13B1; and FIG. 13B1-b shows a larger view of the front view of FIG. 13B1. Example dimensional (e.g., in millimeters) values are provided. However, the dimensions are not particularly limited. As shown in FIG. 13B1-a, the example embodiment of the medical apparatus 3000 includes an imaging optics assembly 3003, a beam combiner 3004, a first display 3005a, and a second display 3006a. In some embodiments, the first display 3005a can be the same size as the second display 3006a. In some embodiments, one of the displays 3005a can be a combination of smaller displays with a corresponding outer dimension equal to the other display 3006a. In some other embodiments, the first display 3005a can have a different size than the second display 3006a. In some embodiments, the imaging optics assembly 3003 can include a mirror 3007 to relocate the optical path from the viewing oculars, chambers, ports or portals to a direction upwards (e.g. vertically) to the displays 3005a, 3006a. This can allow for the optical path from the viewing oculars, chambers, ports or portals to be of a suitable length without moving the oculars, chambers, ports or portals further (e.g., horizontally) from the surgical site. In some embodiments, the imaging optics assembly 3003 can have a periscope design with a first mirror or reflector configured to direct the optical path from the ocular or portal upward or vertically and another reflector, possibly a partially reflecting partially transmitting beamsplitter to reflect at least a portion of the optical path horizontally similar to a periscope. In some embodiments, the surgeon can advantageously be positioned to view the surgical site and to manipulate tools in an ergonomic way with the surgeon's arms sufficiently close to the surgical site so as not to need to stretch his or her arms, which can be especially uncomfortable for long surgical procedures. Accordingly, in some embodiments, 70% to 95% (e.g., 75% to 90%) of the height of the viewing assembly 3000 can be located above the viewing oculars, chambers, or ports. In some embodiments, the horizontal distance from the entrance of the ocular or portal to the display is not larger than the vertical distance from the entrance of the ocular or portal to the display 3005a.

As illustrated in the example embodiments, the distance between the ocular or eye portal optics and the display where the distance is the vertical distance or the distance along an axis perpendicular to the optical axis of the ocular or eye portal can be about 173 mm or between about 100 mm and about 250 mm, between about 120 mm and about 225 mm, or between about 140 mm and about 200 mm or any range between any of these values. The distance between the ocular or eye portal optics and the display where the distance is the horizontal distance or the distance along an axis parallel to the optical axis of the ocular or eye portal can be less than the vertical distance. In some embodiments, the horizontal distance is about 100 mm or between about 50 mm and about 200 mm, between about 75 mm and about 150 mm, or between about 90 mm and about 125 mm or any range between any of these values. In some embodiments, the horizontal distance is about 50% of the vertical distance, or between about 40% and about 90% of the vertical distance, between about 50% and about 80% of the vertical distance, or between about 60% and about 70% of the vertical distance or any range between any of these values. In some embodiments, the display housing of the medical apparatus has greater than or equal to about 50% of the display housing volume above the oculars or eye portals. In some embodiments, the display housing of the medical apparatus has greater than or equal to about 60% of the display housing volume above the oculars or eye portals, greater than or equal to about 70% of the display housing volume above the oculars or eye portals, greater than or equal to about 80% of the display housing volume above the oculars or eye portals, or greater than or equal to about 90% of the display housing volume above the oculars or eye portals, or greater than or equal to about 70% and/or less than or equal to about 95% of the display housing volume above the oculars or eye portals. As described herein, the displays can be positioned above the center of the oculars or eye portals where above the center of the oculars or eye portals can be any position above a plane defined by the optical axis at the exit window (e.g., lens or transparent window) from the display to the eye of the user in the ocular or eye portal. When the plane defined by the optical axis at the exit window is horizontal (e.g., perpendicular to gravity), then an object is above that plane when it is displaced along an axis perpendicular to the defined plane in a direction opposite the direction of gravity. If the display unit rotates to change the orientation of the defined plane, then, in some instances, the relative orientation of the components remains substantially fixed.

FIG. 13B1-c shows the example medical apparatus of FIG. 13B1 with an eye 3001 viewing into an ocular 3002. The medical apparatus includes an imaging optics assembly 3003, a beam combiner 3004, and first and second displays 3005a, 3006a. As described herein, the first display 3005a can display an image with a portion (e.g., bottom ¼ of the display) left black. The second display 3006a can display another image with a portion (e.g., top ¾ of the display) left black. FIG. 13B1-c also shows an alternative example of a first display 3015a with a ¼ corner left black, and a second display 3016a with the remaining ¾ portion left black. Other examples are possible.

As described herein, each eye can merge the two images together such that the two displays appear as one. For example, the eye can form a composite image including a background image and a PIP image. In various embodiments, the predominant image (e.g., from the first display 3005a) can be a non-latent image (e.g., a surgical microscope view of the surgical field), while the supplementary view, supplementary information, supplementary text, and/or supplementary overlays (e.g., from the second display 3006a) can be another non-latent image (e.g., an image of the surgical field from a surgical tool) or a latent image (e.g., a data file, a CT scan, a CAT scan, an MRI, an x-ray, an ultrasound image, etc.). In some embodiments, the two images can be separated from each other by a black bar or the two images can substantially overlap (e.g., in the form of a fluorescence image or a near IR image that goes through a processing box).

FIG. 13B1-d shows an illustration of a beam combiner arrangement 3004, a first camera 3008a, and a second camera 3009a. The first camera 3008a is in communication with a first camera controller 3010a, and the second camera 3009a is in communication with a second camera controller 3011a. The first camera controller 3010a can receive signals from the first camera 3008a, and the second camera controller 3011a can receive signals from the second camera 3009a. A graphical user interface (GUI) controller 3012 and switcher 3013 can communicate how to produce the images on the displays 3005a, 3006a (e.g., which portions to leave black) with the first and second camera controllers 3010a, 3011a. In certain embodiments of the medical apparatus, such processing does not introduce latency for real-time images because such resizing is not a latency-causing activity or function. For example, in some embodiments, the processing can be performed by a video switcher and/or controller and not by a single central processing unit. In various embodiments, the first and/or second camera controllers 3010a, 3011a can include image processors and/or camera control units. In some embodiments, the first and/or second camera controllers 3010a, 3011a can have modest functions. For example, in some embodiments, the first and/or second camera controllers 3010a, 3011a do not have to include computers. As an example, some embodiments include two non-latent lines, signals, or channels.

Certain embodiments of the medical apparatus can receive and display images based on the request from the GUI. For example, upon request, some embodiments can receive a latent image to be displayed. As an example, a static image of an x-ray, a CAT scan, an MRI, or an image from a computer can be received from a source, such as in a format like DICOM (Digital Imaging and Communications in Medicine). A non-latent image can also be received from another source. In some embodiments, the predominant image can be the non-latent image. However, in some instances, the predominant image can be the latent image. For example, a surgeon may wish to view the MRI. The surgeon would know that the MRI is not in real-time. However, the surgeon may wish to have the real-time image of the surgical site in view. In some such instances, the surgeon can switch, via the GUI, the predominant image to the MRI and keep the image of the surgical site as a PIP image. Various embodiments of the medical apparatus do not include a direct optical connection between the two displays (e.g., a decoupled display system) and are not configured in the same way as an operating room microscope.

Certain embodiments of the medical apparatus can include four displays (e.g., two displays for each eye). As disclosed herein, some embodiments can include three or more displays for at least one eye. For example, instead of the second display being as equal to the first, the second display could be a matrix of four smaller screens from four source channels. From a processor standpoint, a section of the display can be designed as non-latent, and can receive a non-latent image from another portion of the display or from another source. In some embodiments, two non-latent real-time images can be imposed as a PIP view in one display, and the transformation can be performed by either the camera or the display system, by multiple cameras or the display system, or by a controller. In some embodiments, when two non-latent images are superimposed and/or overlaid, there can be varying degrees of transparency. In addition, in some embodiments, the images can be registered with both the left and right eyes. For example, the PIP images for the left and right eyes can be placed in the same relative space (e.g., upper right hand corner for both left and right eyes).

In some embodiments, a latent image can be displayed on one display and the non-latent image on another display. In some embodiments, a latent image can be inserted into a non-latent image. For example, the images can be processed through a computer or a computer-like device (e.g., a same computer with the same display). Certain embodiments of the medical apparatus can include two or more displays to provide images (latent and/or non-latent) overlaid or integrated and merged in each eye. The advantage of certain embodiments is the ability to view images (latent and/or non-latent) from multiple sources, e.g., distal cameras, proximal cameras, external sources, etc.

In addition, sources with different formats can be combined. For example, one display can include an image from a digital source and the other display can include an image from an analog source. As one example, one camera can be a digital 3G SDI camera and the other camera can be an analog camera. If one of the displays was set up for an analog format and the other display was set up for a digital format, certain embodiments of a medical apparatus can mix formats without having to convert them into a common format. Accordingly, certain embodiments of a medical apparatus can provide a way of merging digital and analog formats in the same view without translation. In various embodiments, dissimilar and/or incompatible imaging sources can be combined by the user in each eye. In some embodiments, each eye's combined view might differ only by virtue of the convergence angle at the source. As an example, a near IR image can allow one to see within the tissue, e.g., within 1 cm in some cases from the surface. The convergence angles can be parallel, but lie outside the convergence angle of the visible image. The images on the display can be overlaid and displaced to match the convergence depth.

Figure 13C:
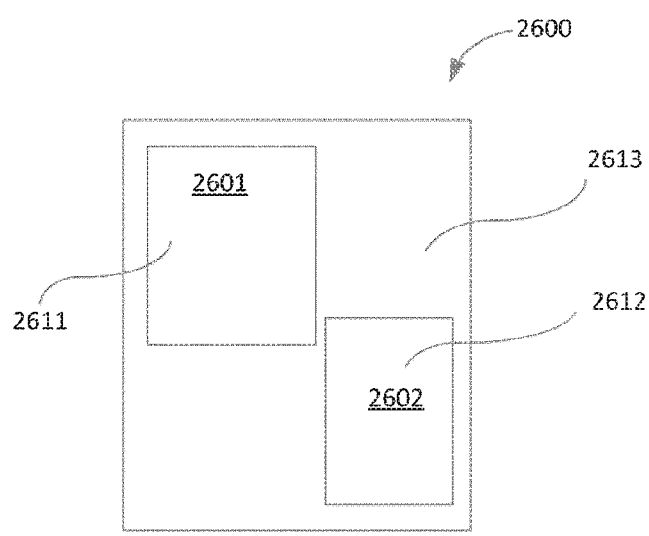
FIG. 13C illustrates a schematic of an example view of multiple images of a surgical field combined adjacent to one another.

FIG. 13C illustrates that the images are not restricted to PIP images. FIG. 13C shows, for example, a schematic of an example view 2600 of multiple images (e.g., from multiple sources) of the surgical field disposed adjacent to one another. For example, a first (e.g., a background) image 2601 is produced on a first portion 2611 of the view 2600, and a second (e.g., a smaller or of similar size) image 2602 is produced on a second portion 2612 of the view 2600 such that the images do not necessarily overlap one another or do not need to substantially overlap, or one image does not need to be substantially contained within the other images. In such embodiments, the images can appear adjacent to one another or tiles in a manner that is not restricted to a PIP arrangement. As described above, more than two images may be included, for example, tiled with respect to each other. Additionally, more than one beam combiner and more than two displays may be employed in various embodiments to combine images, for example, for the left eye (or for the right eye).

As described herein, some embodiments as shown in FIG. 12A-12C can, by the use of beam combiners 2230, advantageously can reduce latency by decreasing the time to produce an image for viewing. For example, multiple images can be tiled to view the multiple images from a variety of sources as opposed to being aligned and combined using an image processing technique that consumes computing power. In addition, an advantage of additional displays in each eye's path in certain embodiments can present to the viewer superimposed images without the complexity of electrical registration and timing issues. In some such embodiments, the brain can also merge the images if the additional displays are reasonably aligned optically.

In some embodiments, the above combination of images can be secondarily or additionally run through a central processor to produce a single composite (e.g., tiled, or picture-in-picture, etc.) view for a single display. Such a combination of differing sources may produce latency, however, the resultant image can be provided to other viewers in the room besides the operating surgeon. Such viewers or observers, such as staff, in the room may have less reason to require a low latency combination of images however such viewers may still benefit from seeing the surgery. For example, staff may be able to anticipate tools that the surgeon will request upon viewing the progress of the surgery. A central processor could produce stereo images for monitors plus goggles and/or auto stereoscopic monitors to be used by the ancillary medical personnel (e.g., staff).

In some embodiments, one or more of the separate signals directed to the separate displays can be accessed for use such as for recording. In some such configurations, one of the outputs from the cameras that are sending video to the respective display(s) could be used separately as the images are electronically separate. For example, the video signal directed to one of the displays can be recorded separately without being combined with images from another display in the recording. A recording device, such as a USB recorder or other storage device could be connected to a port associated with that camera or display allowing recording of the one or more images provided to that display. The user could control the segment of image signal recorded or otherwise used. For example, a still image or a segment of video of any duration (e.g., 1, 2, 3, 4, 5, 10, 20 or more seconds or minutes, or any range between any of these values) could be recorded. Input from the surgeon may be provided via a user interface to record for a certain duration such as for 1 to 10, 20, or 30 seconds or 30 seconds to a minute or from 1 to 2, 3, 5, or 10 minutes or longer. The signal that is recorded or otherwise obtained and used could be obtained from the separate camera or display for any duration and accessed at different times. Such a feature may be provided for one or more of the cameras and/or displays such that the surgeon may select which camera (based on viewing the respective display receiving video from that camera) from which to draw the signal for recording or other use without needing to obtain the signal (video) electronically combined with video displayed on the other displays. Each camera could, for example, have associated therewith a USB recorder or a port for such a recorder. As described above, the recording can be done locally on any or all input signals. The user could therefore edit (and possibly reorient and reposition) and/or emphasize a particular event for teaching or documentation purposes.

In various embodiments, the different displays have stages or platforms or are otherwise configured to be repositioned and/or reoriented mechanically to display for the surgeon respective video at different positions and orientations. In some embodiments, one or more of the different displays could be moved physically with respect to one another by the user. The displays could be mounted so as to be movable and/or reoriented by the surgeon either by hand or electronically. The user could thus move one display from one location on the left or top to another location on the right or bottom (or vice versa) of the view seen by the user. The user can thus reposition so overlay is re-registered. This may be done mechanically and optical (with a beam combiner) rather than electronically (although the displays may be moved electronically). In some cases a camera may be zoomed in (or out) and the zoomed view shown on the display may be repositioned (and/or reoriented) by physically moving the display on which the zoomed image is shown with respect to an image or information provided by another display. This capability may allow the surgeon to selectively emphasize or de-emphasize certain views or inputs from cameras or other sources displayed on the respective displays as desired (for example by placing the display more or less toward the center of the field of view of the viewer). As discussed above, the displays may include images from cameras, images from other sources such as other medical imaging devices (MRI, x-ray, CAT, etc.) or other data. The surgeon may also cause one or more of the inputs to be scaled up or down or enlarged or reduced to an area of interest (for example, reduced to a subset of a fluorescent or narrowband image), which can then be superimposed over another image or moved with respect to another image by moving one display relative to another. The beam combiner will combine the images such that they appear superimposed or otherwise juxtaposed with respect to each other based on the relative locations of the respective displays. In this manner, the surgeon can edit or emphasize particular views, for example, for surgery as well as edit or emphasize a particular event for teaching or documentation purposes.

As described elsewhere in this application and shown, for example, in FIGS. 1 and 11, as well as FIGS. 12A-12O and other figures, the display assembly need not be a direct view display providing an optical path from the user's eye to the surgical site. Instead, the viewer may view displays that show images captured by cameras viewing the surgical site. Likewise, the view can move about more independently and not be limited to the location and/or orientation of the camera. Accordingly, the viewer might be 2, 3, 4, 5 or more feet from the surgical site. The camera may be less than 1 foot or 2 feet (possibly less than 3 feet) from the surgical site in some such cases.

Cooperative Surgical Display Systems

As part of the surgical visualization systems described herein, a surgical display system can be configured to provide advantageous viewing features to a surgeon, assistant, or other operator of the surgical visualization system. A surgical display system can be configured to provide displays and optical components to view the displays. These displays can be configured to provide views of video captured with one or more cameras of the surgical visualization system. These displays can also be configured to provide views of other information, such as text data, images, or the like provided by another electronic device. A surgical display system can provide ports, portals, or oculars, transparent plates, lenses, prisms, mirrors, chambers, baffles, and the like to provide optical paths for a viewer to view the displays of the surgical display system.

In some embodiments, a surgical display system includes one or more displays (e.g., flat panel displays or FPDs) that are configured to be viewed by a surgeon. In the surgical display system, the optical paths to each eye include a combination of lenses configured to provide a view along a right eye optical path and a left eye optical path. Each optical path can be directed to the same display (e.g., to different parts of a single display) or to different displays, for example and without limitation. On the one or more displays, video images can be displayed from a collection of sources. Sources can include camera systems of a surgical visualization system. Examples of sources include one or more cameras on endoscopes, one or more cameras providing surgical microscope views of a surgical site, one or more proximal cameras mounted on a frame near or adjacent to the surgical site, one or more cameras on a surgical tool, and the like.

In some embodiments, a surgical display system includes one or more displays that are viewable in a particular optical path for an eye. For example, the right eye optical path can lead to one or more displays and the left eye optical path can lead to one or more separate displays. In such embodiments, each image acquisition camera system can be registered and aligned to produce a substantially identical view of a scene differing only in waveband selection. The images can be processed to enhance distinctive features or to differentiate between the images provided in the different wavebands. In some implementations, insertion and registration of pre-surgical information produced by an external source can be included on the one or more displays.

In some embodiments, a surgical display system includes one or more displays per eye optical path, wherein a display of information or image in a first display corresponds to a black area in a second display. This can allow the displays to combine to create a seemingly unitary image without ghosting or visual overlapping of different images. The black portion of the screen can be advantageous as it emits little to no light to reduce the contrast of the image provided on the first display.

In some embodiments, a surgical display system is provided that includes one or more displays per eye optical path. In such embodiments, a second image or portion of a second image can be registered to a first image on a first display. In this way, the first and second images can be combined visually to produce a coherent image.

In some embodiments, the surgical display systems disclosed herein are configured so that the right eye path (or right eye view) and the left eye path (or left eye view) provide different perspectives of the same image or images. The surgical display systems can be configured so that the exit pupil produced by the system for each eye path is nominally about 2-9 mm. The surgical display systems can be configured so that the field stop produced by the system for each eye is between about 18 mm and about 28 mm. The surgical display systems can be configured so that the apparent field of view associated with the exit pupil is between about 45 degrees and about 100 degrees. The surgical display systems can be configured so that the eye relief for each eye path is nominally between about 15 mm and about 30 mm. The surgical display systems can be configured so that the total path or track length of the optical path between any display and the viewer's eye (or exit pupil) is at least about 50 mm and/or less than or equal to about 400 mm. The surgical display systems can be configured so that the total track or path length of the optical path between any display and the viewer's eye (or exit pupil) contains one or more reflecting surfaces. The surgical display systems can be configured so that the total path length of the optical path between any display and the viewer's eye (or exit pupil) contains one or more prisms, for example, utilizing total internal reflection. The surgical display systems can be configured so that the one or more displays include more than one display per eye path and two or more displays are combined with a pellicle or thin glass mounted beamsplitter or combiner coating comprising one or more layers. In such embodiments, a thin glass mounted beamsplitter or combiner can be utilized and the ratio of diameter to substrate thickness can be less than about 100 to 1. In such embodiments, the beamsplitter or combiner coating can for example be made of a metalized layer, a patterned layer, or dielectric coating that has multiple layers.

Binocular Display Unit

Various embodiments include a binocular display unit including a pair of oculars that produces (for example, for each eye) an exit pupil in space. This can be a small zone where the marginal rays of the corners of the field of view cross the optical axis. A person's eye naturally chooses this spot when viewing scenes. At this position, a person sees a black margin around the field of view. For a modified Wheatstone configuration, the binocular display unit can be configured to utilize a rectangular display to take advantage of the natural tendencies of the viewer's vision.

Some embodiments employ a display with an exit pupil (as opposed to a large eye box). A rectangular field stop can be included in the ocular. In some implementations, rectangular baffles can be included in the display for rejection of stray light. These features can be combined with a rectangular panel display for each eye wherein the rectangular panel displays its half of a stereo image. The display can be positioned at a conjugate position with the field stop in the ocular. A near-eye display places the display at the field stop of the ocular.

The eye relief, e.g., the position of the exit pupil relative to the last surface of the ocular, is a factor that determines how close a viewer is to the device when viewing the displays. When the eye relief is greater than about 15 mm to about 20 mm, the observer can comfortably wear spectacles during use of the device.

The oculars of the binocular display unit can be used to provide a view with a larger apparent field of view. The ocular can be configured to provide the power and magnification to produce an exit pupil at a desired or targeted location thereby providing desired or targeted eye relief from a field stop. This can produce this apparent field of view.

Beyond a certain field of view (where field of view is inversely proportional to the focal length of the ocular), the output of the ocular does not generally couple with the pupil of an eye and a viewer typically fails to see part of the field. This effect can be referred to as a kidney bean effect, as the portion not seen has a kidney bean shape. A 10× magnification operating room microscope ocular, for example, has a wide field of view and comfortable exit pupil position. In the binocular display unit, the last components of the display system (e.g., the oculars), enable the apparent field of view.

Another consideration when designing a display unit that uses an eye box rather than an exit pupil is illumination. As the apparent field of view increases, the relative brightness of the display decreases. So, as the exit pupil grows until it becomes an eye box, the display panels decrease in apparent brightness because the area (of the eye box) is larger. Accordingly, the disclosed binocular display units put a significant amount of the total illumination into a useful sized exit pupil (as opposed to an eye box). This facilitates interoperability and integration into a surgical environment as the exit pupil of operating room microscopes is a well-established and accepted size.

Various embodiments of the binocular display unit provide a compact unit with ergonomic adjustments at or near the oculars. These display units can be configured to be less massive than other display units meaning that it can be easier to move and adjust.

In some embodiments, a display unit can include a display housing, an opening in the display housing, at least two chambers within the display housing (one for the left eye and one for the right eye), and at least one electronic display disposed the display housing, each of the at least one electronic display comprising a plurality of pixels configured to produce a two-dimensional image. The separate left and right optical paths together provide stereo viewing. The display housing is further configured to separate a right eye path from a left eye path to the at least one electronic display so that light intended to be viewed with a right eye from the at least one electronic display does not travel down the left eye path and vice versa. The medical apparatus includes an imaging system disposed on the display housing, the imaging system configured to generate images of a surgical site from outside the surgical site. The view of the display within the housing can be configured to provide a stereoscopic image to a viewer, as discussed above. In some embodiments, the housing further includes lenses and/or a transparent plate between the eyes of a viewer and the at least one electronic display. In some embodiments, the housing further includes a baffle or other structure to separate the left eye path and the right eye path. In some embodiments, each chamber is baffled to prevent light from one channel to communicate to the other eye path. In some embodiments, at least a portion of the chambers comprise oculars.

In certain implementations, the display unit can be baffled to prevent light communication between the left and right eye channels. To adjust for different accommodations, the displays within the display system can be configured to move toward and/or away from the viewer along the optical path. This can have an effect similar to varying focal lengths of lenses in an ocular system. In some embodiments, the display housing with the electronic displays can change to move the displays closer or further from the viewer along the optical path. In some embodiments, both the display housing and the electronic displays are configured to be adjustable along the optical path to adjust for accommodation.

In certain implementations, the binocular display unit can be configured to receive video images acquired with an endoscope and display these video images within the unit. These images can be combined (e.g., stitched, tiled, switched, etc.) with video from other sources by an operator so that video images from one or more sources, including the endoscope video images, can be viewed with the binocular display unit.

Display Unit with Folded Optical Path

Various embodiments include a display unit including optical elements configured to redirect an optical path from a viewer's eye to a display such that the display is positioned above the viewer's eye when the viewer is looking substantially horizontally (e.g., where horizontal is perpendicular to gravity which is vertical) into the display unit. FIG. 13B1-*a* illustrates an example of such a configuration for a display unit wherein optical components direct and focus images from displays 3005*a* and 3006*a* to the viewer using a beamsplitter/combiner 3004 and mirror or reflector 3007. This allows the displays 3005*a* and 3006*a* to be positioned above the level of the eye when the viewer is looking substantially horizontally (e.g., with gravity vertical) into the display unit. This may also be the case where the majority or all of the optical components are not above the level of the eye when the viewer is looking substantially horizontally into the display unit.

In some embodiments, the display unit includes oculars through which the viewer looks to view images provided by the displays 3005*a*, 3006*a*. In some embodiments, the display unit includes eye portals through which the viewer looks to view images provided by the displays 3005*a*, 3006*a*. In either of these embodiments, the oculars or eye portals and the display unit can include optical components configured to direct the optical path from the displays to the oculars or eye portals as well as to provide imaging functionality. In some embodiments, dimensions of the display housing include the oculars or eye portals and in some embodiments, dimensions of the display housing exclude the oculars or eye portals.

To facilitate the description of the configuration of the display unit, a coordinate system will be adopted that is fixed to the display unit. The coordinate system will take the optical axis through the oculars or eye portals as the x-axis (an example of which is illustrated in FIGS. 13B1-*e* and 13B1-*f*) and the optical axis after the redirection optical component (e.g., the mirror or reflector 3007 in FIG. 13B1-*a*) as the y-axis (an example of which is illustrated in FIGS. 13B1-*e* and 13B1-*f*), the x-axis being perpendicular to the y-axis. The physical distance along the x-axis from the display to the oculars can be a fraction of the distance along the y-axis from the display to the oculars. For example, the distance along the x-axis to the display can be less than or equal to 90% of the distance along the y-axis to the display, less than or equal to 80% of the distance along the y-axis to the display, less than or equal to 70% of the distance along the y-axis to the display, less than or equal to 60% of the distance along the y-axis to the display, or less than or equal to 50% of the distance along the y-axis to the display or any ranges therebetween. In some embodiments, after the optics of the oculars or eye portals, the majority of the optical components can be positioned above (e.g., in a positive direction along the y-axis as defined) the oculars or eye portals. In some embodiments, a majority of the length of the optical path can be positioned above the oculars or eye portals. For example, the total length of the optical path can be taken as the distance from a first optical component (e.g., window where a window may be a lens or planar transparent plate) of the oculars or eye portal to the display 3005*a* or 3006*a*. In some embodiments described herein, less than 50% of that total length is the length of the optical path before the mirror 3007 or the optical component that redirects the optical path from being substantially along the x-axis to being substantially along the y-axis. In some embodiments, the optical axis does not travel downward along the y-axis. In some embodiments, the optical axis does not travel downward along the y-axis prior to being redirected upward along the y-axis toward the displays. These features can allow for a display unit that is larger in height than in depth. This may be advantageous to allow for a display unit that can be moved around in an operating room environment without substantially interfering with the positioning of other display units, camera assemblies, and/or personnel.

To further describe the configuration of the display unit, the coordinate system defined above can include a plane that is perpendicular to the y-axis, referred to as the viewing plane, where the viewing plane intersects the optical axis at the oculars or eye portals. In some embodiments, the display unit can be configured so that a majority of the optical path is not below this viewing plane. In some embodiments, the display unit can be configured so that a majority of the optical path is above this viewing plane. In some embodiments, the display unit can be configured so that at least 40%, at least 50%, at least 60%, at least 70%, at least 80%, or at least 90% of the optical path is above the viewing plane or any value therebetween. In some embodiments, the display unit can be configured so that at least 40% and/or less than or equal to about 99%, at least 50% and/or less than or equal to about 95%, at least 60% and/or less than or equal to about 90%, or at least 70% and/or less than or equal to about 85% of the optical path is above the viewing plane. In some embodiments, the display unit can be configured so that a majority of the optical components are above the viewing plane. In some embodiments, the display unit can be configured so that the displays are above the viewing plane. In some embodiments, the display unit can be configured so that a majority of the display housing volume is above the viewing plane. In some embodiments, the display unit can be configured so that at least 40%, at least 50%, at least 60%, at least 70%, at least 80%, or at least 90% of the display housing volume is above the viewing plane. In some embodiments, the display unit can be configured so that at least 40% and/or less than or equal to about 99%, at least 50% and/or less than or equal to about 95%, at least 60% and/or less than or equal to about 90%, or at least 70% and/or less than or equal to about 85% of the display housing volume is above the viewing plane.

In some embodiments, the display units can be positioned so that their display panels are substantially perpendicular to one another, as illustrated in FIG. 13B1-*e*. In some embodiments, the display units can be positioned so that their display panels are substantially parallel to one another, as illustrated in FIG. 13B1-f. In such an embodiment, an additional mirror 3004b can be included above the beamsplitter/combiner 3004 to redirect the optical axis to the other display.

The display unit can have a depth, d, (e.g., the extent of the display unit housing along the x-axis) and a height, h, (e.g., the extent of the display unit housing along the y-axis) that forms an aspect ratio (d:h) that is less than 1. The aspect ratio of the depth to height can be less than or equal to about 0.95, 0.9, 0.85, 0.8, 0.75, 0.7, 0.65, 0.6, 0.55, 0.5, 0.45, or 0.4 or ranges therebetween any of these values (e.g., 0.95-0.6 or 0.9-0.65).

To facilitate the description of other configurations of the display unit, another coordinate system will be adopted that is fixed relative to gravity. The coordinate system will take gravity as the y-axis and the x-axis lies within the horizontal plane perpendicular to gravity, the x-axis being the projection of the optical axis at the exit window (e.g., final lens element of the oculars or eye portal) on the horizontal plane. In this coordinate system, the height of the display unit can be taken as the dimension of the display housing along the y-axis (e.g., the direction parallel to gravity) and the depth can be the dimension taken along the x-axis (e.g., the direction perpendicular to gravity and parallel to the projected optical path at the ocular or eye portal). With this convention, the display unit can have a depth, d, (e.g., the extent of the display unit housing along the x-axis) and a height, h, (e.g., the extent of the display unit housing along the y-axis) that forms an aspect ratio (d:h) that is less than 1. The aspect ratio of the depth to height can be less than or equal to about 0.95, 0.9, 0.85, 0.8, 0.75, 0.7, 0.65, 0.6, 0.55, 0.5, 0.45, or 0.4 or ranges therebetween any of these values (e.g., 0.95-0.6 or 0.9-0.65). In some implementations, the optical path of the oculars or eye portals can form an angle that is less than or equal to about 30 degrees with the horizontal plane, less than or equal to about 15 degrees with the horizontal plane, less than or equal to about 10 degrees with the horizontal plane, less than or equal to about 5 degrees with the horizontal plane, or less than or equal to about 0 degrees with the horizontal plane.

In some embodiments, the display housing can have a height that is larger than its depth. For example, the depth can be less than or equal to about 90% of the height, less than or equal to about 80% of the height, less than or equal to about 70% of the height, less than or equal to about 60% of the height, less than or equal to about 50% of the height, or less than or equal to about 40% of the height. In some embodiments, the display housing can be longer than it is deep. For example, the display housing can be at least 10% longer than it is deep, at least 25% longer than it is deep, at least 50% longer than it is deep, or at least 100% longer than it is deep. In some implementations, the optical path within the display housing can be longer along its height than along its depth. For example, the optical path along the height can be at least 10% longer than along its depth, at least 25% longer than along its depth, at least 50% longer than along its depth, or at least 100% longer than along its depth or any range of values therebetween.

In some embodiments, the display unit can include an optical system (e.g., lenses) with one or more two-dimensional displays and illumination sources, the optical system configured to direct rays from the displays and illumination sources towards the eyes of a viewer, the optical system configured to produce a collimated virtual image of the one or more displays for each eye. A majority or all of the optical system of the display unit can be near or above a plane that is parallel to the viewer's line of site when looking through oculars or eye portals into the display unit to see the displays. In certain implementations, the collimated rays can be disposed at an angle relative to a vertical plane that is substantially perpendicular to the plane parallel to the viewer's line of site. In some implementations, the display unit includes one or more fold mirrors or prisms or reflectors that are positioned between the displays and the optical system enabling the use of displays that are wider than the center-to-center spacing of the ocular or eye portals or the viewer's eyes, an example of which is illustrated in FIGS. 13B1 and 13B1-b. In some implementations, the one or more fold mirrors or prisms or reflectors lie within the optical system rather than between the optical system and the displays. In some implementations, the optical system includes one or more fold mirrors or prisms or reflectors configured to permit displacement (e.g., in the z-direction) of each eye's opto-mechanical axis to permit a compact overall design and ergonomic adjustment. In some implementations, one or more fold mirrors or prisms or reflectors are positioned between the displays and the optical system, the one or more fold mirrors or prisms configured to permit displacement (e.g., in the z-direction) of each eye's opto-mechanical axis to permit a compact overall design and ergonomic adjustment.

Accommodation Differences

In some embodiments, a display unit can include a display housing, an opening in the display housing, at least two chambers within the display housing, and at least one electronic display disposed in the display housing, each of the at least one electronic display comprising a plurality of pixels configured to produce a two-dimensional image. The display housing is further configured to separate a right eye path from a left eye path to the at least one electronic display so that light intended to be viewed with a right eye from the at least one electronic display does not travel down the left eye path and vice versa. The medical apparatus includes an imaging system disposed on the display housing, the imaging system configured to generate images of a surgical site from outside the surgical site. The view of the display within the housing can be configured to provide a stereoscopic image to a viewer. In some embodiments, the housing further includes lenses and/or a transparent plate between the eyes of a viewer and the at least one electronic display. In some embodiments, the housing further includes a baffle or other structure to separate the left eye path and the right eye path. In some embodiments, each chamber is baffled to prevent light from one channel to communicate to the other eye path. In some embodiments, at least a portion of the chambers comprise oculars.

In certain implementations, the display unit can be baffled to prevent light communication between the left and right eye channels. To adjust for different accommodations, the displays within the display system can be configured to move toward and/or away from the viewer along the optical path. This can have an effect similar to varying focal lengths of lenses in an ocular system. Similarly, lenses or other optical components can be moved in the system to provide for different accommodations. In some embodiments, accommodation adjustment can be made by moving the screens relative to the lenses inside the display unit. In certain implementations, by lengthening the housing with the screens attached, or by moving the screens within a fixed housing relative to the lenses and user, or by moving the position and/or the separation of lenses or groups of lenses, accommodation can be adjusted. Additional adjustments between the two chambers can be accomplished by physically moving the two chambers laterally, e.g., by separating or moving the chambers closer together to adjust for inter pupillary distance differences between users.

In some embodiments, the display housing with the electronic displays can change to move the displays closer or further from the viewer along the optical path. In some embodiments, both the display housing and the electronic displays are configured to be adjustable along the optical path to adjust for accommodation.

In certain implementations, the binocular display unit can be configured to receive video images acquired with an endoscope and display these video images within the unit. These images can be combined (e.g., stitched, tiled, switched, etc.) with video from other sources by an operator so that video images from one or more sources, including the endoscope video images, can be viewed with the binocular display unit.

Camera Providing Surgical Microscope Views

The beginning, middle and end of a surgical case may involve differing visualization goals. As the case begins, the surgeon may be interested in surveying and viewing the area for the surgery. At skin level the surgeon may use surgical tools and the operating room microscope to guide their progress into the body to the surgical site. This means what is desirable is an image acquisition system functioning like an operating room microscope (OR scope) until such time as they choose to use views from other cameras (e.g., one or more cameras on a surgical tool(s), endoscope(s), one or more proximal cameras, etc.).

With this display design a number of surgical microscope camera functions are enabled. As described herein, the difference between using an exit pupil versus using an eye box results in differing apparent fields of view. Similarly, the choice of an electronic acquisition system that is not optically connected to the displays, as is the case in typical OR microscopy, makes many features possible.

An optically coupled microscope may have huge arms and complicated motions to position the microscope in positions required for surgery, in particular for neurosurgery. Some stands give the operating room microscopes a wide range of counterbalanced motions. Decoupling the optical system acquisition from the display, allows for a far greater range of motion, and this motion is closer to the optical elements of the system rather than the stand. Such a decoupled optical system can enable a compact system that can eliminate most or all counterbalancing efforts due at least in part to the reduced size and mass. Similarly, decoupling image acquisition of the surgical microscope view and providing an electronic display with no direct optical path from the oculars to the surgical site affords the opportunity to make a compact and ergonomic system.

Oblique surgical microscope views are useful, for example, for neurosurgery. One challenge to overcome in such systems is if there is a rotation of the surgical microscope views for oblique views there may be a roll component with the following result. The surgeon's eyes are in a plane parallel with the horizon and parallel with the display. Adding an oblique view in the right eye and left eye path's rolling, meaning the right eye and left eye may rock up and down with respect to one another as the mechanism is repositioned.

If the pitch is in a line coincident with the primary surgeon's gaze, from vertical to oblique, yaw around a central axis position-able in x and y, a collar to rotate surgical microscope cameras to switch views between the pairs of optics or alternatively the upper gimbal can be rotated 90 degrees and the view through the right eye left eye pairs can be switched electronically to give a roll motion in a vertical position. The pitch and yaw and collar gimbals are can be motor driven controlled by a joystick on one of the handles that manually control x and y of the assembly. A fine focus z adjustment can be manual or motor driven from controls or mechanisms on one handle or on one of the 2 handles on either side of the assembly. Zoom functions, illumination controls, fixing gaze position etc. can be controlled from the handles as well. The one handle or the 2 handles can reposition the entire mechanism under the display in x and y without disturbing the position of the display.

This assembly does not introduce roll in an oblique view, but could be positioned in a vertical position to have some roll if that is desired. For example, if one wants to roll the view slightly to one side or another so one or the other eye's view is not obstructed by tool use in the surgical opening when the surgical microscope camera is used in a substantially vertical position.

In some embodiments, an electronic surgical microscope for one or more surgeons to view a stereo pair of images in an electronic display from a surgical site is provided that includes a right eye path and a left eye path through a common objective. The electronic surgical microscope can be configured to be used at the focal length of the objective.

In a further embodiment, the electronic surgical microscope can include a right eye path comprising a view through a common objective and an afocal zoom assembly as well as a left eye path comprising a view through a common objective and an afocal zoom assembly.

In a further embodiment, the electronic surgical microscope can include a right eye path comprising a view through a common objective and an afocal zoom assembly and an adjustable diaphragm as well as a left eye path comprising a view through a common objective and an afocal zoom assembly and an adjustable diaphragm.

In a further embodiment, the electronic surgical microscope can include a right eye path comprising a view through a common objective and an afocal zoom assembly and an adjustable diaphragm and a focusing lens assembly as well as a left eye path comprising a view through a common objective and an afocal zoom assembly and an adjustable diaphragm and a focusing lens assembly.

In a further embodiment, the electronic surgical microscope can include a right eye path comprising a view through a common objective and an afocal zoom assembly and an adjustable diaphragm and a focusing lens assembly forming an image on a detector. In a further embodiment, the electronic surgical microscope can include a left eye path comprising a view through a common objective and an afocal zoom assembly and an adjustable diaphragm and a focusing lens assembly forming an image on a detector.

In a further embodiment, the electronic surgical microscope can include 2 or more real time video camera systems coupled to the right eye and left eye paths for processing signals from the right eye and left eye detectors, wherein electronic signals of each eye path produce resolution compatible with HD displays, e.g. 720i, 720p, 1080i, 1080p, and 4k.

In a further embodiment, the electronic surgical microscope can be configured so that neither eye path produces an aerial image suitable for direct viewing.

In a further embodiment, the electronic surgical microscope can include a system to divide the output of each detector, right and left eye, and vertically flip the images to a second right eye and left eye display for an assistant surgeon at 180 degrees to the primary surgeon.

In a further embodiment, the electronic surgical microscope can include a second pair of stereo paths that include a right eye path comprising a view through a common objective and an afocal zoom assembly and an adjustable diaphragm and a focusing lens assembly forming an image on a detector, a left eye path comprising of a view through a common objective and an afocal zoom assembly and an adjustable diaphragm and a focusing lens assembly forming an image on a detector, where both stereo paths are rotated 90 degrees from the first stereo pair paths to permit a second surgeon to view through the common objective and sit at 90 degrees to the primary surgeon. In addition, it can be configured so that neither eye path produces an aerial image suitable for direct viewing. In yet a further embodiment, the right eye path and the left eye path to their respective detectors permit an assistant surgeon to sit at right angles to the primary surgeon. Similarly, the output of the right eye and left eye detector of the assistant surgeon's detector may be vertically flipped to display the stereo scenes appropriately whether the assistant surgeon sits on the right or left side of the primary surgeon. Likewise, the surgical microscope can include a collar to support the stereomicroscope permitting the 4 eye paths to be rotated around the line of sight within the collar plus or minus 90 degrees or more and a system to switch stereo pairs displayed in the viewer from assistant surgeon to primary surgeon.

In some embodiments, a surgical microscope image acquisition system can be provided for acquiring stereo images of a surgical site to be displayed for one or more surgeons without a direct path optically between the lens elements of the acquiring system and surgeon's eyes. In a further embodiment, the surgical microscope image acquisition system can be suspended below an electronic display system for surgery and attached to a plane parallel with the horizon. The plane is the bottom surface of an electronic display for viewing the output of the stereomicroscope image acquisition system. In some embodiments, the plane is integral with a proximal column providing rotation, yaw, for integral displays and one or more stereomicroscope image acquisition systems. In a further embodiment, the column attaches to an arm which provides x y and z positioning movement for entire acquisition and display system at, over or adjacent to the patient. In a further embodiment, the arm attaches to a vertical column supporting all of the above which provides z, rotation and yaw. In some embodiments, the column can provide gross positioning and focusing without the need of counter balance measures as seen in operating room microscope stands, due to the lack of a directly optical pathway from the surgical site to the doctor's eyes.

Decoupling image acquisition from display in a Wheatstone like stereo display results in less mass and less movement of the display(s) that can result in an ergonomic viewing position for long cases. The primary positioning of a surgical view can be by the gimbaled image acquisition system. The positioning elements can be moved from adjacent to column in competing solutions to adjacent to the image acquisition system described herein that provides surgical microscope views.

In some embodiments, a surgical microscope image acquisition system whose stereo pair eye paths view a surgical site through a common objective contains one or more zoom (or just 'lens') assemblies to transform the numerical aperture of one or more fiber optic cables from a remote source(s) also functioning through a common objective. By this means the divergence of the illumination light may be altered to illuminate a scene as either the imaging zoom changes, or to place more energy in an area.

In some embodiments, a surgical microscope image acquisition system is provided where the fiber optic illumination zoom functioning through a common objective has a gimbal mechanism so that the illumination may be steered within the surgical opening, or on the patient.

Various embodiments include a gimbaled image acquisition system, which has a working distance range and stereo separation of an operating room microscope, without an optical through path to the surgeon's eyes. The acquisition system is mounted in a collar (described above) in a gimbal system so that four zoom paths can be rotated 90 degrees around the line of sight to switch stereo paths between assistant surgeon and primary surgeon.

The acquisition system and collar attach to a yoke, which allows the surgical microscope image acquisition system to pitch, e.g., view closer to or further away from the surgeon.

An electronic stereomicroscope for one or more surgeons is provided to view a stereo pair of images in an electronic display from a surgical site having separate right eye and left eye paths (e.g., a Greenough configuration) with a variable convergence. In some embodiments, the electronic stereomicroscope can include a right eye path comprising tilted afocal zoom assembly providing variable convergence angle option as well as a left eye path comprising tilted afocal zoom assembly providing variable convergence angle option.

FIGS. 8A-8B illustrate views of a camera providing a surgical microscope view rotated around a central axis from the point of view of the primary surgeon. The x y stage under the display allows the surgical camera view mechanism to be shifted from one side to another giving the surgeon better access to the surgical site for tool use. The assistant scope can be moved from one side of the device to the other, e.g., +/−90 degrees, from the position of the primary surgeon. The gimbal on the yoke allows the device to see retrograde from vertical. The gimbal system can be positioned for an oblique side view. The device can be configured for oblique views which may be particularly advantageous for neurosurgery.

Frame and Proximal Cameras

Certain embodiments include a medical apparatus comprising one or more proximal and/or distal cameras. In some cases (e.g., in some cases of brain surgery), minimal retraction and/or momentary retraction may be desired. Accordingly, certain embodiments of a medical apparatus comprising a frame, which is not a retractor, can be beneficial. Accordingly, various embodiments of a medical apparatus can comprise a frame that is not a retractor. The frame may be configured to be disposed above a surgical site of a patient. The frame can be mounted to a bed or to the patient and in some embodiments, anchored outside the surgical site of the patient. The medical apparatus can also include one or more cameras (e.g., a stereo camera, a mono camera, a camera providing a surgical microscope view, etc.) mounted to the frame. The one or more cameras can be configured to image the surgical site.

FIG. 14A shows a schematic of an example of such a medical apparatus 500 comprising a frame 510 disposed above a surgical site 501 of mock patient. The mock patient includes an opening 505 in the skull 507, material 509 representing brain, and material 511 representing white tissue. A hand retractor 513 is shown as lifting the material 509 representing brain to show the skull base tissue 511. The frame 510 can be configured to be disposed above the surgical site 501 of the patient. One or more cameras 520 can be mounted to the frame 510. For example, referring to FIG. 14A, one or more cameras 520 can be mounted to the frame 510 via mounts, clamps, and/or fingers 525 (with or without gimbals 530).

In various embodiments, the frame 510 can be configured to be mounted to a bed (e.g., to a gurney) or to the patient. For example, the frame 510 can be configured to be mounted to the bed (e.g., to the bed rail) and/or to the patient via a Mayfield clamp or a Mayfield mount. The frame 510 can be configured to be disposed outside the patient but within a close proximity to the patient and/or surgical site 501. For example, the frame 510 can be configured to be disposed above the surgical site 501 and/or above the patient by a distance of 1 mm, 5 mm, 10 mm, 15 mm, 20 mm, 25 mm, 30 mm, 35 mm, 40 mm, 45 mm, 50 mm, 75 mm, 100 mm, 120 mm, 130 mm, 140 mm, 150 mm, 175 mm, 200 mm, 250 mm, 300 mm or any value in between these values. Accordingly, in various embodiments, the frame 510 can be configured to be disposed, for example, 1 mm to 50 mm, 5 mm to 40 mm, 5 mm to 50 mm, 10 mm to 25 mm, 10 mm to 40 mm, 10 mm to 50 mm, 50 mm to 75 mm, 50 mm to 100 mm, 50 mm to 120 mm, 50 mm to 130 mm, 50 mm to 140 mm, 50 mm to 150 mm, 100 mm to 200 mm, (or any range formed by any of the values from 1 mm to 300 mm) above the surgical site 501 and/or above the patient. In various embodiments, the camera location can be configured to be disposed above the surgical site 501 and/or above the patient by a distance of 1 mm, 5 mm, 10 mm, 15 mm, 20 mm, 25 mm, 30 mm, 35 mm, 40 mm, 45 mm, 50 mm, 75 mm, 100 mm, 120 mm, 130 mm, 140 mm, 150 mm, 175 mm, 200 mm, 250 mm, 300 mm or any value in between these values. Accordingly, in various embodiments, the frame 510 can be configured to be disposed, for example, 1 mm to 50 mm, 5 mm to 40 mm, 5 mm to 50 mm, 10 mm to 25 mm, 10 mm to 40 mm, 10 mm to 50 mm, 50 mm to 75 mm, 50 mm to 100 mm, 50 mm to 120 mm, 50 mm to 130 mm, 50 mm to 140 mm, 50 mm to 150 mm, 100 mm to 200 mm, (or any range formed by any of the values from 1 mm to 300 mm) above the surgical site 501 and/or above the patient. In some embodiments, the camera can extend close to and/or inside the surgical site even if the frame 510 is located above the surgical site.

The one or more cameras 520 can include any of the cameras described herein. For example, the one or more cameras 520 can include a mono view camera, e.g., a single camera with one field of view with a circular, rectangular, or square image output. In various embodiments, the one or more cameras 520 can provide a left-eye view and a right-eye view. In some such embodiments, the one or more cameras 520 can be configured to provide stereo imaging. For example, the one or more cameras 520 can include a stereo view camera, stereo assemblies, a pair of cameras, or a split sensor with one-half providing the right-eye view and the other half providing the left-eye view. The one or more cameras 520 can include one or more illumination sources.

Various embodiments of the medical apparatus 500 include a frame 510 for the purpose, partially or predominantly, of holding one or more cameras 520 (e.g., one or more cameras as described herein). Because the frame 510 is not a retractor and does not move or retract tissue, a hand retractor 513 can be used to move tissue in the surgical site 501. In various embodiments, one or more cameras 520 can be configured to be mounted to the frame 510. In some embodiments, the one or more cameras 520 can face inwardly and/or downwardly into the surgical site. The size of the frame 510 is not particularly limited and can depend on the size of the surgical site 501 and/or the type of surgical procedure. The shape of the frame 510 is also not particularly limited. As some examples, the frame 510 can have a cross-sectional shape comprising a round shape (e.g., a circle, an oval, etc.), a regular polygon (e.g., a square, a rectangle, a hexagon, an octagon, etc.), or an irregular polygon (e.g., an L-type shape). FIGS. 14A1-a, 14A1-b, and 14A1-c schematically illustrate an example circular frame 510a, an example square frame 510b, and an example L-shaped frame 510c respectively.

Various embodiments of the medical apparatus 500 can include one or more cameras 520 mounted to the frame 510 to provide one or more perspectives of the surgical site 501. In some embodiments, proximal cameras can be mounted to the frame 510 providing at least two or at least four different perspectives. As one example, four cameras 520 can be mounted to the frame 510 at 3 o'clock, 6 o'clock, 9 o'clock, and 12 o'clock positions. As shown in FIGS. 14A1-a, cameras 520a are mounted to frame 510a at 3, 6, 9, and 12 o'clock positions. In addition, as shown in FIGS. 14A1-b, cameras 520b are mounted to frame 510b at 3, 6, 9, and 12 o'clock positions. In various embodiments, referring to FIG. 14A, the cameras 520 can be positioned 90 degrees (or other angles) apart from each other. Accordingly, referring to FIG. 14A, the cameras 520 can be positionable around the frame 510, for example, around a ring or around a square. In some instances, the cameras 520 can be symmetrically positioned around the frame 510. In other instances, the cameras 520 can be asymmetrically positioned around the frame 510. As additional examples, cameras 520 can be mounted to an L shape of one kind or another. In FIGS. 14A1-c, cameras 520c are mounted to the L-shaped frame 510c.

By being mounted to the frame 510, the one or more cameras 520 can image the surgical site 501. Certain embodiments described herein can include one or more mounts (or clamps or fingers) 525 connecting the one or more cameras 520 to the frame 510. Although the cross-sectional shape of the mounts 525 in FIG. 14A is schematically shown as rectangular, the shape of one or more mounts 525 is not particularly limited.

Various embodiments of the medical apparatus 500 can include one or more gimbals 530 and/or movement control systems (e.g., other positioning and/or orientation systems similar to any of those described herein) to couple a camera 520 to the frame 510 and to change the positioning and/or orientation of the camera 520. In some embodiments, the one or more gimbals 530 can provide gimballing motions similar to those described for cameras providing a surgical microscope view underneath a display. For example, various embodiments utilize a gimbal system similar to those from under the camera providing a surgical microscope view, yet can be relatively smaller and disposed on mounts, clamps, or fingers 525. As will be described herein, various embodiments can include attachment points 515 for four-bar or other x-y-z mechanisms (see, e.g., FIGS. 14A1-a, 14A1-b, and 14A1-c).

Accordingly, in various embodiments, one or more cameras 520 can include first and second cameras configured to move relative to the surgical site 501. For example, certain embodiments of the medical apparatus 500 include one or more gimbals 530 mounted to one or more mounts 525. The one or more gimbals 530 can be configured to allow positioning of one or more proximal cameras 520, such as those not inside the surgical site 501 but viewing into it. Such embodiments can have some advantageous positions. Thus, in various embodiments, one or more gimbals 530 can be configured to move the one or more cameras 520 relative to the frame 510. Some embodiments can include knobs or heads to turn one or more cameras 520 in and out. Some embodiments can also include some features to drive one or more cameras 520 in a precise manner (e.g., sub-millimeter range of motions). In some embodiments, three, four, or more knobs can be provided on either side on the external side (e.g., the outboard side) of the frame 510. By turning the knobs, one or more gimbals 530 can be oriented to move in one axis or the other axis, or move in an x axis or move in a y axis, or move in a z axis, which can be a very advantageous situation. In some embodiments, one or more cameras 520 can be configured to move electronically.

As described herein, the one or more cameras 520 can include any of the cameras described herein. For example, the one or more cameras 520 can include a stereo view camera, stereo assemblies, a pair of cameras, or a split sensor with one-half providing the right-eye view and the other half providing the left-eye view.

One of the advantages of stereo imaging is the ability to provide great depth perception. One of the downsides of any kind of surgery inside the body is becoming disoriented. To give an orientation of location inside the body, surgeons can look at surgical landmarks, the direction of a light source, an external part of an endoscope (e.g., outside the body), and/or a cable coming out of the scope. Additionally, an anatomical landmark relative to others can also be used. However, tissue with very different functions can look very similar, thus resulting in disorientation. Stereo imaging, while it can give great depth perception, can actually add to confusion. If surgeons can be certain that they are always in a horizontal orientation, it can be an extremely advantageous feature, because at least surgeons can know they were not rotated. For example, surgeons may still have some orientation issue about location. However, knowing that the right eye and left eye are seeing things as though standing on the floor and upright, with the right eye and left eye in the same plane, can be extremely advantageous to avoid becoming disoriented.

Utilizing one or more gimbals 530 (and/or other positioning and/or orientation systems), e.g., including those having six degrees of freedom, can allow the horizontal line of sight, e.g., right eye and left eye, to have the same orientation as the viewer. For example, certain embodiments can maintain the horizontal in a way that does not allow any other motion other than keeping the right eye and left eye horizontal orientation, whether looking straight down or in an oblique situation. As described herein, this can be advantageous in some instances. If a surgeon has an obstruction, it may be desired to angle the surgeon's view to see around the distraction, but to maintain a horizontal line of sight or at least not to introduce roll.

Accordingly, in certain embodiments, the one or more cameras 520 can include first and second cameras configured to move relative to the surgical site 501 and to maintain a same horizontal orientation with respect to each other. For example, referring to FIG. 14A, the mounts 525 can hold the six degrees of freedom (or however many degrees of freedom desired) to create a gimbal that moves around (e.g., to allow a gimbal 530 to move around) but, can in various embodiments, maintain the horizontal orientation of right eye and left eye in the same plane or allow the viewer to not feel the right eye or left eye higher than or lower than the other eye. With continued reference to FIG. 14A, in certain embodiments, a camera 520 can be relatively smaller than the mount 525. The gimbal 530 can have a relatively small pitch yaw rotation structure that can move the camera 520 to direct its line of sight in six degrees of freedom. Certain embodiments provide x-y-z and pitch, yaw, and roll mainly both to position the camera 520 but also to maintain the horizontal axis of the two eye views. For example, in various embodiments, the one or more gimbals 530 can be configured to potentially allow for repositioning in (transverse) x, y, or (longitudinal) z direction as well as pitch or yaw (rotation), or any combination thereof. Various embodiments, however, might not enable roll so as to reduce the disorientation that may result when the left and right channels of a stereo camera are rolled (e.g., the horizontal line through the left and right channels are not parallel to the ground). Accordingly, the one or more cameras 520 can be configured to move with respect to an x direction, a y direction, or a z direction. In some embodiments, one or more cameras 520 can be configured to move with respect to a pitch or yaw. For example, one or more cameras 520 can be configured to move with respect to a pitch and/or yaw, and without roll.

As described herein, in various embodiments, the frame 510 can be configured to be mounted (directly or indirectly) to a bed (e.g., a gurney) and/or to the patient and anchored outside the surgical site of the patient. In some embodiments, the frame 510 can be configured to be mounted to the bed (e.g., to the bed rail) and/or to the patient via a Mayfield clamp or a Mayfield mount. In some embodiments, the frame 510 can be configured to provide a stereotactic planning system. For example, a system that provides a frame of reference, e.g., a coordinate system associated with many positions in that region can be used. Certain embodiments can be drilled right into or otherwise attached to a patient (e.g., skull for brain surgery). If the patient moves (e.g., coughs), the whole device moves. Accordingly, in certain embodiments, the frame of reference may not get disoriented by involuntary or voluntary movement of the patient. In various embodiments, the frame 510 can be a stereotactic frame. In various embodiments, the frame 510 can be mounted to a stereotactic system. In various embodiments, the frame 510 can be mounted to the patient and connected indirectly to a stereotactic system.

Certain embodiments of the medical apparatus 500 can be supported by the bed, by a Mayfield clamp, by a Mayfield mount, or by the frame 510 (e.g., a stereotactic frame). For example, in certain embodiments, a stereotactic frame or the bed provides a supporting structure. In some embodiments, a stereotactic frame can mount on the patient's skull, and some other support mechanism can mount to the bed.

Certain embodiments of the medical apparatus 500 can include more distal cameras than the proximal cameras 520. For example, a more distal camera than the proximal camera 520 can be mounted to the frame 510, e.g., on a finger 525 that goes down into the surgical site 501. The cameras 520 can be mounted to face inward with respect to each other (and/or possibly downward into the surgical site). Various embodiments including cameras 520 on a frame 510, such as a stereotactic frame or a bed-mounted frame, can include features applicable to other technology including but not limited to distal and proximal cameras.

In certain embodiments of proximal cameras 520 on frames 510, the proximal cameras 520 can be positioned just outside and adjacent to the surgical site 501 (e.g., between 5 mm and 50 mm, between 10 mm and 25 mm above the patient, between 10 and 40 mm above the patient, between 10 and 50 mm above the patient, between 50 mm and 75 mm, between 50 mm and 100 mm, between 50 mm and 120 mm, between 50 mm and 130 mm, between 50 mm and 140 mm, between 50 mm and 150 mm, between 100 mm and 200 mm, etc.). Accordingly, the field of view for various embodiments of proximal cameras 520 on frames 510 can be different than the field of view of distal cameras within a surgical site (e.g., distal cameras on a surgical tool). For example, for a distal camera within a surgical site, in order to provide an image from within a surgical site, a wide as possible field of view is desired even if not in the center of field. Whereas for certain embodiments having a proximal camera 520 on a frame 510, the field of view can be narrower because the camera 520 may not be in the surgical site 501.

Accordingly, certain embodiments of a proximal camera 520 on a frame 510 can have a different optical function than a distal camera (e.g., a distal camera on a surgical tool). Some such embodiments of a proximal camera 520 can be relatively small like an endoscope but behave structurally like certain embodiments of a gimbal camera as described herein for a surgical microscope view camera. In certain embodiments, the proximal camera 520 can be used with a camera providing a surgical microscope view, such as for example described elsewhere in this application. Accordingly, a distal camera can be useful for endoscopic procedures. However, certain embodiments having a camera (e.g., a proximal camera and/or a more distal camera than a proximal camera) mounted to a frame 510 can be useful for procedures that are endoscopic, as well as those that are not critically endoscopic, but that are microscopic-like, such as for some brain surgical procedures.

In some instances, cameras positioned within the surgical site may compromise the cameras' imaging ability, e.g., being in the wrong position. For proximal cameras 520 mounted to a frame 510 being just outside and adjacent to the surgical site 501, certain embodiments can include precision controls on the proximal cameras 520 that may not be placed on small distal cameras inside the surgical site 501. For various embodiments including a proximal camera 520, the frame 510 and mount 525 (or clamp or finger) may remain still with only the gimbal 530 being adjusted.

FIG. 14B1-*a* shows an illustration of an imaging system 540 comprising a camera 541, fiber optics 542 and a laparoscope 545 (which can also be representative of an endoscope) going inside the abdomen 546 through the abdominal wall 547 at a port 548 of entry (e.g., a trocar or cannula insertion point). The laparoscope 545 can have a field of view 549 of the area 550 of interest. Because the laparoscope 545 goes inside the body some distance, the port 548 of entry can become a rotation point around that fulcrum (e.g., at the insertion point). Whether the laparoscope 545 is going through a single port, a laparoscope 545 and tools going through the same port, or the laparoscope 545 and tools going through different ports, a lever arm on the laparoscope 545 and/or tools from the point 548 of entry in the imaging system 540 can create disadvantageous imaging issues. Thus, having a lever arm from the port 548 of entry can be an optical disadvantage for endoscopes and laparoscopes. Further, a laparoscope 545 used through the abdominal wall 547 is typically positioned at zero degree, with spin not desired. For example, rotation of the horizon with the laparoscope 545 is typically not desired. Because of the entry point 548 of the abdominal wall 547, a gimbal system and/or imaging movement may generally be not possible in certain embodiments.

FIG. 14B1-*b* shows an illustration of certain embodiments of a medical apparatus having one or more proximal cameras D on a frame G. Some such embodiments can be useful where the surgical site opening is bigger and not similar to an opening through an abdominal wall 547. Certain such embodiments can have an optical advantage of no lever arm from an entry point of the body. Other optical advantages of some such embodiments include the ability to use gimbals F similar to one's own vision (e.g., eye, head, neck combination), a stationary ergonomic display, gimbals for stereo cameras, and/or planar four-bar mechanisms for positioning without disturbing horizontal positions of right and left eye acquisition for horizontal viewing in display.

When not going through the abdominal wall 547, skull-based surgery, sinus surgery, knee surgery, or surgery in various other constrained body passages can be performed without a trocar opening. Often, such surgery (e.g., sinus surgery, neurosurgery, laparosurgery, or orthopedic surgery) can involve rotation and result in disorientation. With such rotation, the surgeon may have to keep the eye/brain combination working to know one's location in space. Thus, in various instances, maintaining the horizon without roll is desired.

In FIG. 14B1-*a*, when viewing the area 550 of interest with a laparoscope 545, a surgeon may be restricted by the port 548 of entry through the abdomen 546. In FIG. 14B1-*b*, when viewing the area E of interest, a medical apparatus 600 including one or more proximal cameras D on a frame G, a gimbal system F can allow maintenance of the horizontal right eye/left eye configuration. A surgeon C can view through an ocular B to view an inside view of the body on the display A. The gimbal system F can comprise a mechanism configured to provide movement of the proximal cameras D while maintaining the horizon (e.g., right eye/left eye parallel with the right eye/left eye in the display).

FIG. 14B2-*a* schematically illustrates imaging optics of an example imaging system compatible with certain embodiments of cameras as described herein. FIG. 14B2-*b* shows an illustration of an example top-down view of certain embodiments disclosed herein. In certain such embodiments, the center I of rotation is at the end of the gimbal of the proximal camera D instead of at the abdomen wall 547. In certain embodiments, such movement H can be analogous to rotating one's eyes in their socket or rotating one's head around the axis of the neck. Movement laterally and longitudinally of the gimbal mechanism can occur at the center I of rotation. The rotation H around the center I (e.g., side-to-side movement) can maintain the horizon in some embodiments. FIG. 14B2-*c* shows an illustration of an example side view of one optical channel of the apparatus shown in FIG. 14B2-*b*. In the example side view, the proximal camera D can rotate around J. Such movement can be analogous to the head-and-neck combination (e.g., up-and-down movement).

FIG. 14B2-*d* shows an illustration of an example proximal camera arrangement. Two proximal cameras D are shown here, e.g., at 12 o'clock and 6 o'clock on a plane of the frame G. There could be four cameras, e.g., also in an orientation of 3 o'clock and 6 o'clock and still maintain their stereo movement. FIG. 14B2-*e* shows an illustration of a display A viewable through portals (e.g., oculars B) by a surgeon C. FIG. 14B2-*f* illustrates a top-view of a left proximal camera $D_L$ providing a left line $L_L$ of sight and a right proximal camera $D_R$ providing a right line $L_R$ of sight. FIG. 14B2-*f* also illustrates an example planar four-bar mechanism K that can allow movement of proximal cameras $D_L$, $D_R$ in one orientation and then tip and turn without inducing roll. For example, yaw (movement around I), pitch (movement around J), and the motion (from the four-bar mechanism K) that can represent the lateral movement around in space are shown. In certain embodiments, motion for the proximal cameras $D_L$, $D_R$ can include pitch and yaw, but not roll. If there were roll on the acquisition cameras, the line-of-sight of the right eye and left eye in the display can be different from the right eye and left eye of the acquisition system. FIG. 14B2-*g* shows an illustration of the side view of FIG. 14B2-*f*. FIG. 14B2-*g* shows pivots P of the four-bar mechanism K and mount M to the frame.

Some embodiments can include sensors and cameras that can be automatically rotated if the right eye and left eye of the display system is rotated (e.g., roll). In some such embodiments, if a camera tipped, the display can follow the camera up to a certain point. For example, if a camera tipped at 15 degrees, the display can tip 15 degrees. If roll were induced in the acquisition system in the proximal cameras and the display were to follow the roll, the cameras providing a surgical microscope view underneath the display can stay constant in certain embodiments (or might roll as well). In some embodiments, the surgical microscope cameras can roll with roll of the display (as may potentially the proximal cameras). However, in many embodiments, the ability for the proximal cameras (and/or the surgical microscope view cameras) to roll may not be provided or may be limited to reduce disorientation.

Figure 3B:
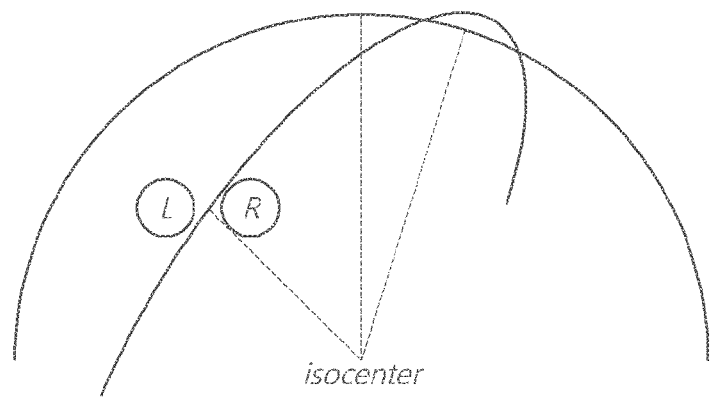

FIG. 14B3 is an illustration of certain embodiments described herein showing an oblique camera orientation. The motion F can allow one or more proximal cameras D to image from multiple views. In some embodiments, unlike the endoscope or laparoscope 545 where pitch can be typically dictated by the port 548 of entry, the pitch is about the point J of rotation at a proximal camera D. Such motion F can be similar to an eye locating in a socket. Motion F can represent the ability of a proximal camera D to move around its own axis, supported by the frame G (e.g., on a non-laparoscopic device). The one or more proximal cameras D can include a relatively small pair of cameras such as stereo cameras. Providing only yaw, only pitch, a four-bar mechanism, and a z motion can maintain the horizontal line through the lines of sight of the left and right cameras, eliminating roll in some embodiments.

As described herein, certain embodiments can include the x and y motion of a four-bar mechanism. In other embodiments, other x-y-z mechanisms besides a four-bar mechanism can be used. In some embodiments, the pitch and yaw can be moved to a proximal camera on a frame independent of a display. By providing one or more proximal cameras with gimballing motion, and in some embodiments, with all motions except roll, near the opening of the body, various embodiments can be different than endoscopes and not comparable with microscopes.

An endoscope typically can have a 50 degree field of view to 110 degree field of view. An operating room microscope (e.g., a camera providing a surgical microscope view) can have typically a smaller field of view, for example, the area of interest can be 50 mm in diameter and 300 mm away from the vertex of the acquisition system.

In some embodiments, a proximal camera as described herein can be in between those two ranges. Thus, some embodiments of a proximal camera can be described as being sometimes endoscope-like and sometimes microscope-like. Some such proximal cameras can have a narrower field of view than an endoscope and a wider field of view than a microscope. Some such proximal cameras can also be positioned closer to the patient than a surgical microscope because the sensors and cameras can be much smaller. In addition, compared to loupes, various embodiments of proximal camera and display can be more advantageous by having the opportunity to be in an ergonomic position and the ability to see additional views.

An endoscope, sinus scope, neuro scope, and/or laparoscope might have a working distance from 10 mm to 100 mm, and might have a field of view between 50 degrees and 110 degrees. An operating room microscope might have a field of view as seen on the patient (e.g., not in an angled space) from 35 mm to 200 mm, and at a working distance of 200 mm to 450 mm. In various embodiments, proximal cameras can be from 10 degree field of view to 50 degree field of view with working distances of 5 mm to 50 mm, 40 mm to 100 mm, 40 mm to 150 mm, 50 mm to 100 mm, 50 mm to 150 mm, 100 mm to 200 mm (e.g., something that allows you to be close to the patient). In some embodiments, the workspace can be determined by the opening into the body, the depth of the wound or the surgical passageway, and the surgeon's hands and tools. Surgeons typically may not take a tool like forceps with scissor action in their hand, but may take a tool like pistol grips. In addition, surgeons typically may not run their hands into the body. Accordingly, there may be a standoff working distance, e.g., a 150 mm tool, at a minimum, for a 100 mm passage. In addition, there may be some surplus of space between the surgeon's hand and the opening of the body, e.g., to accommodate a drape for example. The frame (e.g., 125 mm in diameter) can be positioned above this working distance, e.g., within 10 mm, 25 mm, 40 mm, 50 mm, 75 mm, 100 mm, 130 mm, 140 mm, 150 mm, 175 mm, or 200 mm in some instances, above the surgical opening to have this proximal camera. Thus, certain embodiments of proximal cameras can be disposed at the opening of the passageway and view down in the surgical opening, with a narrower field of view than an endoscope, but a closer working distance than a microscope. In some embodiments, the working distance can be between 1 mm to 50 mm, 5 mm to 40 mm, 5 mm to 50 mm, 10 mm to 25 mm, 10 mm to 40 mm, 10 mm to 50 mm, 50 mm to 75 mm, 50 mm to 100 mm, 50 mm to 120 mm, 50 mm to 130 mm, 50 mm to 140 mm, 50 mm to 150 mm, 100 mm to 200 mm, 100 mm to 300 mm (or any ranges formed by any values between 1 mm and 300 mm). In addition, in some embodiments, the field in the object plane can be between 25 mm to 200 mm or between 25 mm to 250 mm (or any ranges formed by any values between 25 mm and 250 mm).

Additionally, any of the features or embodiments described in connection with the surgical tools, surgical visualization systems and components thereof, may be used with, combined with, incorporated into, be applicable to, and/or are otherwise compatible with one or more embodiments of a medical apparatus including one or more proximal cameras mounted to a frame disposed above the patient and/or surgical site as described herein.

For example, in various embodiments of a medical apparatus can include one or more cameras. At least one of the cameras can include a surgical microscope camera configured to provide a surgical microscope view of the surgical site. In various embodiments, the surgical microscope camera is not coupled to a direct view surgical microscope. As also described herein, the medical apparatus can include a binocular viewing assembly comprising a housing and a plurality of portals (e.g. oculars). The plurality of portals or oculars (e.g., separated left and right portals or oculars) can be configured to provide views of at least one display disposed in the housing. The left and right portals (e.g. oculars) can be separated by sidewalls, baffling, tubing, etc. that reduces optical cross-talk therebetween. For example, light from a display or display portion associated with the left portal or ocular is blocked so as to not propagate into the right portal or ocular, and vice versa. Similarly, light from a display or display portion associated with the right portal or ocular is blocked so as to not propagate into the left portal or ocular. The medical apparatus can further include an image processing system (e.g., comprising processing electronics) in communication with the camera (e.g., the camera including the surgical microscope camera) and the one or more displays. As also described herein, the image processing system can be configured to receive images acquired by the camera (e.g., the camera including the surgical microscope camera), and to present output images based on the received images on the one or more displays so that the output images are viewable through the plurality of oculars.

Mobile Display Devices

As described herein, various embodiments of a medical apparatus can switch between and/or combine (e.g., dispose as adjacent to one another, tile, overlap, superimpose, dispose as PIP, etc.) images from different sources. For example, the images can include a view of the surgical site (e.g., a surgical microscope view, an image from an endoscope, an image from a proximal camera, an image from a surgical tool, an image from a camera on a retractor, etc.) combined with other information such as a data file, a computed tomography (CT) scan, a computer aided tomography (CAT) scan, magnetic resonance imaging (MRI), an x-ray, ultrasound imaging, fluorescence imaging, neuromonitoring, vital sign monitoring, etc. Such information can be images taken in real time or can be stored on a device such as a general all-purpose computer. The device can be a desktop computer, a laptop, or a notebook, etc.

The device can include equipment belonging to the hospital. However, some surgeons (or other medical personnel) may travel between different hospitals and/or offices and have all patient records/data on one's own device. Accordingly, in certain embodiments disclosed herein, the device can include a surgeon's own portable equipment. For example, in certain embodiments as disclosed herein, the medical apparatus can include information from a mobile display device such as a cellular telephone (e.g., a "cell phone" such as a smartphone), a tablet, an Internet enabled portable device, a network connected portable device, or any mobile device with a display capable of displaying images including text (e.g., devices known in the art or yet to be developed). The mobile display device can include software applications (e.g., for navigational guidance and ergonomic control), pre-recorded information, and memory for recording and storing information from other devices. The mobile display device can include 3D volume data sets (e.g., functional MRI, CT, etc.), as well as 2D information.

In certain embodiments, it may be beneficial for a surgeon (or other medical personnel) to view additional information during surgery without having to take one's eyes away from the surgical site (e.g., from the viewing assembly described herein). In one example, the surgeon can view additional information about the same patient undergoing surgery. As another example, in situations where the surgeon could be in the operating room for very long hours, the surgeon can view additional information concerning another patient and/or other important affairs. The additional information can include an e-mail message, a text message, a medical communication, medical data, news, financial data, business information, business data, photographs, etc. For example, the surgeon's mobile display device may include pre-recorded clinical images from medical devices, reference data, navigational device data in real time, streaming text of patient data, hospital or other medical communication, Twitter feeds, and/or other feeds through wired or wireless communication. In some embodiments, the mobile display device could include pico projectors as described herein for projecting fiducials or virtual touch screen images (e.g., buttons, icons, thumbnails, etc.) for the surgeon to see. As described above, some embodiments include a virtual touch screen where the surgeon's or user's movement in free space is detected. The surgeon could move his/her hand or instrument so as to touch an image, e.g., a virtual button, icon, thumbnail, etc. The surgeon's movement could be tracked to record selection of an option and/or to provide an input via the virtual touch screen.

Accordingly, various embodiments of a medical apparatus are configured to allow the surgeon or medical personnel to view an image of the surgical site and additional information from a mobile display device simultaneously. In addition, since the mobile display device has a separate controller (e.g., processing electronics), certain embodiments described herein may reduce latency. In some such embodiments, the medical apparatus can include a docking station configured to receive the mobile display device.

Figure 15:
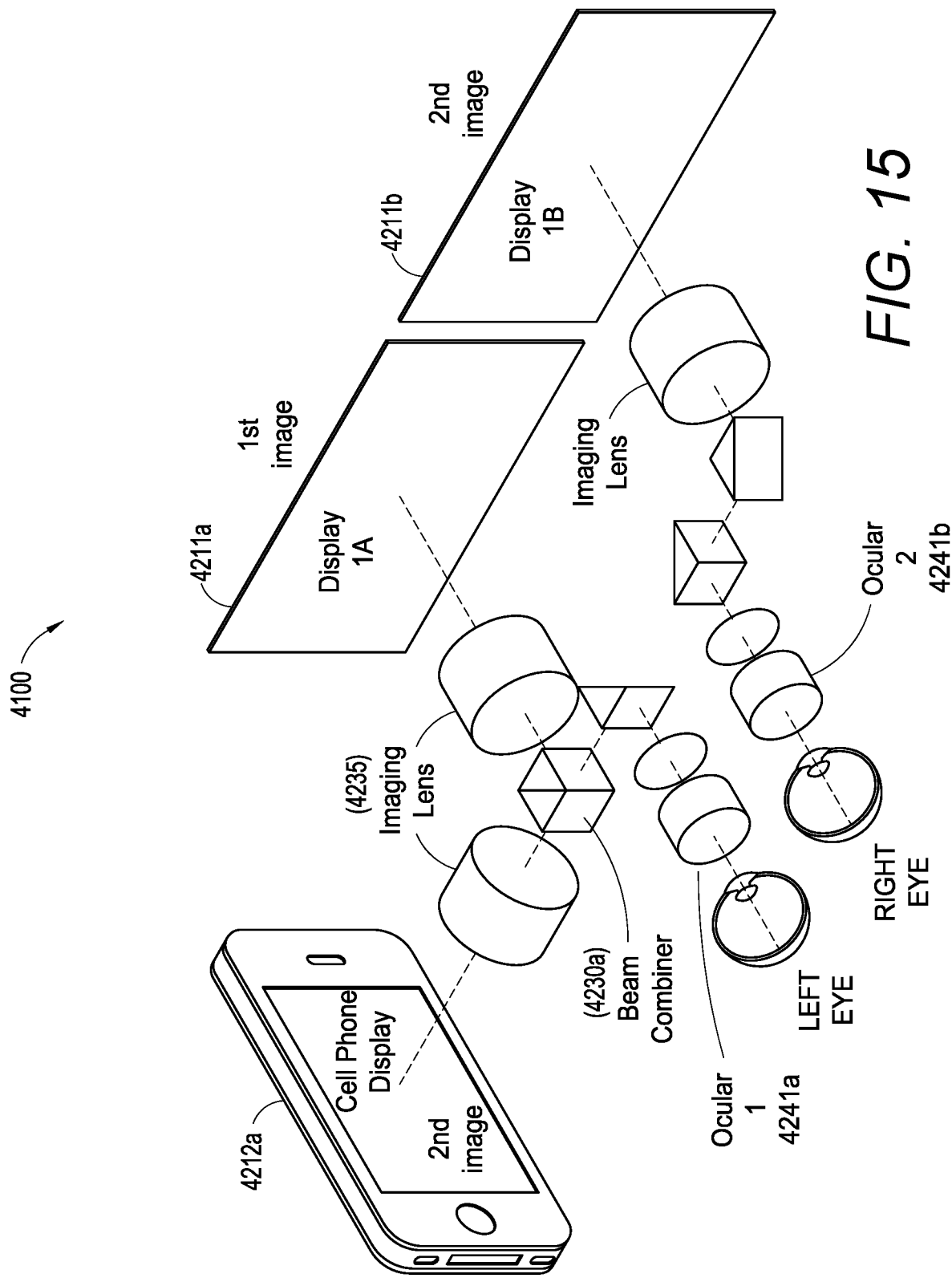
FIGS. 15-21 schematically illustrate examples of a medical apparatus that utilize a mobile display device in accordance with certain embodiments described herein.

FIG. 15 shows an example embodiment of such an apparatus. The medical apparatus 4100 can include a first display 4211a (or display portion) configured to display a first image of a surgical site. The medical apparatus 4100 can also include a controller (e.g., processing electronics) configured to receive one or more signals corresponding to the first image from a camera (not shown) and to drive the first display 4211a to produce the first image. Each signal path from the camera to the first display 4211a can include a control unit to control various parameters (e.g., brightness, intensity, gamma, chroma, area of interest, subtraction, edge enhancement, text forms, graphics, etc. or combinations thereof). The camera can include a camera as described herein. For example, in some embodiments, the camera can include a camera providing a surgical microscope view. The camera can have a work distance between 150 to 400 mm or to 450 mm. Other values outside these ranges are also possible. The camera can provide an image of a field (or lateral dimension). In some other embodiments, the camera can be a visualization device such as an endoscope, a proximal camera, a camera disposed on a surgical tool, a camera disposed on a retractor, etc.

The medical apparatus 4100 can also include a docking station 4230 (shown in FIG. 18) configured to receive a mobile display device (e.g., a cell phone or tablet). The docking station can be disposed on the viewing assembly or at a distance away from the viewing assembly. The location/orientation of the docking station 4230, e.g., with respect to the viewing assembly, is not limited. The docking station 4230 can be in electrical and/or optical communication with the mobile display device. For example, the docking station 4230 can include a port for electrical and/or optical communication with the mobile display device. The docking station 4230 can also include a port providing power to the mobile device. In some embodiments, the docking station can be in wireless communication with the mobile display device. As shown in FIG. 15, the mobile display device can include a second display 4212a (or display portion) having a second image. The second image can include information as described above (e.g., e-mail message, a text message, a medical communication, medical data, news, financial data, business information, business data, photographs, etc.) from the mobile display device.

In some embodiments, the surgeon sees the second display 4212a through a set of lenses and/or mirrors or other optical elements so that the surgeon can be at or near the patient, while the location of the mobile display device and docking station is not particularly limited. Similar to the embodiments shown in FIGS. 12A-130, a beam combiner 4230a can be configured to receive and combine the first image of the surgical site or at least a portion thereof and at least a portion of the second image from the mobile display device. Various embodiments of the medical apparatus 4100 can include imaging lenses for imaging the displays. For example, as shown in FIG. 15, one or more imaging lenses 4235 can be disposed between respective beam combiners 4230a and displays 4211a, 4212a. In various embodiments, pellicle mirrors can also be used.

In certain embodiments, the combined images can be viewed within a housing of a viewing assembly through a first ocular 4241a. In some examples, as shown in FIG. 15, the combined images can be viewed through the first ocular 4241a to provide a left-eye view. In other examples, the combined images can be viewed through the first ocular 4241a to provide a right-eye view. The combined images can be viewed as a picture-in-picture (PIP) as shown in FIG. 13A or as adjacent to one another as shown in FIG. 13C, or can facilitate easy switching from one image to another. For example, in some embodiments, the medical apparatus may darken an image while allowing another image to be visible. Shutters can also be used in some embodiments to block or attenuate one image and not block or not attenuate (or attenuate less) the other image.

In various embodiments, the second image from the mobile display device can change between different images. As an example, the second image can include medical data shown adjacent to the first image of the surgical site or as a PIP or in the same field of view but spaced apart e.g., by borders. During surgery, the surgeon could receive notification of an emergency text message. In some such embodiments, since the latency of the second image from the mobile display device may be less critical than the first image of the surgical site, the surgeon or other medical personnel could switch the second image from the medical data to the text message. For example, some embodiments can be configured to allow the second image to automatically switch to the text message or to a portion of the text message (e.g., while still displaying the first image). As another example, some embodiments can be configured to allow the text message or a portion of the text message to be viewed with the second image as a PIP. In some such embodiments, if desired, the surgeon or other medical personnel could switch the second image from the medical data to the text message (e.g., while still displaying the first image).

Since the surgery room is a sterile environment, in certain embodiments, the medical apparatus 4100 can include a remote control configured to control the mobile display device. As an example, the remote control can be configured to control the second image displayed on the second display 4212a of the mobile display device. For example, the remote control can allow the user to switch the second image and/or adjust the size, contrast, brightness, zoom, etc. The remote control can be any user interface which allows control of the mobile display device, for example, from a distance away from the device (e.g., wirelessly and/or without the user physically touching the device). In some embodiments, the remote control can be disposed on or near the viewing assembly and controls thereof used by the user. For example, the remote control can include one or more handgrips on either side of the viewing assembly. The one or more handgrips can include buttons, a joystick, etc. Alternatively, the remote control can include a joystick (e.g., with buttons), a handle, buttons, haptics, a touchpad, etc. In some embodiments, the remote control or another control can control the first image. Such control can control the camera providing the first image or control the first display producing the first image. For example, the control can adjust size, contrast, brightness, zoom, iris size, auto gain, illumination, etc., e.g., using a series of buttons on a handle such as a handle on the binocular display assembly.

With continued reference to FIG. 15, the medical apparatus 4100 can further include a third display 4211b (or display portion). The third display 4211b can be configured to display a third image. In some embodiments, the third image can be viewed within the housing of the viewing assembly through the second ocular 4241b. The medical apparatus 4100 can include another controller (e.g., additional electronics as described herein) configured to receive one or more signals corresponding to the third image from a camera and to drive the third display to produce the third image. As an example, the third image can comprise another image of the surgical site, e.g., from a camera providing a surgical microscope view, from a visualization device such as an endoscope, from a proximal camera, from a camera disposed on a surgical tool, from a camera disposed on a retractor, etc. The first and third displays 4211a, 4211 b can be configured to provide 3D viewing of the images of the surgical site through the first and second oculars 4241a, 4241b. For example, the cameras can provide different views from different stereo perspectives to produce 3D visualization for a viewer viewing the first and third displays 4211a, 4211b through the first and second oculars 4241a, 4241b. In some embodiments, the viewing assembly can be ergonomically decoupled from the camera that provides video to the first and/or third display 4211a, 4211b. As described herein, in various embodiments, the viewing assembly of the medical apparatus 4100 does not provide a view of the surgical site through the first and second oculars 4241a, 4241b via an optical pathway that passes through the housing. For example, certain embodiments are not associated with a direct view surgical microscope.

In certain embodiments, the mobile display device can operate as a controller, processor, or computer, for the surgical visualization apparatus, possibly assisting for example, in controlling various components (e.g., cameras, motors for orienting cameras, displays, lighting, etc.), performing processing (e.g., imaging processing, graphic user interface control, etc.) and or other electronic functions including electronic computing or process functions. In some embodiments, the docking station 4230 can be configured to allow the mobile display device to provide navigational guidance and/or ergonomic control. For example, using a software application residing on the mobile display device, a user can interact with the mobile display device communicating through the docking station (e.g., via a port) or wirelessly to the medical device to guide the camera units, control their orientation, selection of cameras or view, or other. In addition, the docking station 4230 can be configured to allow the portion of the second image from the mobile display device to be displayed on an external monitor. Furthermore, in various embodiments, the docking station 4230 can be configured to allow the mobile display device to receive and record images, e.g., of the surgical site, using the mobile display device's camera. The mobile display device can also receive and record images from the other displays. In some embodiments, such functions can be controlled by a remote control (e.g., using controls on the viewing assembly) as described herein so as to not need to move locations and/or to touch the mobile display device during surgery.

Figure 16:
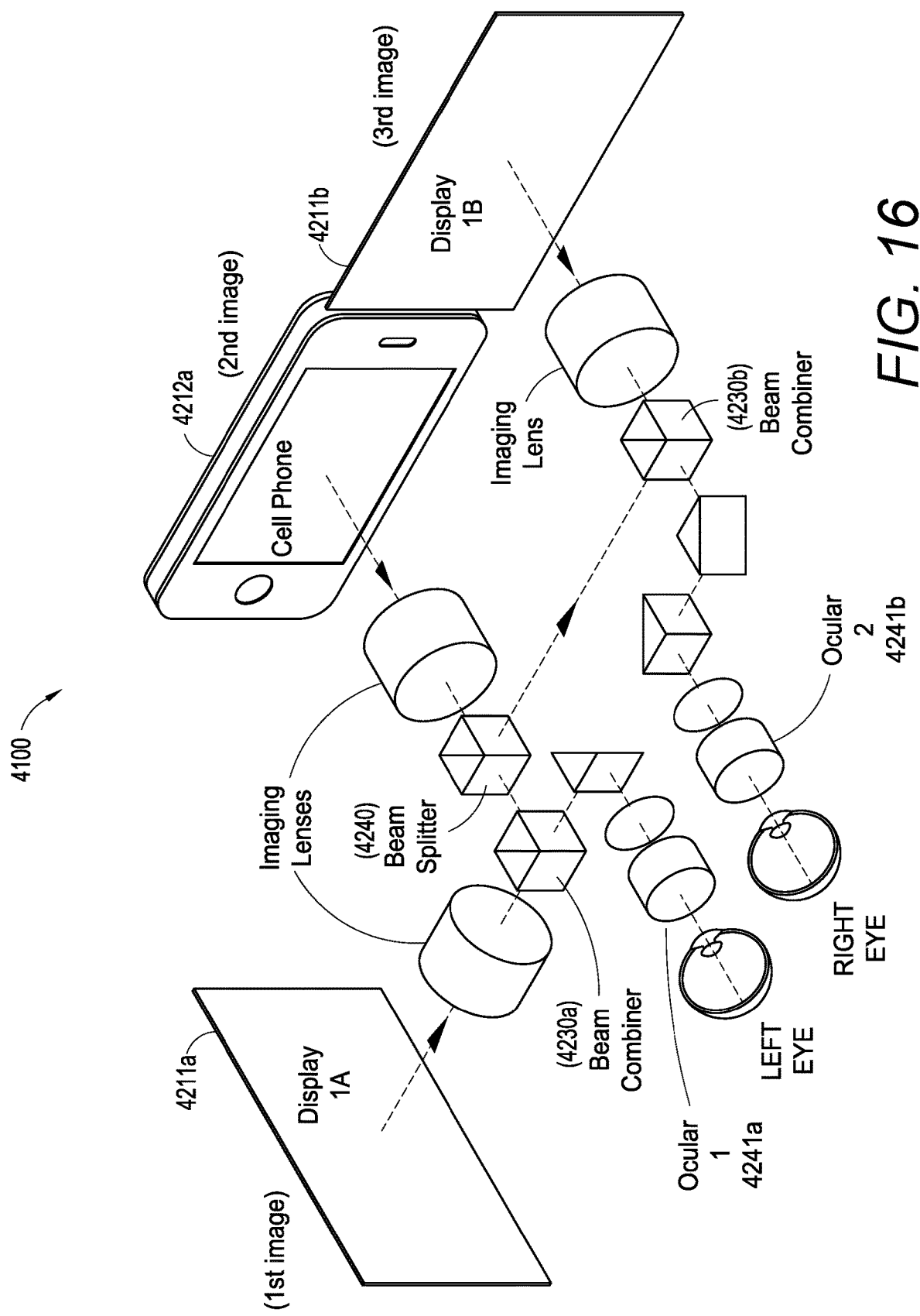

FIG. 16 shows another example embodiment of a medical apparatus 4100. While the schematic of FIG. 15 illustrates that certain embodiments of the medical apparatus 4100 can provide a mono view (as opposed to a stereo view) of the image from the mobile display device in one eye (e.g., in the first ocular 4241a), certain embodiments can provide a mono view of the image from the mobile device in both eyes. As shown in FIG. 16, the image from the mobile display device can be combined with both the first image of the surgical site from the first display 4211a and the third image of the surgical site from the third display 4211b and be viewable within the housing of the viewing assembly through the first ocular 4241a and second ocular 4241b respectively. For example, the medical apparatus 4100 can include a beamsplitter 4240 configured to separate and direct at least a portion of the second image from the mobile display device to two optical paths (e.g., toward the first and second oculars 4241a, 4241b). The medical apparatus 4100 can include a beam combiner 4230a configured to receive and combine at least a portion of the second image from the mobile display device and at least a portion of the first image of the surgical site for viewing through the first ocular 4241a. The medical apparatus 4100 can also include one or more additional beam combiners 4230b configured to receive and combine at least a portion of the second image from the mobile display device and at least a portion of the third image of the surgical site for viewing through the second ocular 4241b. The combined images can be switched in and out of the field of view, viewed as adjacent to one another in the field of view (e.g., space apart but within the field of view), or viewed as a PIP.

Figure 17:
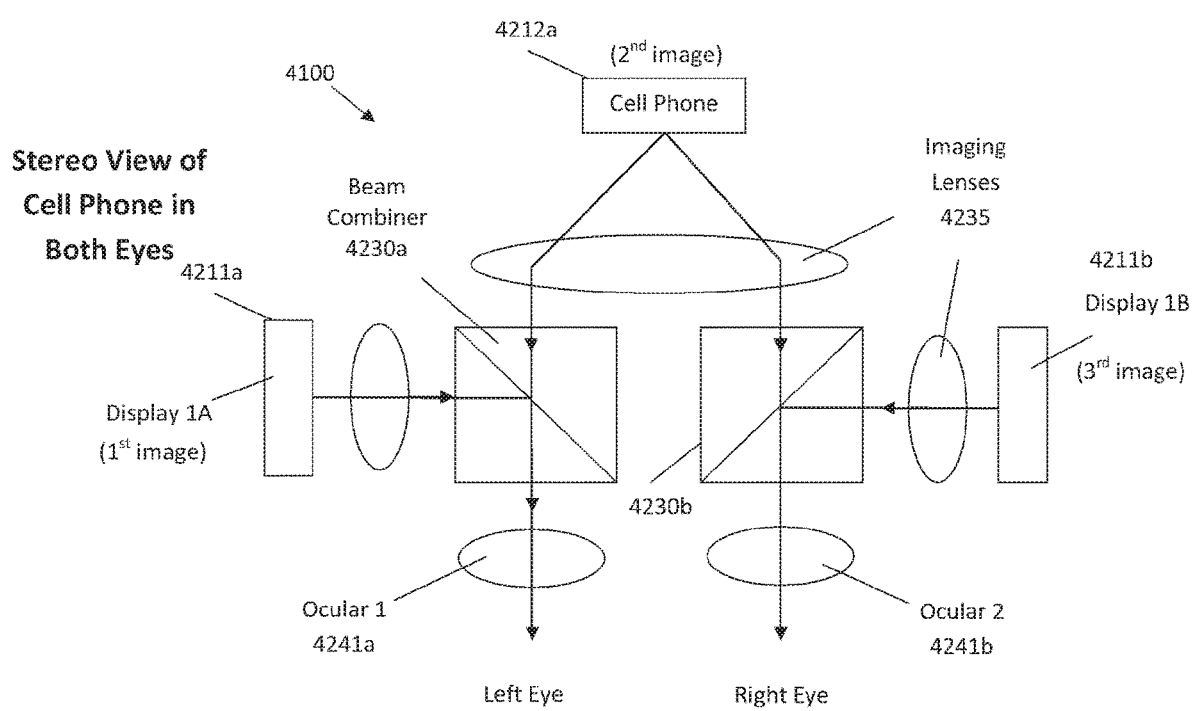
Figure 17B:
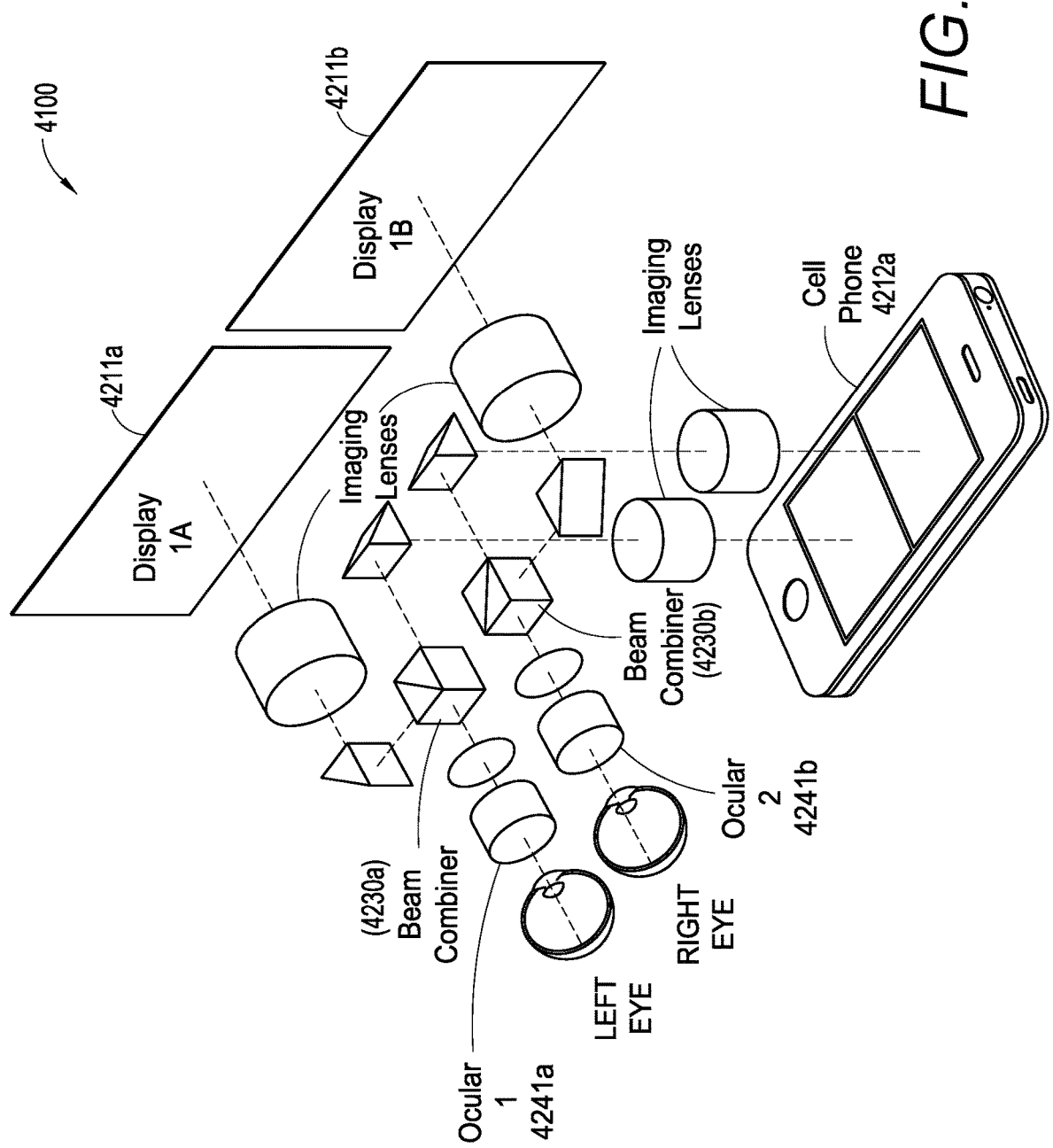

FIGS. 17 and 17B show another example embodiment of a medical apparatus 4100. In this example, the medical apparatus 4100 can provide a stereo view of an image from the mobile display device in both eyes (e.g., using two oculars). Such embodiments can include an imaging lens 4235 configured to provide two different views of the image from the mobile display device, e.g., from two different angular perspectives. In some embodiments, two imaging lenses can be used to provide images from the mobile display device, as shown in FIG. 17B. The medical apparatus 4100 can include a beam combiner 4230a configured to receive and combine an image of the surgical site from a first display 4211a with at least a portion of the image from the mobile display device (e.g., one view from the second display 4212a of the mobile display device). The medical apparatus 4100 can also include another beam combiner 4230b configured to receive and combine a third image of the surgical site from a third display 4211b and at least a portion of the image from the mobile display device (e.g., a different view from the second display 4212a of the mobile display device). The images from the mobile display device combined with the images from the first and third displays 4211a, 4211b can be different perspectives of the image from the mobile display device. The different perspectives can be different stereo views of the image from the mobile display device such as to provide 3D viewing. The combined images can be switched in and out of the field of view, viewed as adjacent to one another in the field of view (e.g., space apart but within the field of view), or viewed as a PIP.

FIG. 17 shows an example embodiment utilizing a single imaging lens 4235 to provide two different angular views of an image from the mobile display device. Some embodiments can include multiple imaging lenses 4235, e.g., an imaging lens for the left eye view and another imaging lens for the right eye view. Furthermore, in some embodiments, the display 4212a of the mobile display device can provide multiple images, e.g., a split screen providing the left and right eye views.

Figure 18:
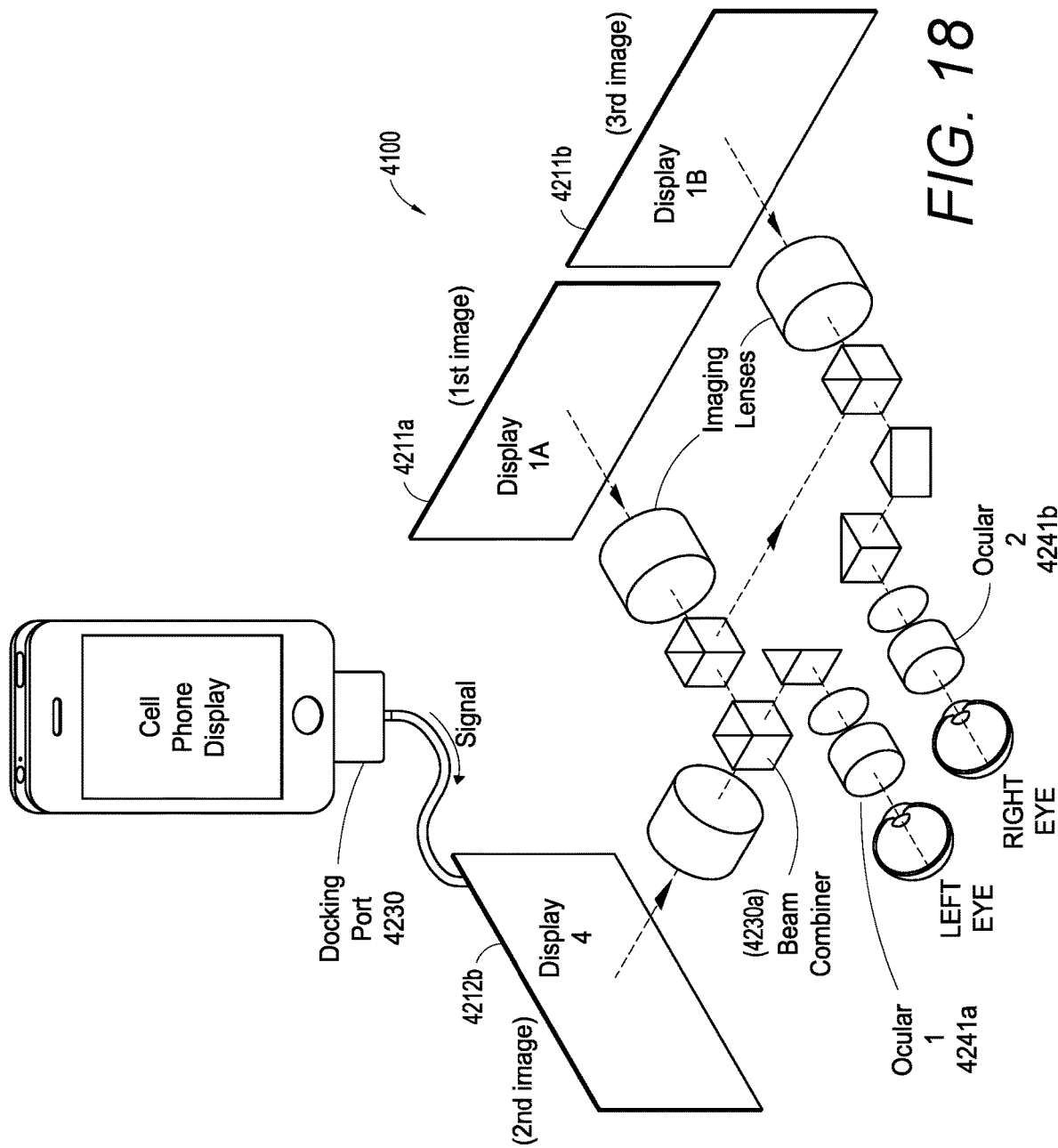
Figure 19:
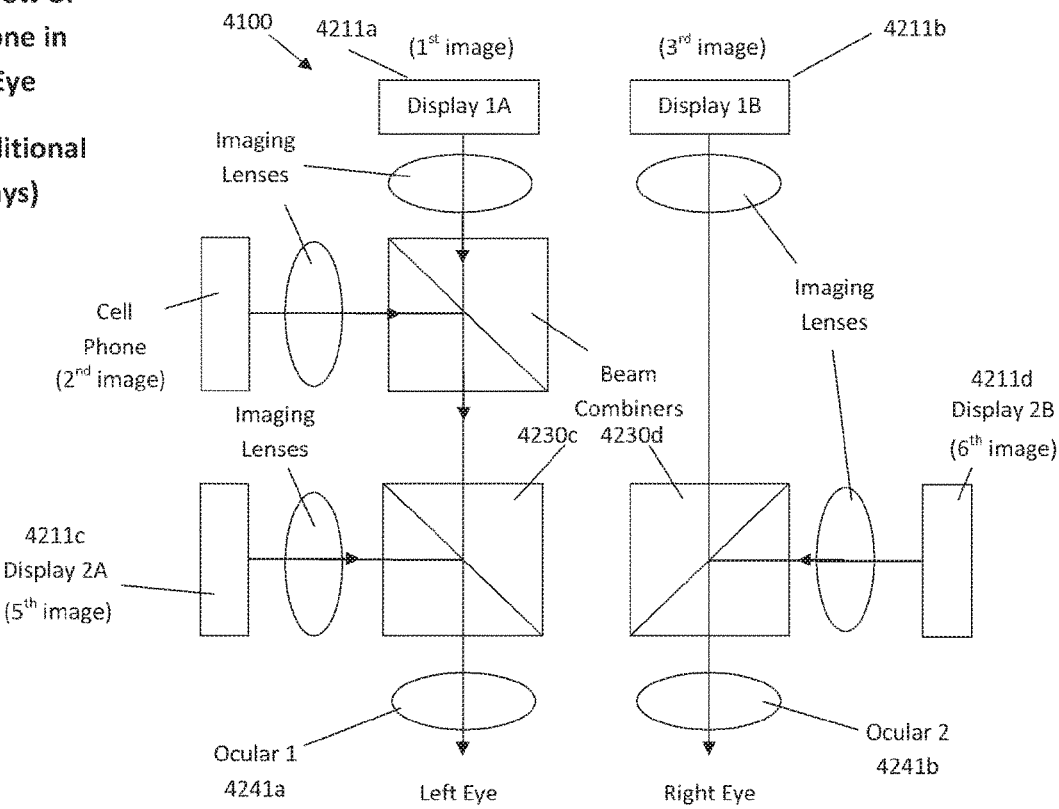

As shown in FIGS. 15-17B, the second display 4212a is a portion of the display of the mobile display device. In some such embodiments, the medical apparatus 4100 can include an optical pathway between the second display 4212a and beam combiner 4230a or 4230b such that the beam combiner 4230a or 4230b is capable of optically receiving the portion of the second image from the second display 4212a. In other embodiments, as shown in FIG. 18, the medical apparatus 4100 can include a fourth display 4212b to display the second image or a portion of the second image. For example, the medical apparatus 4100 can include a controller (e.g., electronics) configured to receive one or more signals corresponding to the second image or a portion of the second image and drive the fourth display 4212b to produce the portion of the second image. In some such embodiments, the docking station 4230 can transmit the signals from the mobile display device to the fourth display 4212b. A beam combiner 4230a can be configured to receive the second image or a portion of the second image from the fourth display 4212b. For example, as shown in FIG. 18, the beam combiner 4230a can be configured to receive and combine the first image of the surgical site from the first display 4211a and the portion of the second image from the fourth display 4212b.

In addition, similar to FIG. 15, a first image from the first display 4211a and a third image from a third display 4211b can comprise images of the surgical site, e.g., from a camera providing a surgical microscope view, from a visualization device such as an endoscope, from a proximal camera, from a camera disposed on a surgical tool, from a camera disposed on a retractor, etc. The first and third displays 4211a, 4211b can be configured to provide 3D viewing of the images of the surgical site through the first and second oculars 4241a, 4241b. For example, the cameras can provide different views from different stereo perspectives to produce 3D visualization for a viewer viewing the first and third displays 4211a, 4211b through the first and second oculars 4241a, 4241b.

Figure 20:
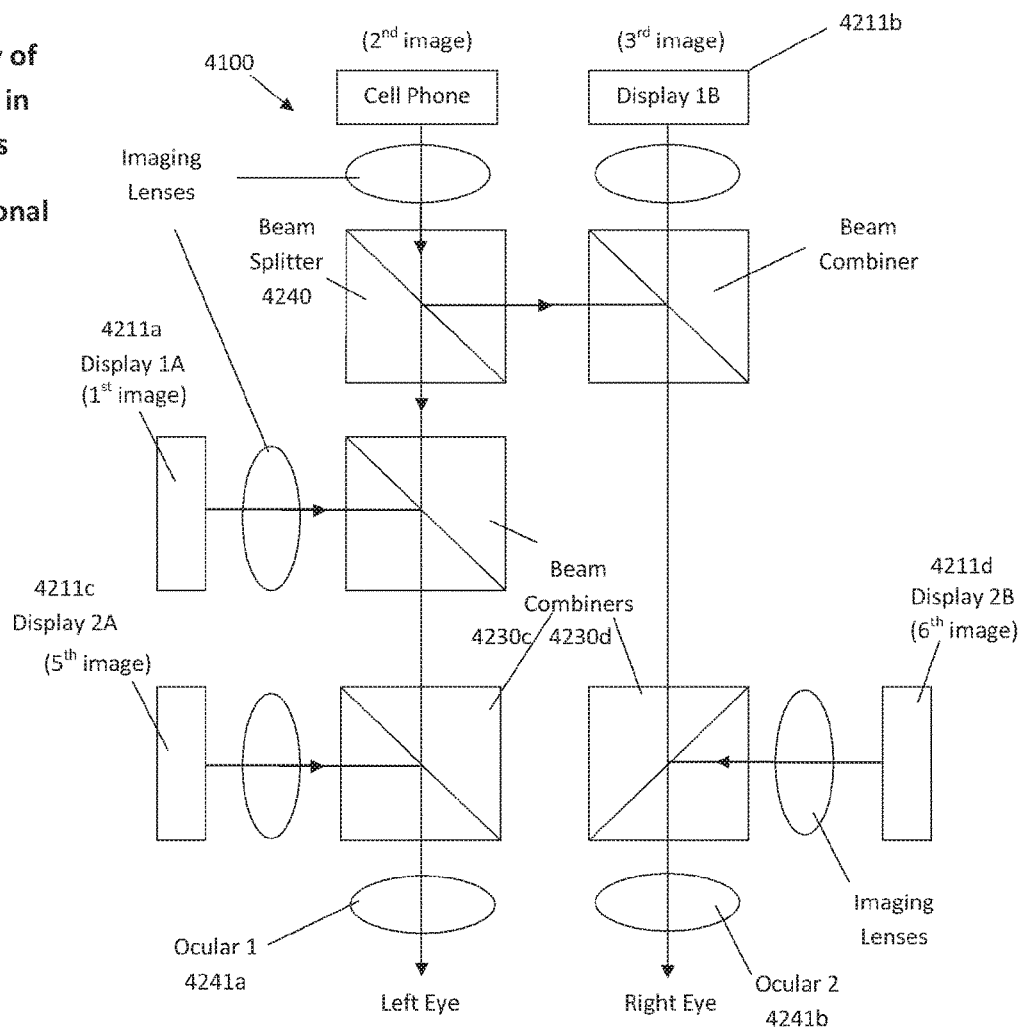
Figure 21:
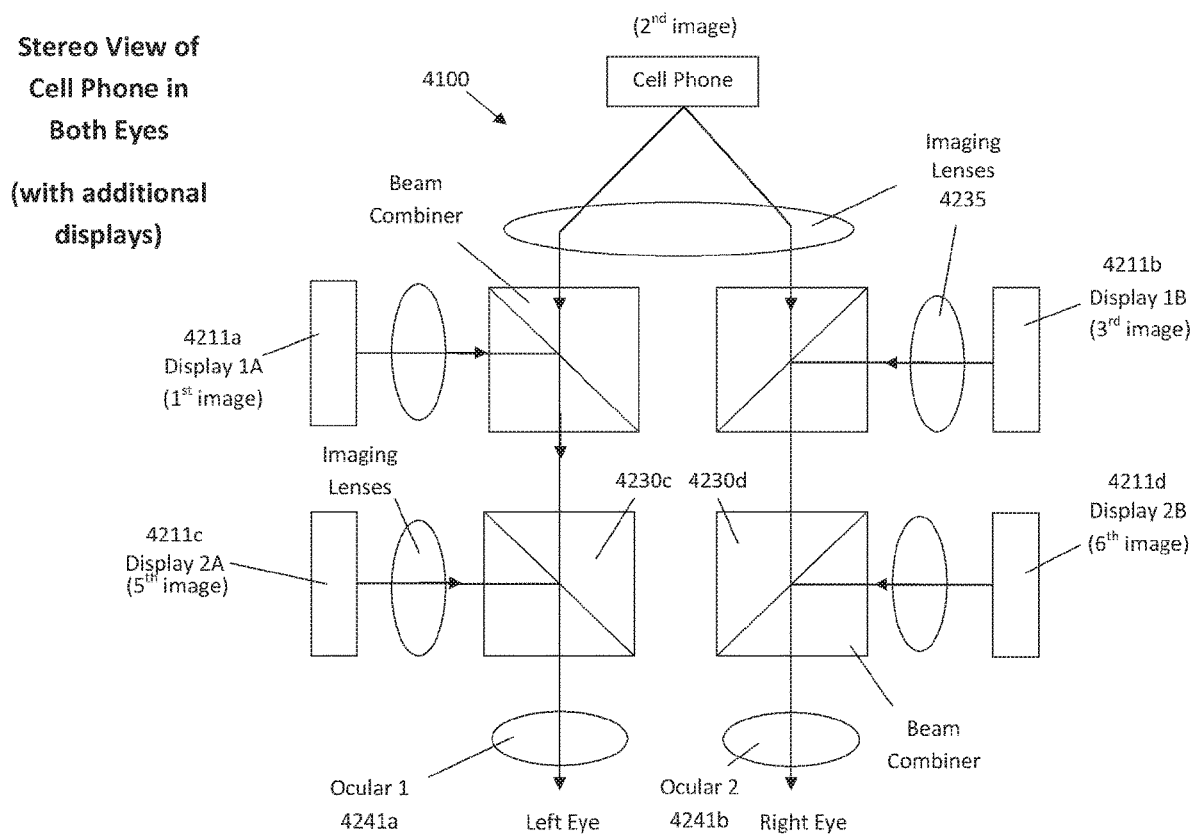
Figure 22:
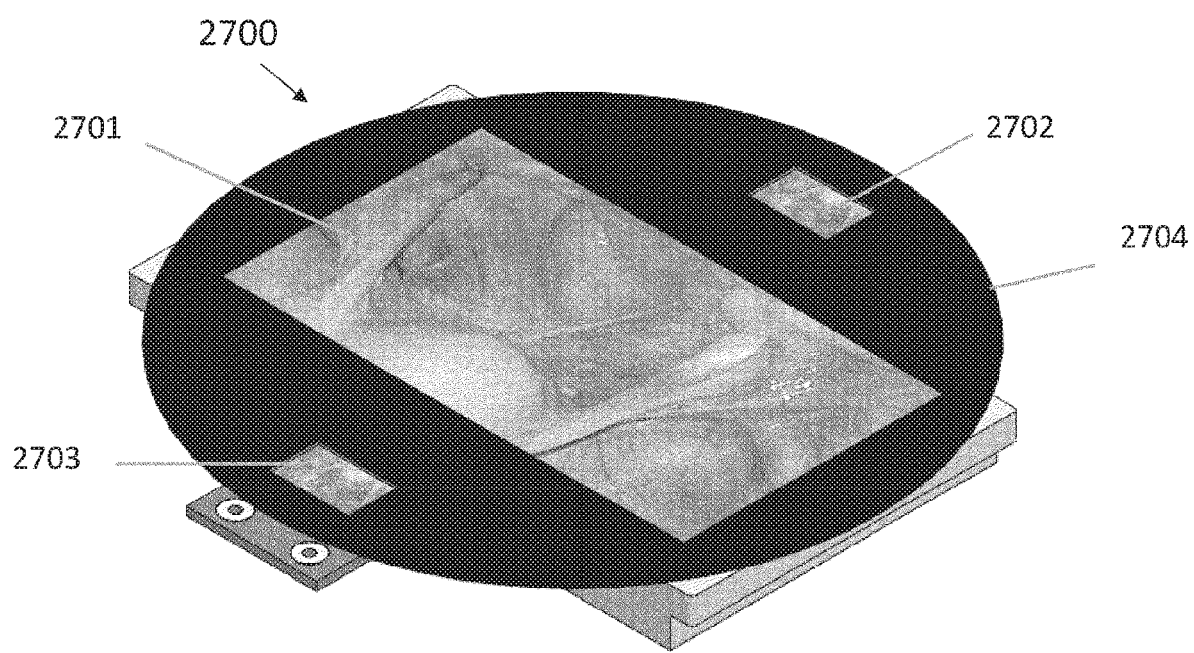
FIG. 22 shows an example medical apparatus having multiple displays within the field of view of an ocular.

Certain embodiments can include additional beamsplitters, beam combiners, mirrors (e.g., pellicle mirrors), lenses, and/or displays. For example, as shown in FIGS. 20-22, the medical apparatus 4100 can include a fifth display 4211c configured to display a fifth image. The medical apparatus 4100 can include an additional controller (e.g., electronics as described herein) configured to receive one or more signals corresponding to the fifth image from a camera and to drive the fifth display 4211c to produce the fifth image. In some instances, the fifth image can include another image of the surgical site. The medical apparatus 4100 can include another beam combiner 4230c configured to receive and combine the first, second, and fifth images or portions of the first, second, and fifth images for viewing within the housing of the viewing assembly through the first ocular 4241a. The medical apparatus 4100 can also include a sixth display 4211d configured to display a sixth image, a controller (e.g., electronics as described herein) configured to receive one or more signals corresponding to the sixth image from a camera and to drive the sixth display 4211d to produce the sixth image, and/or a beam combiner 4230d configured to receive and combine at least the third and sixth images or portions of the third and sixth images for viewing within the housing of the viewing assembly through the second ocular 4241b. In some instances, the fifth and sixth displays are configured to provide stereo images to provide 3D viewing of images of the surgical site through the first and second oculars 4241a, 4241 b. The cameras can provide different views from different perspectives of the surgical site to produce 3D visualization for the viewer viewing the fifth and sixth displays through the first and second oculars

4241*a*, 4241*b*. In other embodiments, the images from the additional display portions can include other information such as a data file, a computed tomography (CT) scan, a computer aided tomography (CAT) scan, magnetic resonance imaging (MRI), an x-ray, ultrasound imaging, fluorescence imaging, information from a mobile display device, neuro-monitoring, vital sign monitoring, etc. The images from the different displays can be switched between different images, disposed adjacent to one another, or disposed as a PIP.

Various embodiments described herein utilizing images from mobile display devices have the advantage of having a separate controller for the image displayed by the mobile display device, which may reduce latency. Certain embodiments described herein can be applied to a primary display, a surgeon display, an assistant display, possibly other displays, or any combination of these. The images that the surgeon sees can also be projected onto other displays for other medical personnel and staff to see.

Figure 23:
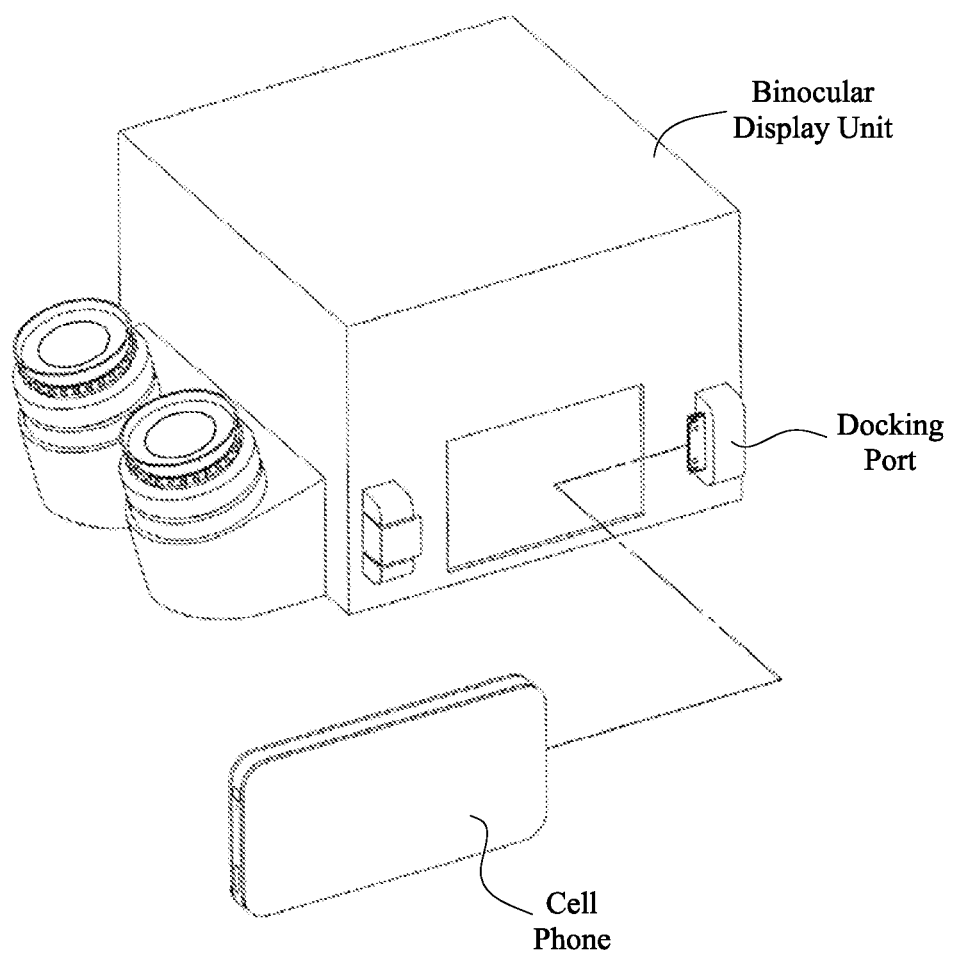
FIG. 23 illustrates an example embodiment of a mobile display device in communication with a docking port disposed on a binocular display unit.

FIG. 23 shows an example embodiment of a mobile display device in communication with a docking port disposed on a binocular display unit. The docking port may comprise an electrical connection for electrical communication with other components in the system. The location/orientation of the docking port and/or mobile display device with respect to the binocular display unit is not limited. In addition, additional docking ports can be disposed on the binocular display unit or at a distance away from the binocular display unit. For example, in various embodiments, a docking port can be provided for the mobile display device of an assistant surgeon (or other medical personnel). In such embodiments, images from the assistant surgeon's mobile display device can be displayed on the assistant display. In some embodiments, the assistant surgeon can view images combined with other images or can switch between images without changing the images seen by the primary surgeon.

Figure 24:
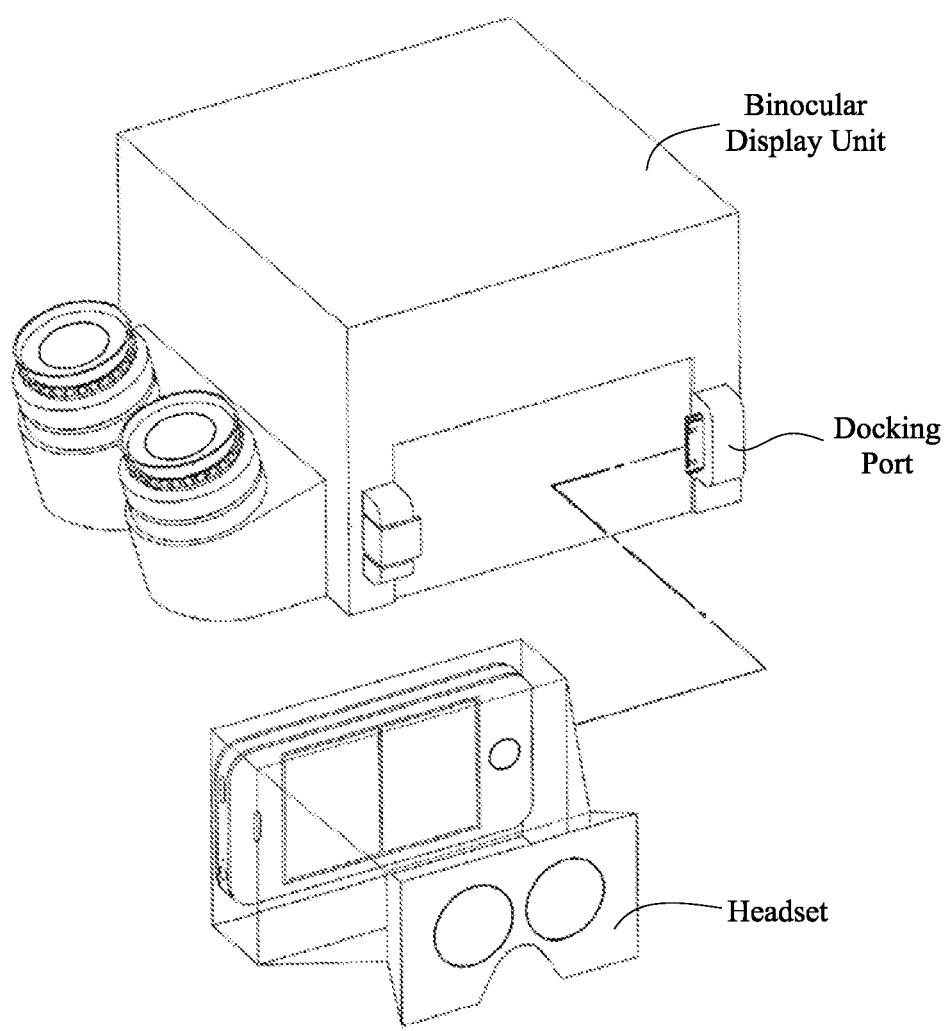
FIGS. 24-25 illustrate example headsets or head mounted displays used to view images from a mobile display device.

Furthermore, FIG. 24 shows an example headset or head mounted display that can be used to view images from a mobile display device (e.g., an Oculus Virtual Reality type display), alone or in combination with other images from other displays or devices. The headset or head mounted display may comprise an immersive display and/or other near eye display. In some such embodiments, the display of the mobile display device can provide multiple images, e.g., a split screen providing left and right eye views, for viewing through the left and right eyepieces of the headset.

In various embodiments, the docking port can be included on any side of the binocular viewing assembly. For example, with reference to FIGS. 23 and 24, the docking port can be on the side opposite to the side where the docking port is shown in FIGS. 23 and 24. The docking port can be on the side opposite to the side where oculars are closest. Similarly, multiple docking ports can be included. For example, one docking port may be on any 1, 2 or 3 of these sides. Such configuration accommodates one or more assistants positioned opposite of the surgeon or on the surgeon's left or right or any combination of these locations.

Figure 25:
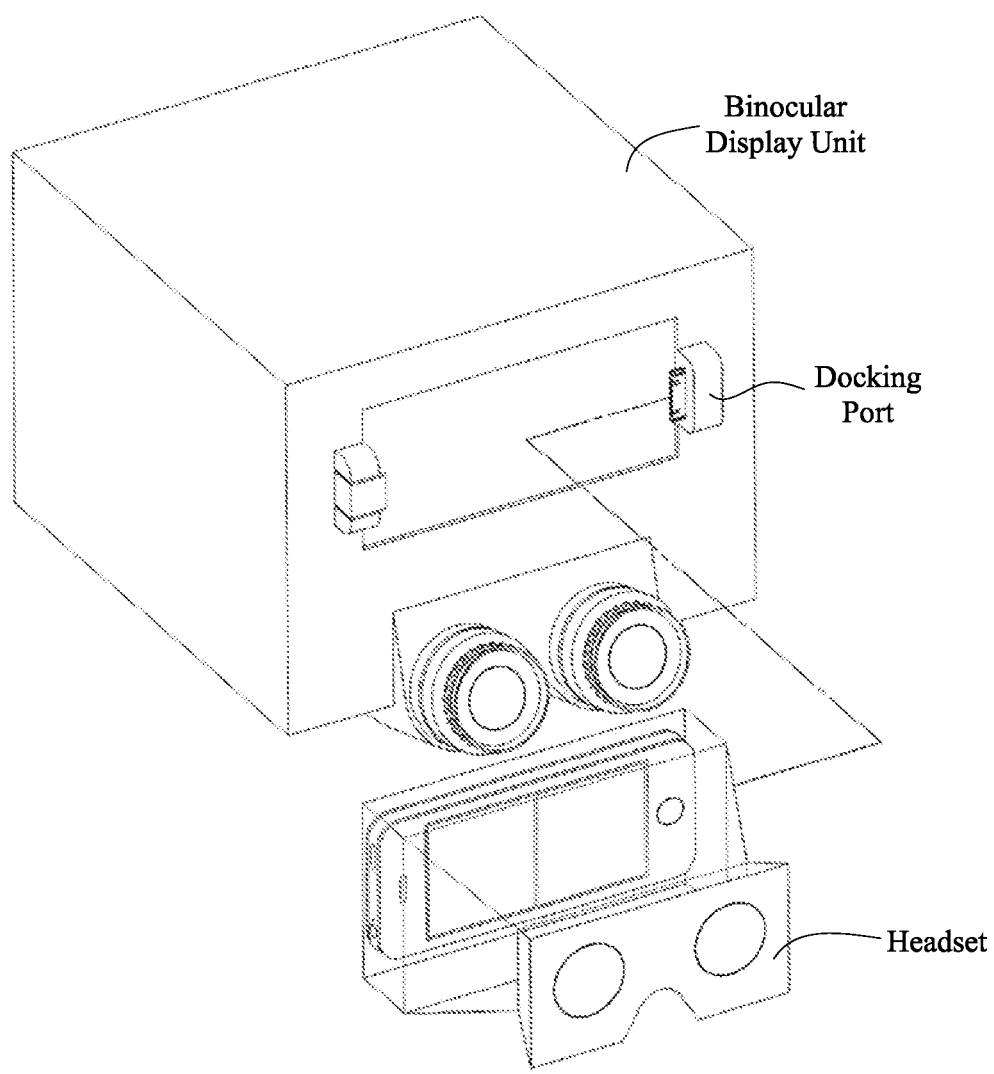

FIG. 25 shows another example headset or head mounted display that can be used to view images from a mobile display device. This example is similar to the embodiments described with respect to FIG. 24, yet the docking port is on the same side of the binocular display unit (and slightly above) as the primary surgeon's oculars. Such embodiments can allow the primary surgeon to view the images on the mobile display device without moving far from the surgical site. Various embodiments can include a headset for the primary surgeon in combination with one or more assistant headsets as shown in FIG. 24. As described herein, various elements and combinations of elements for viewing multiple images from one or more displays, e.g., including one or more mobile display devices, are possible.

Remote Control

As described herein, certain embodiments of a surgical visualization system can include a control (e.g., disposed on the viewing assembly) configured to control a camera, a display, mobile display device, or other medical device. For example, as described herein, the control can adjust size, contrast, brightness, zoom, iris size, auto gain, illumination, etc. In some embodiments, the control can include a pair of handgrips with buttons on either side of the viewing assembly so that the surgeon would not need to move away from the surgical site. In some embodiments, the control can include a single handgrip with buttons which allows the surgeon to not have to move both hands from the surgical site even momentarily.

In further embodiments, the control can allow hands free control so that the surgeon would not need to put down surgical tools from both hands. Such hands free controls can include a virtual touch screen as described herein and/or voice command recognition. Such hands free controls can also include eye and/or head tracking. For example, the control can include eye and/or head tracking systems that monitor the eye movements and/or head movements of the user. An electronic processing system in communication with the control can include algorithms that can interpret the user's eye movements and/or head movements. The control can be configured to vary at least one parameter (e.g., size, contrast, brightness, zoom, iris size, auto gain, illumination, etc.) of a camera, a display, mobile display device, or other medical device based on the eye movements and/or head movements of the user to adjust the displayed images. In some such embodiments, the control can be configured to measure the position and/or movement of one or more of the user's eyes, and/or measure the position and/or movement of the user's head. For example, in some embodiments, the control can monitor the user's gaze interaction with the surgical site, a virtual screen with icons, and/or other object. Based on such interactions, e.g., number of gazes, period of gaze, winking, etc., the control can control the camera, display, or other medical device that the user's gaze is directed towards.

Efficient Surgical Imaging Systems

Various surgical microscopes can provide a direct view of the surgical field. In such microscopes, the visible light from the illumination source is typically split (e.g., via a beamsplitter) between the direct view and the camera. Accordingly, the amount of visible light provided to the camera is reduced, which can affect the quality of the images (e.g., brightness) as seen by the user.

As disclosed herein, certain embodiments of a surgical imaging system providing a surgical microscope view can be configured to be decoupled from the camera providing the video to the display, e.g., FIGS. 2 and 3A. In various such embodiments, since the camera is decoupled from the viewing assembly, a large portion (e.g., substantially all) of the light from a light source can be directed to the camera without the need for a beamsplitter, which can also result in light loss. As such, various embodiments described herein can provide highly efficient surgical imaging systems compared to direct-view surgical microscopes. Quality well lit images can be provided without needing excessive illumination of the patient.

High Intensity Displays

As described herein, certain embodiments can include a plurality of displays (or display portions), e.g., a plurality of displays 2211a, 2212a for a left-eye view and a plurality of displays 2211b, 2212b for a right-eye view as shown in FIGS. 12A-12B. The displays can be illuminated by a source of illumination (e.g., a fiber optic, LED, etc.) or can be emissive displays. In some embodiments incorporating optical elements (e.g., beamsplitter, beam combiners, etc.), the image viewed through an ocular can have a reduction in the screen brightness. Accordingly, in various embodiments, the displays are configured to be brighter than certain conventional displays to compensate for loss in passing through optical elements like beamsplitters and beam combiners. Certain embodiments of the medical apparatus described herein, for example, include one or more displays having a relatively high brightness. In certain embodiments, the medical apparatus can include one or more light sources to illuminate a display. The one or more light sources can provide a power between about 0.5 watt to about 10 watts (e.g., 0.5 watt, 1 watt, 2 watts, 3 watts, 4 watts, 5 watts, 6 watts, 7 watts, 8 watts, 9 watts, 10 watts of power, or any value therebetween) or any ranges in between (e.g., 2-4 watts, 3-7 watts, 5-6 watts, etc.). Consequently, the output from one of the displays can be between about 0.5 watt to about 10 watts (e.g., 0.5 watt, 1 watt, 2 watts, 3 watts, 4 watts, 5 watts, 6 watts, 7 watts, 8 watts, 9 watts, 10 watts of power, or any value therebetween) or any ranges in between (e.g., 2-4 watts, 3-7 watts, 5-6 watts, etc.). In some embodiments, the light source(s) (e.g., an LED) can provide the higher power instead of the typical power (e.g., about 250 mW). In some other embodiments, the one or more light sources can include one or more auxiliary light sources (e.g., an additional LED backlight, edge light, or frontlight) that provide additional power. As one example, the display can include a backlit or edge lit display panel illuminated continuously by a plurality of LEDs on the back side or edge of the panel with power such as 0.5 W, 1 W, 2-4 W, or 5-6 W. Such light sources(s) can be run off a battery or line voltage. Utilizing one or more light sources to provide more power can provide certain embodiments with displays having sufficient and/or relatively higher brightness.

Neuro-Monitoring and Vital Sign Monitoring

As described herein, various embodiments of a medical apparatus can include a view of the surgical site (e.g., from a camera providing a surgical microscope view, from a visualization device such as an endoscope, from a proximal camera, from a camera disposed on a surgical tool, from a camera disposed on a retractor, etc.) combined with other information such as a data file, a computed tomography (CT) scan, a computer aided tomography (CAT) scan, magnetic resonance imaging (MRI), an x-ray, ultrasound imaging, fluorescence imaging, information from a mobile display device, etc. As described herein, the medical apparatus can include additional information stored in a device or received in real time. Furthermore, the medical apparatus can include a view of information providing neuro-monitoring, e.g., using neurological metrics. For example, the information can include electroencephalography (EEG) to record electrical activity of the brain. As another example, the information can include electromyography (EMG) to record electrical activity of muscles to evaluate the muscles and the nerves that control the muscles. The information can also include a monitor of vital signs, such as the heart rate, blood pressure, body temperature, weight, etc. In some embodiments, the information provided in various embodiments can include a graph of signals as a function of time. In some other embodiments, the information can be colored light, an LED light, a signal, graphics, or text when a certain threshold has been reached as the surgeon takes action during the procedure. With neuro-monitoring and/or vital sign monitoring in real time, the surgeon and/or other medical personnel can receive direct feedback during the surgery, e.g., when surgery is near a nerve, or otherwise to give biofeedback or status of vital signs. The information can viewed on a primary display, surgeon display, and/or assistant display, etc. Neuro-monitoring information can be provided on a separate display, a same display as the image or a separate display and a beam combiner as described herein.

Pair of Mobile Display Devices

As described herein, various embodiments of a medical apparatus, e.g., a binocular display, can provide a stereoscopic view of the surgical site using a pair of displays (e.g., left and right displays) for viewing through a pair of oculars (e.g., left-eye view and right-eye). Some examples are shown in FIGS. 9A-9B. Each of the pair of displays can display an image from a respective camera. One or more optical elements can be included in each optical path to direct light from each respective display to the respective ocular. In certain embodiments described herein, a cell phone (or other mobile display device such as a tablet) including a camera and display can be used for left and right channels. For example, the display of a first cell phone can be used as the display for the left-eye view (e.g., to display the image for the left-eye view). The display of a second cell phone can be used as the display for the right-eye view (e.g., to display the image for the right-eye view). The cameras of the first and second cell phones can provide the image of the surgical site to be displayed on each respective display (e.g., may be a surgical microscope having a work distance between 150 and 450 mm). In some embodiments, one or more optical elements can be added to one or both of the cameras. For example, a lens could be added to provide increased or decreased magnification or work distance. In addition, one or more optical elements (e.g., one or more mirrors, lenses, etc.) can be included in each optical path to direct light from each respective cell phone display to the respective ocular. The provided images can be different perspectives of the surgical site to provide a stereo view (e.g., 3D viewing) of the surgical site. In some embodiments as described herein, the cell phones can be controlled by a remote control (e.g., a handgrip, a joystick, a handle, buttons, haptics, a touchpad, etc.). In certain embodiments, also as described herein, each cell phone can have its own controller (e.g., processing electronics) to receive signals corresponding to the image from its camera and to drive its display to produce the image. Advantageously, having separate controllers for each of the left and right cameras and displays may reduce latency.

Separate Display Controllers

As described herein, certain embodiments of surgical visualization systems may reduce latency by using one or more beam combiners, e.g., FIGS. 12A-13C and 15-21, to receive images from displays and to combine the images for viewing through oculars. In such embodiments, the images are provided optically for viewing. In various other embodiments, the images can be provided electronically by separate controllers (e.g., processing electronics) to separate displays in the left and right eye channels. For example, different displays in the left and right eye channels can have a separate dedicated controllers which can allow for reduced latency. Furthermore, with separate controllers for the separate displays, if one of the controllers were to fail, the controller in the other channel can continue to provide images to the surgeon. Likewise the left and right eye channels have separate controllers which can also allow for reduced latency.

Multiple Displays in Field of View

As described herein, various embodiments of a medical apparatus can switch and/or combine (e.g., dispose as adjacent to one another, tile, overlap, superimpose, dispose as PIP, etc.) images (including graphics and/or text) from different sources as shown in FIGS. 13A and 13C. In some such embodiments, the images can be presented within a central portion of the view of an ocular. For example, the images can be visible within a central rectangular portion within a circular or oval field of view of an ocular because displays are typically rectangular. The shapes and sizes of the central portion and/or the field of view of the ocular are not particularly limited.

In some embodiments as shown in FIG. 22, the medical apparatus 2700 can include multiple displays 2701, 2702, 2703 within the field of view 2704 of the ocular. In this example, a first image is displayed on a first display 2701. A second image is displayed on a second display 2702, and a third image is displayed on a third display 2703. A first controller can receive one or more signals corresponding to the first image from a camera or display and drive the first display 2701 to produce the first image. A second controller can receive one or more signals corresponding to the second image from a camera or display and drive the second display 2702 to produce the second image. Furthermore, a third controller can receive one or more signals corresponding to the third image from a camera or display and drive the third display 2703 to produce the third image. Utilizing separate displays with separate controllers for each display may reduce latency. The example shown in FIG. 22 illustrates a first display 2701 as a central rectangular display extending over a substantial portion of the view with the second and third displays 2702, 2703 as smaller peripheral rectangular displays.

However, the displays can be in any location and have any shape, size, and/or aspect ratio. In addition, the displays can have the same or different shape, size, and/or aspect ratio from each other. The number of displays within the field of view is also not limited. For example, the number of displays can include 2, 3, 4, 5, 6, 7, 8, etc. The displays can be, for example, an LED light, an LCD, an LED display, an OLED display, a DMD display, or an emissive display although other displays are possible. The images can include a view of the surgical site (e.g., a surgical microscope view, an image from an endoscope, an image from a proximal camera, an image from a surgical tool, an image from a camera on a retractor, an image from a mobile display device, etc.). The images can also include information such as a data file, a computed tomography (CT) scan, a computer aided tomography (CAT) scan, magnetic resonance imaging (MRI), an x-ray, ultrasound imaging, fluorescence imaging, information from a mobile display device, neuro-monitoring, vital sign monitoring, graphics, text, etc.

As an example, an image of the surgical site can be presented on a display within a central portion of the field of view of the ocular. Another image can be presented on a smaller peripheral display outside the central portion but within the field of view of the ocular. The peripheral image can be, for example, a text message provided by a cell phone. The cell phone can have for example, a four inch, five inch, six inch, or any size display. The text message displayed on the cell phone can be presented on a smaller (e.g., 1 inch, 1.5 inch, 2 inch, etc.) display within the field of view of the ocular. Accordingly, some such embodiments can include a docking station as described herein, configured to receive the mobile display device. As also described herein, since the latency of one of the images may not be as critical as the image of the surgical site, certain embodiments can include a switching system configured to switch an image to another image (e.g., from another source). In some such embodiments, the displays can be controlled by a remote control (e.g., a handgrip, a joystick, a handle, buttons, haptics, a touchpad, etc.). For example, the images can be switch from one image from one source to another image from a different source. Thus, various embodiments include multiple displays in the field of view of a single ocular to provide multiple images simultaneously with reduced latency.

Certain embodiments can include another ocular having a plurality of displays within the field of view. For example, the medical apparatus can include first and second oculars (e.g., left-eye view and right-eye view). As an example, both the left-eye view and right-eye view can have four displays each within its field of view, for a total of eight displays. Various displays within certain embodiments of the medical apparatus can be configured to provide 3D viewing of the images of the surgical site through the first and second oculars. As described herein, in various embodiments, the medical apparatus can include a viewing assembly comprising a housing and the oculars. In some embodiments, the medical apparatus does not provide a view of the surgical site through the first and second oculars via an optical pathway that passes through the housing. For example, certain embodiments are not associated with a direct view surgical microscope. In some instances, the medical apparatus can provide a mono view of the surgical site. Various examples are possible.

Computer-Assisted Surgery including Surgical Navigation

In certain embodiments described herein, one or more displays can present images for computer-assisted surgery including for example, surgical navigation. In some instances, medical images (e.g., from one or more CT scans, CAT scans, MRI scans, x-rays, ultrasound imaging techniques, etc.) can be used to generate a 3D image dataset. The 3D dataset can be presented on one or more displays. In various examples, the 3D dataset can be generated into a 3D model of the surgical site. In some such embodiments, the 3D model can be manipulated (e.g., segmented into 2D images, rotated, enlarged, reduced, etc.) to provide different views of the surgical site.

The 3D model can be combined with other images (e.g., images from one or more cameras) on any of the embodiments described herein. In some examples, the 3D model and one or more images may be combined using one or more beam combiners (such as discussed with reference to FIGS. 12A-13C). With reference to FIG. 13A, some embodiments can present the 3D model as a PIP image. For example, a background image from a camera providing a surgical microscope view of the surgical site can be presented on a first portion 2511 of a composite image 2500 with the 3D model presented on a second portion 2512 of the composite image 2500. With reference to FIG. 13C, some embodiments can present an image from a camera providing a surgical microscope view of the surgical site on a first portion 2611 of a view 2600 adjacent with the 3D model presented on a second portion 2612 of the view 2600.

With reference to FIG. 22, some embodiments can present the 3D model on one or more of the multiple displays 2701, 2702, 2703 simultaneously with one or more other images (e.g., images from one or more cameras) in the field of view of an ocular. As an example, images from a camera providing a surgical microscope view of the surgical site can be shown on display 2701, while the 3D model can be shown on a separate display 2702 or 2703. As another example, images from a camera providing a surgical microscope view of the surgical site can be shown on display 2701, and the 3D model can be shown on the same display 2701. In some such examples, the 3D model can be combined (e.g., superimposed or presented adjacent) with the images from the camera providing a surgical microscope view of the surgical site (e.g., as shown in FIGS. 13A and 13C).

In various embodiments, user controls as described herein can be used to manipulate the 3D model on the display. In some embodiments, the dataset used to generate the 3D model can be pre-recorded images of the surgical site such that the 3D model can also be used preoperatively for diagnosis and planning. In some embodiments, the dataset used to generate the 3D model can be intraoperative images such that the 3D model can be generated from real-time images of the surgical site.

Certain embodiments described herein can provide surgical navigational guidance by presenting the 3D model as a map to the surgeon, assistant, or other medical personnel during the surgical procedure. In some embodiments, a surgical navigational system can track a surgical tool being used by the surgeon, assistant, or other medical personnel, and the system can provide images relating to the surgical site from the 3D model with respect to the tool (e.g., the images can change with movement of the tool). For example, a 3D model generated from pre-recorded images can be sliced or manipulated to provide a 2D or 3D view of the surgical site adjacent the tool (e.g., either alone or in combination with other images). As another example, a 3D model generated from intraoperative images (e.g., from a proximal camera, a camera on the surgical tool, etc.) can provide a 2D or 3D view of the surgical site adjacent the tool in real-time (e.g., either alone or in combination with other images). In some instances, the 3D model generated from intraoperative images can be combined with the 3D model generated from preoperative images, for example, to update the preoperative images. Accordingly, as described herein, various embodiments can present images for surgical navigational guidance where images can be provided with respect to movement of a surgical tool.

With reference to FIGS. 13A, 13B, and 22, for example, images from the 3D model for surgical navigational guidance can be displayed alone or in combination with other images (e.g., images from a camera providing a surgical microscope view) in the field of view of the ocular. Some such embodiments can advantageously allow the surgeon, assistant, or other medical personnel to view images of the surgical site (e.g., images from a camera providing a surgical microscope view) and images for surgical navigation simultaneously while not having to move his or her head from the ocular.

Robotic Surgery

In general, surgery requires few gross motor skills. It can be predominately comprised of fine motor skills, e.g., the skillful motions that are the coordinated movements of small muscles of the fingers, hands, and wrists. The principal interaction with surgical tools is typically between the thumb and fingers, supported by the hand and wrist. The degrees of freedom in the hands and wrists are many and complex. In some instances, robotically assisted surgery may help compensate for the difficulties of minimally invasive endoscopic surgery performed through one or more small openings in the body giving fine motor-like skills to surgical tool tips. The body openings, or ports, required for endoscopic surgical access can form a spatial constraint, orientation problem, lever arm, and fulcrum at the body opening which robots can ably compensate for in some cases.

In the case of surgery where ports are not used, robots can be configured or optimized instead to reduce the spatial relationships and physical size between finger, thumb, and wrist-like functions while retaining or enhancing dexterity, removing tremors, and the like. Robots can be used to give a surgeon a third and/or fourth hand to manipulate tools (or to give a surgeon a third and/or fourth tool), and to displace tissue for visual and or surgical access, among other functions, within a surgical site. This miniaturization of hands and/or tools, such as actuators, jaws, claws, clamps, and the like can allow master slave or other robotic methods to complement the fine motor skills of the surgeon. A mechanical third and/or fourth hand and/or tool can involve another surgeon (e.g. assistant) to remotely control the third and/or fourth hand and/or tool movement in coordination with the first surgeon.

The distinction between the above method and some present robotic surgery, for example, is that the surgery is performed through ports or minimally sized openings by one surgeon remotely, not at the patient's side. The robotic arms that compensates for the fulcrum of the port produce a device which is relatively too large to have either the surgeon or an assisting surgeon directly over or adjacent the patient. Accordingly, in various embodiments described herein a surgeon or assistant can control at least one robotic surgical device while being at the patient's side. For example, while viewing through oculars of a viewing assembly disposed over or adjacent the surgical site, the surgeon or assistant can also operate a control system (e.g., disposed on the side of a viewing assembly) to operate one or more robotic surgical devices.

In certain embodiments of a medical apparatus as described herein, miniaturized third and/or fourth hand robotic surgical devices or robots of many functions, e.g., not requiring large motions in some instances to compensate for port access, can be above or within a surgical site, supported by stereotactic frames, or proximal camera frames, frames and support attached to beds, arms and stands, and the like. The work performed by the assisting surgeon in coordination with the first surgeon can be made possible by each surgeon having a view of the surgical site. Surgical visualization systems such as described herein can be used by the surgeon and assistant together with the robotic surgical devices. In various embodiments, the viewing assembly of the display can be comprised of two chambers or portals (such as oculars), one for each eye of the viewer. Each chamber can be baffled to prevent light from one channel to communicate to the other eye path. Each surgeon can have access to a plurality of input cameras attached or within an imaging acquisition apparatus. Examples include cameras that provide surgical microscope views, cameras with the surgical site that are mounted on retractors, proximal cameras disposed proximal to and above the surgical site (e.g., mounted on frames above the surgical site), endoscopes, exoscopes, cameras mounted on surgical tools, etc. In some embodiments, all the viewers can see stereo imagery.

With two or more surgeons having visual access to the surgical site, the first surgeon with direct control over his or her hands and tools can direct the actions of the assisting surgeon having control over the third and/or fourth hand robotic surgical device or robot, by voice or other communication, to position, reposition, hold, move, cut, clamp, irrigate, aspirate, rotate, measure, biopsy or in any another manner to assist in the actions of the first surgeon. While the surgeon with direct access to the surgical site can be positioned at the patient, the second or other surgeon can be remotely stationed at some distance away in the case of a larger master robot slave arrangement for third and/or fourth hand functions where the assisting surgeon can use the master robot hand controls conveniently without interfering with the first surgeon and/or the patient.

In some embodiments, a first and second surgeon can have direct access to the patient. Each can have an electronic binocular display at or over the patient. In addition, each can be assisted by a third surgeon or assistant remotely located from the patient with a third electronic binocular display controlling a master slave robot, or other, for example, used surgically in a manner as described above.

In some embodiments, the second or third surgeon with an electronic binocular display can use haptic controls, joysticks, or other controls, to position intraoperative imaging such as ultrasound, fluorescence imaging, and real time navigation results, and/or 3D volume data sets or other images collected preoperatively; e.g., all to be displayed within the electronic binocular displays of the active surgeons in a manner of their choosing.

In some embodiments, a first surgeon and/or a first surgeon and second surgeon each with the electronic binocular display at or adjacent the patient with surgical tools can be assisted or coordinate with an additional surgeon and an endoscope, such a steerable flexible endoscope inserted in a body opening and guided to a first surgical site from within the patient where images from both surgical approaches can be viewable by the surgical team.

In some embodiments, the first surgeon and/or a first surgeon and a second surgeon each with the electronic binocular display at or adjacent the patient with surgical tools can be assisted or coordinate with an additional surgeon and a 'port' based robot, whose access to the patient is through another access point, such as a port, or body orifice. Images from both surgical approaches can be viewable by the surgical team.

Display Designs

Figure 26:
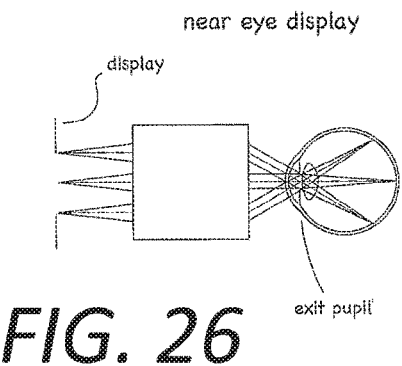
FIGS. 26-30 illustrate various example display optics designs in accordance with certain embodiments described herein
Figure 27:
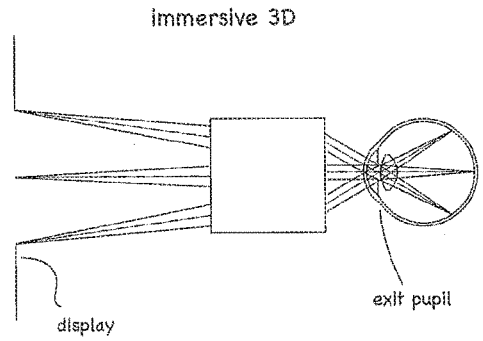

Various embodiments of the binocular display assembly described herein form a real image of first and second displays (e.g., LCD) displays. This real image is imaged onto the retina of a viewer (e.g., the surgeon) with the aid of the oculars. FIG. 26 shows a system that does not form real image. Instead, a virtual image that is viewed by the eye is formed by the optics. Similarly the system in FIG. 27 is not configured to form a real images, rather a virtual image that is viewed by the eye is formed by the optics.

Figure 28:
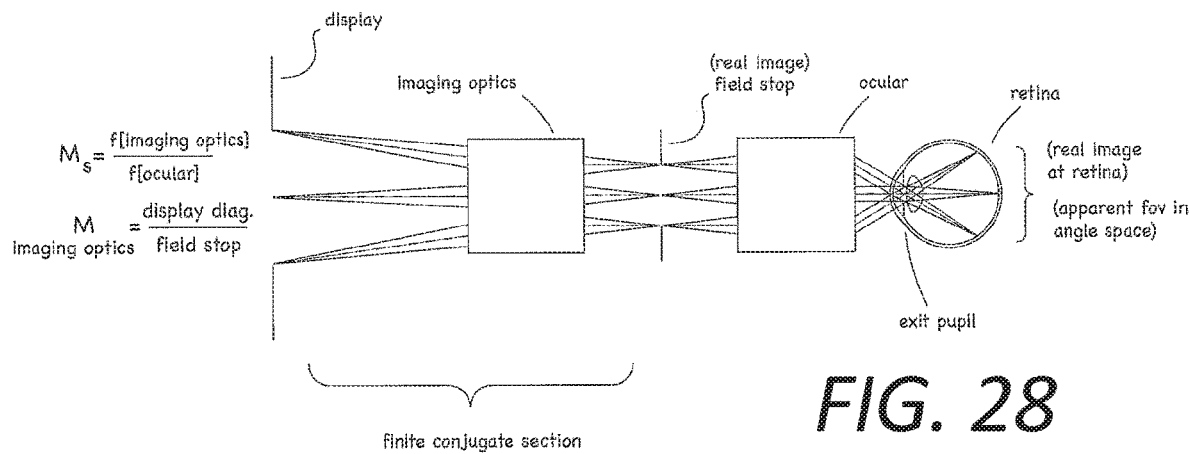

In contrast, FIG. 28 illustrates an embodiment such as described herein wherein a real image is formed by the imaging optics. This real image of the display is formed at the location of the field stop by the imaging optics. In FIG. 28, this field stop is shown located between the imaging optics and the oculars. A conjugate image of the real image located at the field stop is formed onto the retina with the aid of the oculars. Advantageously, in various embodiments, the ocular can be adjusted for doctors having impaired visual acuity such as myopia or hyperopia. The optical path distance through the ocular may be adjusted, for example, to bring the intermediate real image at the field stop in focus for the surgeon even when the surgeon is not wearing corrective eyeglasses. Such adjustments may be made without creating vignetting problems.

Figure 29:
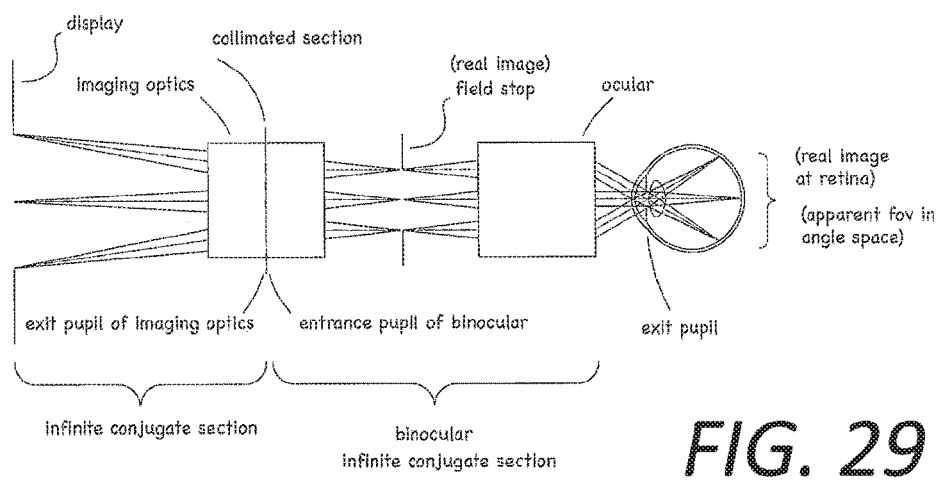

FIG. 29 illustrates another embodiment such as described herein wherein the optics that images the display has an exit pupil where the image of the display is collimated. This portion of the system is referred to in the drawing as an infinite conjugate section as collimated light is output by the optics. The exit pupil can match up with entrance pupil of the ocular or binocular assembly including the ocular. In this system, a real intermediate image of the display is formed at the field stop. This real image is imaged onto the retina of the viewer with the aid of in the binocular assembly. The binocular assembly including the oculars is referred to as a binocular infinite conjugate section as the collimated light is received by this section. In some embodiments described herein, a mounting fixture enables the binocular assembly including the ocular to be connected to the display assembly that forms a collimated image of the display. As discussed above, in various embodiments, the ocular can be adjusted for doctors having impaired visual acuity such as myopia or hyperopia. The optical path distance through the ocular may be adjusted, for example, to bring the intermediate real image at the field stop in focus for the surgeon even when the surgeon is not wearing corrective eyeglasses. Such adjustments may be made without creating vignetting problems.

Figure 30:
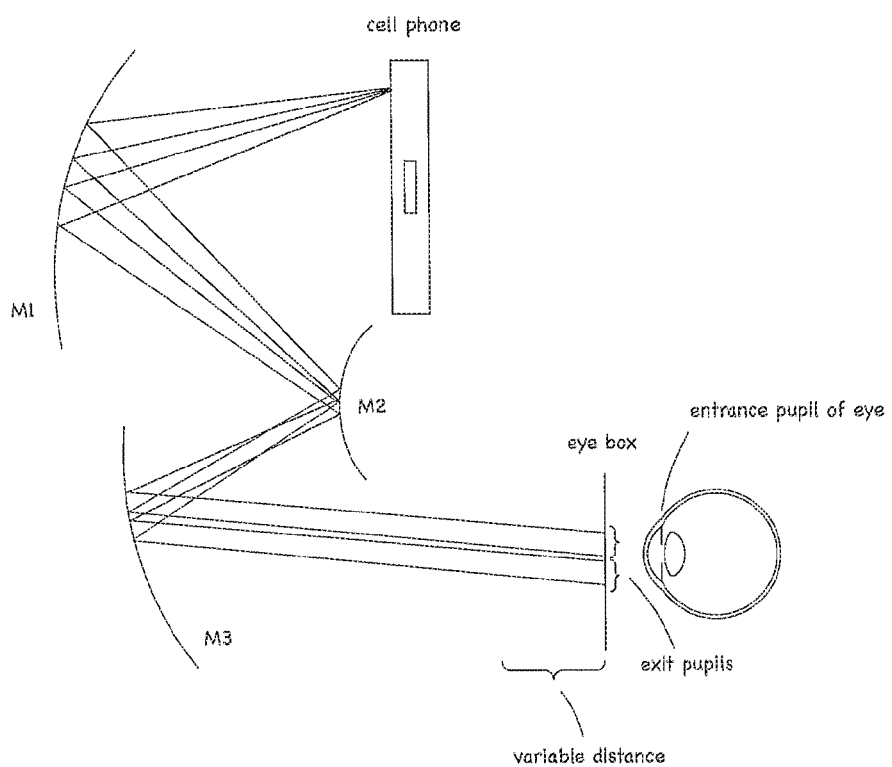

In some embodiments, an eye box can be created that allows the eye to move about a distance from the display assembly and still see the image produced by the display. FIG. 30 illustrates a configuration for producing such an eye box. In this example, a cell phone is shown as the display as is described herein, however, other displays may be employed. As shown in FIG. 30, a combination of optical elements forms a collimated beam, e.g., an image at infinity. The eye can focus this beam down onto the retina and thereby see an image of the cell phone display.

As illustrated, multiple laterally disposed pupils are created such that the eye can see the display over a range of lateral positions. Excessive lateral movement may produce vignetting. However, the image will be visible to the viewer for a range of head positions.

Three optical elements are shown in FIG. 30, each comprising reflective optical elements (e.g., mirrors). However, a different number of optical elements may be employed. Lens may also be used. A combination of elements make up of one or more reflective elements and one or more lenses may also be used. The curvatures of the optical elements may be aspherics and may be freeform shapes.

In the configuration shown, a real image of the object (e.g., the cell phone) is formed between in the optical path between M1 and M3.

Such a display configuration may be useful for an assistant display. Such an assistant display can be provided, as described herein, for assistants and other allied health professional to view during surgery. The display may be located, for example, on the outside of the binocular viewing assembly that the primary surgeon views through or otherwise (e.g., on different arms and/or stands). The display can be in various locations/orientation including for example, 90°, 180°, −90° with respect to the view of the surgeon viewing through oculars. One or more such display may be used. Such a display as shown in FIG. 30 can allow the viewer to stand off at some distance and still see stereo. This may permit the viewer to move more freely and provide increased situational awareness.

In certain configurations, mirror M3 could be semitransparent, meaning you could see the patient through the mirror. Such a design might additionally provide increased situational awareness.

In some embodiments, one or more of the optical elements could be adjustable, for example, to allow the user to adjust the distance at which the user can see the image.

Decrees of Freedom of Movement

In various embodiments described herein the binocular display assembly is configured to move in five degrees of freedom as seen from the position where the eyes meet the oculars. In particular, the binocular display unit can translate up/down (x), left/right (y) and forward or backward (z) and can pitch (tilt upward or downward) and yaw (rotate left or right). In various embodiments, the binocular display unit and the oculars cannot roll, that is rotate clockwise or counter-clockwise as seen from the position where the eyes meet the oculars. Roll can cause the viewer, e.g., surgeon, to become nauseas. Accordingly, in various embodiments the binocular display assembly (and oculars) are physically restricted from roll movements. For example, arms from which the binocular display assembly is supported may restrict roll from degrees of freedom of movement and keep the combination of the left and right oculars horizontal (parallel with the floor).

Similarly in various embodiments described herein the stereo cameras (such as the cameras that provide surgical microscope views) are configured to move in five degrees of freedom as seen from the view provided by the stereo camera. In particular, the stereo cameras can translate up/down (x), left/right (y) and forward or backward (z) and can pitch (tilt upward or downward) and yaw (rotate left or right). In various embodiments, the cameras cannot roll, that is rotate clockwise or counter-clockwise as seen from the view provided by the cameras. As discussed above, roll can cause the viewer, e.g., surgeon, to become nauseas. Accordingly, in various embodiments the cameras are physically restricted from roll movements. For example, the cameras may be disposed on arms, positioners and/or mounts that restrict roll from the degrees of freedom of movement and that keep the combination of the left and right camera views horizontal (parallel with the floor).

In various embodiments, the five degrees of freedom of movement of the binocular display assembly and oculars are decoupled from the five degrees of freedom of movement of the surgical microscope view cameras and/or other cameras. Accordingly, in certain embodiments, the oculars and/or binocular display assembly can move in five degrees of freedom without relying on movement of the surgical microscope view cameras or other cameras. Similarly, in certain embodiments, the surgical microscope view cameras and/or other cameras can move in five degrees of freedom without relying on movement of the oculars and/or binocular display assembly.

In various embodiments, mechanical fixtures can limited the degrees of freedom of movement of stereo cameras to, for example, avoid roll of that would cause the viewer to become nauseas. For example, mechanical fixtures can limit the roll of stereo endoscopes. In some embodiments, for example, the stereo endoscope or other stereo camera can be affixed to a mount such as a ring in a manner to restrict roll and keep the horizon of the stereo camera substantially constant. Other types of guides that limit the stereo camera from rolling can also be used. Accordingly, for some embodiments, five degrees of freedom or less (e.g., one or more of x, y, z translation and pitch and yaw) may be provided to the stereo cameras such as for stereo endoscope. Limiting to five degrees of freedom instead of six degrees of freedom, such as by removing roll and keeping the horizon substantially constant can reduce discomfort and disorientation for the viewer such as the surgeon or assistant.

Fixed Working Distance Objectives

In various embodiments, the camera configured to provide surgical microscope views may include a microscope objective with a fixed working distance. This fixed working distance may correspond to a fixed focal length. This objective, may have for example a work distance or focal length, of 150 mm to 450 mm, such as 150 mm, 200 mm, 250 mm, 300 mm, 350 mm, 400 mm, 450 mm, or values therebetween. Other work distances, including those described elsewhere herein may be possible. Although the objective may have a fixed work distance, the objective may permit zoom/variable magnification. The camera may be configured to receive different objectives having different working distances, which may be selected by the surgeon for different surgical procedures. One objective with a fixed working distance or focal length of 400 mm may be switched out for another objective having a fixed working distance or focal length or 150 mm to accommodate different circumstances, different types of surgery or based on the surgeons preference. Other objectives with different working distances or focal lengths may be used. In various embodiments, therefore the surgical microscope camera is configured to have the objective conveniently be removed and replaced with another microscope objective having a different working distance or focal length. The mechanical interface, for example, threading to screw the objective in place, clamps, etc. may be configured to facilitate such convenient interchangeability. As described herein, in certain embodiments for a stereo system, light for both left and right channels pass through a single objective. In other embodiments, two objectives, one for the left channel and one for the right channel, may be used.

Laser Distance Positioning Guide

As discussed above, various embodiments include at least one camera that provides surgical microscope views. Some of these cameras have a work distance between 175 mm and 450 mm. Certain embodiments are equipped with a system for enabling the user to set the proper distance between the cameras and the surgical site. The camera providing a surgical microscope view may, for example, be suspended from an articulated arm which enables the distance of the surgical microscope camera from the patient and surgical site to be adjusted to match the working distance of the surgical microscope camera. A system that informs the person (e.g., physician, nurse, technician, etc.) positioning the surgical microscope camera with respect to the patient may be useful for giving that person guidance as to whether to increase or decrease the separation of the between patient and the surgical microscope view camera. Such a system may also aid in lateral alignment.

Some such systems rely on projecting beams of light onto the patient at the surgical site. For example, lasers may be mounted on the assembly with the left and right surgical microscope view stereo cameras. The lasers may be configured to direct a pair of laser beams that converge onto a spot at the proper distance between the surgical site and the cameras. Accordingly, if the distance between the camera(s) and the surgical site is not correct, the beams will be incident on the patient at two spaced apart locations. Two separate laser beam spots will be formed on the patient. In contrast, if the distance between the patient at the surgical site and the camera that provide a surgical microscope view are correct, the laser beams are configured to overlap. In some embodiments, one laser beam may be configured as a line oriented in one direction while the other laser bean is configured as a line oriented in a perpendicular direction. Likewise, when the two laser beams overlap, a crosshair pattern is formed.

Figure 31:
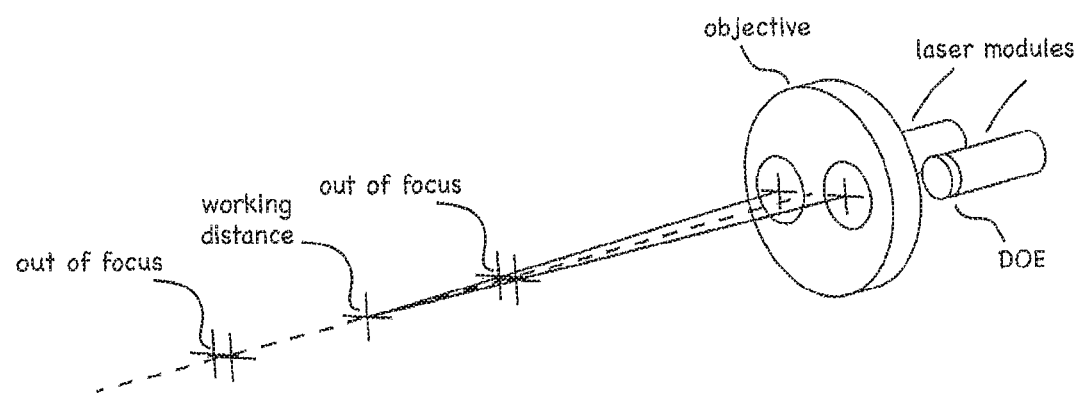
FIG. 31 illustrates a laser distance positioning guide in accordance with certain embodiments described herein.

In other embodiments, both beams may be cross-hairs that overlap when the proper distance is established between the patient and the surgical microscope view cameras. Other configurations and beam patterns are possible. In some embodiments, the laser outputs an infrared laser beam and is visible by viewing a display such as in the binocular display assembly that is coupled to an infrared sensor that may form part of the surgical microscope view camera assembly. In other cases, visible light sources can be used. The person positioning the surgical microscope view camera with respect to the surgical site may see the light beams on the patient without the aid of a display In some embodiments as shown in FIG. 31, light sources can emit light that passes through the objective and are thereby focused by the objective down to a spot, which corresponds to the work distance and/or the proper distance between the cameras and the surgical site. In some cases, the laser module output collimate beams that are parallel to each other. These parallel beams are focused by the objective (and thereby caused to overlap) at a distance that corresponds to the focal length and, hence working distance, of the surgical microscope cameras. Accordingly, for such systems, if the objective is switched out, for example, for another procedure, the beam will be focused by the new objective at the focal length and working distance of that new objective. This feature is convenient as the distance where the beams converge to a common location will chance to the proper location when the objective is switched out to a new objective for a different procedure or preference of the surgeon.

The systems described above that employ light beams such as laser beams to establish the proper distance between the patient/surgical site and the surgical microscope view cameras may also be configured to provide for laterally aligning the surgical microscope view camera as well. The location where the beams overlap may, for example, correspond to the field of view (e.g., the center of the field of view) of the surgical microscope view camera. Thus, one can use the position where the beams overlap on patient to laterally align the surgical microscope camera as well. Other laser beam pointing based systems can be use.

Other types of systems to aid in positioning the surgical microscope view camera with respect to the patient may also be employed. For example, a range finder may be used to establish the proper distance between the patient and the surgical microscope view camera. A laser rangefinder may, for example, be incorporated into the assembly in some embodiments. In certain implementations, the output of the rangefinder can be displayed using the binocular display and be viewable by looking through the oculars. In some implementations, the output of the rangefinder may be viewed without looking through the oculars. For example, a display may be disposed on the outside of the binocular viewing assembly (e.g., on the housing) that provides distance or positioning data based on the laser rangefinder. This display may indicate whether to increase or decrease the separation and may show when the separation is correct and matched to the working distance of the surgical microscope view camera. A display located elsewhere may also be used. For example, this information may alternatively or in addition be sent to a panel display. In certain embodiments, this information may be projected onto a surface such as onto the patient for viewing.

Accordingly, in various embodiments, feedback for setting the proper distance (and possibly lateral alignment) may be provided by looking at a display in the binocular viewing assembly such as when looking through one or both of the oculars. Additionally, feedback for setting the proper distance (and possibly lateral alignment) without looking through one or both of the oculars and may be provided by looking at the patient or a display, for example, located on the binocular viewing assembly or elsewhere.

Software/Image Processing

In some embodiments as described herein, multiple displays can be utilized together to allow viewing of an image of the surgical field. The images can thereby be superimposed over each other. The multiple displays and images can provide features that would be helpful for the user or assist in the surgical procedures. For example, a two display system can be used where one of the displays allows viewing of an image of the surgical field. The second display can superimpose an image over the first surgical field display using a beam combiner as described in detail herein. The ability to superimpose or display both images at the same time utilizing the beam combiner as described herein can allow for the elimination of the delay present when images are added through the use of a computer processor. By allowing for the multiple displays to be superimposed or adjacent to each other through combination of the multiple displays, the multiple displays can be viewed together as a single real time image. This can allow for viewing of fiducials, drawings and/or annotations, virtual alignment of implants, and/or display of other features in coordination with a display of an image of the surgical field. In various embodiments, the image of the fiducial, drawings, annotations, implants, etc., can also appear on one or more assistant displays, and/or on a panel display viewable by others in the room or by one or more displays located remotely. In some embodiments, an image can be projected directly onto the patient and/or surgical site. This can allow viewing of fiducials, drawings and/or annotations, virtual alignment of implants, and/or display of other features directly onto the surgical site or patient's body. This method of projecting directly onto the surgical site may eliminate the need for the second display of the surgical site as described previously and utilize only the overlaid image and/or images onto the surgical site itself. In some embodiments, a projector system may including a small projector such as a handheld projector, a pico projector, mobile projector, pocket projector, mini beamer, or other projector can be used.

In some embodiments, an image can be used to measure features of the surgical field. The image can be superimposed or adjacent to a first surgical field display or projected adjacent to and/or on the surgical field itself. Fiducials as described herein can be used in the image to measure portions or positioning of multiple aspects of the surgical field. The fiducial markers can be a marking or pattern on the image displayed, for example, the fiducial markers can be a mark, a line, a set of marks, a set of lines, image, and/or set of images. Other known points or features can be used as a fiducial markers as well. In some embodiments, for example, the image can include a ruler or grid pattern that can be displayed adjacent to and/or superimposed on the first displayed image of the surgical field or projected adjacent to and/or on the surgical field.

The multiple images or a single image can be calibrated and/or scaled to the same size or to a known size to ensure accurate measurements and/or accurate viewing of the images. Additionally, the overlaid images can be calibrated to the surgical site itself. The calibration can involve employing a calibration piece, e.g., a ruler or grid, and placing the calibration piece at the location of the surgical site and imaging the calibration piece to obtain the proper image size for the fiducial. An image of the fiducial of proper size can then be stored and the stored image of the fiducial can be reproduced on the second display. Proper adjustment of the scaling of the first and second display, to match each other may be undertaken as well. Other approaches to calibration may also be employed. The calibration can utilize predetermined distances automatically applied or applied through user input. The calibration can be performed electronically by electronics that identifies the image of the surgical field, the surgical field itself, and/or an aspect of the image or surgical field and provides scaling or magnification accordingly. Additionally, input controls can be utilized by the user to calibrate or scale the images to match each other in size or match the scale of the surgical field itself or features therein. For example, a user (e.g., a technician) can manipulate the displays by moving them in any direction increasing or decreasing the magnification so that the image fields of the display(s) are lined up and scaled to the correct size. This can be done by utilizing knobs, buttons, touch screens, virtual touch screens, voice or other input controls from a control unit and manipulated by the user. The control unit can be integrated into the binocular display assembly. In other embodiments, the control unit can be remote from the binocular display assembly.

In some embodiments, an image can be used to display drawings or other markings drawn by or inserted by the surgeon or assistant on the surgical field. The drawing(s) and other marking(s) can be superimposed on or displayed adjacent to a display of an image of the surgical field or projected adjacent to and/or on the surgical field. For example, a surgeon can introduce a drawing and/or annotation onto an image of the surgical field to annotate the image as desired. In some embodiments, the drawings or annotations can be projected onto the surgical field or onto the patient. In some embodiments, a computer processor receives the drawings or annotation produced or selected by the surgeon and identify where the annotations or drawings are being inserted relative to the display of the surgical field image or relative to the surgical field itself. In some embodiments, the computer processor can save and/or reuse these drawings or annotations. In various embodiments, the drawings and/or annotation can also appear on one or more assistant displays, and/or on a panel display viewable by others in the room or by one or more displays located remotely.

In some embodiments, an image can be used to simulate placement of implants in the surgical field. The image of the implant can allow for the implant to be aligned virtually with an image of the surgical field and/or the surgical field. For example, an overlay of a spinal implant can be used to illustrate and/or determine the desired positioning of the spinal implant within the surgical area. In some embodiments, the spinal implant image can be manipulated by the user to move the implant image over the surgical area or surgical field display. In various embodiments, a variety of implant images can be stored or retrieved based on user selection of the type of implant. In some embodiments, input controls can be utilized by the user to move the image of the surgical implant relative to the surgical field. In some embodiments, the movement of the image of the surgical implant can be performed by an input of the user to move the image of the surgical implant in any direction as desired by the user. For example, the user can manipulate the image displays by moving them in any direction. This can be done by utilizing knobs, buttons, touch screens, virtual systems and methods, voice, or other input controls from a control unit manipulated by the user. The control unit can be integrated into the binocular display assembly. In other embodiments, the control unit can be remote from the binocular display assembly. In some embodiments, the image of the implant can be magnified or scaled to the appropriate size by a computer processor or by other mechanical control or inputs as described previously. Alternatively, the implant image can be displayed at a predetermined size corresponding to the actual size of the implant. In various embodiments, the image of the implant can also appear on one or more assistant displays, and/or on a panel display viewable by others in the room or by one or more displays located remotely.

Illumination

Figure 43:
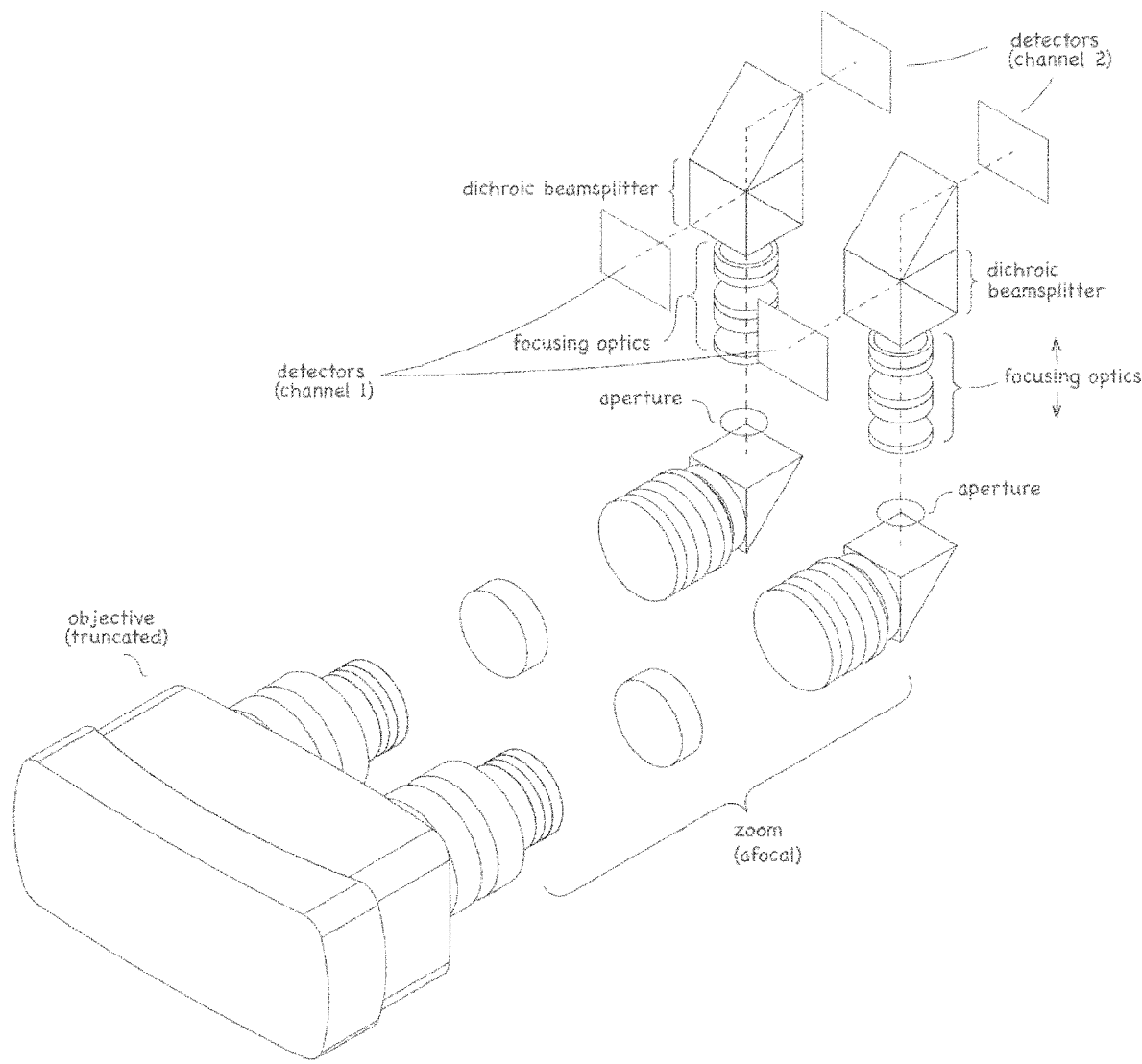
FIG. 43 illustrates an example optical imaging system for providing a surgical microscope view of a surgical site using a common objective for left and right optical paths, wherein each optical path is split to at least two image sensors.

Various implementations described herein can include an imaging system to generate images of a surgical site. The imaging system can include a common objective for left and right eye optical paths. The common objective can collimate light from the surgical site. The optical path of the collected collimated light can be redirected by a prism, fold element, or beamsplitter. The collimated light can be configured to pass through a zoom lens group (e.g. afocal zoom), an aperture, and other optical elements to direct portions of the collimated light within the left and right eye optical paths, as shown in FIG. 43 described herein and/or FIGS. 29A and 29B of U.S. application Ser. No. 14/581,779 filed on Dec. 23, 2014 entitled "SURGICAL VISUALIZATION SYSTEMS," which published as U.S. Publication No. 2015/0297311. U.S. application Ser. No. 14/581,779 and U.S. Publication No. 2015/0297311 is incorporated by reference herein in its entirety for all that it discloses. For each left and right eye optical paths, the imaging system can be configured to generate images of the surgical site. The imaging system can include a sensing system configured to detect the images formed in the left and right eye optical paths. For example, in some embodiments, the sensing system can be configured to detect the images formed in the left eye optical path on portion of the sensing system, and to detect the generated images in the right eye optical path on another portion of the sensing system.

Each left and right eye optical paths of the imaging system can include a plurality of optical paths for imaging at different wavelength ranges. In some embodiments, the optical paths can lead to sensors sensitive to the different wavelength ranges. In various embodiments, the plurality of optical paths can be used for imaging, for example, in infrared (IR), near infrared (NIR), visible wavelengths or bands (about 400 to about 700 nm). As described herein, features (e.g., tumors) could be made to fluoresce by injecting fluorescent chemical (e.g., dye) and illuminating the feature with light that induces fluorescence (e.g., UV, visible, or in IR radiation). As another example, imaging at blue (about 440 to about 460 nm) and/or green (about 540 to about 560 nm) wavelengths can improve visibility of features since the peak light absorption of hemoglobin occurs at these narrow band wavelengths. Use of other bands of wavelengths are possible.

In certain embodiments, the imaging system can switch between imaging at different wavelengths. For example, in some embodiments, the imaging system can switch between imaging at narrow band wavelengths and visible wavelengths. As another example, in some embodiments, the imaging system can switch between imaging at NIR and IR. Thus, certain embodiments can switch between wavelengths or wavelength bands in two or more or all of infrared (IR), near infrared (NIR), visible, and ultraviolet (UV). By switching between different wavelength ranges (e.g., illuminating the surgical site with different wavelength ranges in sequence), the surgeon or assistant may be able to detect subtle differences between the two images. If the images are registered, the surgeon would be able to see and know a sense of direction. Also, by switching illumination on and off, the sensors can remain on and detect the appropriate wavelengths when present based on the illumination that is switched on. As an example, certain embodiments can include a sensor sensitive to visible light and another sensor sensitive to IR light. When the visible light source is on, the sensor sensitive to visible light can detect the visible light, and when the IR light source is on, the sensor sensitive to IR light can detect the IR light. Furthermore, some embodiments can include a single sensor with multiple illumination (e.g., dual visible illumination).

In some such embodiments, the imaging system can include an illumination control configured to control the light provided to the surgical site such that the provided light switches between the light of different wavelength ranges. For example, the surgical site can be illuminated by at least one illumination source, such as one or more lasers, light emitting diodes, or white-light light sources. The illumination source can include multi-spectral illumination sources to provide visible light or white light whose color temperature can be varied. The illumination source can also include other sources configured to provide infrared, near infrared, visible, ultraviolet, and or other bands of wavelengths. The illumination control can control the light provided to the surgical site by controlling one or more illumination sources. For example, the illumination control can adjust the position of an illumination source (e.g., position of a fiber optic) and/or turn on/off an illumination source or block the illumination (e.g., with a shutter or modulator). As another example, the illumination control can include a filter (e.g., a bandpass, low pass, or high pass filter) such that the sensors are provided light of the different wavelength ranges. The illumination control can include at least one knob, dial, button, handle, switch, joystick, haptic, or touchpad. In some embodiments, the illumination control can be disposed on the binocular viewing assembly including a housing and oculars such as on handles on the housing such that the user need not remove one's eyes from the oculars.

Alternatively, instead of controlling the light being provided to the surgical site, some embodiments of imaging systems can control the received light from the surgical site. For example, each of the left eye and right eye optical paths can include one or more filters (e.g., a notch filter) configured to remove unwanted wavelengths from the received light to remove unwanted wavelengths from the light being provided to the surgical site. For example, a notch filter may be used in front of the different sensors to block the pump light uses to excite fluorescence, which may possibly saturate the sensors. The different wavelengths ranges can include wavelengths in two or more or all of infrared (IR), near infrared (NIR), visible, and/or ultraviolet (UV), as described herein.

Various embodiments described herein include an imaging system configured to generate images of the surgical site at different wavelength ranges. The imaging systems can be used for the primary display, surgeon display, the assistant display, possibly other displays, or any combination of these. For example, in some embodiments, the assistant can switch to and from a fluorescence image on the assistant display. In some cases, the assistant can switch the images that the assistant sees from fluorescence images to visible images and back or combinations of thereof, without changing the images seen by the primary surgeon. In various embodiments described herein, the generated images in the left eye and right eye optical paths can be different stereo views of the surgical field. In some embodiments, the imaging system can provide a surgical microscope view. As for various embodiments described herein, the imaging system need not be associated with a direct view surgical microscope.

Additional Discussion on Producing Multiple Images in Different Wavelength Bands Accordingly, in various embodiments, one or more cameras, such as the camera that provides a surgical microscope view (e.g. having a working distance and/or focal length of 150-450 mm) can be configured to receive images of different wavelengths. The cameras may, for example, receive fluorescence images as well as non-fluorescence images or narrow band images such as blue images (e.g., about 440 to about 460 nm wavelength) and/or green image (about 540 to about 560 nm wavelength) as well as broad band visible wavelength images (e.g., that extend across the visible spectrum) wherein the surgical site is illuminated with white light. Such a visible wavelength image may be used as a reference view used by the surgeon most of the time in performing the surgery. This view may resemble the view seen through a direct view surgical microscope.

Likewise, the cameras may have sensors that are sensitive to different wavelength bands. For example, a visible detector array and an infrared detector array (e.g., NIR) may be employed. Or different types of sensors sensitive to different portions of the infrared spectrum may be used. Similarly, different types of sensors sensitive to different portions of the visible spectrum may be used.

Alternatively (or in combination), multiple sensors having similar spectral response can be used. Additional wavelength selective optics may be used to enable the different sensors to detect different wavelengths. For example, multiple visible detectors with the same spectral responsivity can be used. Similarly, multiple infrared detectors with the same spectral responsivity may be use. One or more wavelength selective filters may be associated with one or more of the sensors and may be included in the optical path to the respective sensors. For example, a first filter or filter combination may be included in the optical path to a first sensor and a second different filter or filter combination may be included in the optical path to a second sensor. In this manner, the two sensors may be sensitive to two different spectral bands, e.g., blue and green respectively. In some cases, one of the sensors may not have any filters associated therewith or may otherwise be configured to be sensitive to a broader wavelength spectrum that is different from the other optical sensor. For example, a first filter or filter combination may be included in the optical path to a first sensor and while no filter is included in the optical path to a second sensor. Again, the two sensors will be sensitive to two different spectral bands, e.g., green and the entire visible spectrum respectively. This later configuration may be useful, for example, to see a fluorescence peak on a first sensor and a broad band image (e.g., reference view) across the entire visible spectrum that is produced by illuminating the surgical site with white light on a second sensor.

Accordingly, one or more of the sensors may have associated therewith a filter or filter combination to provide wavelength selectivity. The different filters for the sensors may comprise band pass filters, low pass filters, high pass filters, notch filters, or any combination thereof.

In some embodiments, the wavelength selectivity may be included in one or more beamsplitting element (e.g., a beamsplitter such as a dichroic beamsplitter). Such an optical element may enable the separation of light having two different spectra into two separate beams. For example, light of having a first spectra may be directed (e.g., reflected) in a first direction while light having another different second spectra may pass through. Accordingly, additional filters need not be added in the optical paths of the sensors although in some embodiments such additional filters may be included. Use of wavelength selective beamsplitters or deflectors can provide increased efficiency in comparison to a 50:50 beamsplitter with filters to remove unwanted light. Instead of removing unwanted wavelengths, such as by using absorption filters, the wavelengths are redirected. However, in various embodiments that employ wavelength selective beamsplitters or deflectors, filters may still be employed to further tailor the spectrum.

Additionally, as described herein switching illumination on and off may provide the wavelength selectivity. For example, a first light source having a first wavelength spectra may be turned on while a second light source having a second spectra is shut off or blocked from reaching the surgical site at a first time. The light or resulting fluorescence response signal reaches the one or more sensors to provide an image corresponding to the first wavelength spectra. At a second later time, the second light source is turned on or permitted to reach the surgical site while the first light source is turned off or blocked from reaching the surgical site. This light then reaches the one or more sensors to provide an image corresponding to the second wavelength spectra.

In some such embodiments, a single sensor may be used to collect light from either light source if the sensor is sensitive to both light sources. In other embodiments multiple sensors may be employed. One sensor may, for example, be more sensitive to the first wavelength spectra and another sensor may be more sensitive to the second wavelength sensor. One or more wavelength selective beamsplitter or deflector may be used to direct the light of the different wavelengths to the different sensors.

Instead of switching the light sources on and off, in certain embodiments both light sources can remain on and the images from respective sensors can be sent to different displays. Or the viewer can switch from showing the image from the first sensor on the display to showing the image from the second sensor on the display and vice versa. Accordingly, the viewer can switch back and forth between views of the surgical site having different wavelength distributions. Switching back and forth may enable the viewer to more readily detect distinctions between the two images.

Alternatively, in certain embodiments, the viewer can view both images from both cameras at the same time, for example, in a picture in picture (PIP) configuration or next to each other, etc. As described herein, the surgical visualization system may be configured for the viewer to select which format to view the images, for example, one at a time with ability to switch from one image to the other, or both at the same time juxtaposed on the display.

The visualization system may be configured to provide the primary surgeon these different images in different spectral images either at the same time or to switch between them. The surgeon can control what image he or she sees.

Similarly, the visualization system may be configured to provide the assistant or other viewer besides the primary surgeon the ability to view the different images in different spectral either at the same time or to switch between them. The assistant or other viewer can control what image he or she sees regardless of what views or images that primary surgeon elects to see. For example, the assistant may be interested in seeing only a fluorescence image or only a narrow band blue or green image while the primary surgeon is interested in switching back and forth between the fluorescence image or a narrow band blue or green images and a broad band visible image covering the width of the visible spectrum.

In some embodiments, the illumination directed onto the surgical site passes through the imaging optics for receiving light from the surgical site before being incident on the surgical site. For example, the light source is disposed with respect to the imaging optics (or a portion thereof) to form a path from the light source through the imaging optics (or a portion thereof) to the surgical site. This light may first then pass through, for example the objective and/or the zoom system prior to being incident on the surgical site. A portion of this light after being reflected or a fluorescence response signal from the surgical site will then pass again through the imaging optics and be directed to the one or more sensors.

Additionally, in various embodiments more than two optical sensors may be employed. For example, more than two detector arrays for the left channel in a stereo camera may be employed. Likewise, more than two detector arrays for the right channel in a stereo camera may be employed. As discussed above, multiple sensors may increase the spectral information provided by the system as many spectral regions may be separately measured and be available to the viewer for comparison.

In certain embodiments, for example, 4 cameras sending signal to 4 displays (e.g., 2 cameras and displays for each of left and right channels). Alternatively, 6 cameras could send signal to 6 displays (e.g., 3 cameras and displays for each of left and right channels). Alternatively, 8 cameras could send signal to 8 displays (e.g., 4 cameras and displays for each of left and right channels). The number of cameras and displays may be more or less. Additionally, mono cameras (as compared to stereo cameras) may be included. The number of cameras and displays also need not be the same. Similarly, the number of camera's and/or displays associated with the left channel need not be identical to the number of camera's and/or displays in the right channel.

Various combination of the features described above and elsewhere herein may be used.

Example Embodiments on Producing Multiple Images in Different Wavelength Bands

Figure 32:
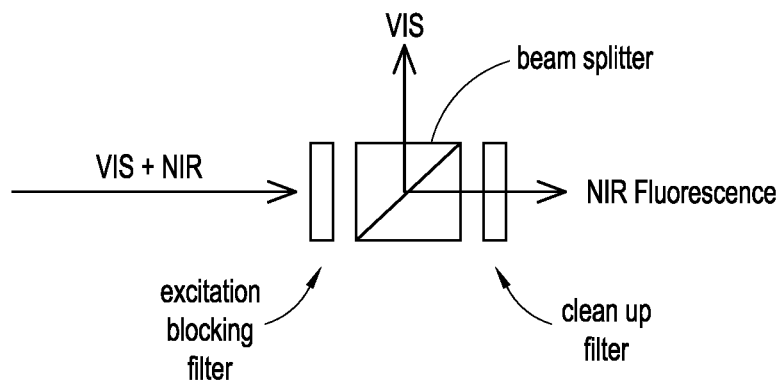
FIGS. 32-33 illustrate example embodiments on producing multiple images in different wavelength bands.
Figure 33:
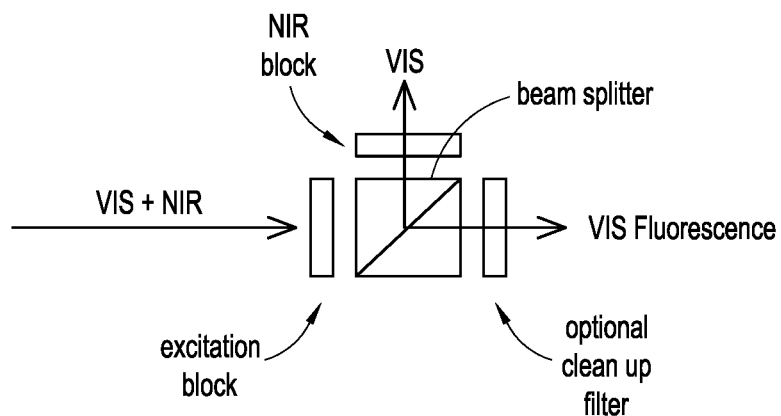
Figure 34:
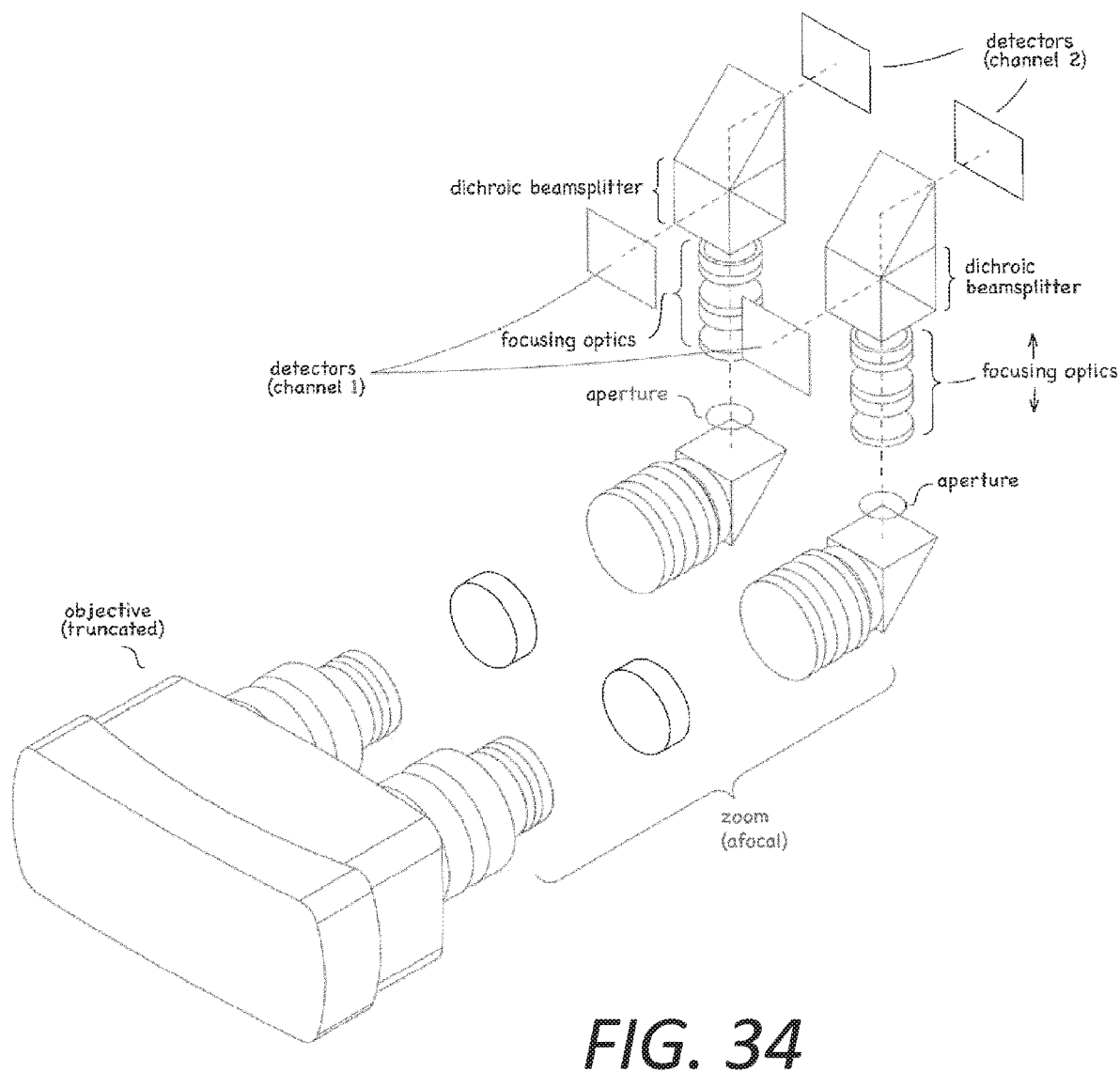
FIG. 34 illustrates an example optical imaging system or camera in accordance with certain embodiments described herein

FIGS. 32 and 33 show example embodiments of a combination of a beamsplitter and one or more filters which can be used in an imaging system as described herein to generate images of a surgical site in different wavelength ranges. In certain embodiments, the imaging system can include a filter block (or a filter cube, cartridge, or assembly) to hold a beamsplitter and one or more filters. For example, as shown in FIG. 34, the filter block or assembly can be placed in the optical path from the surgical site to the sensing system. In particular, the filter assembly comprising the dichroic beamsplitter is shown in the optical path between the focusing optics and the sensing system. The filter block can be moved in and out of the imaging system allowing the beamsplitter and one or more filters to be changed or allowing the filter block comprising the beamsplitter and one or more filters to be replaced with another filter block comprising a beamsplitter and one or more filters.

As shown in FIG. 32, the filter block, cartridge, or assembly can include an excitation blocking filter, a dichroic beamsplitter, and a clean-up filter. In this example, one or more light sources can provide visible light and near infrared (NIR) light to illuminate the surgical site. This visible and NIR may include pump light for exciting fluorescence. Optical fluorescence in the form of NIR light in this example may be emitted from the surgical site. As described herein, an excitation blocking filter can be used in front of the sensing system to block the pump light used to excite fluorescence, which may possibly saturate the sensing system. The dichroic beamsplitter (used alone or in combination with one or more filters) can separate the visible light and NIR light into two optical paths. In this example, a clean-up filter is used in one of the optical paths. Such a filter may, for example, reduce contribution from wavelengths different from the fluorescence signal. The sensing system, which may include one or more sensors in each optical path, can be used to detect the separated visible and/or NIR fluorescence light. The imaging system can generate the images of the surgical site based on the detected light. For example, the imaging system can generate an image of the surgical site in the visible range, and another image of the surgical site in the near infrared range. This visible image may be a useful reference view which the surgeon uses for most of the surgery and provides a visible image akin to what the surgeon is accustomed to when viewing a patient through a surgical microscope with a white illumination light source.

As shown in FIG. 33, one or more light sources can be used to illuminate the surgical site with visible and near infrared light. This visible and NIR may include pump light for exciting fluorescence. Optical fluorescence in the form of visible light in this example may be emitted from the surgical site. The dichroic beamsplitter can separate the light into two optical paths with one or more filters in each optical path. In this example, in one optical path, a NIR blocking filter is used to block the NIR light such that only the visible light is sent to the first optical path. In the other optical path, a clean-up filter is used such that mostly only or only the visible fluorescence light is sent to the other optical path. The sensing system, which may include one or more sensors, can be used to detect the light in each of the two paths.

Advantageously one filter block or assembly having first spectral characteristics can be switched out (e.g., by a nurse, technician, orderly, doctor or surgical staff) for a second filter block or assembly having second spectral characteristics. Accordingly, different filter assemblies can be used for different circumstances, for example, if different fluorescence dyes and fluorescent peaks are used such as for different procedures. In some embodiments, the filter block or assembly may simply comprise a dichroic or wavelength selective beamsplitter. In other embodiments, the filter block or assembly may comprise filters such as band pass filters and/or notch filters. As described above, one filter assembly can be switched out for another filter assembly for different circumstances. For example, the dichroic beamsplitters in FIG. 34 can be switched out for other dichroic beamsplitters having different spectral properties such that although the first dichroic filter might split light into first and second beams having first and second spectral distributions, the second dichroic filter might split light into first and second beams having different third and four spectral distributions. An opening or door in the side or top or bottom of the housing of the camera may permit the filter assembly to be switched out.

Other combinations of light sources, beamsplitters, filters, and wavelength bands are possible. As described herein, in various embodiments, the imaging system can generate images in different wavelength bands. The imaging system can combine (e.g., dispose as adjacent to one another, tile, overlap, superimpose, dispose as PIP, etc.) and/or switch between the images.

Fluorescence and Narrow Band Imaging

Figure 35:
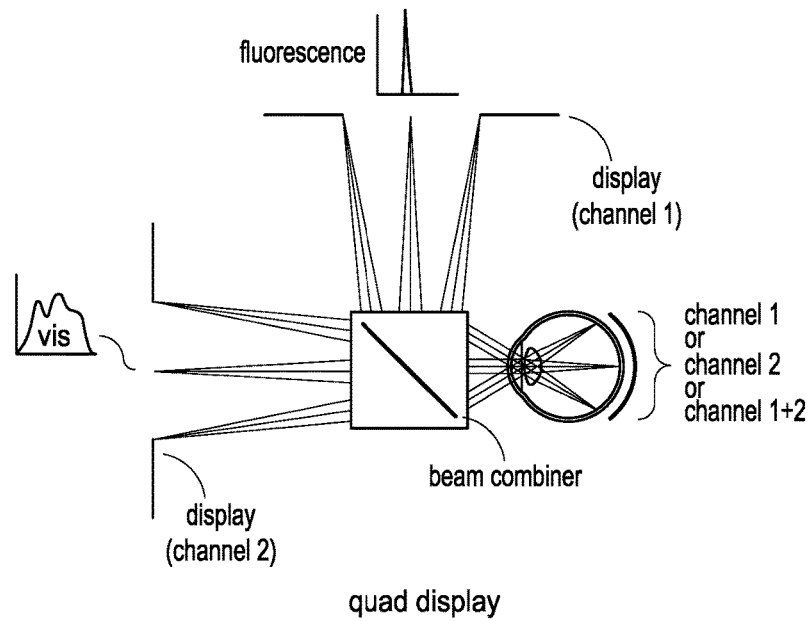
FIG. 35 illustrates various embodiments for fluorescence imaging.
Figure 35:
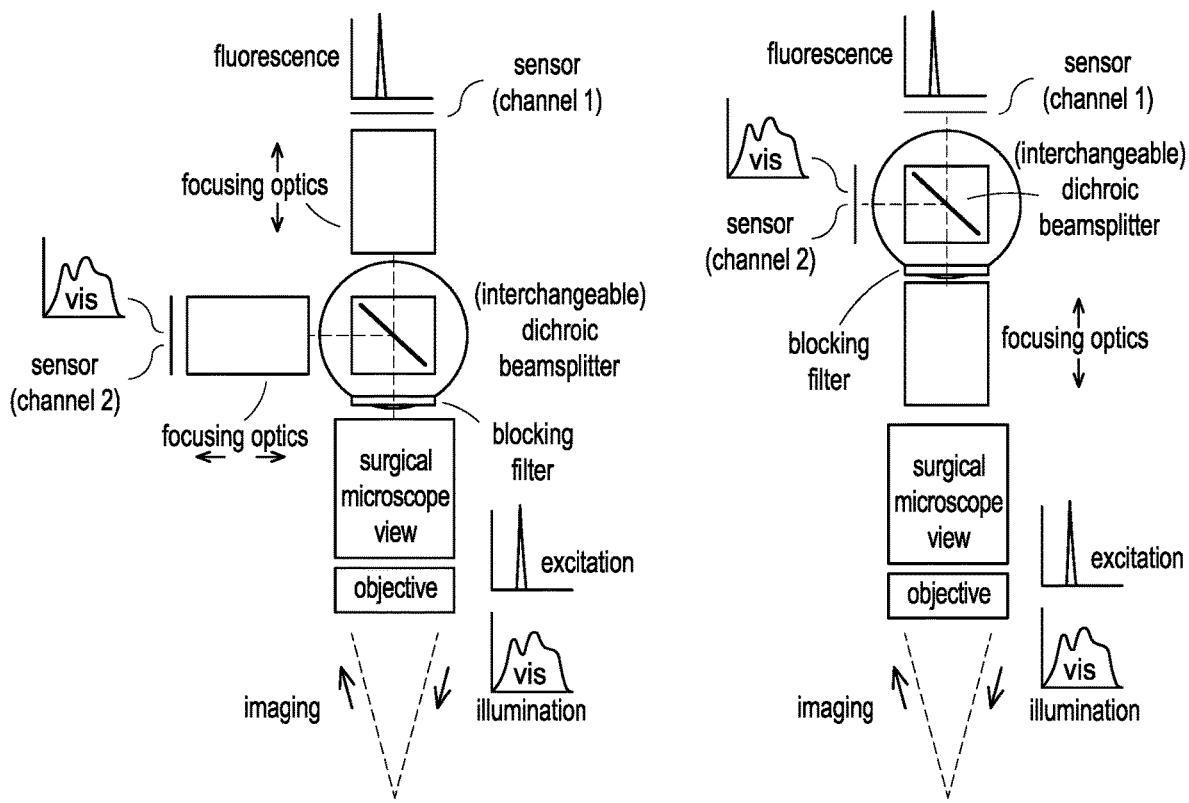

FIG. 35 (lower portion) illustrates various embodiments where the surgical microscope view camera obtains a fluorescence image as well as a visible reference image. Light collected by the microscope objective is passed through a dichroic beamsplitter and directed into two paths. The first path (channel 1) for light passing through the beamsplitter is for the fluoresce signal. A sensor is included in channel 1 that is sensitive to the fluorescent signal. The second path (channel 2), reflected by the beamsplitter, is for a broad band visible wavelength reference view. The broad band image might resemble an image seen by a surgeon when viewing a patient illuminated with white light through a direct view surgical microscope. A sensor is included in channel 2 that is sensitive to visible light. The wavelength selective beamsplitter may be used to separate the light into the two paths. A blocking filter configured to block the pump wavelength used to induce fluorescence is also included.

As discussed elsewhere herein the dichroic beamsplitter may be interchangeable. For example, one dichroic beamsplitter can be switched out for another if a different fluorescence wavelength is to be examined or a different type of image or images are to be obtained. For example, different procedures using different fluorescing materials such as dyes may result in different fluorescent wavelengths. Accordingly, the wavelength selective beamsplitter may be different. An opening in the housing for easy substitution of one dichroic filter for another may be used. Similarly, the blocking filter may be switched out, for example, if the pump wavelength is different. The blocking filter and dichroic beamsplitter may be included in a single assembly that is switched out in certain embodiments.

FIG. 35 (upper portion) also shows a display assembly such as a binocular display assembly that includes multiple optical channels (channel 1 and channel 2) and associated display screens (e.g., LCD, OLED). A beam combiner combines the optical paths to each of the display screens. One of the display screens (channel 1) can be in electrical communication with the sensor receiving the fluorescence signal. The other display screen (channel 2) can be in electrical communication with the sensor receiving the visible reference image.

Figure 36:
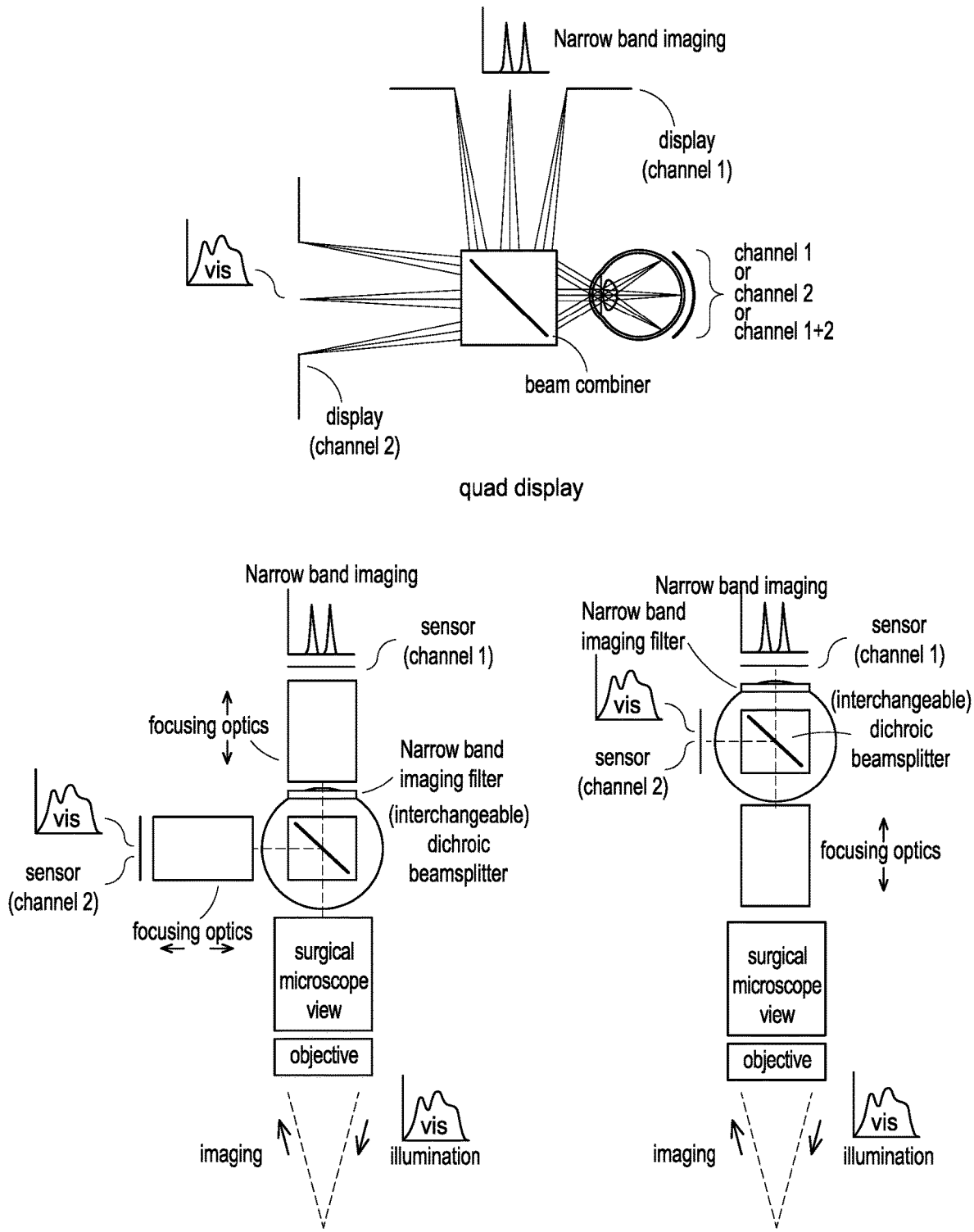
FIG. 36 illustrates various embodiments for narrow band imaging.

FIG. 36 (lower portion) illustrates various embodiments configured for narrow band imaging, for example, using blue and green wavelengths. These wavelengths may, for example, be between 440 to 460 nm and 540 to 560 nm, respectively. FIG. 36 shows the surgical microscope view camera configured to obtain narrow band images as well as visible reference images. Light collected by the microscope objective is passed through a dichroic beamsplitter and directed into two paths. The first path (channel 1) for light passing through the beamsplitter is for the narrow band imaging signal. A sensor is included in channel 1 that is sensitive to the narrow band imaging signal. The second path (channel 2), reflect by the beamsplitter is for a broad band visible wavelength reference view. The broad band image might resemble an image seen by a surgeon when viewing a patient illuminated with white light through a direct view surgical microscope. A sensor is included in channel 2 that is sensitive to visible light. The wavelength selective beamsplitter may be used to separate the light into the two paths. A narrow band imaging filter configured to further attenuate unwanted wavelengths, for example, outside 440 to 460 nm and 540 to 560 nm, is also included.

As discussed elsewhere herein the dichroic beamsplitter may be interchangeable. For example, one dichroic beamsplitter useful for narrow band imaging can be switched out for another useful for fluorescence imaging. Accordingly, the wavelength selective beamsplitter may be different. An opening in the housing for easy substitution of one dichroic filter for another may be used. Similarly, the filter may be switched out through an opening. The filter and dichroic beamsplitter may be included in a single assembly that is switched out in certain embodiments.

In certain embodiments, a beamsplitter that is not a dichroic beamsplitter may be used. The narrow band imaging filter may be used to filter our light outside the narrow band imaging wavelengths to accomplish narrow band imaging.

FIG. 36 (upper portion) also shows a display assembly such as a binocular display assembly that includes multiple optical channels (channel 1 and channel 2) and associated display screens (e.g., LCD, OLED). A beam combiner combines the optical path to each of the display screens. One of the display screens (channel 1) can be in electrical communication with the sensor receiving the narrow band imaging signal. The other display screens (channel 2) can be in electrical communication with the sensor receiving the visible reference image.

A wide range of variations are possible. Various features may be excluded and/or combined with other features disclosed elsewhere herein.

Binocular Viewing Assembly

The disclosure generally describes a binocular viewing assembly for providing a surgeon with video of a surgical site. The binocular display can include a plurality of displays in a housing and a plurality of oculars for viewing those displays. The binocular viewing assembly can be configured to show views of video images of the surgical site. The binocular viewing assembly can be further configured to show images from the surgeon's cell phone or tablet. In some embodiments, the binocular viewing assembly includes optical components configured to direct video images from the plurality of displays to the oculars, wherein the video images are acquired with stereo electronic microscope cameras configured to provide a surgical microscope view of the surgical site. The optical components can be configured so that the optical axis from the oculars is not aligned with (e.g., does not intersect) the stereo electronic microscope cameras.

In some embodiments, the binocular viewing assembly can be combined with one or more displays positioned outside of the housing, wherein the display can be viewed by an assistant or other personnel in the operating room. The one or more displays can be flat panel displays or images projected onto a screen or other surface so that a person not looking through the oculars of the binocular viewing assembly can see video images on the one or more displays. In certain implementations, the video images on at least one of the one or more displays can include the view that is being provided in the binocular viewing assembly. In some implementations, a plurality of displays can be configured to display the video images provided by the plurality of displays in the binocular viewing assembly. In certain embodiments, the displays are mounted on the housing. In some embodiments, one or more of the displays can be configured to provide stereo video images. In some embodiments, the binocular viewing assembly can include a fiber optic light source to direct light to the surgical site. In some embodiments, the binocular viewing assembly can be configured to provide views of video acquired with one or more endoscopes.

In some embodiments, the surgical visualization system can include one or more endoscopes, one or more cameras positioned on a retractor and/or one or more cameras positioned proximal to the surgical site in addition to the stereo microscope camera. The various cameras can have different optical properties to provide different imaging functionality to the surgical visualization system. For example, the one or more cameras positioned on the retractor can have a relatively wide field of view and can be positioned at a distance that is multiple focal lengths from the surgical site. The one or more cameras on the retractor can thus be configured to provide a relatively short focal length and wide field of view, to provide images suitable for working more obliquely. As another example, the stereo microscope camera can be configured to have a longer focal length than the cameras on the retractor and/or the proximal cameras. The stereo microscope camera can be configured to be positioned about one focal length away from the surgical site. The stereo camera can be configured to provide zooming functionality. The stereo microscope camera can be positioned to allow a surgeon to put tools and/or proximal cameras between the surgical microscope camera and the surgical site. The stereo microscope camera can have a relatively narrow field of view. In certain implementations, the proximal cameras can be positioned on a structure so that the proximal cameras are positioned outside of the surgical site and below the stereo microscope camera and the binocular viewing assembly, wherein the structure is positioned so that a surgeon can put tools between the structure and the stereo microscope camera.

In certain implementations, the surgical visualization system can include one or more projectors configured to project images on a patient. The images can be of user interface elements to allow virtual manipulation by a surgeon utilizing the binocular viewing assembly. The surgical visualization system can include a user interface camera configured to acquire video images of the patient and the hands of the surgeon with the projected images. The user interface camera can be operably coupled to an image processing system to determine whether movements by the surgeon's hands correspond to virtual manipulation of the user interface elements of the projected images.

The disclosure also provides for a binocular viewing display having oculars beneath corresponding displays. The binocular viewing display can be configured in a manner similar to a periscope. For example, the displays can be positioned above the oculars with optical components configured to deliver images of the displays positioned underneath the displays.

The disclosure also provides for a binocular display assembly comprising a contoured housing. The contoured housing can include, for example, at least an indentation on a bottom portion of the housing, wherein the indentation is configured to provide a place to attach or otherwise position a camera for acquiring images of a surgical site.

The disclosure also provides for a surgical visualization system that includes a primary surgeon camera and an assistant camera, the primary surgeon camera and the assistant camera positioned to acquire images of a surgical site from outside the surgical site. The surgical visualization system can include an optical system associated with the primary surgeon camera and the assistant camera, wherein the optical system includes a central objective that is rotatable around a central aperture. The primary surgeon camera and the assistant camera are configured to rotate about the central aperture that encircles the common objective or pairs of converging optical trains.

The disclosure also provides for a microscope head that can be used with one or more of the surgical visualization systems disclosed herein, wherein the microscope head is autoclavable. For example, the microscope head can be made of materials that can withstand heats and pressures present in an autoclave used to sterilize devices and/or objects for use in surgery. The materials can include polymers such as, for example and without limitation, polypropylene, polymethylpentene, PTFE resin, polycarbonate, polymethyl methacrylate, and the like. Other materials include, for example and without limitation, metals, plastics, rubber, and other such materials or combinations of materials.

Example Binocular Viewing Assembly

Figure 37A:
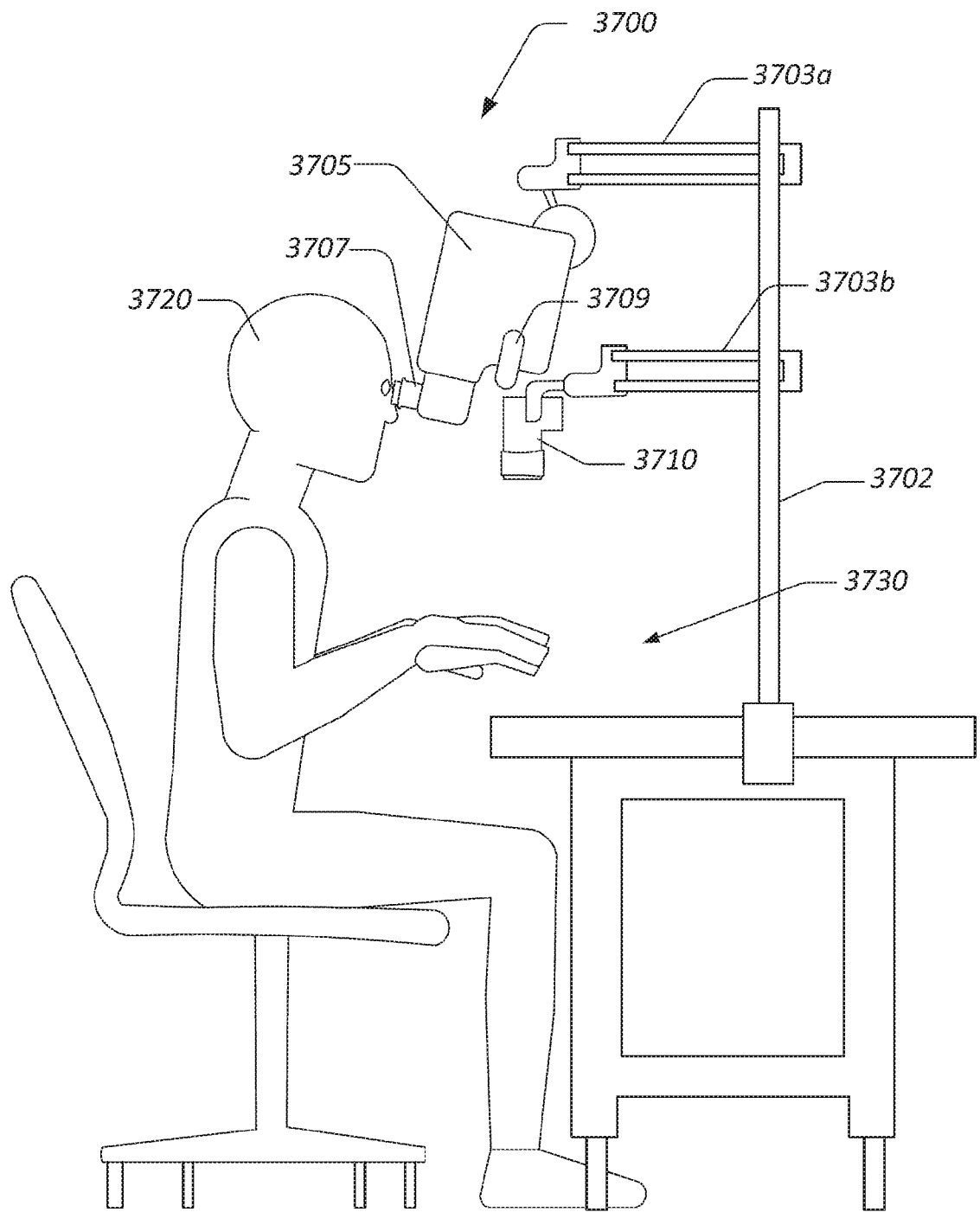
FIGS. 37A-B illustrates an example ergonomically beneficial binocular viewing assembly for providing a surgeon with video of a surgical site.
Figure 37B:
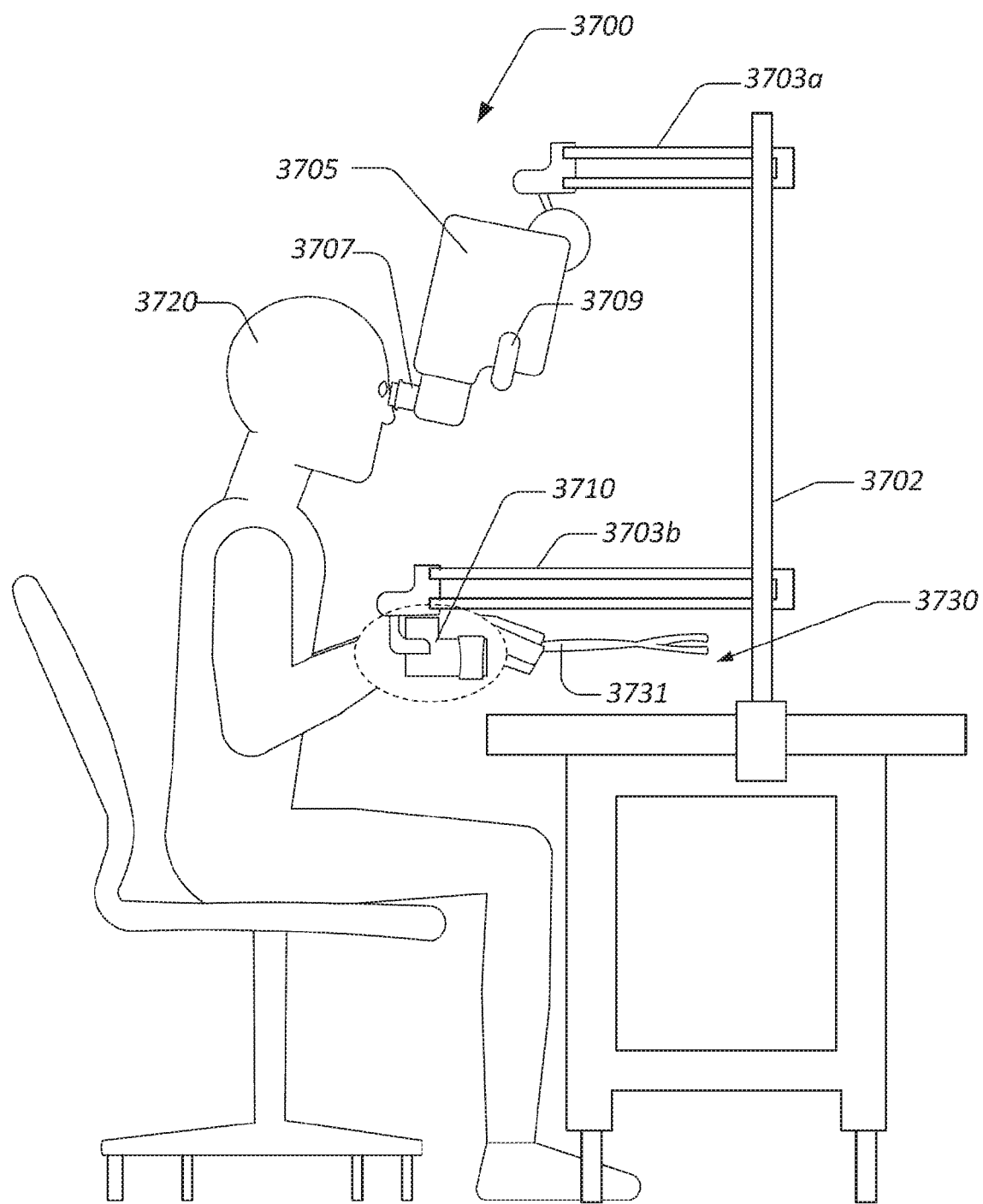

FIGS. 37A-B illustrate an example binocular viewing assembly 3700 for providing a surgeon 3720 with video of a surgical site 3730. The binocular viewing assembly 3700 can include a housing 3705 attached to a support structure 3702 through arm 3703a that allows a position and/or orientation of the binocular viewing assembly 3700 to be manipulated. The binocular viewing assembly 3700 includes oculars 3707 configured to provide a view of a binocular display positioned in the housing 3705. The binocular display can comprise one or more electronic displays. The binocular display can comprise one or more electronic displays for each of a left eye and a right eye optical viewing path from the oculars 3707. The binocular viewing assembly 3700 includes a stereo surgical microscope camera assembly 3710 coupled to the support structure 3702 through arm 3703b. The housing 3705 can include handles 3709 to facilitate manipulation of the housing 3705. The arm 3703b can allow for independent manipulation of the position and/or orientation of the stereo surgical microscope camera assembly 3710 (e.g., independent of the movement, position, and/or orientation of the housing 3705).

The stereo surgical microscope camera assembly 3710 can include a stereo microscope camera configured to acquire video images of a surgical site or other work site. The stereo microscope camera can be configured to provide a surgical microscope view of the surgical site. The stereo microscope camera can be configured to be positioned from the surgical site at least about 150 mm and/or less than or equal to about 450 mm, at least about 175 mm and/or less than or equal to about 400 mm, or at least about 200 mm and/or less than or equal to about 300 mm. By providing these ranges of working distance, this can allow the surgeon to place tools and/or other cameras between the stereo surgical microscope camera assembly 3710 and the surgical site. The stereo microscope camera can be configured to have a focal length that is about the same as the working distance. The stereo microscope camera can be configured to provide a zoom functionality to allow for magnification of video images of the surgical site. For example, at a fixed working distance the stereo microscope camera can be configured to zoom in and out of the surgical site to allow magnification of different portions of the surgical site. The stereo microscope camera can be configured to have a relatively narrow field of view. For example, where the working distance and/or focal length of the stereo microscope camera is about 300 mm, the field of view of the stereo microscope camera can allow visualization of an area of about 30 mm in diameter. The field of view of the stereo microscope camera can be between, for example and without limitation, about 50 mm and about 100 mm. The field of view of the stereo microscope camera can be, for example and without limitation, at least about 5 degrees and/or less than or equal to about 15 degrees.

In some embodiments, the binocular viewing assembly 3700 provides a view of one or more additional cameras. For example, one or more cameras can be positioned on an endoscope or a retractor and at least one of the plurality of displays of the binocular viewing assembly 3700 can be configured to display images from the one or more cameras on the endoscope or retractor. The one or more cameras on the endoscope or retractor can be configured to have a relatively short focal distance and/or a relatively wide field of view, compared to the stereo microscope camera. For example, a camera positioned on the endoscope or retractor can have a focal length of about 3 mm. The one or more cameras positioned on the endoscope or retractor may also be positioned multiple focal lengths from the portion of the surgical site to be imaged. For example, where the focal length of an endoscope or retractor camera is about 3 mm, the camera can be positioned about 10 mm from the patient or portion of the patient to be imaged. Thus, the endoscope or retractor cameras can be in relatively close proximity to the object to be imaged and provide a wide field of view.

In some embodiments, the binocular viewing assembly 3700 provides a view of one or more additional cameras positioned on a standoff structure, positioned proximal to the worksite or surgical site. These proximal cameras can be configured to provide images of a human body or part thereof from outside of the surgical site, but from a relatively close distance thereto. For example, the standoff structure and/or the positioning of the proximal cameras can be such that a surgeon cannot easily put a tool or their hands between the structure (or the cameras) and the surgical site so that the surgeon can work freely in that space.

The binocular viewing assembly 3700 can be configured to show views of video images of the surgical site. The video images can be acquired with the stereo microscope camera, endoscope cameras, retractor cameras, proximal cameras, or any combination of these. The plurality of displays can be configured to provide images acquired with a particular camera. For example, one display can be configured to provide images from a single camera (e.g., a stereo camera). In certain implementations, the oculars 3707 provide views of a plurality of displays, each display configured to display video images acquired by a particular camera. In some embodiments, the oculars are configured to combine first and second video images at the oculars from first and second displays to provide a combined image to the viewer. This can be done to optically superimpose images with a relatively small latency between image acquisition and image display. This can be beneficial for a surgeon due to rapid or nearly instantaneous visual feedback between actions and what is viewed through the oculars 3707.

In some embodiments, the optical axis from the oculars 3707 does not form a straight line to the stereo electronic microscope cameras to provide a surgical microscope view. For example, the stereo electronic microscope camera can be positioned below the line of sight of the oculars 3707 and be directed at different pitch angles (and/or yaw angles) and possibly be offset in x, y, and/or z.

FIG. 37B illustrates the surgical microscope camera assembly 3710 configured for providing a surgical microscope view of a surgical site 3730 from a temporal approach. The surgical microscope camera assembly 3710 can be rotated and positioned to acquire video images of the surgical site 3730 wherein the optical axis from the surgical microscope camera assembly 3710 to the surgical site is substantially horizontal. In some embodiments, the optical axis can be inclined with respect to the horizon. In certain implementations, the optical axis is substantially orthogonal to the surgical site.

When configured for use with a temporal approach, the surgical microscope camera assembly 3710 can be configured to be positioned substantially below the housing 3705. In certain implementations, the surgical microscope camera assembly 3710 can be positioned between a surgeon's hands and/or arms during surgery. The surgical microscope camera assembly 3710 can be configured to be relatively small so that the surgical microscope camera assembly 3710 does not significantly impede with free movement of the surgeon's hands, arms, and/or tools. In certain implementations, the surgeon can use tools 3731 that are relatively long (e.g., between about 150 mm and about 300 mm). Thus, the surgical microscope camera assembly 3710 can be positioned to provide a working distance between about 150 mm and about 450 mm when positioned between the surgeon's hands or arms and long tools are utilized.

Figure 44:
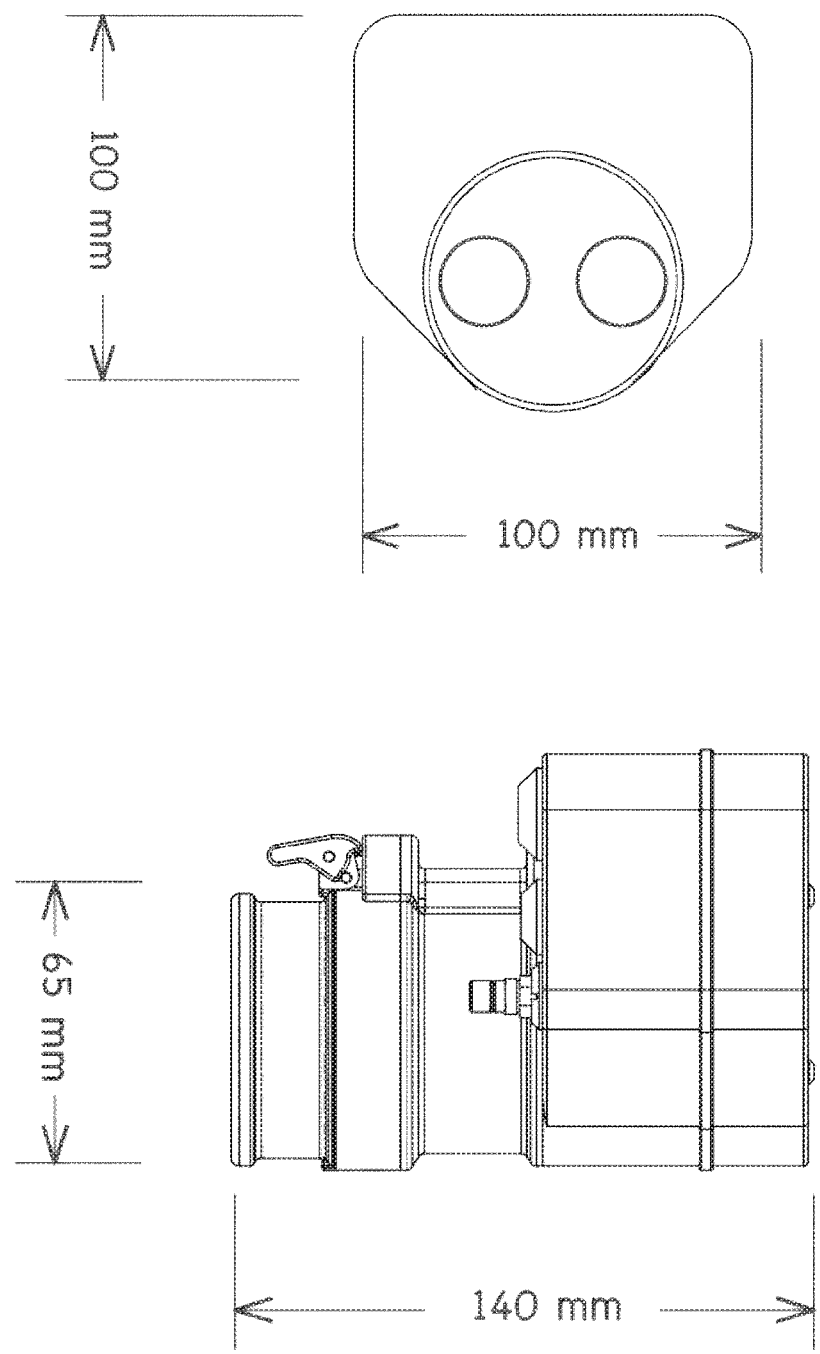
FIG. 44 illustrates an example of a low profile surgical microscope camera assembly including a housing.

The surgical microscope camera assembly 3710 can be configured to be smaller than the binocular viewing assembly 3700. For example, the surgical microscope camera assembly 3710 can have a linear dimension of less than or equal to about 6 inches and at least 4 inches or less than or equal to about 140 mm and at least about 65 mm. In particular, some embodiments of the surgical microscope camera assembly 3710 include a housing with a depth of about 5.5 inches, a height of about 5.2 inches, and a width of about 4 inches or a depth of about 140 mm, a height of about 100 mm (or about 65 mm for a lens assembly), and a width of about 100 mm, as illustrated in FIG. 44. The dimensions of surgical microscope camera assembly 3710 can be larger or smaller. For example, a height of the surgical microscope camera assembly 3710 housing can be less than or equal to about 9 inches, less than or equal to about 8 inches, less than or equal to about 7 inches, less than or equal to about 6 inches, less than or equal to about 5 inches, less than or equal to about 4 inches, or less than or equal to about 3 inches or any range between any of these values. For example, a depth of the surgical microscope camera assembly 3710 housing can be less than or equal to about 9 inches, less than or equal to about 8 inches, less than or equal to about 7 inches, less than or equal to about 6 inches, less than or equal to about 5 inches, less than or equal to about 4 inches, or less than or equal to about 3 inches or any range between any of these values. For example, a width of the surgical microscope camera assembly 3710 housing can be less than or equal to about 9 inches, less than or equal to about 8 inches, less than or equal to about 7 inches, less than or equal to about 6 inches, less than or equal to about 5 inches, less than or equal to about 4 inches, or less than or equal to about 3 inches or any range between any of these values. As another example a volume of the surgical microscope camera assembly 3710 housing can be less than or equal to about 730 in$^3$, less than or equal to about 525 in$^3$, less than or equal to about 350 in$^3$, less than or equal to about 225 in$^3$, less than or equal to about 115 in$^3$, less than or equal to about 100 in$^3$, less than or equal to about 75 in$^3$, or less than or equal to about 50 in$^3$ or any range between any of these values. The surgical microscope camera assembly 3710 can weigh less than or equal to about 7 kg, less than or equal to about 6 kg, less than or equal to about 5 kg, less than or equal to about 4 kg, less than or equal to about 3 kg, less than or equal to about 2 kg, or any range between any of these values. The surgical microscope camera assembly 3710 with the housing conforming to the above size restrictions can be configured to capture video images with a resolution of at least 1920 pixels by 1080 pixels (e.g., "HD" video). The surgical microscope camera assembly 3710 with the housing conforming to the above size restrictions can be configured to have a working distance of at least 150 mm and/or less than or equal to about 450 mm, at least 200 mm and/or less than or equal to about 400 mm, at least 250 mm and/or less than or equal to about 350 mm, or at least 275 mm and less than or equal to about 325 mm. When the surgical microscope camera assembly 3710 is thus configured in a compact housing, the surgical microscope camera assembly 3710 can be positioned near the binocular viewing assembly 3700 and/or near the surgeon 3720 without significantly impeding free movement of the surgeon's hands and/or tools during surgery (e.g., when the surgeon is operating and looking through the oculars 3707 of the binocular viewing assembly 3700).

In some embodiments, the binocular viewing assembly 3700 can be configured such that the surgeon 3720 can look at the surgical site 3730 (e.g., directly look at the surgical site without the use of the binocular viewing assembly 3700) without visual obstructions from the binocular viewing assembly 3700. In various embodiments, the surgeon 3720 can switch between looking through the oculars 3707 and directly looking at the surgical site 3730 without having to move components of the binocular viewing assembly 3700 and/or without having to significantly move from their body (e.g., their hands and arms can remain relatively stationary, which can be important when performing surgery).

In some embodiments, the binocular viewing assembly 3700 is configured for use with a tube access approach. For example, where tools are used in combination with a tube access approach, the surgeon's tools can be configured to push the surgeon's hands away from the tube opening to allow the surgeon to view down the tube. With the binocular viewing assembly 3700, the surgical microscope camera assembly 3710 can be configured to provide the view through the tube. For example, the surgical microscope camera assembly 3710 can include an objective lens positioned about 100 mm from the tube opening and configured to have an optical axis through the tube to the surgical site 3730.

In some embodiments, the binocular viewing assembly 3700 can be further configured to show images from a cell phone, tablet, or other computing device, such as, for example, described above. In certain embodiments, the computing device can be placed within or near the housing 3705 so that the user can see the display of the computing device. For example, an optical system can be provided that relays an image of the computing device to the oculars 3707. In certain embodiments, the computing device can be communicably coupled to the binocular viewing assembly 3700 to allow for images to be electronically communicated to at least one of the displays viewable through the oculars 3707. In certain embodiments, the computing device can be positioned so that a camera images the device and those video images are presented on one of the plurality of displays viewed through the oculars 3707.

In certain embodiments, a surgical visualization system can comprise the binocular viewing assembly 3700 in addition to one or more displays configured to be viewed by an assistant or other personnel that are not looking through the oculars 3707. In some embodiments, one or more of these displays can be mounted near the surgical site 3730. For example, one or more displays may be mounted to the support structure 3702 or the housing 3705. In some implementations, the one or more displays can be flat panel displays or images projected from one or more projectors possibly projecting images on a wall or screen. In some embodiments, at least one of the one or more displays provides images of the surgical site acquired with the stereo microscope camera, endoscope, a retractor camera, a proximal camera, or any combination of these. In certain embodiments, at least one of the one or more displays is configured to provide a similar or equivalent view of what is seen through the oculars 3707. For example, the display can be configured to present the same video images provided on one of the plurality of displays in the binocular viewing assembly 3700 and may provide the same field of view. As another example, where multiple displays are viewed through the oculars 3707, one display or a combination of displays outside of the binocular viewing assembly 3700 can be configured to provide the same video images viewed on the multiple displays viewed through the oculars 3707.

In some embodiments, the additional displays can comprise 1, 2, or 3 flat panel displays. The additional display(s) can be arranged at angles relative to the oculars 3707, wherein the angle is about ±90 degrees or about 180 degrees. In some embodiments, the additional display(s) can be configured to provide stereo video images. This can allow an assistant or other personnel to view the same or similar stereo video image that can be seen through the oculars 3707. In some embodiments, the additional displays include one or more cameras or other similar devices configured to track the gaze or eyes of a user. This can be used to enhance, tailor, or optimize the view of an assistant or other surgeon by shifting a portion of a display relative to another display or by shifting a film layer(s) above one or more of the displays to achieve a desirable or suitable convergence. This can provide a suitable or desirable 3D-effect to be rendered.

In some embodiments, the additional displays (e.g., displays mounted on the housing 3705) have back- or edge-lit LED illumination sources that have an output of about 1 W, 2 W, 5 W, 6 W, or greater than 6 W of power to drive the displays in a well-lit surgical environment.

In some embodiments, the additional displays have optics (e.g., lenses and mirrors) to produce a relatively large eye box for each eye. This can be done to allow the assistant or other user some degree of head motion while still seeing stereo video images. This can also be done to allow the stereo view to be seen at a relatively large distance from the display. For example, stereo video images may be seen at a distance of about 5 cm from the display, about 10 cm from the display, about 30 cm from the display, or greater than about 30 cm from the display, or any range between any of these values. This arrangement facilitates the primary surgeon positioning the binocular assembly 3700 for their convenience and the assistant can still see stereo images from a different position (e.g., the other side of the patient and/or table).

In some embodiments, the binocular viewing assembly 3700 includes a fiber optic light source or other type of light source. The fiber optic light source can be configured to provide illumination to one or more parts of the object being imaged.

In some embodiments, the binocular viewing assembly 3700 includes a virtual user interface system comprising a user interface projector and a user interface camera. The user interface projector can be configured to project images onto the surgical site. The images can include user interface elements such as, for example and without limitation, virtual buttons, icons, thumbnails, arrows, text, or the like. The user interface camera can be configured to acquire images of the surgical site and motions may be made by the user (e.g., the surgeon's hand or tool), wherein the user interface camera acquires images of the projected images. An image processing system can be operably coupled to the user interface camera and/or the user interface projector. The image processing system can be configured to determine whether actions taken by a user (e.g., the surgeon or assistant) corresponds to virtual manipulation of at least one element of the virtual user interface. In some embodiments, the stereo microscope camera can be used as the user interface camera.

Figure 41:
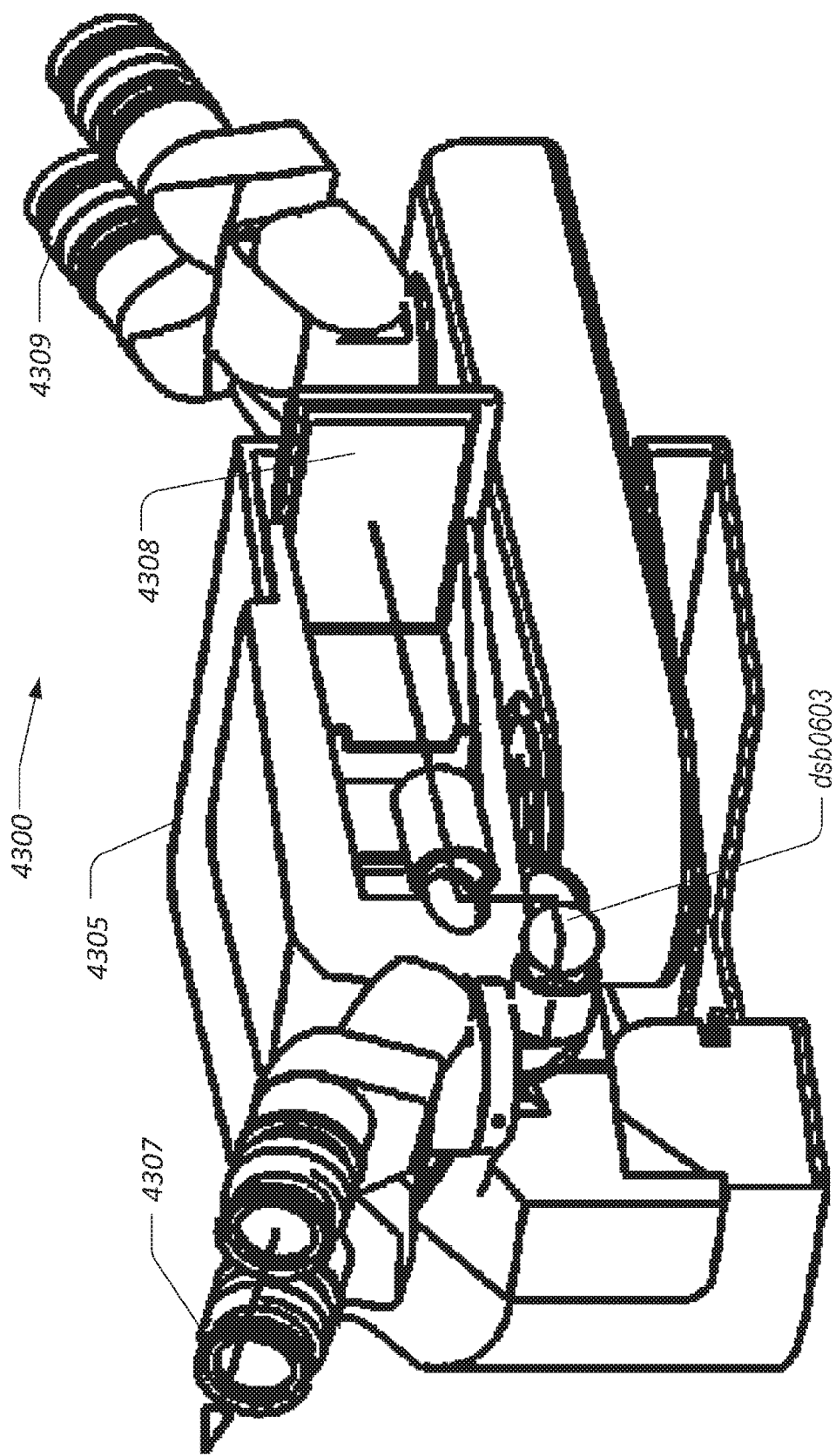
FIG. 41 illustrates an example binocular viewing assembly that includes surgeon oculars and assistant oculars.

FIG. 41 illustrates an example binocular viewing assembly 4300 that includes surgeon oculars 4307 and assistant oculars 4309. The surgeon oculars 4307 can be configured to provide a view of one or more surgeon displays 4308 positioned within a housing 4305 of the binocular viewing assembly 4300. The view of the one or more surgeon displays 4307 can be provided by optical components 4303. Similarly, the assistant oculars 4309 can be configured to provide a view of one or more assistant displays (not shown) positioned within the housing 4305 of the binocular viewing assembly 4300. The assistant oculars 4309 can be rotated relative to the housing 4305 independently of the surgeon oculars 4307.

Example Binocular Viewing Assembly with Displays Above Oculars

Figure 38:
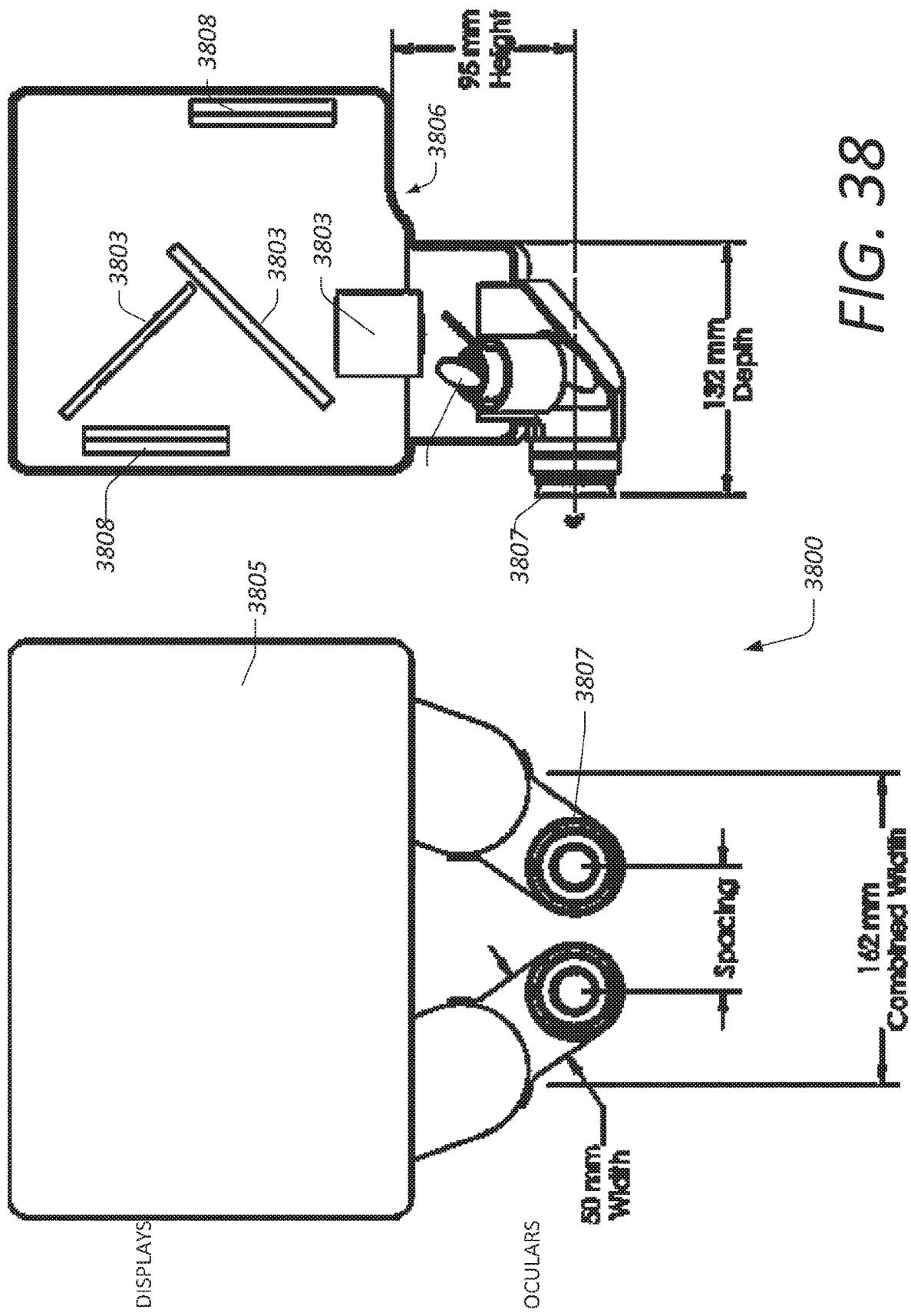
FIGS. 38-39 illustrate an example ergonomically beneficial binocular viewing display having oculars beneath corresponding displays.
Figure 39:
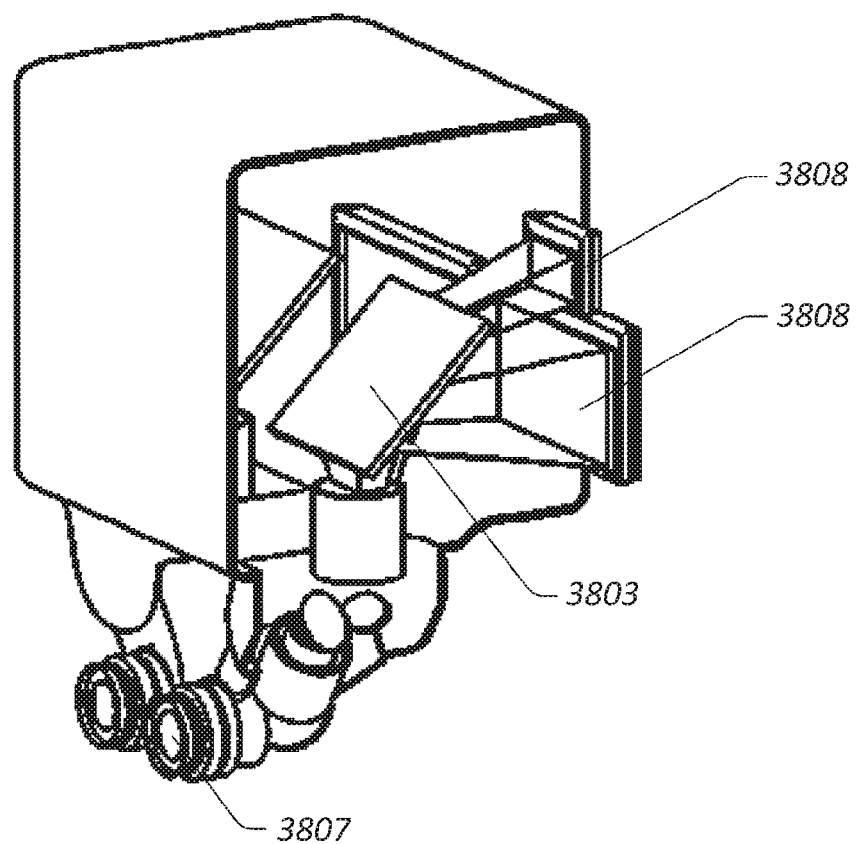
Figure 39:
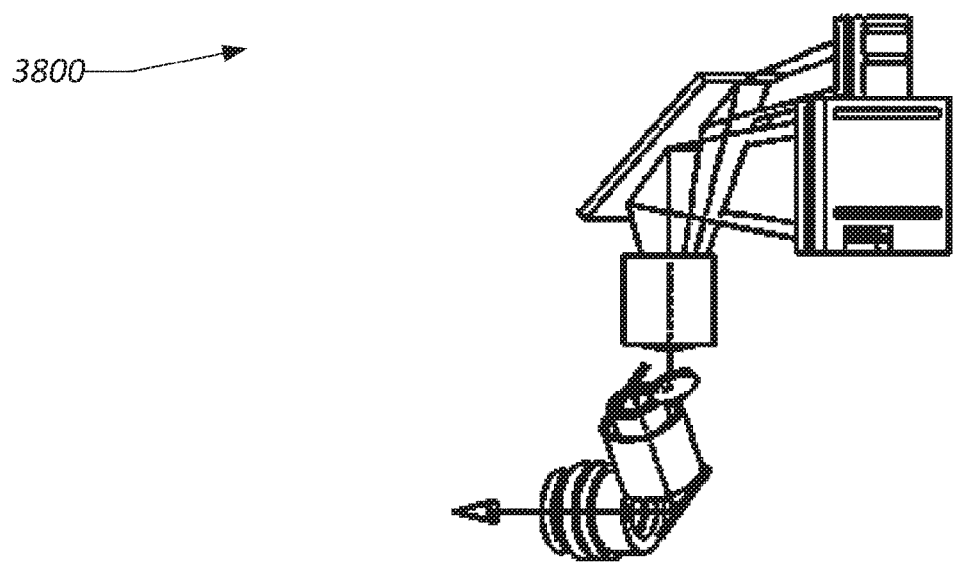

FIGS. 38-39 illustrate an example binocular viewing display 3800 having oculars 3807 beneath corresponding displays 3808. The binocular viewing assembly 3800 includes housing 3805 configured to house displays 3808 along with optical components 3803 configured to direct images from the displays 3808 to the oculars 3809 for viewing by a surgeon or other user.

In this manner, the binocular viewing display 3800 can be configured in a manner similar to a periscope. This allows for the optical path from the oculars 3807 to the displays 3808 to be of a suitable length without moving the oculars further from the surgical site. For example, the housing 3805 can include a contoured portion 3806 configured to allow a surgical microscope camera to be positioned near the housing 3805. Thus, the surgical microscope camera can be positioned near the housing to provide a surgical microscope view of the surgical site. Advantageously, the surgeon can be positioned near the surgical site while viewing the surgical microscope view of the surgical site through the oculars 3807. By positioning the displays 3808 above the oculars, the optics, electronics, housing 3805, and the like can be positioned so as to allow the surgeon to be positioned and to manipulate tools in an ergonomic way during surgery, reducing fatigue and discomfort.

The contour 3806 can be configured to allow movement of the surgical microscope camera independent of movement of the binocular viewing assembly 3800. This independent movement can allow the surgeon to position the binocular viewing assembly 3800 in a way that is comfortable and ergonomically advantageous while allowing for independent adjustment of the stereo microscope camera without disruption of the ergonomic positioning of the binocular viewing assembly 3800. For example, this can allow the surgical microscope camera to be placed in a way that allows the surgeon to position their body close to the surgical site. This can improve or enhance the ergonomics associated with performing surgery with a surgical visualization system.

The binocular viewing assembly 3800 thus configured can provide a number of advantages. For example, the binocular viewing assembly 3800 can provide situational awareness the surgeon being able to attend to both viewing the surgical site through a microscope or viewing system and being cognizant of the whole patient, the activities of other allied health personnel, and other medical equipment in the room. Therefore, the binocular viewing assembly 3800 and the other various devices described herein provide both the ergonomic benefit of decoupled, displayed surgical images from the acquiring cameras and the ability to readily see much of the patient and operating room.

FIG. 39 illustrates the binocular viewing assembly 3800 with the housing 3805 cut away to show the optical components 3803 providing a view of multiple displays 3808 for each of a left eye and right eye view through the oculars 3807. For example, in the field of view of a single eye of the oculars 3807, the electronic displays 3808 can be arranged so that the user sees both displays 3808.

Example Contoured Binocular Viewing Assembly

With reference to FIGS. 37A-39, example binocular viewing assemblies 3700, 3800 are illustrated that include a contoured housing 3705, 3805. This contoured housing can be configured to allow for independent movement and adjustments of a binocular viewing assembly and a surgical microscope assembly. With specific reference to FIGS. 37A and 37B, the binocular viewing assembly 3700 includes housing 3705 with a contoured portion 3706 configured to allow movement of the surgical microscope assembly 3710. This advantageously decouples movement of the surgical microscope camera assembly 3710 and the viewing assembly 3700. Accordingly, a user (e.g., a surgeon) can position the binocular viewing assembly 3700 in an ergonomically satisfactory way. The user can also position the surgical microscope viewing assembly 3710 to provide the desired or targeted view of the surgical site 3730. Adjustment of the position and/or orientation of either assembly can be done without or with reduced effect on the position and/or orientation of the other assembly. Thus, adjusting the surgical microscope assembly 3710, for example, does not require the user to move the binocular viewing assembly 3700.

The housing 3705 can include the contoured portion 3706 that can be configured as an indentation on a bottom and distal portion of the housing 3705. The indentation is configured to allow free movement of the surgical microscope camera relative to the viewing assembly. This can allow the user to position the surgical microscope camera assembly 3710 to acquire desirable or targeted images of the surgical site 3730.

In some embodiments, the binocular viewing assembly 3700 includes handles 3709 to facilitate movement of the housing 3705. The housing 3705 can be coupled to an arm 3703a of the support 3702, the arm configured to allow a user to position and/or orient the housing 3705 within a range of positions and orientations. The surgical microscope camera assembly 3710 that provides surgical microscope views can be coupled to a different arm 3703b to allow independent movement of the surgical microscope camera assembly 3710 relative to the housing 3705. The contoured portion 3706 allows the surgical microscope camera assembly 3710 to be positioned relatively closely to the housing 3705. This can advantageously allow the surgical microscope camera assembly 3710 to be positioned above the surgical site 3730 close to the oculars. For example, where the surgical site is directly below the housing 3705, the surgical microscope camera assembly 3710 can be configured to have an optical axis that is nearly parallel to gravity for certain surgeries.

Advantageously, this can allow the surgeon and/or assistant to position their body close to the surgical site to improve comfort and the ergonomics of performing surgery. In some embodiments, the housing 3705 is thinner at the bottom than at the top. The contoured portion 3706 can be formed at the bottom of the housing 3705 with electronic displays positioned above the contoured portion 3706 within the housing 3705. In some embodiments, the binocular viewing assembly 3700 includes the housing 3705 and a plurality of oculars, the plurality of oculars configured to provide views of at least one display in the housing 3705. The plurality of oculars include a left ocular and a right ocular similarly disposed left and right with respect to a surgical site so as to coincide with a corresponding left eye camera and right eye camera. The at least one display can be configured to receive output video images based on stereo video images produced by the left and right eye cameras. The binocular viewing assembly 3700 can be attached to a viewing arm configured to position the binocular viewing assembly 3700. The left-eye camera and the right-eye camera have optical inputs for receiving light from the surgical site and the distance from the left and right oculars to the optical input of the left-eye camera and the optical input of the right-eye camera is not larger than the size of the housing 3705 of the binocular viewing assembly 3700. Advantageously, this allows a surgeon to ergonomically perform surgery at a surgical site beneath the auxiliary optical assembly (comprising the cameras) while viewing through the plurality of oculars the output video images of the surgical site displayed on the at least one display. In certain implementations, the left-eye camera and the right-eye camera are not coupled to a direct view surgical microscope. In some embodiments, the binocular viewing assembly 3700 and associated auxiliary optical assembly are configured so that a surgeon can ergonomically perform surgery at a surgical site that is lateral to the auxiliary optical assembly while viewing through the plurality of oculars output video images of the surgical site displayed on the at least one display. In certain implementations, the auxiliary optical assembly is smaller than the binocular viewing assembly 3700.

Figure 40:
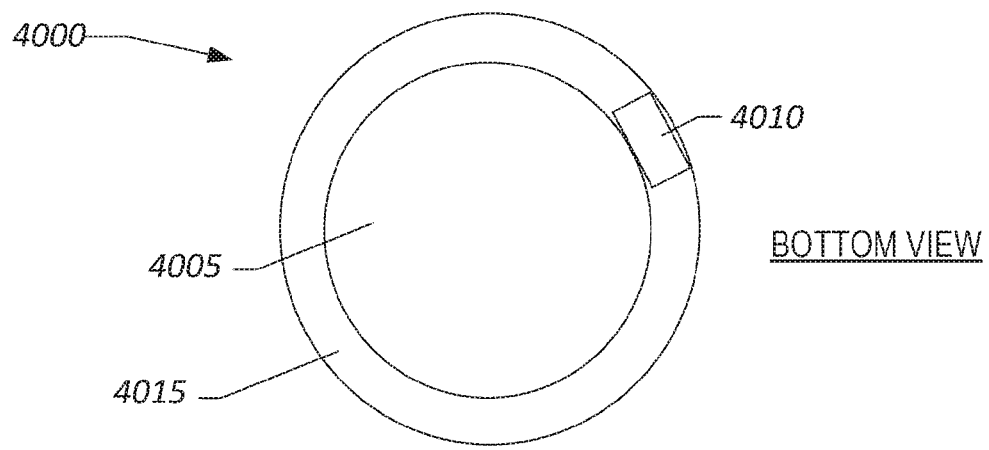
FIG. 40 illustrates an example surgical visualization system that includes a primary surgeon camera and an assistant camera that is rotatable around a central aperture.
Figure 40:
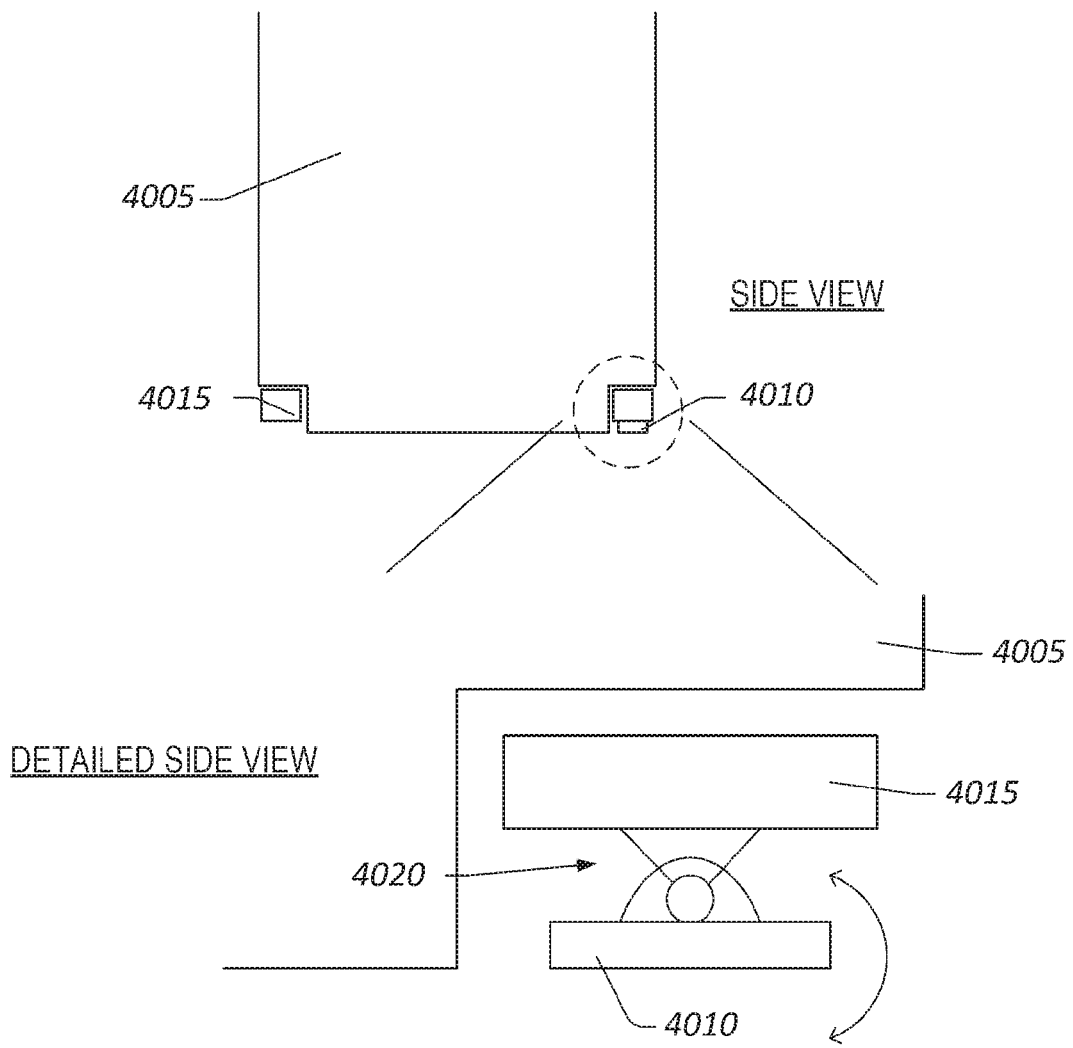

Example Surgical Visualization System with Cameras Rotating about Central Aperture FIG. 40 illustrates an example surgical visualization system 4000 that includes a primary surgeon camera and an assistant camera 4010, each of the primary surgeon camera and the assistant camera positioned to acquire images of a surgical site from outside the surgical site. The assistant camera 4010 can be mounted on a rotating ring 4015 or other similar structure. The rotating ring 4015 can be configured to rotate about an objective lens 4005 or pairs of converging optical trains, the objective lens 4005 or pairs of converging optical trains being part of an optical system of the primary surgeon camera. For example, the objective lens 4005 can be used to form images of the surgical site onto the image sensor of the primary surgeon camera.

In some embodiments, the objective lens 4005 or pairs of converging optical trains is rotatable and is coupled to the ring 4015. In some embodiments, the objective lens 4005 pairs of converging optical trains is configured to be able to remain stationary while the rotating ring 4015 rotates. The assistant camera 4010 can be configured to acquire images of the surgical site as the optical axes of the assistant camera 4010 and the primary surgeon camera can be configured to be substantially parallel and/or can be configured to be directed to the same or similar region of the surgical site.

The primary surgeon camera can be configured to have a fixed central area with one or more sensors and zoom functionality. The objective lens 4005 or pairs of converging optical trains can be positioned in the middle of the rotatable ring 4015 such that the assistant camera 4010 on the rotatable ring 4015 rotates around the objective lens 4005. The ring 4015 can be manually manipulated and/or powered by an electronic motor. In some embodiments, the assistant camera can pivot in addition to being rotated by the ring 4015. For example, a pivoting system 4020 can be included to allow additional degrees of freedom in the movement of the assistant camera 4010 relative to the objective lens 4005 or pairs of converging optical trains. In some embodiments, the surgical visualization system includes software to reduce the likelihood that cables will become entangled upon rotation of the ring 4015.

Example Optical Systems for Binocular Viewing Assemblies

FIGS. 26-29 illustrate example optical systems for use with the binocular viewing assemblies described herein. The optical systems can include a binocular optical system and a display optical system, wherein the display optical system is configured to generate a real image of the display at the field stop between the display optical system and the binocular optical system. The binocular optical system is configured to generate a real image of the field stop at a retina of a user. The optical system can be configured to have a magnification proportional to the ratio of the focal length of the binocular optical system to the display optical system. The magnification of the binocular optical system can be proportional to a ratio of the display diagonal to the field stop diagonal.

In some embodiments, the optical systems can include a display with an optical system configured so that an exit pupil of the optical system is within an eye of a user viewing the display through the oculars (e.g., where the oculars form at least part of the optical system). This is referred to as a "near eye display" or an "immersive display" in FIGS. 26-29. A difference between the near eye display and the immersive display is a size of the display. The display in the immersive display can be larger than the display in the near eye display.

In some embodiments, the optical systems can include a finite conjugate section comprising the optical components from the display to the field stop. In some embodiments, the optical systems can include an infinite conjugate section comprising the optical components from the display to a collimated section, and a binocular infinite conjugate section comprising the optical components from the collimated section to before the eye of the user. The exit pupil of the display optics can be within the collimated section and the entrance pupil of the binocular optics can be within the collimated section. The apparent field of view can be the angular extent of the image of the field stop within the eye of the user looking at the display through the oculars (e.g., wherein the oculars are part of the binocular optical system).

Optical Systems for Surgical Microscope Cameras

In some embodiments, optical components directing images from the surgical site to the surgical microscope stereo cameras can include a field stop positioned after zoom optics of the optical train. This can be different from an optical system where the field stop is positioned within the zoom optics. Advantageously, the field stop after the zoom optics positions the field stop nearer the image sensor. As the beam (e.g., ray bundle of light through the optical system) size expands and contracts, the extent of the beam (or beam cross-section) gets larger and smaller. Placing the field stop after the zoom optics allows the optical system to be compact, making lenses and image sensors smaller (e.g., the lenses can have a diameter of about 0.25 inches and the image sensor can be about 0.5 inches across). In addition, this allows for optical components to be inserted to split the beam into different spectral components, such as visible, near IR, red, green, blue, UV, yellow, etc. This also allows for filter blocks to be easily added to the optical train. This can result in a relatively small auxiliary optical assembly, for example. This can advantageously allow a surgeon to position the auxiliary optical assembly comprising the optical systems described here closer to a viewing assembly (e.g., one or more of the viewing assemblies described herein). With the auxiliary optical assembly positioned closer to the viewing assembly, this can allow the surgeon to position the viewing assembly, the auxiliary optical assembly, and the surgeon's body closer to the surgical site. Advantageously, this allows the surgeon to perform the surgery more ergonomically and comfortably.

Autoclavable Microscope Head

The surgical visualization systems disclosed herein, such as the systems that include a binocular viewing assembly, can include a microscope head made of materials so that it can be sterilized using an autoclave. The materials used in the microscope head can be configured to withstand heats and pressures present in an autoclave. The microscope head can be configured to maintain its optical and mechanical characteristics after the autoclaving process. For example, the optical systems of the microscope head can be configured to maintain alignment (e.g., an optical axis of the optical system does not significantly deflect or change after undergoing the autoclaving process). Similarly, the optical systems of the microscope head can be configured to maintain configured imaging characteristics (e.g., a focal location of the optical system does not significantly change after undergoing the autoclaving process). The mechanical properties of the microscope head can be configured to not significantly deteriorate after undergoing the autoclaving process. For example, the structural integrity (e.g., brittleness, deformability, elasticity, rigidity of the materials, etc.) can remain within a suitable tolerance after undergoing the autoclaving process. In some embodiments, the microscope head is resistant to significant deterioration after at least 100 times through an autoclaving process, after at least 200 times through an autoclaving process, or after at least 300 times through an autoclaving process. The microscope can be made of materials or combinations of materials to provide the targeted or desired characteristics. For example, the materials can include polymers such as, for example and without limitation, polypropylene, polymethylpentene, PTFE resin, polycarbonate, polymethyl methacrylate, and the like. Other materials can include, for example and without limitation, metals, plastics, rubber, and other such materials or combinations of materials. In some embodiments, the microscope head is sealable, to make it autoclavable.

Field of View of Primary and Assistant Displays

As described elsewhere herein, the various surgical visualization systems that include a binocular viewing assembly can include one or more additional displays. The additional displays can be configured to be viewed through an assistant ocular system or the additional displays can be positioned on a housing of the binocular viewing assembly, on a support structure near the binocular viewing assembly, on a wall, or projected onto a wall or screen. In certain implementations, the field of view of video images presented on the displays viewed by the surgeon through the binocular viewing assembly is the same as the field of view of the video images presented on one or more of the additional displays. For example, one or more of the additional displays can present an identical view as that being provided by the displays viewed by the surgeon. This can include stereo images and/or monocular images. In some embodiments, where the binocular viewing assembly provides a view of more than one display, individual displays of the additional displays can be configured to present video images having the same field of view as the displays in the binocular viewing assembly.

Stereo and Spectral Imaging

As described elsewhere herein, the optical systems of the cameras (e.g. the surgical microscope camera) can include a common objective and one or more image sensors. In certain implementations, a single objective can be used for left and right imaging channels, wherein additional optics focus light from the single objective onto left and right image sensors. In some implementations, the optical systems can further include optical components that split optical paths of light based at least in part on the spectral composition of the light. For example, optical systems can be configured to allow visible light to pass through an optical component while this same optical component redirects the optical axis for light caused by fluorescence (e.g., near infrared light). This can be used to provide an image acquisition system with four image sensors, with two image sensors for the left channel and two image sensors for the right channel, a first image sensor in the left channel being configured to receive light within a first spectral band and a second image sensor in the left channel being configured to receive light within a second spectral band. The right channel can be similarly configured.

This can allow stereo images to be produced for both visible and near infrared spectral bands, for example. This can also allow for images acquired in different spectral bands to be displayed superimposed (e.g., either superimposed on a display or superimposed through the use of multiple displays and optics, as described herein). For example, a display left channel can include a first display configured to display video images acquired with the first image sensor in the left image sensor channel and a second display configured to display video images acquired with the second image sensor in the right image sensor channel. A display right channel can be similarly configured.

Figure 42:
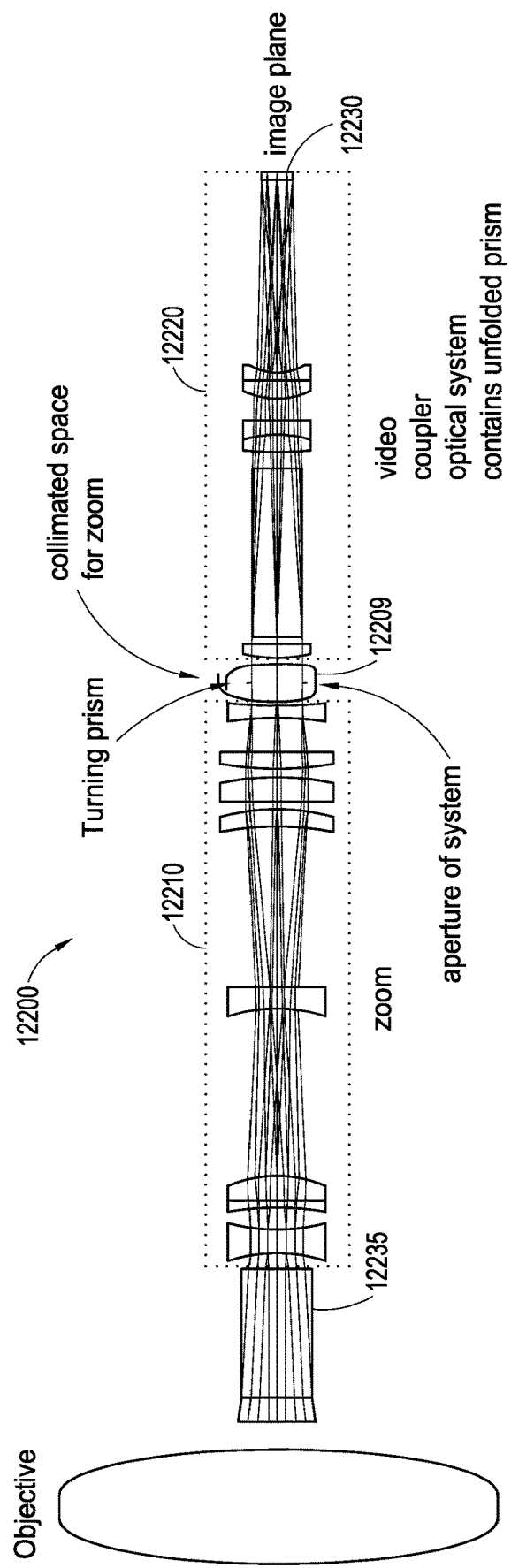
FIG. 42 illustrates an example optical imaging system for providing a surgical microscope view of a surgical site.

FIG. 42 illustrates an example optical system 12200 for providing a surgical microscope view of a surgical site. The optical system 12200 can include an objective lens, a zoom lens group 12210, an aperture 12209, a turning prism, and a video coupler optical system 12220 comprising a focus lens group. The focus lens group can focus images of the scene onto the image plane where there is an image sensor 12230. This optical system 12200 can be configured, in some embodiments, as illustrated in FIG. 43 to include at least two beam redirection elements, or beam deflectors, for each of a left optical path and a right optical path. The optical system can redirect the respective optical paths at least twice to provide a compact envelope for the optical system. This can allow the camera system, e.g., the surgical microscope camera system, to be compact relative to the binocular viewing assembly. Advantageously, a smaller surgical microscope camera system can allow for greater freedom of movement and positioning of the camera. Thus, a surgeon can position the surgical microscope camera assembly to achieve a desired or suitable view into the surgical site with little or no interference with the position of the binocular viewing assembly. Additionally, the compact size surgical microscope view camera can provide for increased situational awareness and access to the surgical site for the surgeon. The smaller size reduces the likelihood that the surgical microscope will block view or access by the surgeons hands to the surgical site (unlike a large bulky surgical microscope view camera). With the surgical microscope positioned closer to the viewing assembly, this can allow the surgeon to position the viewing assembly, the surgical microscope, and the surgeon's body closer to the surgical site. Advantageously, this allows the surgeon to perform the surgery more ergonomically and comfortably.

The optical system illustrated in FIG. 43 includes left and right optical paths. In some embodiments, at least one of the beam deflectors is a dichroic element configured to provide a first optical path for light within a first spectral band and a second optical path for light within a second spectral band. For example, the dichroic beam deflector can allow visible light to substantially pass through a redirection element while this same redirection element folds the optical axis of infrared light 90 degrees relative to the optical path for the visible light. The respective first and second optical paths generated at the dichroic beam deflector can each be directed onto respective image sensors. Accordingly, the optical system can be configured to acquire video images of a surgical site using left and right optical paths with each optical path acquiring light in at least two spectral bands. This can advantageously allow the surgeon to view stereoscopic images in two or more wavelength bands. This may be useful in visualizing fluorescence within a surgical site, for example. The surgeon may also have a visible wavelength reference view akin to the view seen from a direct view surgical microscope view of a patient illuminated with white light. As illustrated, each of the left and right optical paths can utilize a common objective lens. The optical paths can include at least two redirection elements to fold the optical axis of the various optical paths (e.g., left and right optical paths, first and second optical paths branching from respective left or right optical paths, etc.) so that the optical axis prior to the image sensors is substantially parallel to the optical axis after the objective lens. As illustrated, the edge of the objective lens may be truncated to reduce size and form factor. Accordingly, in various embodiments, the objective lens does not have a clear aperture that is circular or rotationally symmetric. Rather the clear aperture is wider than tall to accommodate both the left and right channels disposed left and right with respect to each other.

The optical paths can include a zoom lens group positioned after the objective lens. Each of the left and right optical paths can include a zoom lens group. On an image side of the zoom lens group, a redirection element or beam deflector can be positioned to bend the optical axis about 90 degrees. On an image side of the beam deflector, the optical system can include an aperture. On an image side of the aperture, the optical system can include focusing optics. As indicated by the double-sided arrow, in some embodiments, the focusing optics can be configured to move along an optical axis that is perpendicular to the optical axis of the zoom lens group to provide focus adjustment and bring into focus an image. On an image side of the focusing optics, the optical system can include a dichroic beamsplitter to generate first and second optical paths. Light from the first optical path can be directed and focused onto a first image sensor while the second optical path can be redirected by a beam deflector positioned on an image side of the dichroic beamsplitter. Light from the second optical path can be directed and focused onto a second image sensor. In some embodiments, the optical axis at the second image sensor is parallel to the optical axis at the first image sensor. The optical axis at the first and second optical sensors can, in some embodiments, further be parallel to the optical axis between the objective lens and the first beam deflector.

The optical designs provide for a relatively compact surgical microscope camera assembly while providing a suitable optical path for acquiring video images with left and right channels with each channel acquiring images of at least two spectral bands. In some embodiments, the surgical microscope camera assembly can weigh less than about 1.5 kg. In some embodiments, the image sensors of the surgical microscope camera assembly each have a diagonal measurement that is less than about an inch, ⅔ inch, ½ inch, ⅓ inch, or ¼ inch or ranges in between any of these values. In some embodiments, the surgical microscope camera assembly can be separated from the binocular viewing assembly by less than about 2 feet, less than about 1.5 feet, or less than about 1 foot. In certain embodiments, movement of the surgical microscope camera assembly can be decoupled from movement of the binocular viewing assembly. For example, in certain implementations, the surgical microscope camera assembly can move independently of the binocular viewing assembly in the z direction (e.g., directly towards and away from a person looking through the oculars of the binocular viewing assembly). In certain implementations, the surgical microscope camera assembly can move independently of the binocular viewing assembly in the x direction (e.g., left or right with respect to from a person looking through the oculars of the binocular viewing assembly). In certain implementations, the surgical microscope camera assembly can pitch and/or yaw independently of the binocular viewing assembly. In various embodiments, roll of the surgical microscope camera and oculars is restricted to avoid inducing nausea. In certain embodiments, the surgical microscope, when in use can be separated from the binocular viewing assembly by a space such as a space of at least 6 inches, 1 foot, 1.5 feet, 2 feet, 3 feet, 4 feet, 5 feet, etc. or any range between any of these values. Such an open space can provide for increased situational awareness and increase access of the surgeon to the surgical site. For example, the surgeon may have more room to reach toward the surgical site without hitting large bulky equipment. Similarly, reduction of form factor can create a more open environment where the surgeon has more unobstructed views and increase situational awareness. This configuration provides the surgeon with clearer paths to view, for example, the patient for example when the surgical microscope camera is situated above the patient and the surgical site is directly underneath.

In various embodiments, the surgical microscope camera and/or the binocular viewing assembly is not attached to the ceiling of the operating room.

Switchable Views Between Surgical Microscope Camera and Endoscope Camera

In some embodiments, a surgical visualization system can include one or more connection ports configured to receive video image data from one or more sources. For example, the connection port can be configured to receive input from an endoscope. The surgical visualization system can be configured to switch between providing video images received from a surgical microscope camera and a camera on an endoscope.

A video coupler can be configured to be part of the surgical visualization system, wherein the video coupler is configured to convert a device meant for viewing with an eye to a device that is configured for acquisition with a camera. The video coupler, for example, can be coupled to an endoscope that is configured to provide images suitable for viewing with an eye. The video coupler, for example, can be configured to acquire images suitable for display from the endoscope. In some embodiments, the endoscope can be a stereo endoscope having an isocenter and intended for use where the horizon is level. The video coupler can be configured to acquire stereo images from such an endoscope.

Example Visualization System with Multi-View Switching

Figure 45:
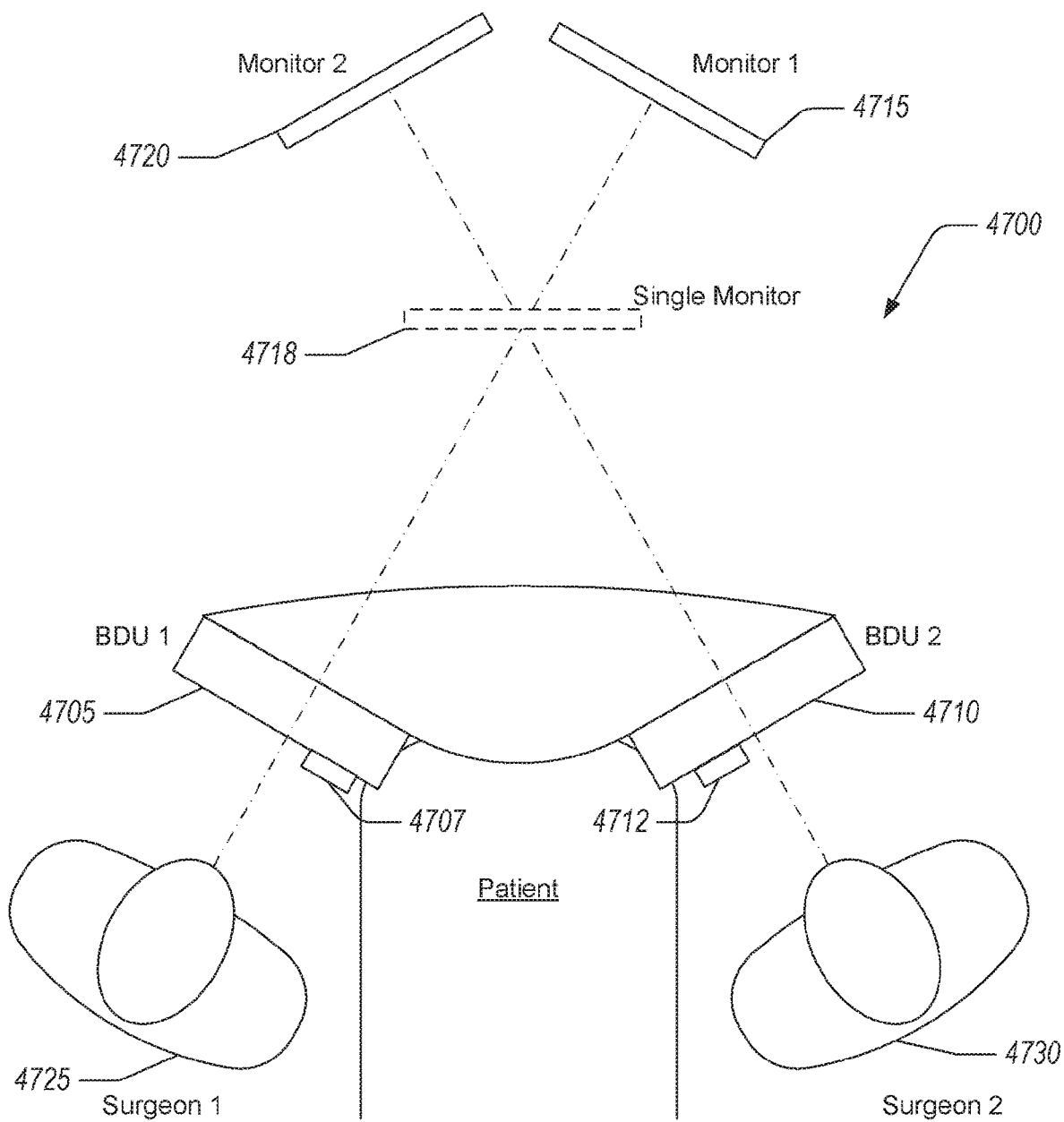
FIG. 45 illustrates an example visualization system with two binocular display units configured for multi-view switching.

FIG. 45 illustrates an example visualization system 4700 with two binocular display units 4705, 4710 configured for multi-view switching. The electronic visualization system 4700 with multi-view switching is shown with 2 binocular display units 4705, 4710 (e.g., BDU), which have stereo or 3D viewing, with 2D monitors 4715, 4720 (in a two-monitor configuration) or 2D monitor 4718 (in a single monitor configuration) shown behind each BDU in the line of sight of two surgeons 4725, 4730. The BDUs can include user interface features 4707, 4712 configured to allow one or both of the surgeons 4725, 4730 to control what is displayed within the respective BDU 4705, 4710, on the monitors 4715, 4718, and/or 4720, or any combination of these. The user interface features 4707, 4712 can include buttons, switches, foot pedals, touch screens, or the like. The user interface features 4707, 4712 can be attached to the BDU 4705, 4710 or they can be removable or separate from the BDUs. In certain implementations, the user interface features 4707, 4712 comprise a single button on a handle or other feature of the respective BDU 4705, 4712.

For certain surgical procedures, two surgeons can work together simultaneously. In one portion of the procedure a first surgeon can take the lead. In a second portion of the procedure, a second surgeon can take the lead. For example, when two endoscopic surgeons work sequentially, such as an ENT and Neurosurgeon (e.g., in an endoscopic endonasal transsphenoidal surgery) they may use a single endoscope with 2 monitors. The ENT can initiate the case and the Neurosurgeon can assist. Then, when they enter the cranial cavity, the Neurosurgeon can lead and the ENT can assist. In such an example, there is a single imaging modality which they hand off (e.g., an endoscope view). The monitors 4715, 4720 can be positioned directly in front of each surgeon 4725, 4730 for advantageous viewing. The surgeons themselves can be positioned on either side of the patient for surgical work.

For certain surgical procedures, two surgeons can use an operating room microscope. The surgeons may be positioned at 180 degrees apart from one another, e.g., two neurosurgeons in a spine case where they are on opposite sides of the table, or two neurosurgeons at 90 degrees in some skull base surgeries. In either scenario, the surgeon orientation is dictated by the nature of using one imaging modality, e.g., the microscope, and positioning the surgeons for surgical work. The visualization system 4700 can improve this situation by providing comfortable and/or convenient viewing assemblies and monitors to allow each surgeon to be positioned comfortably and appropriately during a surgical procedure.

The visualization system 4700 can be used to enhance the capabilities of other visualization systems by allowing multi-view switching between respective surgeons, where multi-view switching includes the ability to switch between imaging modalities and/or views within a particular imaging modality. For example, to facilitate a simultaneous endoscopic- and microscopic-like approach to surgery through an integrated visualization system 4700 with multi-view switching, two binocular display units 4705, 4710 can be positioned in front of respective surgeons 4725, 4730. The work space orientation of the two surgeons can be preserved, if desired, and the viewing can be configured to be directly in front of each surgeon in a line of sight familiar to them. In certain implementations, other surgeon positions relative to each other may be used due to the independence provided by the electronic visualization system 4700 with multi-view selection. In various implementations, two or more imaging modalities can be used simultaneously, or alternately, with stereo or 3D capabilities by two surgeons acting independently or assisting one or the other.

The electronic visualization system 4700 with multi-view switching allows the assistant or co-surgeon to work independently in the same imaging modality view as the surgeon, or in an alternative imaging modality view. The co-surgeon or assisting surgeon can select their own view and monitor the view of the other surgeon in a picture in picture. In some implementations, the co-surgeon or assisting surgeon can switch to a view of another imaging modality, or to another reference image modality, such as a 3D volume data set of pre-surgical images. Such flexibility advantageously circumvents limits of using a single imaging modality by two surgeons.

To control switching between views, imaging modalities, and the like, any suitable user interface can be implemented. As a particular, non-limiting example, a single button on a handle of the BDU, a foot-switch, or a control panel, connected in parallel, can be used by a respective surgeon or assistant to control the view of the respective BDU and/or the view of the other surgeon to cycle through the viewing options, e.g., endoscope, exoscope, camera on a tool, electronic surgical microscope, or reference pre-surgical imaging.

For example, the default mode can be a single button press cycles the imaging modalities for both surgeons in their respective BDUs. If there is an exoscope and surgical microscope attached to the system, for example, pressing the selection button cycles through those two choices. If a Dicom image, for example, is added then each use of the button brings up the next of these three options. In certain implementations, the button (or other user interface element) can be configured to independently control video displayed within the BDUs 4705, 4712 and/or displays. For example, each BDU may include a user interface element that controls what is seen on the corresponding display in the BDU and/or the display outside the BDU. As another example, each BDU may include a user interface element that controls what is seen on the display in the other BDU and/or the other display outside the BDU associated with the user interface element. In this way, an assistant or co-surgeon can control what is displayed to each surgeon. In some embodiments, the output video is the same for both surgeons. In some embodiments, the output video is different for the surgeons. In some embodiments, a single user can control the disparate displays/BDUs to display the same video or to display different videos on each display/BDU.

Additionally, by holding the single button on the handle or foot switch down for a longer duration, such as 1.5 seconds, for example, a single button control can be made to function as an alternate button. This would facilitate another degree of functionality in image choice in the BDU. Users may configured the system 4700 so that the alternate function is used to control picture in picture. So that with a simple actuation of the button, the view can cycle through the modalities as full views with the next view as a picture in picture in both BDUs. Or in another configuration, the 1.5 second selection can be configured to control the BDU's independently, allowing one surgeon to use a microscope view and the other surgeon to use an endoscope view (or other modality).

The views can be cycled by depressing a single button by either surgeon. With a 'timed' depression of a single button the view choices can be cycled by an individual surgeon, independent of the other. With a 'timed' depression of a single button the view choices can be displayed as picture in picture. This facilitates dependent and independent multi-view for multiple surgeons in an electronic visualization system.

Display Mounted Image and Camera Controls

Figure 46:
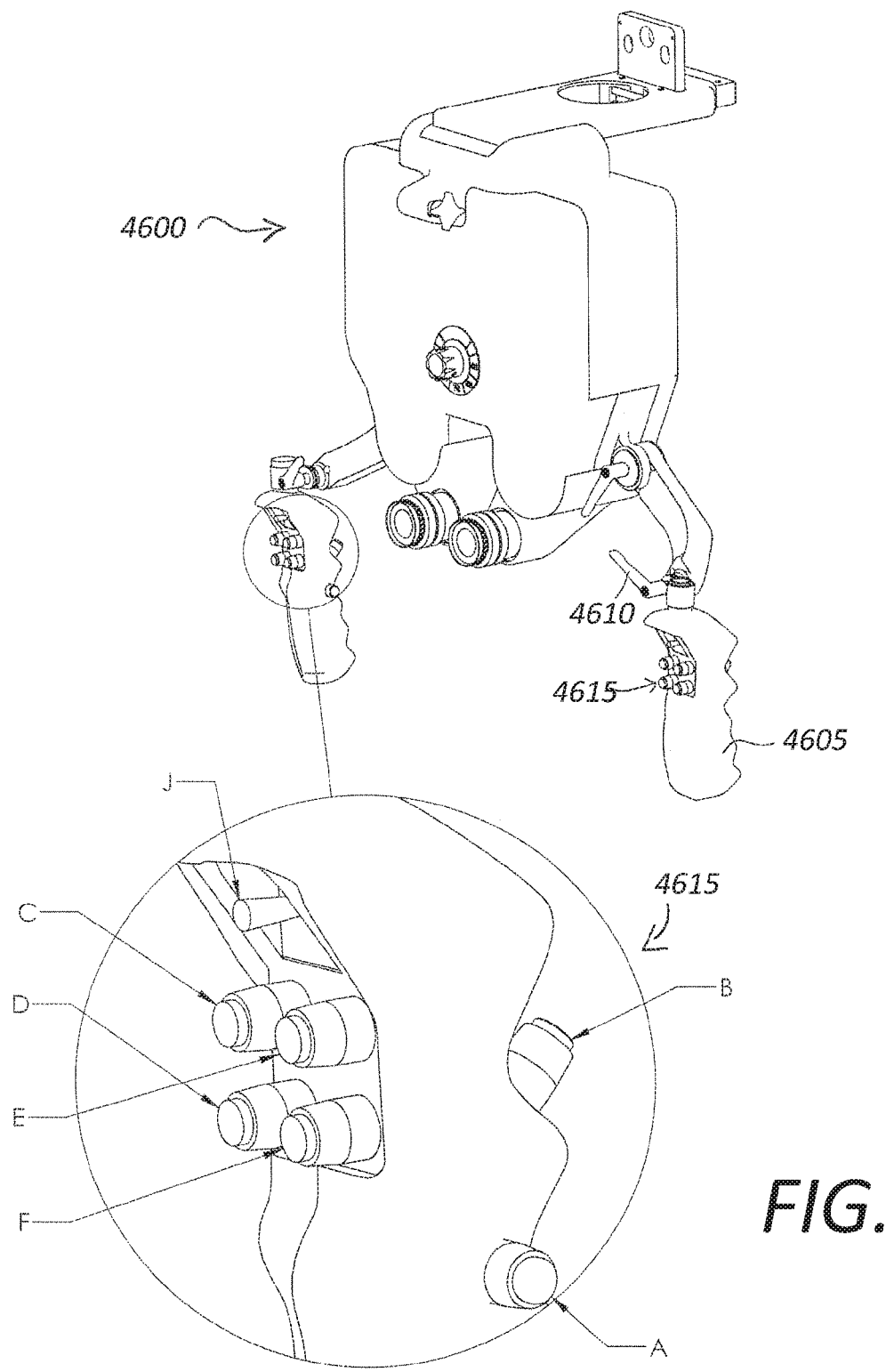
FIG. 46 illustrates an example binocular viewing display unit with camera controls integrated with a handle.

FIG. 46 illustrates an example display unit 4600 with camera controls 4615 integrated with a handle 4610. The display 4600 unit can display one or more images using one or more screens to provide a stereo image which is viewable by the user. The images can be generated by a camera mounted to the same stand that holds the display (e.g., a camera that provides a surgical microscope view of the surgical site), by a camera mounted near the patient (e.g., proximal cameras), by a camera placed in the patient (e.g., an endoscope, a camera on a retractor or on a surgical tool), by a graphical display system such as a computer or picture archiving and communication system (PACS system), or by another image generating source. The display unit 4600 can include a handle mounted 4605 to the display unit 4600 that allows the user to easily position the display unit 4600 in an ergonomic and functional position. The handle 4605 includes a button, switch, or lever 4610 that when engaged releases a brake. This brake holds the display unit still. The brake release button, switch, or lever 4610 is positioned on the handle 4610 such that the user can release the brake while holding the handle firmly and using the handle 4605 to manipulate the display 4600, then the user can activate the brake by disengaging the button, switch or lever 4610. In some embodiments, the brake on the surgeon display handle is configured to release a brake that allows the display unit to be moved. In some embodiments, the brake on the assistant display handle is configured to release a brake that allows the assistant display to be moved but leaves the surgeon display locked in place.

Also included on a control panel attached to the display unit or on a handle is a series of controls 4615 that affect the image seen by the user. These controls can be buttons, switches, toggles, dials, joysticks, levers, touch pads, or other devices. The controls 4615 can provide a number of different functions that affect the image. One control can switch which image or image set is being viewed by the user, switching for example from the stand mounted camera to a camera placed in the patient, to a PACS system to view the radiology data, to a computer that displays other pertinent data, or to another image source.

Another set of controls can modify the image that is being displayed. The cameras that are connected to the system may have the ability to adjust zoom, focus, iris diameter, color saturation, or other functions. The controls on the display can be configured to communicate with these remote cameras to adjust some or all of these functions. For example, there could be a toggle or a set of buttons that adjust the zoom of the camera in or out, and another set that adjusts the focus of the camera.

Another set of controls can modify the position of the camera by activating a motor to move the camera. For example, a stand mounted or table mounted camera could have motors that control the position and rotation of the camera. The controls could activate the motors, moving the camera. The user can thereby be looking at or into the display while moving the camera so that the camera can be accurately aimed at the area of interest.

The display unit 4600 can have multiple control panels 4615. These can be mounted on multiple handles 4605, for example, one on the right side and one on the left. For example, as illustrated in FIG. 46, mounted on the left handle are controls which include buttons A through F and joystick J. In these embodiments, a similar set of buttons, but in the mirror image orientation, are included on the right handle. The controls on the different handles can be different, for example, the left handle can be used to move the camera and the right handle could be used to zoom and focus the camera. Alternatively, some or all of the controls on the display unit or the different handles can be duplicated such that either handle can be used to control a function. Further, a duplicate set or subset of controls can be provided in other locations, such as near an assistant or in a control panel intended for use by the user's foot.

The controls can be configured so that one set of controls can perform multiple functions. For example, a multi-position switch can be used to determine which image input is displayed in the display. This same switch can be configured so that a particular control, say a camera zoom control, only activates the feature of the displayed image generator, for example, only the zoom on the currently activated camera changes position. In this example, the amount of zoom of any other camera connected to the system would be unchanged. To change the zoom of the other cameras, they would need to be activated. It would be possible in this system to also have some or all of the zooms activated at the same time, but this would probably be undesirable.

Each individual camera may have a number of operations that need to be controlled. Some of these operations are zoom, focus, iris diameter, light source intensity, light source wavelength, moving in space in the x, y, or z direction, rotating about the x, y or z axis, activating or removing a filter, taking a still picture, and other standard camera operations. Similar types of operations may be needed to manipulate graphical images from other sources, such as zooming into a radiograph, rotating a reconstructed CT scan model, or paging through the patient's records. Further operations may be needed for other image sources so that the user can navigate the graphical user interface of the image source. For the most complicated devices, there may be the desire control a large number of different operations. One method to accomplish this would be to have a matching number of controls. Some embodiments are configured to have a method to change what the controller activated depending upon need. For example, if the camera mounted to the stand was capable of being moved by a motor forward and back as well as to the left and to the right, this could be controlled easily by a four-way-joystick. If the same camera could also be panned to the left and right and tilted up and down, a second four-way-joystick could be used to control that. Another embodiment would be to have a switch that changed which circuits were affected by the first four-way-joystick so that it could control movement in one instance and could control rotation in a second instance. This same switch could toggle the circuit to another location so that the same four-way-joystick could be configured to drive the zoom and focus motors of the camera, or the iris diameter and light source intensity, or other functions that would be desired.

Figure 47:
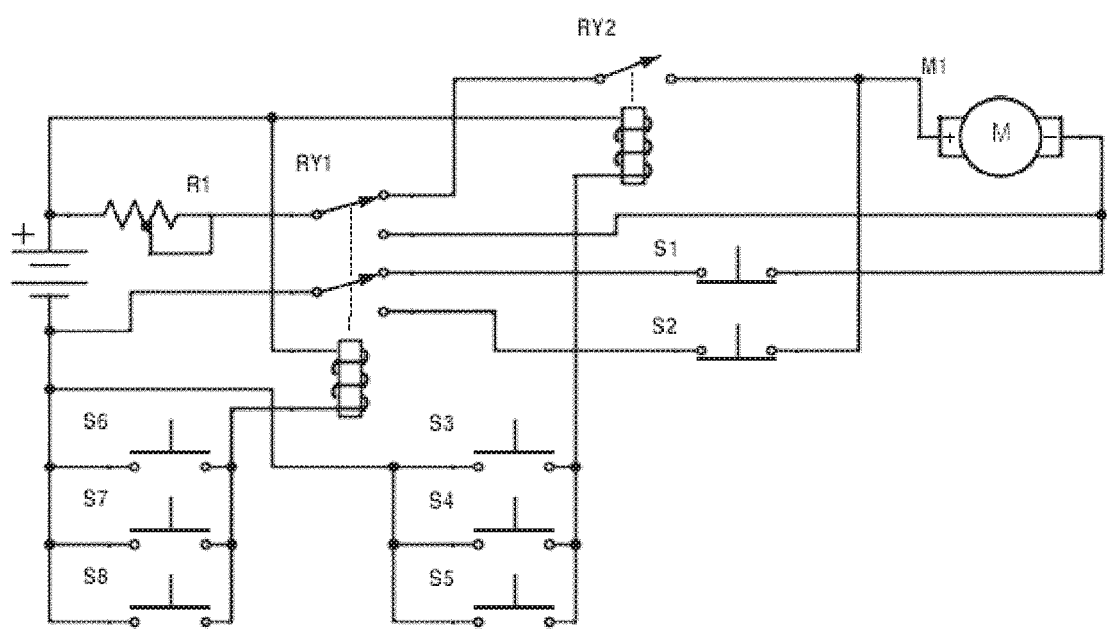
FIG. 47 illustrates an example embodiment of an electro-mechanical circuit diagram that has multiple switches which control one function.

FIG. 47 illustrates an example embodiment of an electro-mechanical circuit diagram that has multiple switches which control one function. Normally Open switches S3, S4, and S5 are connected in parallel so that should at least one of them be closed, Normally Open relay RY2 closes, completing the circuit for Motor M1. If any of the Normally Open switches S6, S7, or S8 are closed, the circuit is completed in reverse polarity for Motor M1, running it in reverse. The normally closed switches 51 and S2 open the circuit when the motor has moved its target to one or the other limit. A potentiometer, R1, is included to adjust the speed at which the motor runs. Switches S3 through S8 can be located in various locations. Each switch S3, S4, and S5 can be located in a different location, and another switch from S6, S7, and S8 can be located in the similar location. For example, S3 can be located next to S6. Switch S4 could one pole of a multi-pole joystick, while S7 is the opposite pole. Switch S5 could be one side of a foot-operated toggle, while switch S8 is the other side of that toggle.

To change which circuit is affected by the switch sets, a double pole multi-position switch can be placed in the circuit between Relay RY2 and Switches S3, S4, and S5 and between Relay RY1 and Switches S6, S7, and S8. This could be a rotary switch, a linear switch, or a single pole relay activated switch. Multiple multi-position switches could be tied to the same control knob or button so that changing the switch to a particular position could both set the image displayed to a specific input source and set the controls to operate features related to that image source. For example, the first position on a slider could move multiple linear multi-pole switches to a first position. One of the switches, in this first position, would send the signal from a specific camera to the display, while others of the switches, in this first position, would set some or all of the controls to affect functions on this first camera, such as zoom, focus, position, rotation, etc. Moving the slider to a second position would change a first switch to a position that sends a signal from a second camera to the display while other switches would set some or all of the controls so that they affected functions on this second camera. Additional multi-pole switches could be used in series to switch whether the control affected one function or another, for example, a second multi-pole switch could change the control switch to affect zoom in one position, x-position in a second position, pan rotation in a third position, and other functions in other positions. The setting of each multi-pole switch would control which image generating device was active and which function was being manipulated.

Figure 48:
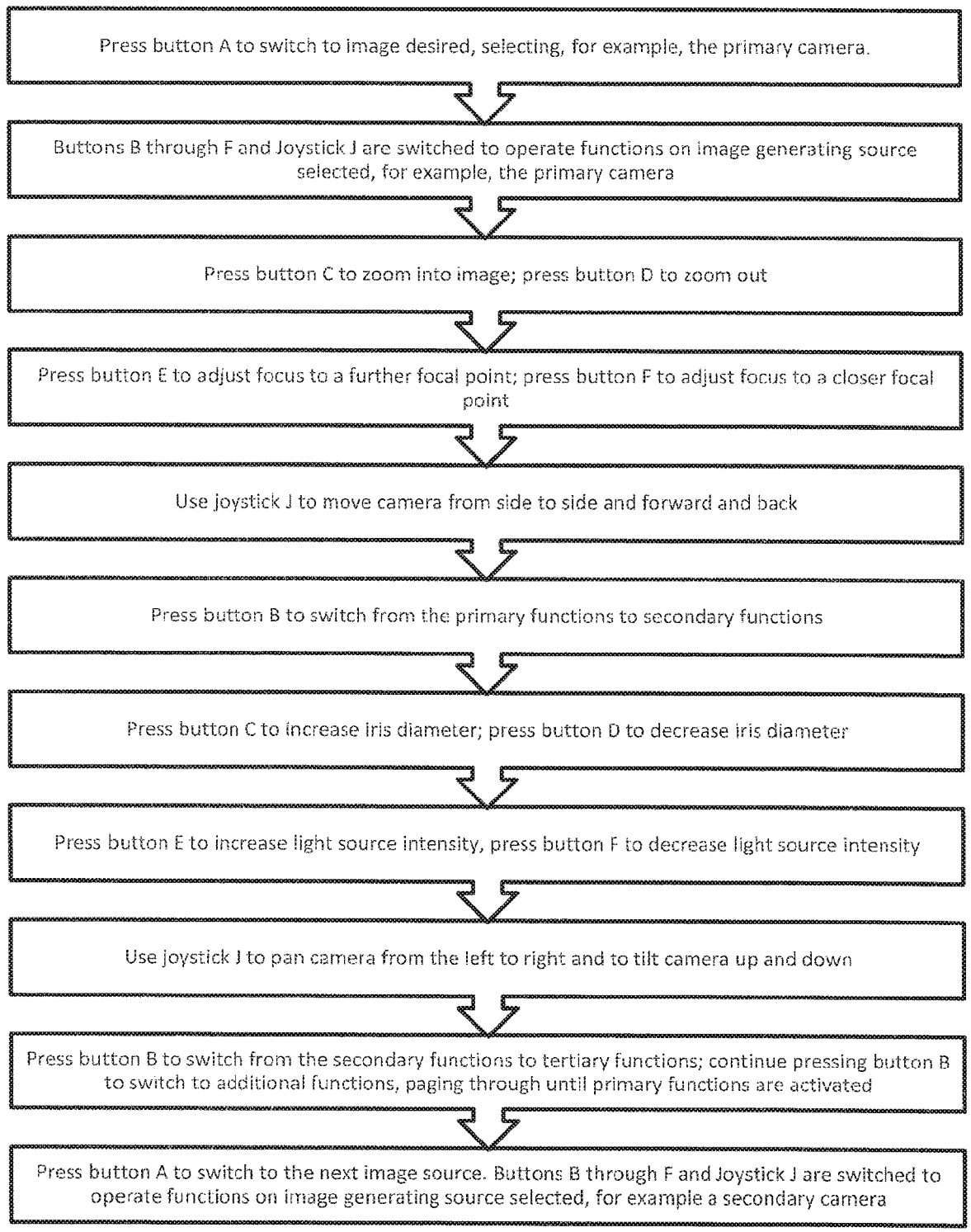
FIG. 48 illustrates an example algorithm that demonstrates how a small set of buttons can be configured to operate a larger number of functions.

In some embodiments, a single pole switch can be used to activate a relay that toggles the multi-pole switch to the next position. This same single pole switch can be configured to activate a series of relays in parallel so that the multi-pole switches would not need to be physically connected to the same slider. An algorithm that demonstrates how a small set of buttons could operate a larger number of functions is shown in FIG. 48.

An alternative embodiment would be to use a microcontroller to simulate the desired circuitry. A program simulating the motor control circuit and the multi-pole relay switch described above can be installed onto the microcontroller, which can be connected to the multiple display inputs and the multiple motors or other controlled features. The program could follow the same algorithm or an algorithm optimized for a microcontroller. This could have numerous advantages. For example, the microcontroller could be programmed so that potentiometer switches or Hall Effect switches could be used to control both the speed and direction of a motor in one setting, while being used purely as an on/off switch in another setting. Further, the simulated multi-pole switch could be programmed so that it is operated by a button and only toggles between active sources. In this example, when operating with three cameras, a PACS system and a computer connected to the display, the button would toggle between five different inputs, while when operating with just two cameras connected, the button would only toggle between two inputs.

In some embodiments, a medical apparatus is provided that includes a stereoscopic display, at least one camera remote to the display that is an image source for the display, and a control panel integral with the display that controls functions on the camera. The control panel can be mounted to a handle attached to the display. The handle can include a method for releasing brakes on the display stand so that the display can be manipulated to an ergonomic position using the handle. A second control panel can be mounted to a second handle. The second control panel can be configured to duplicate the controls of the first control panel. The second control panel can be configured to operate different functions from the first control panel. The control panel can be configured to operate functions on the camera that include one or more of the following: zoom, focus, iris diameter, light source intensity, light source wavelength, moving the camera in space in the x, y, or z direction, rotating the camera about the x, y or z axis, activating or removing a filter, taking a still picture, and other standard camera operations. A first control panel can operate a first subset of possible functions. A setting can be changed so that the first control panel can operate a second subset of possible functions wherein some or all of the functions are different than the first subset of functions. The specified subset of possible functions can vary depending upon the type of camera that is providing images to the display. At least one additional image source can be included that can supply images to the display. The at least one additional image source can be at least one of an additional camera, a radiology viewing system, and a computer display. Switching from one image source to another can change the functions that the control panel operates. Switching from the first camera to an additional camera can be configured to change the control panel from operating functions on the first camera to operating functions on the additional camera. Switching from a camera to another type of image source changes the controls so that they operate as input devices which can navigate the graphical user interface of the image source. The control panel includes a control mechanism that allows the user to switch which image source is being displayed. The control panel includes a control mechanism that allows the user to switch which functions the control panel can operate. An example of functionality includes pushing a button to cycle through available views. For example, switching of images can be accomplished by GUI or by handle mounted control. Pressing the button once provides a view of the surgical microscope view, pressing the button again provides a view of the proximal camera, pressing the button again provides a picture in picture view, pressing the button again switches the larger and smaller videos in the picture in picture, and pressing the button again returns back to the surgical microscope view.

The control panel can include at least one control mechanism chosen from buttons, switches, toggles, dials, joysticks, levers, or touch pads. The control mechanism can be part of an electro-mechanical circuit that operates a function on a camera or imaging device. The control mechanism operates a relay that is part of an electro-mechanical circuit that operates the function. A switch can be used to set which electro-mechanical circuit the control mechanism is connected to. The switch can be a multi-position switch so that the control mechanism can be switched among a plurality of electro-mechanical circuits. The switch is a single pole switch that operates a multi-position relay so that the control mechanism can be switched between a plurality of electro-mechanical circuits. The control mechanism is connected with a microcontroller that operates functions on one or more cameras or imaging devices. A second control mechanism is connected with a microcontroller that operates functions on one or more cameras or imaging devices. The microcontroller is programmed to control the switching of the image source and on which functions the control panel operates. The stereoscopic display can be a binocular display device.

Video Coupler

Accordingly, the surgical visualization systems described herein can be configured to generate or acquire video images from a variety of sources. In some embodiments, a surgical visualization system can include one or more video couplers that are configured to receive optical input from a variety of sources. For example, a video coupler can comprise a camera attachment that has a fixed focal length or that includes zoom optics, the camera attachment can also be a mono or stereo configuration wherein the camera attachment forms an entrance pupil that is configured to coincide with an exit pupil of an imaging system intended to be coupled to the visualization system, such as an endoscope or an exoscope.

An exoscope can be a device similar to an endoscope whose field of view and distribution of illumination is narrower than an endoscope and attached to a positionable arm attached to a bed or stand. Typically, an exoscope views a surgical site surgery from outside of the surgical opening. An example of an exoscope is described in U.S. Pat. No. 8,702,602 to Berci et al., entitled "Exoscope," issued Apr. 22, 2014. For example, an exoscope can serve to observe and illuminate an object field on a patient from a position set apart from the patient's body. The exoscope can include a lens system configured to observe the object field and an illumination configured to illuminate the object field. The exoscope can be mounted by using a bracket in such a way that, through the lens system, an object field can be observed at a distance of a few centimeters, such as in the range of about 20 cm, from the distal light outlet or image entry end. Exoscopes may for example include devices that are observation instruments based closely on successful invasive endoscope technology but serving for extracorporeal illumination and observation of an object field.

For many endoscopes and exoscopes, there is no integrated image sensor. However, these devices generally include exit pupils to be viewed by an eye or to couple to a video coupler. Accordingly, the surgical visualization systems disclosed herein can include a video coupler having an image sensor and imaging optics configured to receive optical information from an external device (e.g., an endoscope or exoscope) that does not include an imaging sensor to generate video images of the field of view viewed by the external device. These video images acquired with the video coupler can then be used in the way other camera systems are used in the disclosed surgical visualization systems.

For example, a surgical visualization system can be configured to switch between different image sources or cameras. Examples of the cameras include proximal cameras, surgical microscope cameras, endoscopes (potentially through the use of a video coupler), retractor cameras, surgical tool cameras, exoscopes (potentially through the use of a video coupler), and the like. The video acquired with the variety of sources can be displayed on one or more displays within a display unit, such as a binocular display unit or other display unit described herein.

In some embodiments, the video coupler is configured to optically couple to the exit pupil of the endoscope or exoscope wherein the optical information from the endoscope or exoscope may be divided using a prism or beamsplitter or mirror and a lens assembly to form a right eye and left eye path to a stereo sensor(s) within the video coupler. Such an arrangement can be used to produce stereo views within a display unit.

In a stereo embodiment with visible light and near infrared light, e.g., for fluorescence imaging, each eye path can be configured to contain a dichroic beamsplitter directing light to a sensor, or group of sensors, for each respective waveband. For example, a video coupler containing a pair of 3-chip visible cameras can be coupled with one or more sensors for acquiring near infrared video.

In a stereo embodiment with visible light and near infrared light, e.g., for fluorescence imaging, each eye path can be configured to contain a dichroic beamsplitter directing light to a group of sensors for each respective waveband. For example, a video coupler can contain a pair of 4-chip prisms with sensors for RGB and NIR for each eye path.

In a stereo embodiment with visible light and near infrared light, e.g., for fluorescence imaging, a timing and control system configured to accept/acquire image information at a portion of a sensor for each respective waveband can be implemented. For example, a timing and communication system can be configured to start and stop the respective wavebands of the illumination source or sources. For example, a video coupler can be configured to include a pair of single sensors with RGBW pixels, with one channel for each eye path.

These example embodiments may be implemented by dividing a sensor or group of sensors to a right eye and left eye area, respectively.

In some embodiments, the video coupler can include a notch or blocking filter for fluorescence excitation. This may be advantageous where the exoscope or endoscope does not include such a filter.

User Control Systems & Control of Image Intensity

As discussed above, there have been a variety of imaging systems developed to enhance the surgeon's view of the surgical site. These imaging systems can include optical surgical microscopes or digital video cameras and display systems. The digital video cameras can be used as endoscopes, which are placed inside the patient and are used in keyhole type surgery, or can be used as exoscopes, which are placed at or near the surgical wound to focus on the surgical site.

Figure 49:
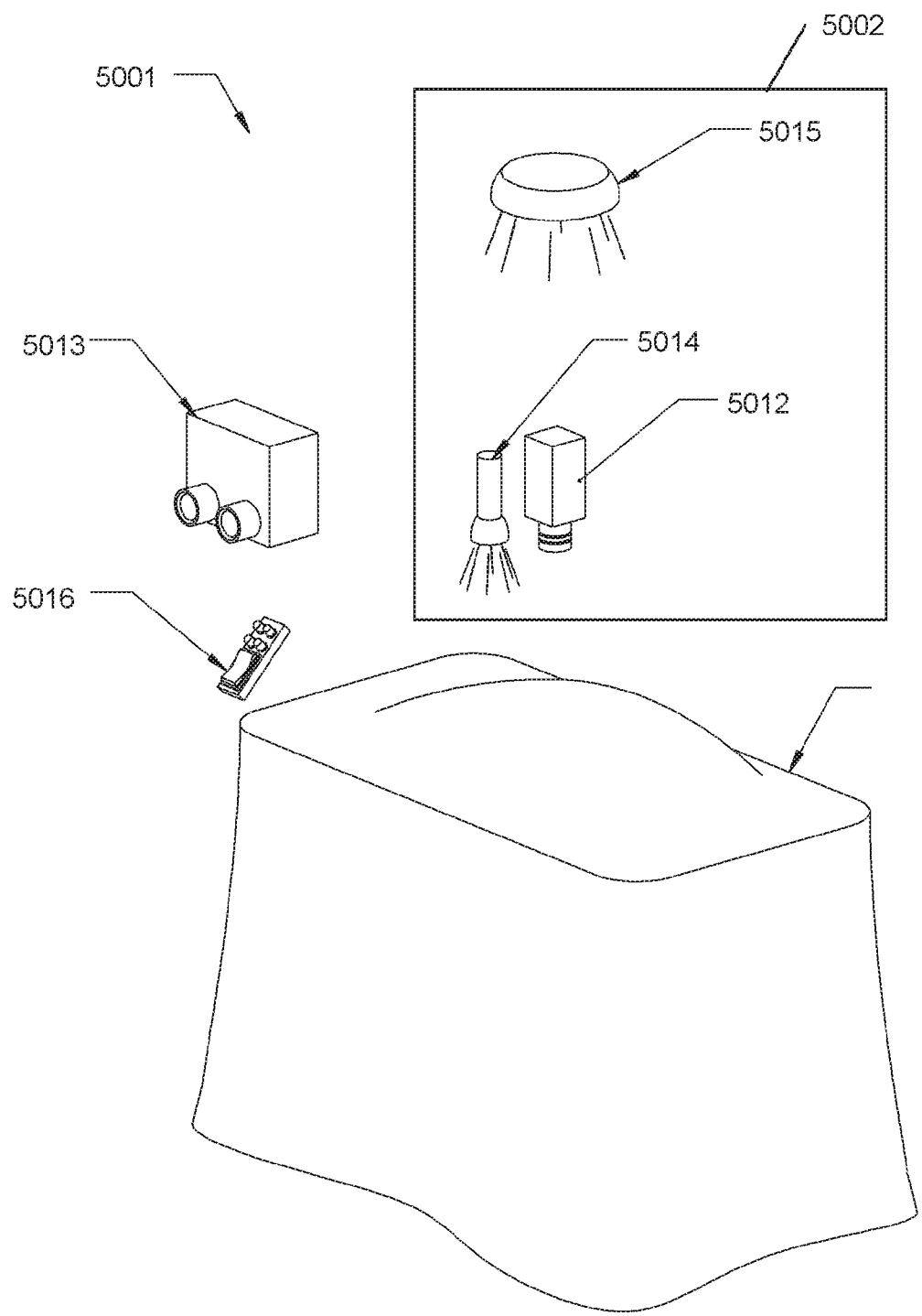
FIG. 49 schematically illustrates an example of an imaging system in a simplified operating room configuration.

FIG. 49 schematically illustrates an example of such an imaging system 5001 in a simplified operating room configuration. The imaging system 5001 includes an image acquisition subsystem 5002 having a digital camera 5012 and one or more light sources, such as lights 5014, 5015. The digital camera 5012 and lights 5014, 5015 are focused on an area of interest (e.g., a surgical site) of the patient on the table 5011. The user (e.g., surgeon) can look into the display 5013 to see a magnified view of the surgical site. The imaging system 5001 also includes a remote control 5016 which allows the user to adjust the digital camera 5012 as needed.

As discussed above, these imaging systems can incorporate optical or digital filters to enhance the image. One type of filter can enhance the view using false-color imaging where information resulting from the measurement of non-visible light is used to produce images in the visible spectrum. For example, near-infrared light can be measured by a digital sensor, a digital transformation can be applied to the measured data, and light in the visible spectrum corresponding to light in the near-infrared spectrum can be presented on the display.

In certain embodiments described herein, an integrated visualization system is provided which advantageously permits switching among different surgical views to facilitate the surgeon's own viewing options, to coordinate the work with assistants or other surgeons, or both. The integrated visualization system may advantageously use less space than would separate visualization systems and may advantageously incorporate convenient controls for multiple visualization modalities (e.g., when comparing or alternating between microscopes, endoscopes, or other visualization modalities).

In certain embodiments, a visualization system advantageously allows for viewing and switching between multiple visualization modalities using only a single stand or cart with the multiple visualization modalities attached via arms or other connections.

In certain embodiments, a visualization system advantageously assists a range of users (e.g., surgeons, assistants) and can be tailored for one or more approaches or surgical sites. The visualization system can be used by a single surgeon or simultaneously by one or more surgeons or co-surgeons working on the same patient (e.g., three- or four-handed surgery).

In certain embodiments described herein, a visualization system is provided that utilizes some or all of the features of surgical visualization systems, as disclosed elsewhere herein. In certain embodiments described herein, the visualization system can advantageously combine certain functionalities and advantages of the surgical visualization systems disclosed above and elsewhere herein (e.g., utilizing a surgical microscope and an exoscope). For example, the visualization system can include a 3D digital camera that can be placed near the surgical site (e.g., like a standard exoscope) or can be placed above the site (e.g., like a surgical microscope). In either of these modes, the user can look into a display that provides a 3D view of the surgical site, with the display placed in an ergonomic position for the user, unrelated to the position of the digital camera.

Using these visualization systems, multiple cameras can be placed about the surgical site and can be viewable in the same display. These cameras can include one or more of: a digital microscope, an e-scope, a surgical microscope, an exoscope, an endoscope, or other surgical microscopes or cameras that provide a view of a surgical site. To avoid having to disconnect one camera and connect another to the display each time the user wants to change views, a video switch can be employed. All video signals can go to the switch, and the desired video signal can be output to the display.

Some of the cameras contemplated to be used with the visualization system described herein have adjustments like zoom, focus, iris diameter that can be controlled. Further, some of these cameras are mounted to systems that allow adjustment of the camera's position, for example, panning the camera left or right or adjusting the up and down tilt of the camera. In certain embodiments described herein, the visualization system can be configured such that these adjustments can be done remotely via a remote control device (e.g., a panel comprising switches) that send electronic signals to motors or other electronic devices located on or in the camera. As the number of cameras and the number of adjustable options per camera grows, the number of switches of the remote control device could be expected to increase. At some point, however, the increased number of switches would make ease of operation become a challenge. When that happens, the user may decide to look at the remote control device instead of maintaining the user's view of the surgical site. Certain embodiments described herein advantageously provide a way to simplify the remote control device so that the user can operate the remote control device through memory without having to look away from the surgical site, yet can retain the ability to operate any desired functions of the cameras.

In some configurations, the different camera settings may utilize different light conditions to facilitate viewing. The different camera settings can include different zoom levels, where a tighter zoom utilizes a more focused light and a wider zoom utilizes a more diffuse light. The different camera settings can include different light spectra. For example, instead of broad spectrum visible light (white light), it could be desirable to use blue light or non-visible light, such as near infrared. Some existing surgical visualization systems are already configured such that changing a camera setting may change a light setting (e.g., changing the focus on some optical microscopes changes the light intensity and spread). Yet, these systems are not configured to work with other cameras or multiple camera visualization systems. Further, some cameras may utilize more light than others to achieve the desired quality of visualization. Smaller cameras, with their smaller diameter objectives and smaller sensor chips, can often utilize more illumination of a subject for the same clarity. When switching from a smaller camera (e.g., an exoscope) to a larger camera (e.g., a digital surgical microscope camera), the intense light utilized for the exoscope may appear very bright when the surgical microscope camera image is shown in the display. This effect could wash out the digital display in the area that is illuminated such that the worksite cannot be adequately visualized, or worse, this effect could cause flash blindness to the user when switched. Additionally, bright light, whether visible or non-visible light, can cause warming or even burning of the patient's tissue. Even though flash blindness may not occur with unused lights being left on, there are advantages to having the unused lights dimmed or turned off when not being utilized. Certain embodiments described herein advantageously provide a system which can adjust the settings on the integrated lights, for example, automatically to programmed settings for the camera selected by the user from which the image is being displayed. In certain embodiments, when the display is changed to a different camera view from a different camera selected by the user, the system can advantageously automatically change the settings on the integrated lights to the programmed settings for the different selected camera.

When switching among different cameras or adjusting the cameras, other factors can affect the lighting to be utilized as well. For example, additional issues that can affect the desired lighting conditions to be used can include camera position, distance to the workspace, and type of tissue being imaged. Because the state of the surgical site can be changed constantly, when switching to a particular camera, the desired lighting conditions may have changed. For example, the surgeon may use an endoscope to create a channel for further surgical steps, and may then use a different camera with a wider field of view to reposition the endoscope in the channel. The desired lighting conditions for the new endoscope position may be different and therefore, when the surgeon switches back to the endoscope, the image being viewed may be too dark, too bright, washed out, or may have other problems related to the lighting conditions. Certain embodiments described herein advantageously provide a system which adjusts the lighting conditions being utilized in response to one or more of: changes of camera position, distance to the area of interest, type of tissue being imaged, or other conditions.

Viewing in surgical sites can utilize supplemental illumination (e.g., lighting in addition to room or overhead lighting). An endoscope-like visualization modality can be selected by the user when the area of interest is not directly viewable from outside the body (e.g., looking off at an angle behind an anatomical structure or within a body cavity). In such a case, the lighting can be generally directed along the view of the endoscope-like device. A microscope-like visualization modality can benefit from supplemental illumination since an image of a small site can be greatly magnified, and the desired amount of illumination often increases as an image is magnified. Certain embodiments described herein advantageously provide a system which controls the supplemental illumination in response to the selected visualization modality.

Large changes in illumination levels between modalities can be related to the field of view of the camera relative to its working distance. The intensity of illumination is proportional to the inverse square of the distance from the light source, which is known as the inverse-square law (e.g., expressed for light intensity as intensity=power/area). The consequence of this relationship is that illumination varies with a change in position. For example, when the illumination level of the light source is held at a constant output level and a change of working distance is made, the effect on the resulting image can be far more pronounced when the tissue being viewed is close to the light source, e.g., when the field of view and illumination mapping are from endoscope-like devices (e.g., wide field of view). Conversely, when the tissue being viewed is far from the tip of the device, the effect on the resulting image from small variations of either the illumination level or the working distance can be dramatically reduced.

If the illumination emanating from the tip of an endoscope-like device, or the illumination utilized with a microscope or its digital equivalent, is not held at a constant output level and a change of working distance is made, the illumination level at the area of interest as seen by an imaging system can be manipulated to appear similar. Such a change can utilize the intervention of the user. However, certain embodiments described herein advantageously provide a system which can change the illumination automatically so that the switching of one modality to another can be seamless or substantially seamless, relative to light levels viewed on an electronic display.

In certain embodiments described herein, the camera gain levels can be changed automatically when the light sources are switched in the visualization system. By changing the camera gain levels instead of changing the illumination, certain embodiments described herein advantageously provide a system which reduces the potential to overexpose tissue to heat, whether the illumination is white light for imaging or near-infrared for excitation. In certain embodiments, the imaging field of view and the illumination field of coverage can be adjusted to be approximately equal, even as magnification changes.

However, the cone of imaging optics and illumination between modalities can differ. For example, operating room (OR) microscopes can have cones of imaging optics and illumination that vary between negative angles of a few degrees to a small number of positive degrees. Typically, the area viewed on the patient can be smaller than the size of the objective lens of the OR microscope-like device at high magnification. At the lowest magnification, the area viewed can be at most several times larger than the objective lens. OR microscopes and digital equivalents can have long working distances relative to the area observed. For cameras of these types, a change of 10 mm in distance can represent a small percentage change in the illumination level. Such long working distances can result in a shallow depth of field, so the user can find focus and can stay in a standoff position. Typically, OR microscopes are relatively stationary (e.g., held by an arm from a stand), and can be positioned in a favorable viewing position and the surgical work can then proceed.

In contrast, endoscopes or wide angle cameras on tools or retractors can experience significant movement during operation. Endoscopes and cameras on tools and retractors can have wide fields of view (e.g., 70 to 110 degrees) and are often hand-held, can be smaller, and can be used much closer to the area of interest than can an OR microscope-like device. As a result, the endoscope or cameras on tools and retractors can be positioned and repositioned as the surgical procedure is performed to view what the surgeon deems relevant. Endoscopes and cameras on tools and retractors also can have short working distances relative to OR microscopes and working distances that approximate the area observed. The illumination power can vary widely (e.g., to keep the illumination level constant as distance to the subject changes). In particular, for imaging modalities that are considered wide angle (e.g., endoscopes and cameras on tools and or retractors), a change of 10 mm in the working distance represents a large percentage change in illumination. For example, moving closer by 10 mm from a 25 mm nominal working distance can yield a nearly 3× increase in illumination level, and moving away 10 mm from a nominal 25 mm working distance can yield a nearly 2× decrease in illumination level. This effect can cause viewing issues when switching the display to the view of a handheld camera such as an endoscope. Certain embodiments described herein advantageously provide a system that can properly adjust for the variation in effective illumination automatically when the user switches imaging modality.

Near infrared imaging utilizing exogenous dyes can utilize one or more excitation sources in the infrared, a wavelength domain not seen by the human eye. Excitation sources in the 700-800 nm range are invisible, but safety for the patient, operator and allied health personnel can be considered (e.g., by accounting for excitation levels reaching skin or other tissue). The amount of excitation relative to emission level in the imaging domain is known as Stokes shift and can be large, even orders of magnitude larger than ambient levels. Therefore, excitation illumination can be blocked (e.g., using an optical filter) from returning to any sensor so that only the fluorescence output or emission of the dye is received by the cameras.

In addition, the infrared source can generate heating of the patient's tissues. Also, fluorescence quenching, due to prolonged exposure of the dye to the emission source, can make imaging more difficult as time goes on. Certain embodiments described herein advantageously provide a system and method to pulse the emission such that sufficient photon energy is supplied to the fluorescent dye, but a minimum of energy is transferred through radiative heating. A duty cycle where the infrared source is cycled on and off can be used to reduce (e.g., minimize) heating while maintaining sufficient visible emission from the dye while at a rate such that the excitation response is captured in the camera. Certain embodiments described herein advantageously provide a system and method in which pulsing of the emission source is performed with the pulses timed so that the video frame is taken by the camera when the excitation response occurs.

Figure 50A:
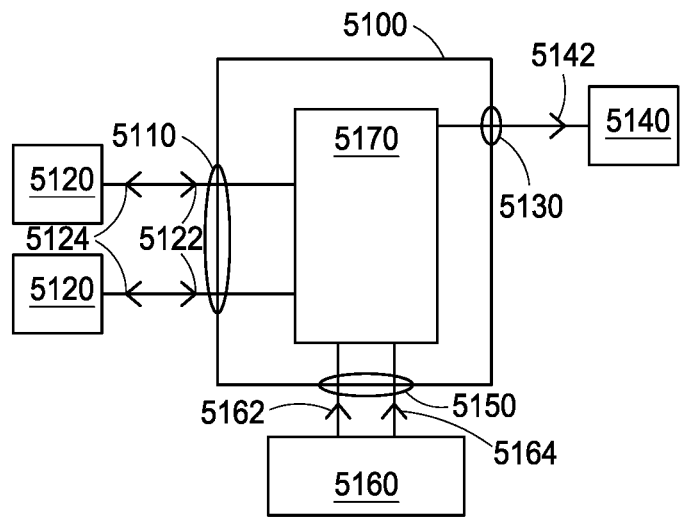
FIG. 50A schematically illustrates an example visualization system controller in accordance with certain embodiments described herein.

FIG. 50A schematically illustrates an example visualization system controller 5100 in accordance with certain embodiments described herein. The visualization system controller 5100 comprises a plurality of communication ports 5110 configured to be operatively coupled to a plurality of image acquisition subsystems 5120. The visualization system controller 5100 further comprises at least one image output port 5130 configured to be operatively coupled to at least one image display subsystem 5140. The visualization system controller 5100 comprises at least one user input port 5150 configured to be operatively coupled to at least one user input device 5160. The visualization system controller 5100 further comprises at least one circuit 5170 operatively coupled to the plurality of communication ports 5110, the at least one image output port 5130, and the at least one user input port 5150. The at least one circuit 5170 is configured to receive data signals 5122 from the plurality of image acquisition subsystems 5120, to transmit control signals 5124 to the plurality of image acquisition subsystems 5120, and to transmit output image signals 5142 to the at least one image display subsystem 5140. The at least one circuit 5170 is further configured to receive at least one first user input signal 5162 and a plurality of second user input signals 5164 from the at least one user input device 5160. The at least one circuit 5170 is responsive at least in part to the received at least one first user input signal 5162 by: selecting an image acquisition subsystem 5120 from the plurality of image acquisition subsystems 5120, transmitting the output image signals 5142 to the at least one image display subsystem 5140 in response to the data signals 5122 received from the selected image acquisition subsystem 5120. In certain embodiments, the at least one circuit is responsive that least in part to the received at least one first user input signal by generating the control signals 5124 and transmitting the control signals 5124 to the selected image acquisition subsystem 5120. In certain such embodiments, the at least one circuit 5170 generates the control signals 5124 in response to the at least one first user input signal 5162 and the received plurality of second user input signals 5164.

Cameras

Figure 50B:
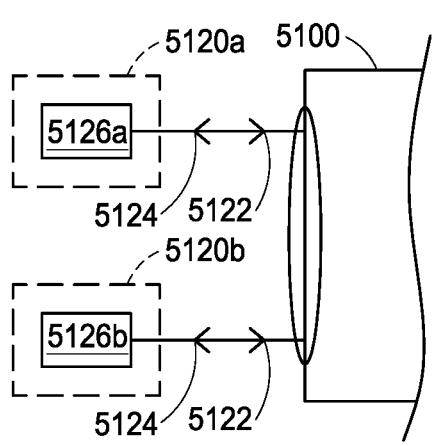
FIG. 50B schematically illustrates a partial view of an example visualization system controller operatively coupled to a first image acquisition subsystem comprising a first camera and to a second image acquisition subsystem comprising a second camera in accordance with certain embodiments described herein.

The plurality of image acquisition subsystems 5120 of certain embodiments are configured to be operatively coupled to the visualization system controller 5100. For example, the image acquisition subsystems 5120 can be in wired communication with the visualization system controller 5100 (e.g., via wired communication ports 5110) and/or in wireless communication with the visualization system controller 5100 (e.g., via wireless communication ports 5110). In certain embodiments, the plurality of image acquisition subsystems 5120 comprises a plurality of cameras 5126. FIG. 50B schematically illustrates a partial view of an example visualization system controller 5100 operatively coupled to a first image acquisition subsystem 5120*a* comprising a first camera 5126*a* and to a second image acquisition subsystem 5120*b* comprising a second camera 5126*b* in accordance with certain embodiments described herein. The plurality of cameras 5126 can be selected from the cameras described herein, including but not limited to: endoscopes, exoscopes, cameras providing surgical microscope views, digital microscopes that are placed about the surgical site at various positions and angles, and other surgical cameras.

In certain embodiments, the camera 5126 generates data signals 5122 indicative of an image of the surgical site and provides the data signals 5122 to the visualization system controller 5100, with the visualization system controller 5100 responding at least in part to the data signals 5122 to generate and provide the output image signals 5142 to the at least one image display subsystem 5140 (e.g., a display 5140). The camera 5126 may capture three-dimensional (3D) video and the display 5140 may be capable of displaying video in 3D. The camera 5126 and the display 5140 can also be capable of displaying alternate color images or video, for example, false color images based on infrared light imaging. In certain embodiments, the cameras 5126 are configured to show the surgical field from different angles, different fields of view or magnification, or different options such as false color imaging.

In certain embodiments, the cameras 5126 can all be the same type of camera, while in certain other embodiments, the cameras 5126 are of different types. A simple camera can be used which has a fixed focal length, zoom, light level to the image sensor, and spectrum of light recorded. The camera 5126 can also be mounted in the desired position and can be manually moved if the position is to be adjusted. Some cameras can have one or only a few possible adjustments. For example, a camera 5126 can have a focus adjustment, since the surgical works space distance from the camera may vary as the operation proceeds. A more complex camera 5126 can have adjustment of two or more of: focus, zoom, iris opening, color or filter controls, pan, tilt, or other rotations about an axis, and other functions.

One or more cameras 5126 can comprise adjustment mechanisms or systems configured to control various features of the camera 5126, including but not limited to, position (e.g., panning the camera 5126 left or right or adjusting the up and down tilt of the camera 5126), zoom, focus, iris diameter. In certain embodiments, the visualization system controller 5100 provides the ability to control the features of the cameras 5126 (e.g., to adjust the zoom and focus) remotely. For example, the cameras 5126 can be motorized and configured to receive the control signals 5124 from the visualization system controller 5100 which are generated in response at least in part to the first user input signal 5162 and the plurality of second user input signals 5164 from the at least one user input device 5160 (e.g., a remote control device comprising one or more switches which can be activated to adjust these functions). By placing the camera controls in a location remote from the camera 5126, certain embodiments described herein advantageously provide the ability to do one or more of the following: to avoid jostling the camera 5126 while adjusting a function of the camera 5126, to avoid blocking other cameras or users while adjusting a function of the camera 5126, to provide the ability for the user to look at the display while making the adjustment, and to more easily control the sensitivity of the adjustment. For example, having remote control over camera positioning can allow the user to look at the display 5140 while adjusting the aiming of the camera 5126 so that the center of the workspace can be placed in the center of the displayed image. Any or all of these functions can be incorporated into a camera 5126 through the use of motors or other actuators adjusting the position of parts of the camera (such as lenses) in accordance with certain embodiments described herein.

Figure 51:
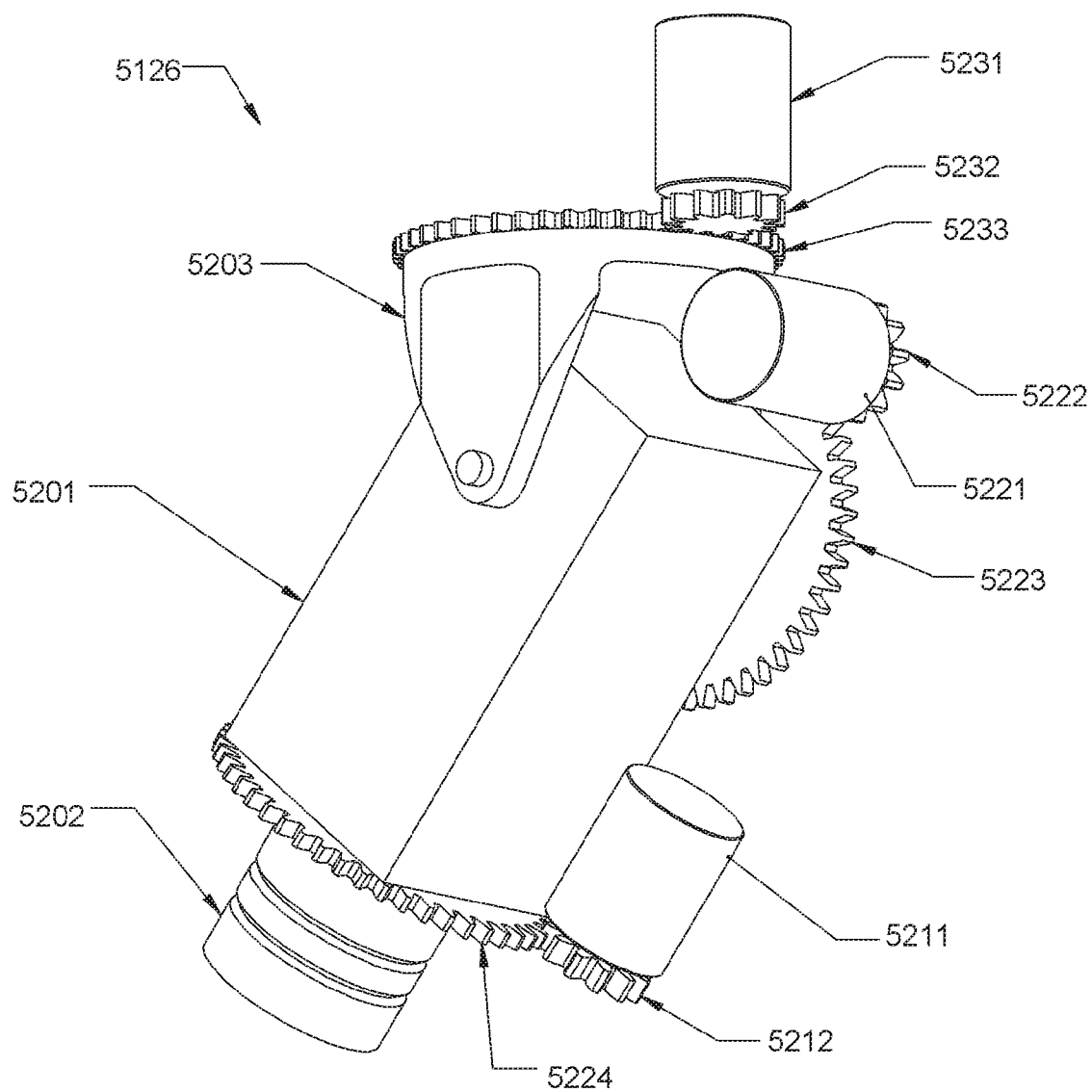
FIG. 51 schematically illustrates an example camera comprising motors and gears mounted to adjust pan, tilt, and focus in accordance with certain embodiments described herein.

FIG. 51 schematically illustrates an example camera 5126 comprising motors and gears mounted to adjust pan, tilt (e.g., pitch), and focus in accordance with certain embodiments described herein. While the example camera 5126 schematically illustrated by FIG. 51 only has motors that operate three functions, in certain other embodiments, the camera 5126 can include other adjustable functions, such as zoom and iris diameter. Other mechanisms, systems, arrangements, or configurations for adjusting the functions of the camera 5126 are contemplated (e.g., not only making adjustments via operation of motors and gears). For example, some functions may be adjusted electronically (e.g., switching the output from the visible light sensor to an infrared sensor).

The motors and gears are schematically illustrated in FIG. 51 as being external to the camera body, yoke, and mount, in accordance with certain embodiments described herein, and to demonstrate how they may operate. In certain other embodiments these motors and gears can be mounted internally to the camera body. The camera 5126 can comprise a body 201 that houses at least one sensor that detects light.

The camera 5126 can further comprise a lens housing 5202 that holds one or more optical lenses, a motor 5211, a pinion gear 5212, and a gear 5213 mechanically coupled to the lens housing 5202. When the housing 5202 is turned, cams can move the lenses in a predetermined path to adjust focus. The motor 5211 can be mechanically coupled to the camera body and can turn the pinion gear 5212 which, in turn, moves the gear 5224. In this way, running the motor 5211 can adjust the focus of the camera 5126.

The camera 5126 can further comprise a yoke 5203 that is mechanically coupled to the camera body and to a camera mount (not shown), a second motor 5221 mechanically coupled to the yoke 5203, a pinion gear 5222, and a gear 5223 mechanically coupled to the camera body. The yoke 5203 holds the camera 5126 in place. When activated, the second motor 5221 can turn the pinion gear 5222 which, in turn, moves the gear 5223, causing the camera 5126 to tilt. The camera 5126 can further comprise a third motor 5231 mechanically coupled to the same camera mount as is the yoke 5203, a pinion gear 5232, and a gear 5233 rigidly connected to the yoke 5203. The third motor 5231 can be rigidly connected to the camera mount, while the yoke 5203 is free to rotate about the axis of the yoke 5203. When activated, the third motor 5231 can turn the pinion gear 5232 which, in turn, moves the gear, 5233, causing the camera 5126 to pan.

Lights

A well-lit operating field is desirable during surgery. Achieving a well-lit operating field can be a challenge when operating deeply in a small wound. Multiple light sources can be utilized so that different parts can be easily visualized. In certain embodiments described herein, the plurality of image acquisition subsystems 5120 can comprise a plurality of light sources 5128. The plurality of light sources 5128 of certain embodiments are configured to be operatively coupled to the visualization system controller 5100 (e.g., in wired communication with the visualization system controller 5100 via wired communication ports 5110 and/or in wireless communication with the visualization system controller 100 via wireless communication ports 5110). The light sources 5128 can be selected, for example, from the light sources described herein.

Figure 50C:
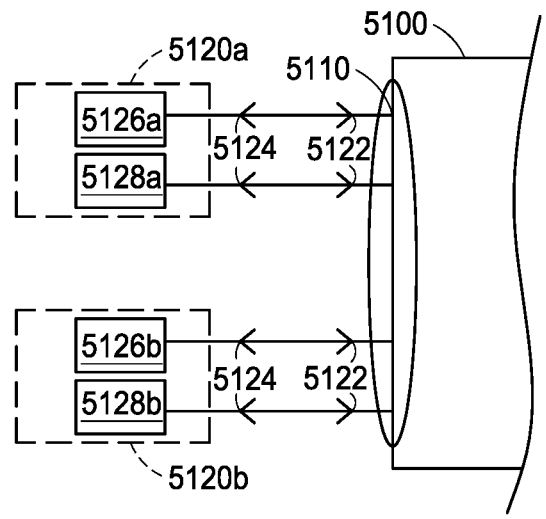
FIG. 50C schematically illustrates a partial view of an example visualization system controller operatively coupled to first and second image acquisition subsystems each comprising a camera and a light source in accordance with certain embodiments described herein.

In certain embodiments, each image acquisition subsystem 5120 can comprise a camera 5126 and a corresponding light source 5128. For example, in accordance with certain embodiments described herein, FIG. 50C schematically illustrates a partial view of an example visualization system controller 5100 operatively coupled to a first image acquisition subsystem 5120a comprising a first camera 5126a and a first light source 5128a. The example visualization system controller 5100 is also operatively coupled to a second image acquisition subsystem 5120b comprising a second camera 5126b and a second light source 5128b. In certain embodiments, the light source 5128 can be integrated with the corresponding camera 5126, while in certain other embodiments, the light source 5128 can be separate from the corresponding camera 5126.

In certain embodiments, the visualization system controller 5100 is responsive at least in part to the data signals 5122 from the camera 5126, the first user input signal 5162, and/or one or more of the plurality of second user input signals 5164 to generate and provide control signals 5124 to the light source 5128. When using a camera 5126, it can sometimes be desirable to have a light source 5128 located near the camera 5126 and oriented in a similar direction to the camera 5126. A light source 5128 with such an orientation can be least likely to cast shadows that cause visualization problems. Therefore, in certain embodiments, one or more cameras 5126 can each have an associated light source 5128.

When using one camera 5126, the light emitted from the light source 5128 associated with another camera 5126 may cause unwanted shadows. Also, intense light from a light source 5128 can cause heating of the patient's tissue, so it can be desirable to turn off a light source 5128 during times that the light source 5128 is not needed for the selected camera 5126. In certain embodiments, one or more light sources 5128 can emit non-visible spectrums of light (e.g., infrared) which can be used with a camera 5126 that can provide false-color images of infrared light views of the surgical site. Infrared light can cause tissue heating, although an infrared light source generally would not cause shadows when viewing the surgical site through a separate visual-light-based camera 5126. In certain embodiments, the visualization system controller 5100 can advantageously turn off the infrared light source when not in use so as to reduce (e.g., minimize) heating of the patient's tissue and potentially avoid harm resulting from such heating.

Display

The at least one image display subsystem 5140 can include one or more displays as described herein. The at least one image display subsystem 5140 of certain embodiments is configured to be operatively coupled to the visualization system controller 5100 (e.g., in wired communication with the visualization system controller 5100 via at least one wired image output port 5130 and/or in wireless communication with the visualization system controller 5100 via at least one wireless image output port 5130). In certain embodiments, the at least one image display subsystem 5140 can be integrated with the visualization system controller 5100.

In certain embodiments, the image display subsystem 5140 (e.g., display 5140) can comprise a binocular display device (e.g., a display configured to display 3D images, such as one or more LDC or LED displays disposed in a housing which are viewed through a pair of oculars) or a display screen configured to be viewed by a user at a distance from the display screen). In various embodiments, such a display is not a direct view display, where an optical path is provided from the ocular through the housing to the surgical site. The display 5140 can be configured to respond to the output image signals 5142 received from the visualization system controller 5100 to generate and display an image to be viewed by the user. In certain embodiments configured for use by multiple surgeons, each surgeon can have a display, and the surgeon can choose which camera image would be fed into the display being used by that surgeon.

Remote Control Devices

In certain embodiments, the at least one user input device 5160 (e.g., at least one remote control device) is configured to generate the first user input signal 5162 and the plurality of second user input signals 5164, and is configured to be operably coupled to the visualization system controller 5100 so as to transmit the first user input signal 5162 and the plurality of second user input signals 5164 to the visualization system controller 5100. The at least one user input device 5160 of certain embodiments is configured to be operatively coupled to the visualization system controller 5100 (e.g., in wired communication with the visualization system controller 5100 via at least one wired user input port 5150 and/or in wireless communication with the visualization system controller 5100 via at least one wireless user input port 5150). The at least one user input device 5160 can comprise one or more selector mechanisms, actuation devices, or other input device components including but not limited to: buttons, toggle buttons, switches, toggle switches, rocker switches, triggers, knobs, dials, relays, joysticks, touchpads, and touchscreens. The at least one input user device 5160 can include one or more remote control devices as described herein.

In response to the user manipulating one or more of the selector mechanisms, the at least one user input device 160 can generate and transmit the first user input signal 5162 and the plurality of second user input signals to the visualization system controller 5100. The at least one user input device 5160 can be integrated with the at least one image display subsystem 5140, with the visualization system controller 5100, or both. Example user input devices 5160 in accordance with certain embodiments described herein are also referred to herein as remote control devices 5160.

For example, the remote control device 5160 can comprise one button or a pair of buttons configured to run a specified motor of a camera 5126 in a forward direction and a backward direction (e.g., the one button or a pair of buttons can be dedicated to activating the appropriate motor for increasing and decreasing the focal distance of the camera 5126). The remote control device 5160 can be configured such that, in response to the user pressing a button, the remote control device 5160 is configured to generate and transmit appropriate user input signals to the visualization system controller 5100, which is configured to respond to these user input signals by generating and transmitting appropriate control signals 5124 to the specified motor of the camera 5126, which then moves in accordance with the control signals 5124. In certain embodiments, the button of the remote control device 5160 can be connected to circuitry (e.g., a relay or control board) of the remote control device 5160 that generates and transmits the user input signals to the visualization system controller 5100, and the specified motor of the camera 5126 can comprise circuitry (e.g., a relay or control board) that activates the motor in response to receiving control signals 5124 indicative of the button having been actuated.

For another example, the remote control device 5160 can comprise a toggle button, joystick, or variable level rocker switch that operates via the visualization system controller 5100 to increase the focal distance of the specified camera 5126 when operated in one direction and to decrease the focal distance of the specified camera 5126 when operated in another direction. In certain embodiments, the toggle button, joystick, or variable level rocker switch are configured to operate via the visualization system controller 5100 to change the focus of the camera 5126 at varying speeds depending upon how far or how hard the toggle button, joystick, or variable level rocker switch is pushed by the user. Depending upon the number of camera functions to be controlled, the remote control device 5160 can comprise a plurality of switches.

For still another example, the remote control device 5160 can comprise a switch to be actuated (e.g., moved) by the user for designating which of the multiple cameras 5126 is to be used as the video source by providing video images to be presented on the display for viewing (e.g., which input signals 5122 from the multiple cameras 5126 are to be transmitted via the plurality of communication ports 5110 to the visualization system controller 5100 to be used as the video source). In response to the user input signal generated and transmitted by the remote control device 5160 due to the switch being activated by the user, the visualization system controller 5100 can respond to the camera input signals 5122 from a selected camera 5126 and can generate output image signals 5142 based on the camera input signals from the designated source and transmit the corresponding output image signals 5142 to the at least one image display subsystem 5140. Certain such embodiments can advantageously avoid disconnecting and reconnecting display cables when switching among camera views to be displayed.

Figure 52:
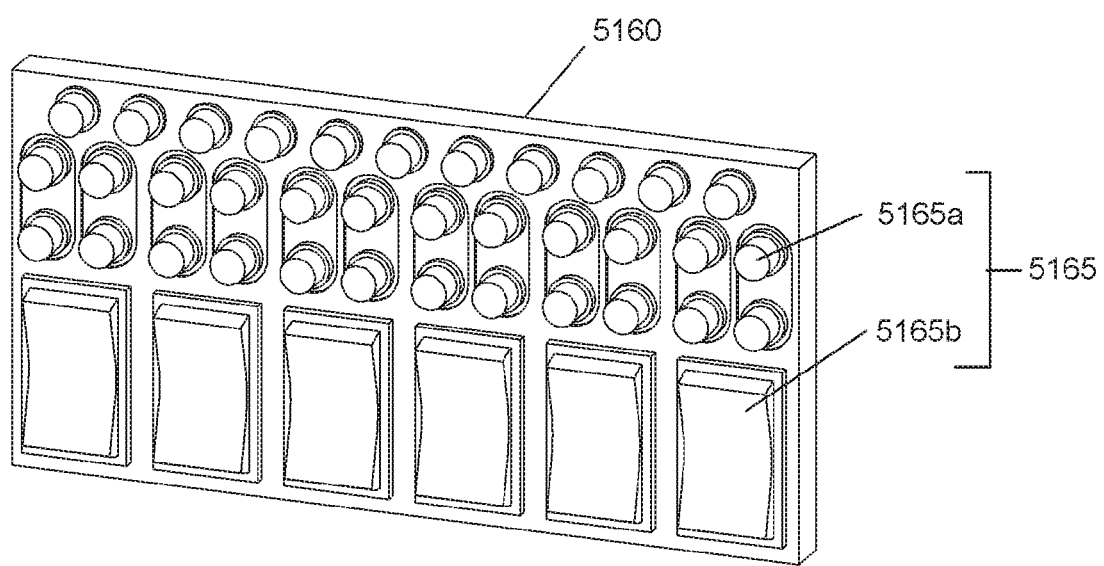
FIG. 52 schematically illustrates an example remote control device comprising a plurality of selector mechanisms (e.g., switches and buttons) in accordance with certain embodiments described herein.

FIG. 52 schematically illustrates an example remote control device 5160 comprising a plurality of selector mechanisms 5165 (e.g., switches 5165a and buttons 5165b) in accordance with certain embodiments described herein. The example remote control device 5160 of FIG. 52 comprises switches 5165a and buttons 5165b configured to allow adjustment of zoom, focus, pan, tilt, other rotations, iris diameter, and false color imaging. In certain embodiments (e.g., using the example remote control device 5160 of FIG. 52), the remote control device 5160 has sufficient switches 5165a and buttons 5165b so that each function on each camera has a dedicated switch. The example remote control device 5160 also comprises one or more selector mechanisms (e.g., switches 5165a) configured to transmit the first user input signal 5162 to the visualization system controller 5100, which responds to the first user input signal 5162 by selecting the data signals 5122 from a selected one of the cameras 5126 for use in generating the output image signals 5142 transmitted to the display 5140. In this way, certain such embodiments advantageously allow the user to toggle the viewed video between the different image acquisition subsystems 5120 (e.g., cameras) that are available. In certain such embodiments, besides toggling the selected camera, the visualization system controller 5100 further responds to the first user input signal 5162 by acting upon only the second user input signals corresponding to the selected one of the cameras 5126 and generating control signals 5124 (e.g., focus, zoom, etc.) transmitted to the selected one of the cameras 5126. In this way, certain such embodiments disable the selector mechanisms corresponding to non-selected cameras 5126 so that the settings of these cameras 126 remain unchanged until selected by the user.

In certain embodiments having a large number of image acquisition subsystems 5120, the at least one remote control device 5160 may have an excessive number of selector mechanisms. For example, if there is a remote control device 5160 dedicated to each camera, the user may need to keep track of where each remote control device 5160 is located or may need to break eye contact from the display in order to verify which remote control device 5160 is being operated. One alternative may be to have one remote control device 5160 with a large number of selector mechanisms (e.g., as schematically illustrated in FIG. 52) so that all the cameras functions are accessible on the one remote control device 5160. However, this configuration may also be problematic because the user may break eye contact from the display to find the appropriate selector mechanism, as it would be difficult to memorize the location of each switch, button, etc. of the remote control device 5160 when there are a large number of them. In both configurations, the user may not remember which camera is active in the display when wanting to make an adjustment to the camera since it can be difficult to remember which switch operates which function.

In certain embodiments, the remote control device 5160 advantageously has a number of remote control selector mechanisms that are configured to control the same camera functions (e.g., one or more remote control devices that have a limited number of easy-to-remember selector mechanisms), and configured to vary the function for which the selector mechanisms modify when activated. For example, the user may prefer to perform a primary adjustment with a dominant hand, but while performing the surgical operation, may want to perform minor adjustments with the other hand to avoid having to interrupt the surgical operation. For another example, the user may want to make the adjustments using a remote control device configured to be used with the foot so that both hands of the user can be used on the surgical procedure without interruption. In such situations, the user may want to maintain eye contact on the subject matter shown in the display and not break away to look at the selector mechanisms (e.g., control switches) mounted on the remote control device 160.

In certain embodiments, the remote control device 5160 advantageously has a limited number of selector mechanisms (e.g., switches) mounted on the remote control device 5160 that perform the known functions, and each of one or more of the selector mechanisms is configured to perform multiple functions. In certain embodiments described herein, the visualization system controller 5100 can respond to the plurality of second user input signals 5164 depending upon the information of the first user input signal 5162. Certain such embodiments advantageously allow the user to actuate a first selector mechanism which selects the desired camera function (e.g., selects a desired camera, selects a desired function, or both) that is controlled by activating a second selector mechanism. For example, the visualization system controller 5100 can advantageously determine which camera feed is sent to the display and can set the appropriate relays so that the selector mechanisms (e.g., switches) of the remote control device 5160 operate the desired functions on only that camera. Certain such embodiments advantageously allow the remote control device 5160 to have only the selector mechanisms needed to adjust one camera, and the user can adjust the camera of interest by operating those selector mechanisms without changing the settings for the other non-selected cameras. In this way, when switching back to a first camera after adjusting a second camera, the settings of the first camera are advantageously unchanged from when it was previously used. In certain embodiments in which the displayed image is a selected previously-stored image or image otherwise imported from a source other than the camera (e.g., MRI, CT, x-ray, DICOM image, etc.), the user can actuate a first selector mechanism which selects a desired source of images (e.g., selects a camera, selects a desired previously-stored image, or both) that is controlled by activating a second selector mechanism. For example, the visualization system controller 5100 can advantageously determine which source of images (e.g., camera, or previously-stored image, etc.) is selected to be sent to the display and can set the appropriate relays so that the selector mechanisms (e.g., switches) of the remote control device 5160 operate the desired functions (e.g., zoom; pan; contrast; brightness) to operate only on that selected previously-stored image or camera or other source of images. Certain such embodiments advantageously allow the remote control device 5160 to adjust the functions for the desired previously-stored image or camera by operating those selector mechanisms without changing the settings for the other non-selected previously-stored images or the non-selected cameras. In this way, when switching back to a first camera after viewing and adjusting a previously-stored image, the settings of the first camera are advantageously unchanged from when it was previously used. Likewise, when switching back to the previously-stored image, the settings of the previously-stored image are advantageously unchanged from when it was previously used. Depending on the configuration, the first selector mechanism that selects a desired source of images (e.g., selects a camera, selects a desired previously-stored image, or both) that is controlled by activating the second selector mechanism may be on the same remote control that the second selector mechanism is located, or may be on a different selector mechanism. For example the first selector mechanism may be a foot pedal and the second selector mechanism may be on a handle of the display assembly. For example, the foot pedal may be used to switch between the image source, for example, between a camera that provides a surgical microscope view, an endoscope, and electronics that is configured to store and/or provide stored images such as MRI images, CT images, X-rays images, DICOM images, etc.). In some instances, the foot pedal may enable the user to toggle between multiple different stored images, such as between a plurality of MRI images, or a plurality of x-ray images, or a plurality of CT images, or a plurality of DICOM images. Similarly the foot pedal may enable the user to toggle between different types of images such as to select either an MRI image, an X-ray image, or a CT image. The switching need not however be limited to a foot pedal and selection can be indicated by the user using, for example, a switch on a handle of the display assembly. Conveniently, in various implementations, when a different image source or image is selected with one of the selectors (foot pedal, switch on the handle of the display assembly, etc.), the other switches may automatically be reconfigured to control that particular source or image (e.g., that camera which is being used to acquire the image or the stored image provided by the electronics). As described above, when switching between cameras, one or more parameter may automatically change. For example, the illumination may change when switching between cameras. Similarly, a parameter (e.g., zoom, focus, iris, tilt, pan, brightness, contrast, etc.) of the image that is displayed may change automatically when switching between cameras and/or a stored image that is stored on electronics. As described above, such images may be x-rays, CT (computed tomography) images, MRI (magnetic resonance imaging) images, etc. Switching may thereby be provided between different image acquisition systems (e.g. cameras) well as image storage systems (e.g., electronics that stores or provides stored images). In some instances, the system can be configured to maintain a consistent parameter (e.g., zoom, focus, iris, tilt, pan, brightness, contrast, etc.) of the image. The overall system need not include the different image acquisition systems (e.g., cameras) but may be configured to communicate with such image acquisition systems. Similarly, the overall system need not include the different image storage system but may be configured to communicate with such image storage system.

As described above, a camera 5126 can have a large number of functions, at least some of which can be operated infrequently, while others may be used extensively. For example, zoom, focus, pan, and tilt may be adjusted frequently while the surgeon operates on different parts of the anatomy, while iris control, false color imaging, and other functions may be adjusted based upon the operating room conditions, camera type, and type of procedure being performed. To simplify the remote control device 5160 so that there are a limited number of selector mechanism (e.g., switches), each selector mechanism can be configured to operate more than one function. A first selector mechanism can be configured to operate a primary function, such as zoom, and then, when a second selector mechanism has been activated, the first selector mechanism can be configured to operate a secondary function different from the primary function. Multiple levels of functions can be incorporated into a remote control device 5160 with a limited number of selector mechanisms.

Figure 53A:
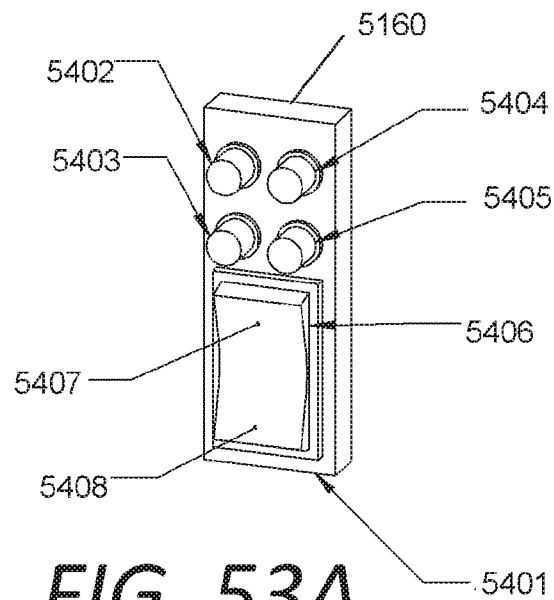
FIGS. 53A and 53B schematically illustrate example remote control devices comprising a plurality of selector mechanisms (e.g., a rocker switch and a plurality of buttons) configured to be operated by hand and by foot, respectively, in accordance with certain embodiments described herein.
Figure 53B:
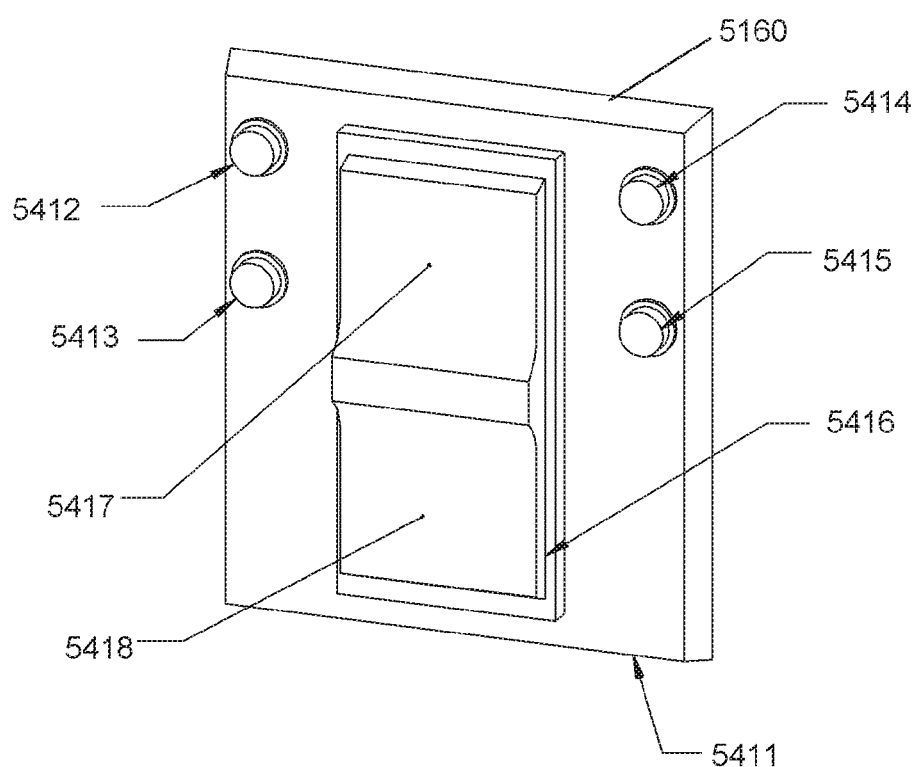

FIG. 53a schematically illustrates an example remote control device 5401 comprising a plurality of selector mechanisms (e.g., a rocker switch 5406 and a plurality of buttons 5402, 5403, 5404, 5405) configured to be operated by hand in accordance with certain embodiments described herein. The remote control device 5401 of FIG. 53a can advantageously allow adjustment of any of the camera functions. One set of buttons 5402, 5403 are configured to provide the first user input signal 5162 to the visualization system controller 5100 so as to select the camera 5126 providing the data signals 5122 to be used by the visualization system controller 5100 to generate the output image signals 5142 that are transmitted to the display 5140. For example, pushing a first button 5402 can switch to the next camera 5126 of the set of available cameras 5126, and pushing a second button 5403 can switch to the previous camera 5126. Pressing the button 5404 can switch the function of the selected camera 5126 that is to be adjusted to the next function of a predetermined list of functions (e.g., from zoom to focus, or focus to pan), and pressing the button 5405 can switch the function of the selected camera 5126 that is to be adjusted to the previous function of the predetermined list. Rocker switch 5406 can be configured such that when the user pushes on the first surface 5407 of the rocker switch 5406, the selected function of the selected camera is operated in a first direction. When the user pushes on the second surface 5408 of the rocker switch 5406, the selected function of the selected camera 5126 is operated in a second direction opposite to the first direction. The rocker switch 5406 of certain embodiments can be a simple single pole, dual throw rocker, providing second user input signals 5164 to the visualization system controller 5100 such that the control signals 5124 transmitted to the selected camera 5126 control the motor to turn at a fixed speed in each direction. In certain other embodiments, other switches (e.g., hall effect sensors) can be employed to provide second user input signals 5164 to the visualization system controller 5100 such that the control signals 5124 transmitted to the selected camera 5126 control the speed of the motor based on how hard the user pressed on the switch. FIG. 53b schematically illustrates an example remote control device 5411 comprising a plurality of selector mechanisms (e.g., a rocker switch 416 having a first surface 5417 and a second surface 5418 and a plurality of buttons 5412, 5413, 5414, 5415), configured similarly to the example remote control device 5401 of FIG. 53a, but with the switch and button sizes and locations configured to be operated with the user's foot instead of by hand.

Figures 54A, 54B:
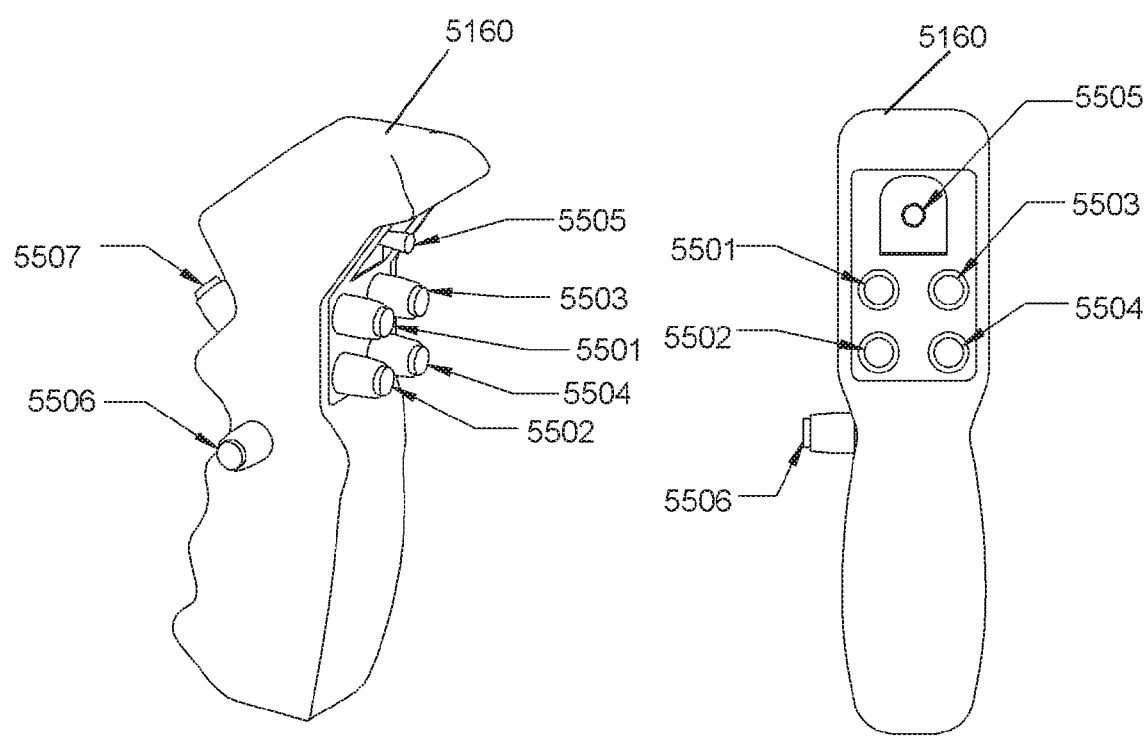
FIGS. 54A and 54B schematically illustrate an example remote control device configured to be operated by hand in accordance with certain embodiments described herein.

FIGS. 54A and 54B schematically illustrate an example remote control device 5160 configured to be operated by hand in accordance with certain embodiments described herein. FIG. 54a is an isometric view and FIG. 54b is a front view. This remote control device 5160 has multiple functions for most of the selector mechanisms (e.g., buttons, switches). For example, the button 5501 can be used to increase the zoom of a selected camera 5126, while the button 5502 can be used to decrease the zoom of the selected camera 5126. Similarly, the button 5503 can be used to increase the focal distance of the selected camera 5126 while the button 5504 can be used to decrease the focal distance of the selected camera 5126. The switch 5505 can be a four-way joystick that, when pressed to the left, makes the selected camera 5126 pan left and, when pressed to the right, makes the selected camera 5126 pan right. When the switch 5505 is moved up, the selected camera 5126 can tilt up, and when the switch 5505 is moved down, the selected camera 5126 can tilt down. The button 5506 can switch the selected camera 5126 that is used to generate the output image signal 5142 shown in the display 5140 to the next camera 5126 in the list of possible cameras 5126.

In certain embodiments, the button 5507 can be a switch that works like a shift key on a typewriter or computer keyboard, whereby pressing the button 5507 (or holding the button 5507 down) can change what function the visualization system controller 5100 adjusts when the buttons 5501, 5502, 5503, 5504 are pressed or when joystick 5505 is moved. When the button 5507 is depressed or not depressed, the remote control device 5160 transmits a corresponding first user input signal 5162 to the visualization system controller 5100. The visualization system controller 5100 responds at least in part to the first user input signal 5162 by applying a corresponding interpretation to the second user input signals 5164 received from the actuation of the other selection mechanisms of the remote control device 5160. For example, upon pressing the button 5507, instead of adjusting the zoom of the selected camera 5126, the button 5501 can adjust the iris diameter of the selected camera 5126 in one direction and the button 5502 can adjust the iris diameter of the selected camera 5126 in another opposite direction. As another example, upon pressing the button 5507, instead of panning the selected camera 5126 left or right, moving the joystick 5505 left or right can cause the selected camera 5126 to tilt, adjusting the view of the horizon on the displayed image. As a further example, upon pressing the button 5507, pressing the button 5506 can switch the selected camera 5126 that is used to generate the output image signal 5142 shown in the display 5140 to the previous camera 5126 in the list of possible cameras 5126. In certain other embodiments, the functionality of the buttons 5503, 5504 and moving the joystick 5505 up and down can also be dependent on whether the button 5507 is depressed or not.

Controller Circuitry

In certain embodiments, the visualization system controller 5100 comprises at least one circuit 5170 (e.g., one or more microprocessors). The at least one circuit 5170 can comprise one or more modules and can be programmed or configured by software code. The at least one circuit 5170 can take a wide variety of forms, including processors, microprocessors, specific-purpose computers, network servers, workstations, personal computers, mainframe computers and the like. The at least one circuit 5170 can be operatively coupled to other hardware of the visualization system controller 5100, examples of which include but are not limited to: a computer-readable memory media, such as random-access memory (RAM) integrated circuits and a data storage device (e.g., tangible storage, non-transitory storage, flash memory, hard-disk drive). It will be appreciated that one or more portions, or all of the at least one circuit 5170 and the software code may be remote from the user and, for example, resident on a network resource, such as a LAN server, Internet server, network storage device, etc. The software code which configures the at least one circuit 5170 and other hardware to perform in accordance with certain embodiments described herein can be downloaded from a network server which is part of a local-area network or a wide-area network (such as the internet) or can be provided on a tangible (e.g., non-transitory) computer-readable medium, such as a CD-ROM or a flash drive. Various computer languages, architectures, and configurations can be used to practice the various embodiments described herein.

In certain embodiments, the at least one circuit 5170 can comprise a plurality of modules (e.g., circuits). For example, the at least one circuit 5170 can comprise a data signal module (e.g., circuit) configured to receive the data signals from the plurality of image acquisition subsystems 5120 and to provide (e.g., generate) the output image signals 5142 transmitted to the at least one image display subsystem 5140. The at least one circuit 5170 can further comprise a control signal module (e.g., circuit) configured to generate and transmit the control signals 5124 to the selected image acquisition subsystem 5120 (e.g., the selected camera, the selected light source, or both) of the plurality of image acquisition subsystems 5120.

The data signal module can be responsive to the first user input signal to determine which data signals 5122 are to be used to provide the output image signals 5142 to the at least one image display subsystem 5140. The control signal module can be responsive to the first user input signal to determine which image acquisition subsystem 5120 (e.g., which camera 5126 and/or which light source 5128) is selected to receive the control signals 5124 and to determine which functionality of the selected image acquisition subsystem 5120 is to be adjusted. In certain embodiments, the at least one circuit 5170 comprises an integrated circuit that includes both the data signal module and the control signal module, and well as other circuitry used during operation of the visualization system controller 5100. In certain other embodiments, the at least one circuit 5170 can be distributed among separate circuits. For example, at least a portion of the at least one circuit 5170 can be integrated in a common housing with the at least one user input device 5160, with the at least one image display subsystem 5140, or both. In certain embodiments, the at least one circuit 5170 is in a different housing spatially separate from that of the at least one user input device 5160, the at least one image display subsystem 5140, or both, while being operatively coupled (e.g., via wired communications or wireless communications) to the at least one user input device 5160 and the at least one image display subsystem 5140. The at least one circuit 5170 can be configured to receive signals (e.g., the data signals 5122, the first user input signal 5162, the plurality of second user input signals 5164) and configured to transmit signals (e.g., the control signals 5124, the output image signals 5142) via one or more wired communication channels (e.g., over wires physically connected to the at least one circuit 170) and/or one or more wireless communication channels (e.g., Bluetooth, WiFi, IR, or others).

In certain embodiments, the at least one circuit 5170 is configured to allow the user to select which video is being viewed by controlling (e.g., switching) which camera 5126 provides the data signals 5122 used to provide the output image signals 5142 to the display 5140. The at least one circuit 5170 can also be used to change which functions will be active when the switches, buttons, etc. of the remote control device 5160 are operated. In certain such embodiments, the remote control device 5160 comprises sets of multi-pole switches, while in certain other embodiments, greater versatility can be made available by utilizing the at least one circuit 5170 (e.g., comprising a microcontroller integrated with the remote control device 5160 and programmed to generate the appropriate user input signals). For example, the microcontroller of the at least one circuit 5170 can be programmed such that actuating a selector mechanism (e.g., a switch closing a circuit) of the remote control device 5160 activates a process that sends a control signal 5124 to an appropriate camera 5126, light source 5128, or camera mount of the selected image acquisition subsystem 5120 (e.g., turning on a relay to operate a motor).

In certain embodiments, the at least one circuit 5170 is configured to accept a series of user input signals to then initiate an activity. For example, a button of the remote control device 5160 can be considered a "second function" button. When the button is pushed, the at least one circuit 5170 receives a first user input signal 5162 in response to which the at least one circuit 5170 accepts any other second user input signal 5164 as a command to initiate a different function than what was first programmed. For example, the at least one circuit 5170 can be programmed such that a primary switch of the remote control device 5160 initiates a second user input signal 5164 which commands the at least one circuit 5170 to move the focus motor forward when pressed, but upon pressing the "second function" button of the remote control device 5160, the at least one circuit 5170 can be programmed to instead respond to the second user input signal 5164 to move the iris diameter motor forward. In certain embodiments, the at least one circuit 5170 can be programmed to switch to the "second function" mode for all selector mechanisms (e.g., buttons, switches) until the "second function" button is pressed again, while in certain other embodiments, the at least one circuit 5170 can be programmed to switch back to the primary functions once one secondary function has been performed. Certain embodiments provide multiple "second function" buttons, while certain other embodiments provide a "second function" button that can advance the at least one circuit 5170 to different sets of secondary functions (e.g., if there are many additional functions relative to the number of buttons put on the remote control device 160).

In certain embodiments, instead of using a button as a "second function" button as described above, the button can operate like a "shift" button to select between first functions and second functions. The at least one circuit 5170 can be programmed to note the position of the "shift" button. When the button is in a first position (e.g., open), the at least one circuit 5170 can respond to user input signals initiated by the other selector mechanisms (e.g., switches) to generate control signals 5124 which operate the first functions, and when the button is in a second position (e.g., closed), the at least one circuit 5170 can respond to user input signals initiated by the other selector mechanisms (e.g., switches) to generate control signals 5124 which operate the second functions. Once the "shift" button is released and returns to the first position, the at least one circuit 5170 can respond to user input signals initiated by the other selector mechanisms to generate control signals 5124 which operate the first functions (e.g., thereby re-enabling the selector mechanisms to perform the first functions). In certain embodiments, the remote control device 5160 can comprise multiple "shift" buttons or a mix of "shift" buttons and "second function" buttons. In certain such embodiments, the set of "shift" buttons and/or "second function" buttons is advantageously designed to provide a beneficial or an optimal configuration for the user. However, for the same reason it can be desirable to limit the overall number of buttons, it can also be desirable to limit the number of buttons used to execute a function.

Example System Configuration

Figure 55:
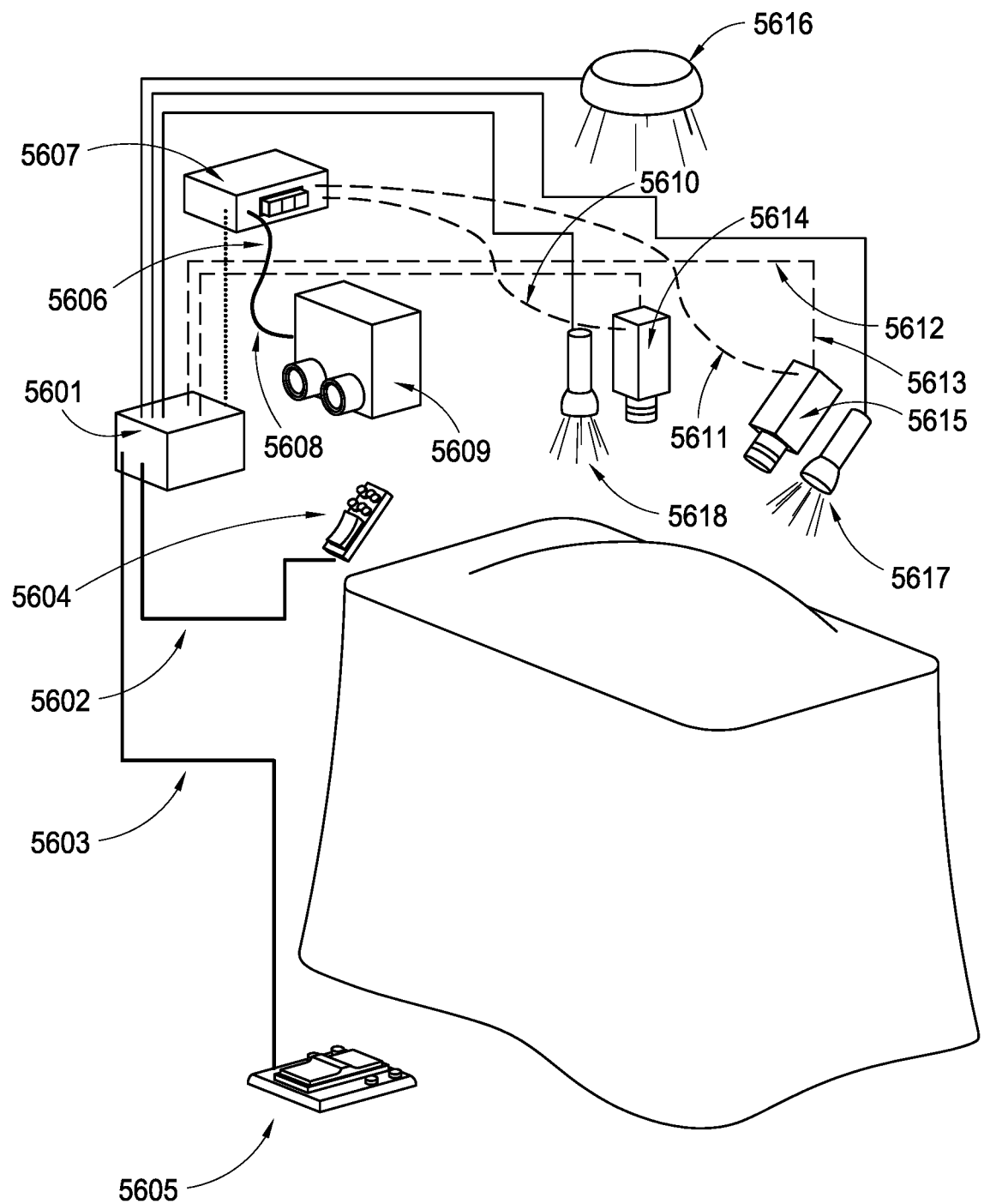
FIG. 55 schematically illustrates an example surgical visualization system utilizing a visualization system controller in accordance with certain embodiments described herein.

FIG. 55 schematically illustrates an example surgical visualization system utilizing a visualization system controller 5100 in accordance with certain embodiments described herein. The example surgical visualization system comprises a plurality of image acquisition subsystems 5120 (e.g., cameras 5614, 5615 and light sources 5616, 5617, 5618), at least one user input device 5160 (e.g., hand-operated remote control device 5604 and foot-operated remote control device 5605), at least one circuit 5170 (e.g., controller 5601 and video switch box 5607), and at least one image display subsystem 5140 (e.g., display 5609). Separate components are shown schematically in FIG. 55, with lines indicating communication channels for signals to be communicated between the different components. As described herein, the at least one circuit 5170 can be configured to receive and transmit signals via one or more wired communication channels (e.g., over wires physically connected to the at least one circuit 5170) and/or one or more wireless communication channels (e.g., Bluetooth, WiFi, IR, or others). In certain embodiments, the individual components of the visualization system controller 5100 can receive power to operate from these same wires, separate power cables, via batteries contained in the units, or other ways to supply power.

The controller 5601 is configured to receive user input signals 5162, 5164 (e.g., signals 5602, 5603, denoted by heavy solid lines) from the remote control devices 5604, 5605 and to transmit control signals 5124 (e.g., signals 5612, 5613, denoted by heavy dashed lines) to the proper camera components to operate a particular function and to transmit control signals 5124 (denoted by light solid lines) to the proper light sources 5616, 5617, 5618. The video switch box 5607 is configured to receive data signals 5122 (e.g., signals 5610, 5611, denoted by light dashed lines) from the cameras 5614, 5615, respectively, and to transmit output image signals 5142 (e.g., signals 5608, denoted by a curved heavy solid line) to the display 5609.

The controller 5601 is shown in FIG. 55 as a separate component, but in certain other configurations, the controller 5601 can be housed in one of the other components (e.g., the display 5609, the video switch box 5607, or one of the remote control devices 5604, 5605). The controller 5601 can comprise solid-state components, a programmable circuit board controller, a more complex programmable device such as a personal computer, or a combination of devices.

Upon using one of the remote control devices 5604, 5605 to change the camera 5614, 5615 used to provide video signals 5608 to the display 5609, the controller 5601 can send a signal 5606 to the video switch box 5607 to change the video signal 5608 sent to the display 5609. The user can therefore look into the display 5609 and press a button in a known location without having to look at it to switch which camera 5614, 5615 is used as the video source that is viewed in the display 5609. The video signals 5610, 5611 from the cameras 5614, 5615 continuously go into the video switch box 5607. In addition, while the user is looking into the display 5609, the camera that is used as the video source being viewed can have one of its functions adjusted. The user can operate the proper buttons on the remote control devices 5604, 5605 and the controller 5601 can send the signal 5612, 5613 to the selected camera 5614, 5615 to be adjusted. Besides setting the video signal to be viewed in the display 5609, the controller 5601 can respond to the signal or signals 5602, 5603 received from the remote control devices 5604, 5605 to allow only the selected camera to be adjusted, with no signals being sent to any other cameras.

Control of Lights

In certain embodiments, the light sources can be controlled through the at least one circuit 5170 so that only the appropriate light sources are turned on at the appropriate intensity for the selected camera that is being used as the video source for the displayed image. As the user switches which cameras are selected, the light sources can be turned up, down, on, or off, to facilitate imaging while avoiding unduly heating the patient's tissue. The at least one circuit 5170 of certain embodiments can also pulse any of the light sources for proper visualization and to synchronize with the camera image.

The at least one circuit 5170 of certain embodiments can also assess the image from each camera for brightness. With that information, the at least one circuit 5170 can adjust the illumination intensity and the camera gain to provide the user with a preferred image quality. For example, this assessment and adjustment can be performed each time the display is switched from the image from one camera to another, or can be performed dynamically as a camera is adjusted (e.g., by the remote control device or by physical manipulation). This brightness adjustment can be set to periodically adjust the lighting and camera gain so the brightness among the images remains relatively constant. For example, the periodic adjustments can be performed automatically at a frequency of 1 Hz (once per second) or more frequently (e.g., between 1 Hz and 100 Hz, between 1 Hz and 10 Hz, between 10 Hz and 100 Hz). In certain other embodiments, the brightness adjustment can be done selectively (e.g., with just certain cameras, only when particular camera settings are being changed by the user, or when switching between cameras to be used as the video source for the display). In similar manner, the at least one circuit 5170 of certain other embodiments can assess the images from each camera for other parameters which can be adjusted by periodically adjusting the light sources and/or the cameras, either automatically or selectively, such that the other assessed parameters of the images remain relatively constant.

As described above, in certain embodiments, the at least one circuit 5170 is configured to transmit control signals 5124 to the light sources 5128 of the surgical visualization system. For example, as schematically illustrated by FIG. 55, the same controller 5601 that switches between video signals 5610, 5611 used to provide the signals 5608 to the display 5609 can also switch which light sources 5616, 5617, 5618 in the surgical visualization system are turned on and at what brightness. In certain such embodiments, the controller 5601 can store desired light settings (e.g., can have previously stored or preprogrammed light settings) for each of the light sources that are part of the system. The user can send a signal 5602, 5603 to the controller 5601 to switch the video signal 5608 being sent to the display 5609. When the signal is received to switch video sources, the light sources can be adjusted to the desired light settings. For example, in certain embodiments, a single light source is associated with each camera. When the controller 5601 receives a user input signal indicative of selecting one of the cameras as the video source to be displayed, the light source associated with that selected camera is turned on and the light sources associated with other cameras are turned off. In certain embodiments, the light source associated with the selected camera is adjusted to maintain a consistent brightness or other parameter with that of the image from the previously-selected camera.

In certain other embodiments, additional light settings may be desired. For example, visualization may be improved by using a light source that is not associated directly with any camera (e.g., light source 5616 of FIG. 55). A high level of brightness of this light source may improve the image of one camera, while a lower level of brightness of this light source may improve the image of another different camera. Also, an ancillary light source may aid people who are directly viewing the surgical site, in which case this ancillary light source may be turned on as long as it does not cause viewing difficulties (e.g., bright spots or shadows) for the surgeon using the display. In such cases, dimming or turning off these ancillary lights can be beneficial.

In certain embodiments, the visualization system controller 5100 advantageously utilizes the different light sources (e.g., an overhead surgical light source 5616 and other light sources 5617, 5618 either associated with a camera or placed to illuminate the surgical site) which are each controlled by the at least one circuit 5170 (e.g., controller 5601). The at least one circuit 5170 can comprise different light settings for each of the light sources of the system, particularly for the light sources corresponding to each camera, and the at least one circuit 5170 (e.g., controller 5601) can switch the light settings for the light sources associated with all cameras each time the video source is switched. The user can also use a switch on the remote control device 5160 to turn the light sources on or off or to change the intensity of a light source as desired.

In certain embodiments, the preprogrammed light settings for the different light sources can be selected to illuminate at different levels depending upon which camera signal is being viewed and the settings for that camera, and/or the preprogrammed light settings can be selected to place the light sources at the desired levels for a known camera condition. For example, if one of the cameras is using a large magnification, a bright focused light source may be used. A second camera, however, may be configured to take in a lot of light. If the light source is left very bright when switching to the second camera, the brightness can be uncomfortable for the user. By presetting the light source to decrease intensity when switching from one camera to another, certain embodiments described herein can avoid such discomfort. In certain embodiments in which false color imaging with non-visible light (e.g., infrared light) is being used with one of the cameras, when switching from that false color image to a visible light image, the non-visible light source can be turned off. For example, turning off an infrared light source when not being used to generate an image being displayed can advantageously reduce the heating of the patient's tissue from the infrared light source. When switching back to the infrared camera, the infrared light source can be turned back on automatically by the at least one circuit 5170 (e.g., controller 5601).

Sometimes a camera being used as the video source is in a different condition than is compatible with the preprogrammed light settings. For example, this condition can be due to a camera being manually placed in a position not compatible with the preprogrammed light settings or due to the camera imaging different types of tissue in a manner that is not compatible with the preprogrammed light settings. Such conditions may lead to an image that is darker or brighter than is desired, causing viewing issues, discomfort for the user, or distraction from the surgical procedure being performed. In certain embodiments, the user may intervene in such conditions to change the brightness, while in certain other embodiments, the visualization system controller 5100 may automatically change the brightness.

In certain embodiments, the at least one circuit 5170 is configured to receive the data signals 5122 from the image acquisition subsystems 5120 and to generate control signals 5124 configured to improve the resulting output image signals 5142 transmitted to the display 5140. For example, the at least one circuit 5170 can assess the brightness of the image provided by the selected camera and can adjust the light source settings and/or the camera settings to bring the brightness of the image from the selected camera into a desired or predetermined range. Alternatively, the at least one circuit 5170 can be configured to receive the data signals 5122 from the image acquisition subsystems 5120 and to generate output image signals 5142, based on the received data signals 5122, that are configured to improve the image being displayed on the display 5140. For example, the at least one circuit 5170 can assess the brightness of the image provided by the selected camera and can generate output image signals 5142 which adjust the brightness of the image to be displayed into a desired or predetermined range. Certain such embodiments advantageously enable the user to view a displayed image while avoiding distracting or uncomfortable levels of brightness.

In certain embodiments, the at least one circuit 5170 compares one or more attributes (e.g., brightness) of the image provided by a first camera and one or more attributes (e.g., brightness) of the image provided by a second camera and automatically adjusts the light source settings and/or the camera settings to bring the displayed images from the first camera and the second camera closer to having the same attributes. Alternatively, the at least one circuit 5170 can compare one or more attributes (e.g., brightness) of the image provided by the first camera and one or more attributes (e.g., brightness) of the image provided by the second camera and can generate output image signals 5142 based on the received data signals 5122, that are configured to bring the displayed images from the first camera and the second camera closer to having the same attributes. Certain embodiments advantageously enable the user to switch the displayed image between images from the first and second cameras while avoiding distracting or uncomfortable differences in attributes (e.g., brightness) between the images.

Figure 56:
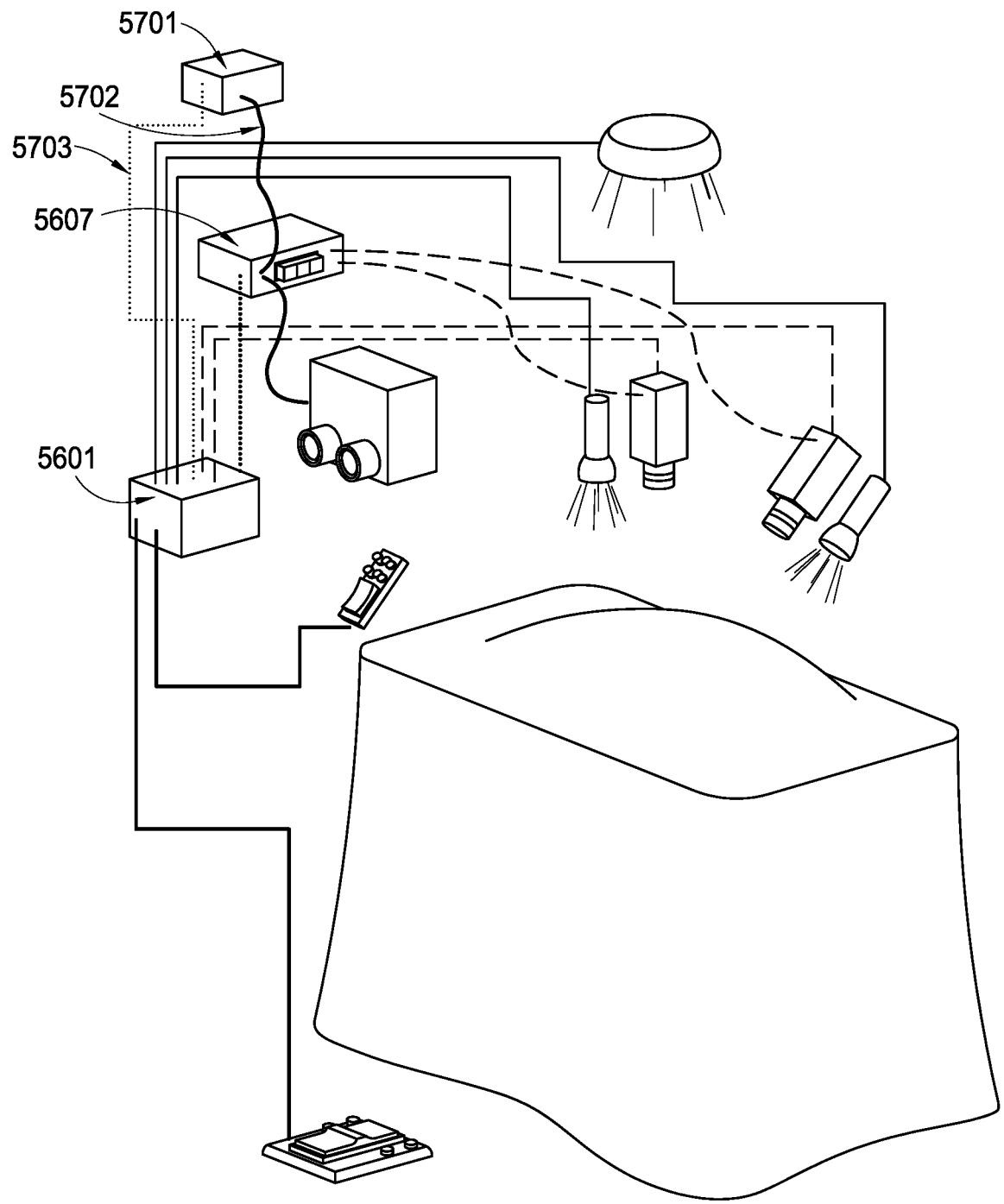
FIG. 56 schematically illustrates an example surgical visualization system utilizing a visualization system controller comprising an image analyzer in accordance with certain embodiments described herein.

FIG. 56 schematically illustrates an example surgical visualization system utilizing a visualization system controller 5100 comprising an image analyzer 5701 in accordance with certain embodiments described herein. The example system of FIG. 56 is similar to that of FIG. 55, but includes the image analyzer 5701. The image analyzer 5701 can comprise a portion of the at least one circuit 5170. While the image analyzer 5701 is shown separately from the controller 5601 in FIG. 56 (e.g., the image analyzer 5701 having its own control board that is configured to transmit a signal to the controller 5601). In certain other embodiments, the image analyzer 5701 can be incorporated into the controller 5601 (e.g., incorporated into the same circuit board). For example, if using a full computer processor such as a Raspberry Pi, the video signal and the switching can all be run in the same processor using one program with multiple subroutines. In certain embodiments, the image analyzer 5701 receives the data signals 5702 from the selected camera, analyzes a selected parameter (e.g., the brightness, intensity, optical power) of the image, and transmits information 5703 regarding the selected parameter to the controller 5601. This information 5703 can be an average value of the selected parameter, a peak value of the selected parameter, or a combination of average and peak values, as well as with other values. The controller 601 then adjusts the selected parameter of the displayed image based upon this information 5703. This process can be repeated as many times as is appropriate to get the selected parameter to match the user's preferences.

Control of Display Image

Figure 57:
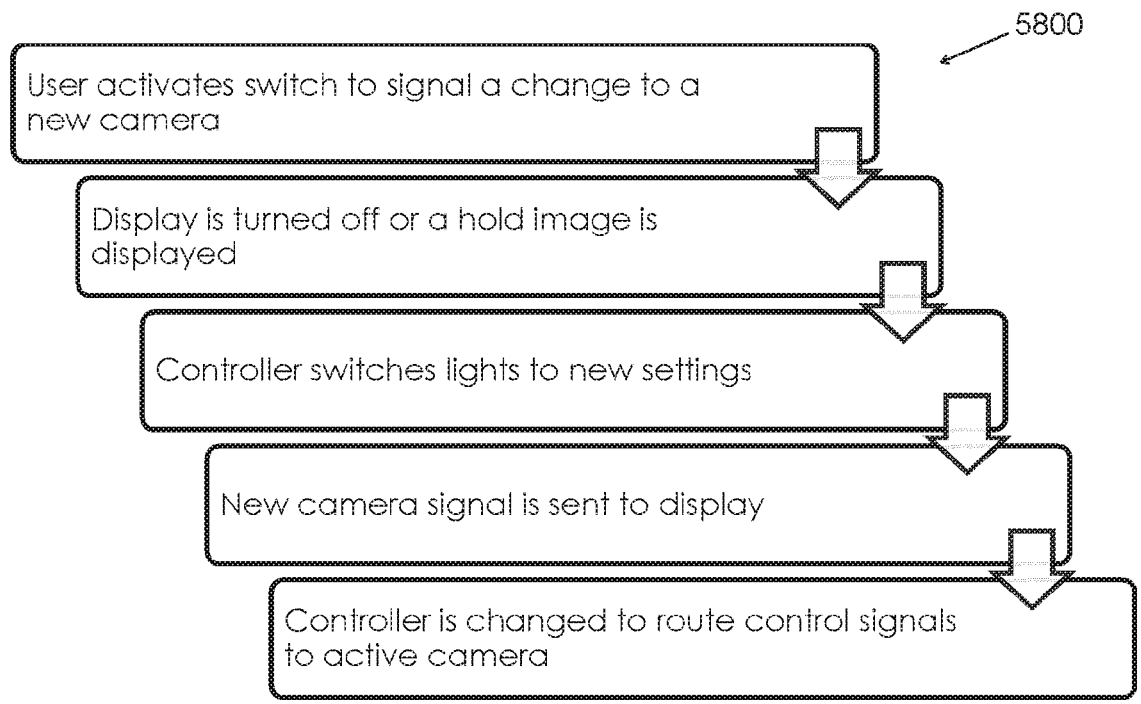
FIG. 57 is a flowchart of an example process for switching the image acquisition subsystem selected to be the video source for the displayed image in accordance with certain embodiments described herein.

FIG. 57 is a flowchart of an example process 5800 for switching the image acquisition subsystem 5120 (e.g., camera 5126 and light source 5128) selected to be the video source for the displayed image in accordance with certain embodiments described herein. The process 5800 comprises switching the lighting system to the desired state, switching the connections from the remote controls and switching what is shown in the display. The switching can comprise a transition from a first modality to a second modality (e.g., switching from a microscope-like modality to an endoscope-like modality, or switching from an endoscope-like modality to a microscope-like modality).

In certain embodiments, switching views among different imaging modalities in an electronic visualization system can be initiated when the system is in one modality and the user chooses the next or desired modality by contacting a button, foot switch, or other selector mechanism of a remote control device 5160. For example, upon the user activating a switch to change to a new camera, the at least one circuit 5170 can respond by comparing the desired next view to the current view for compatibility of the overall illumination intensity. Such a comparison can be performed in a manner unseen by the user (e.g., using only a few milliseconds of the desired next view for the comparison). If the illumination level of the second view is greater than that of the first view, the light source level of the second view can be lowered. If the illumination level of the second view is lower than that of the first view, the light source level of the second view can be increased. Such a comparison and adjustment can be applied when performing complete view switching or picture-in-picture or multiple views per screen. In certain embodiments in which full screen switching takes place, the light source associated with the view that is not displayed can then be disabled, shut off, or set to a lower power setting. In certain embodiments in which two or more scenes are both displayed concurrently, the associated light sources can remain on.

In certain embodiments, the process can proceed as follows:

1) Initiate switching, for example, by selecting a next or desired second modality (e.g., second camera) different from the present first modality (e.g., first camera) by actuating a button, foot switch or other selector mechanism of the remote control device 5160.
2) Detect and possibly modify a level of the second modality before displaying an image of the second modality on the display. For example, the level of the second modality can be modified by either varying the illumination output level, aperture setting, or camera gain of the second modality, and such adjustments may involve several cycles or iterations before displaying the image of the second modality.
3) Display the image of the second modality (e.g., in full, partial, or picture in picture view).

Various methods can be used in accordance with certain embodiments described herein to accomplish apparent light level balancing between views besides changing the illumination levels of the light sources. In certain embodiments, the f-number of the optics of any of the modalities can be varied as the working distance is changed and the light source intensity held constant. In certain other embodiments, the f-number of the optics of any of the modalities can be held constant as the working distance is changed and the light source intensity is varied.

In certain embodiments, the light sources can be set at a constant output and attenuated (e.g., using a variable filter or screen depending on illumination requirements). This attenuation can be controlled by a drive circuit and stepper motor with optional feedback loop for control. The advantage of mechanically or optically attenuating the constant output in this manner can be speed of change without color shift. In certain other embodiments, the light source itself can have its power raised or lowered to the desired output level. In certain embodiments, the light sources associated with each visualization modality can be operated in one of these two ways, in a combination thereof, or in other ways.

Figure 58:
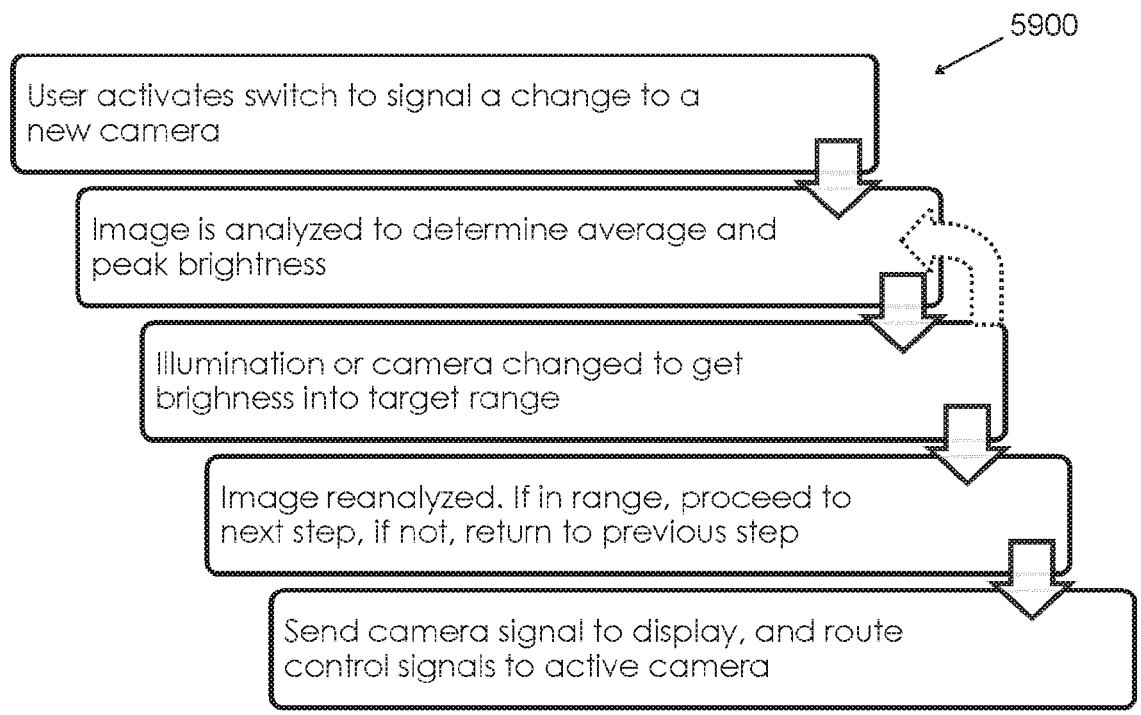
FIG. 58 is a flowchart of an example process for analyzing the image to be displayed and adjusting the brightness of the image to be displayed in accordance with certain embodiments described herein.
Figure 59:
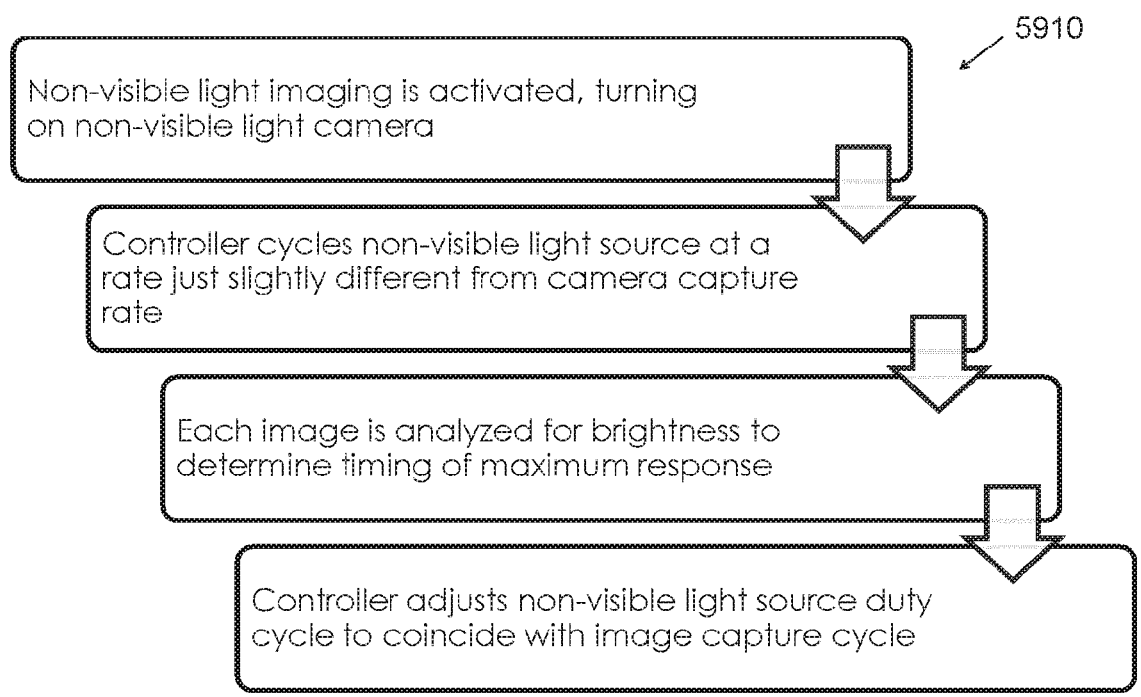
FIG. 59 is a flowchart of an example process for analyzing the image to be displayed for peak emission response due to a duty cycle on a non-visible light source in accordance with certain embodiments described herein.

FIG. 58 is a flowchart of an example process 5900 for analyzing the image to be displayed and adjusting the brightness of the image to be displayed in accordance with certain embodiments described herein. The dashed arrow of FIG. 58 is indicative of a loop in which the lighting is analyzed and adjusted until a satisfactory value is reached. FIG. 59 is a flowchart of an example process 5910 for analyzing the image to be displayed for peak emission response due to a duty cycle on a non-visible light source in accordance with certain embodiments described herein.

To have the at least one circuit 5170 (e.g., controller 5601) automatically adapt the lighting to account for the brightness of the image to be displayed, the at least one circuit 5170 can measure the brightness of the image, for example, by reading the image displayed or to be displayed and determining a parameter (e.g., the luminance, brightness, intensity, optical power, or other metric) measured for each pixel in the image. If the average parameter value is higher or lower than a preprogrammed target range, the image may be brighter or darker than desired. In certain embodiments, the at least one circuit 5170 can adjust the brightness of the different light sources in the system while the brightness of the image is read. Once the average brightness of the image meets a preprogrammed target or range, the at least one circuit 5170 can stop adjusting the lighting. When switching from one camera view to another, the at least one circuit 5170 can read the image from the new camera, assess the brightness, adjust the light sources via a predetermined algorithm, then switch to the new view. The at least one circuit 5170 can continue to display the previous view on the display until the switch occurs, can switch to a blank view (no signal), or can show a preset image on the display while making the change.

In certain embodiments, the at least one circuit 5170 can determine the average brightness of the image to determine whether the image has bright or dark spots. For example, if there is excessive brightness in the center of the image and a lot of darkness at the edges, the at least one circuit 5170 can adjust a focus lens in front of the primary light source which can change the focus of the light, diffusing it across the field of view better. This same technique can be employed if there are multiple light sources and one portion of the view has significantly different luminance relative to other portions.

In certain embodiments, the at least one circuit 5170 can determine the average brightness of the image to dynamically adjust the brightness while the image is being viewed to reduce (e.g., minimize) visualization problems. Such dynamic adjustment can be helpful for cameras that are moved manually where the working distance or type of tissue being imaged changes dramatically. The at least one circuit 5170 can constantly monitor the brightness and when the brightness changes away from a desired level, the at least one circuit 5170 can change the light intensity appropriately.

In certain embodiments, the at least one circuit 5170 can aid in the use of non-visible light, such as infrared, in another way. When viewing fluorescence generated by infrared light, leaving the infrared light source on continuously can lead to patient heating issues. In certain embodiments, the at least one circuit 5170 generates and transmits appropriate control signals 5124 to the infrared light source to pulse the infrared light source at a rate that synchronizes with the camera being used to view the fluorescence. In certain such embodiments, the at least one circuit 5170 can control the pulsing of the infrared light source and can capture the peak emission response.

In certain embodiments, the at least one circuit 5170 can control the switching of the video source and the light sources, and can serve as a central camera clock, timecode, record trigger, or synchronizing reference between multiple cameras. The at least one circuit 5170 of certain embodiments can also provide synchronization between the cameras and light sources.

Digital video technology, whether recording the video or immediately transmitting the video, can be done by capturing "still" images at a constant rate. A video that is captured with a shutter speed of $\frac{1}{125}$s (seconds) at a frame rate of 30 fps (frames per second) can have the image being captured for 8 milliseconds, then the shutter can be closed for 25⅓ milliseconds, then another image can be captured for 8 milliseconds as another cycle begins. This cycle can be termed the "duty cycle" of the camera. The cycle described is one possible cycle, and some cameras can have their duty cycles adjusted via settings that can be controlled.

When the fluorescence response is near instantaneous and potentially short lived, the synchronized cameras can be viewing, their sensors active, during the excitation and during the emission pulse. If the cameras are not synched to the duty cycle of the excitation light source, the result can appear as dropped frames. To avoid such dropped frames, the duty cycle can be set at a rate so high as to not produce video frames without excitation. For example, if the camera is running at 30 fps with a shutter speed of $\frac{1}{125}$s, an excitation pulse rate of 120 pulses per second would ensure that there is an excitation pulse occurring every time the shutter is open. In this example, there can also be approximately three pulses occurring when no image is being captured.

In certain embodiments, the at least one circuit 5170 can be configured to measure the brilliance of the illumination and to adjust the timing of the light sources so as to adjust (e.g., optimize) the lighting duty cycle to correspond with the digital video capture rate. The at least one circuit 5170 can set the duty cycle of the emission source to match in rate the capture rate of the camera. For example, if the camera is set to 30 fps, the emission is pulsed 30 times per second. If the camera is set to 60 fps, the pulse rate will be doubled. The at least one circuit 170 can then start measuring the brilliance of the image captured on the video sensor (e.g., measuring brilliance of just the image values in the spectrum of the excitation response). The at least one circuit 5170 can then adjust the start time of the duty cycle of the emission source. When the timing of the duty cycles are matched, the maximum brilliance can be measured. The at least one circuit 5170 can then adjust the duty cycle of the emission source, changing the length of time that the source is emitting versus the length of time that the source is off. The at least one circuit 5170 can select the shortest time that the source is on that provides an increased (e.g., maximal) brilliance, thereby reducing (e.g., minimizing) the amount of light exposed to the patient without decreasing the fluorescence imaging quality.

By having control over the illumination sources in the lighting system, the visualization system controller of certain embodiments described herein can generate the pulsed illumination for properly visualizing the fluorescence. The at least one circuit 5170 can also turn on, off, or dim the illumination sources in the lighting system to meet the parameters of the various cameras in the system. In certain embodiments, the at least one circuit 5170 can incorporate a feedback loop to assess the image brightness and color qualities, and can modify the light sources or adjust the camera settings to provide a preferred visualization of the workspace.

Headings are used throughout this application as an organizational aid for the reader. These headings may group together examples of methods, apparatuses, and structures that may generally relate to a particular topic noted in the headings. It will be appreciated, however, that while the various features discussed under the heading may relate to a particular topic, the headings should not be understood to indicate that the features discussed under a given heading are limited in applicability only to the topic or topics that listed in the heading. For example, a heading may be labeled "Remote Control". However, the subject matter included under this heading may equally be applicable to subject matter contained in any other section, such as content under the heading "Control of lights," "Example System Configurations," "Controller Circuitry," "Pair of Mobile Devices," and other sections. Alternatively, subject matter from other sections may also be applicable to the "Remote Control" sections.

Although described above in connection with particular embodiments of the present invention, it should be understood the descriptions of the embodiments are illustrative of the invention and are not intended to be limiting. Various modifications and applications may occur to those skilled in the art without departing from the true spirit and scope of the invention.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

It should be emphasized that many variations and modifications may be made to the above-described embodiments, the elements of which are to be understood as being among other acceptable examples. All such modifications and variations are intended to be included herein within the scope of this disclosure and protected by the following claims.

CONCLUSION

Various modifications to the implementations described in this disclosure may be readily apparent to those skilled in the art, and the generic principles defined herein may be applied to other implementations without departing from the spirit or scope of this disclosure. Thus, the claims are not intended to be limited to the implementations shown herein, but are to be accorded the widest scope consistent with this disclosure, the principles and the novel features disclosed herein.

Certain features that are described in this specification in the context of separate embodiments also can be implemented in combination in a single embodiment. Conversely, various features that are described in the context of a single embodiment also can be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

What is claimed is:

1. A surgical visualization system comprising:
at least one image acquisition system and at least one image storage system configured to provide images to be displayed, the at least one image storage system configured to provide previously-stored images from a source other than the at least one image acquisition system;
an electronic display system with one or more displays;
an electronic video switching system;
a controller; and
one or more remote control units that provide remote control of one or more of the following functions for one or more of the images provided by the at least one image acquisition system and the at least one storage system: zoom, focus, iris, tilt, pan, brightness, contrast, and acquisition selection, wherein the one or more functions provided by the one or more remote control units automatically change to an image acquisition or storage system selected for display, such that the one or more remote control units are able to function for multiple image acquisition or storage systems, and
wherein the system is configured to maintain automatically at least one parameter at a consistent level when switching between the images provided by the at least one image acquisition system or the at least one storage system, the at least one parameter comprising contrast.

2. The system of claim 1, wherein the image acquisition or storage systems comprise at least one camera, at least one sensor, at least one image storage medium, or electronics accessing at least one image storage medium.

3. The system of claim 1, wherein the one or more remote control units incorporate one or more indicators that operate the same function on each image acquisition or storage system.

4. The system of claim 3, wherein the one or more indicators comprise one or more switches, buttons, or touchscreens.

5. The system of claim 1, wherein the one or more remote control units incorporate one or more indicators that operate a first function when a first image acquisition or storage system is selected and a second function when a second image acquisition or storage system is selected.

6. The system of claim 1, wherein a first remote control unit operates a variety of functions with a reduced number of indicators by using a first indicator to change the function of a second indicator.

7. The system of claim 6, wherein when the first indicator is open, the second indicator affects a first function and when the first indicator is closed, the second indicator affects a second function.

8. The system of claim 6, wherein initially the second indicator affects a first function, but when the first indicator is operated, the controller is changed so the second indicator affects a second function, and when the first indicator is operated again, the controller is changed so the second indicator operates a third function.

9. The system of claim 8, wherein after further operation of the first indicator, the controller is changed so the second indicator operates the first function.

10. The system of claim 1, wherein the multiple image acquisition or storage systems comprise one image acquisition system and one image storage system.

11. The system of claim 1, wherein the at least one parameter comprises one or more of zoom, focus, iris, tilt, pan, or brightness.

12. A surgical visualization system comprising:
    at least one image acquisition system and at least one image storage system configured to provide images to be displayed, the at least one image storage system configured to provide previously-stored images from a source other than the at least one image acquisition system;
    an electronic display system with at least one display;
    an integrated lighting system comprising a plurality of light sources;
    an electronic video switching system; and
    a control unit that allows the user to switch which of the at least one image acquisition system or of the at least one storage system presents an image in the display, wherein the lighting system has programmed settings for a particular light intensity of each light source to match the optical demands of each image acquisition system, and wherein the control unit switches the lighting system to the programmed setting for the selected image acquisition system in conjunction with switching to the selected image acquisition system, and wherein the system is configured to maintain automatically a consistent brightness on the display when switching to the selected image acquisition or storage system.

13. The system of claim 12, wherein the image acquisition or storage systems comprise at least one camera, at least one sensor, at least one image storage medium, or electronics accessing at least one image storage medium.

14. The system of claim 12, wherein the light intensity is adjusted by turning a portion of the light sources in the system on while leaving an additional portion off.

15. The system of claim 12, wherein the light intensity is adjusted by cycling at least one light source rapidly between off and on with the apparent intensity related to the ratio of the cycle time the light is on versus the cycle time the light is off.

16. The system of claim 12, wherein the light intensity of at least one light source is variable.

17. The system of claim 12, wherein at least one light source generates non-visible light.

18. The system of claim 17, wherein the non-visible light is in the infrared spectrum.

19. The system of claim 17, wherein the non-visible light has a wavelength from about 700 nm to about 1000 nm.

20. The system of claim 17, wherein the non-visible light is in the near infrared spectrum.

21. The system of claim 17, wherein the non-visible light has a wavelength from about 700 nm to about 800 nm.

22. The system of claim 17, wherein the non-visible light is in the ultraviolet spectrum.

23. The system of claim 17, wherein the non-visible light has a wavelength from about 10 nm to about 400 nm.

24. The system of claim 17, wherein the non-visible light is in the near ultraviolet spectrum.

25. The system of claim 17, wherein the non-visible light has a wavelength from about 300 nm to about 400 nm.

26. The system of claim 17, wherein the control unit cycles at least one non-visible light source with a rapid rate between off and on.

27. The system of claim 26, wherein the rate is concurrent with and synchronized to the image capture rate of a camera.

28. The system of claim 26, wherein the rate is selected such that fluorescence response is captured by the image acquisition system.

29. The system of claim 12, wherein the control unit allows for adjustment of the programmed settings of the lighting system.

30. A surgical visualization system comprising:
    at least one image acquisition system and at least one image storage system configured to provide images to be displayed, the at least one image storage system configured to provide previously-stored images from a source other than the at least one image acquisition system;
    an electronic display system with at least one display;
    an electronic video switching system; and
    a control unit that allows the user to switch which of the at least one image acquisition system or of the at least one storage system presents an image in the display, wherein the system is configured to vary at least one parameter of the image in the display, wherein the system is configured to maintain automatically the at least one parameter at a consistent level, and wherein the at least one parameter comprises contrast.

31. The system of claim 30, wherein the image acquisition or storage systems comprise at least one camera, at least one sensor, at least one image storage medium, or electronics accessing at least one image storage medium.

32. The system of claim 30, wherein the at least one parameter comprises one or more of zoom, focus, iris, tilt, pan, or brightness.

33. A surgical visualization system comprising:
    at least one image acquisition system and at least one image storage system configured to provide images to be displayed, the at least one image storage system configured to provide previously-stored images from a source other than the at least one image acquisition system;
    an electronic display system with one or more displays;
    an electronic video switching system;
    a controller; and
    one or more remote control units that provide remote control of one or more of the following functions for one or more of the images provided by the at least one image acquisition system and the at least one storage system: zoom, focus, iris, tilt, pan, brightness, contrast, and acquisition selection, wherein the one or more functions provided by the one or more remote control units automatically change to an image acquisition or storage system selected for display, such that the one or more remote control units are able to function for multiple image acquisition or storage systems, wherein the system is configured to maintain automatically a parameter at a consistent level when switching between the images provided by the at least one image acquisition system or the at least one storage system, the parameter comprising one or more of zoom, focus, iris, tilt, pan, brightness, or contrast, wherein a first remote control unit of the one or more remote control units operates a variety of functions with a reduced number of indicators by using a first indicator to change the function of a second indicator, and wherein when the first indicator is open, the second indicator affects a first function and when the first indicator is closed, the second indicator affects a second function.

34. The system of claim 33, wherein the image acquisition or storage systems comprise at least one camera, at least one sensor, at least one image storage medium, or electronics accessing at least one image storage medium.

35. The system of claim 33, wherein the first and/or second indicator comprises one or more switches, buttons, or touchscreens.

36. The system of claim 33, wherein the first and/or second indicator operates a first function when a first image acquisition or storage system is selected and a second function when a second image acquisition or storage system is selected.

37. A surgical visualization system comprising:
at least one image acquisition system and at least one image storage system configured to provide images to be displayed, the at least one image storage system configured to provide previously-stored images from a source other than the at least one image acquisition system;
an electronic display system with one or more displays;
an electronic video switching system;
a controller; and
one or more remote control units that provide remote control of one or more of the following functions for one or more of the images provided by the at least one image acquisition system and the at least one storage system: zoom, focus, iris, tilt, pan, brightness, contrast, and acquisition selection, wherein the one or more functions provided by the one or more remote control units automatically change to an image acquisition or storage system selected for display, such that the one or more remote control units are able to function for multiple image acquisition or storage systems, wherein the system is configured to maintain automatically a parameter at a consistent level when switching between the images provided by the at least one image acquisition system or the at least one storage system, the parameter comprising one or more of zoom, focus, iris, tilt, pan, brightness, or contrast, wherein a first remote control unit of the one or more remote control units operates a variety of functions with a reduced number of indicators by using a first indicator to change the function of a second indicator, and wherein initially the second indicator affects a first function, but when the first indicator is operated, the controller is changed so the second indicator affects a second function, and when the first indicator is operated again, the controller is changed so the second indicator operates a third function.

38. The system of claim 37, wherein the image acquisition or storage systems comprise at least one camera, at least one sensor, at least one image storage medium, or electronics accessing at least one image storage medium.

39. The system of claim 37, wherein the first and/or second indicator comprises one or more switches, buttons, or touchscreens.

40. The system of claim 37, wherein the first and/or second indicator operates a first function when a first image acquisition or storage system is selected and a second function when a second image acquisition or storage system is selected.

41. The system of claim 37, wherein after further operation of the first indicator, the controller is changed so the second indicator operates the first function.

* * * * *